US011254640B2

(12) United States Patent
Olson et al.

(10) Patent No.: US 11,254,640 B2
(45) Date of Patent: Feb. 22, 2022

(54) N-SUBSTITUTED INDOLES AND OTHER HETEROCYCLES FOR TREATING BRAIN DISORDERS

(71) Applicant: The Regents of the University of California, Oakland, CA (US)

(72) Inventors: David E. Olson, Davis, CA (US); Lee Dunlap, Davis, CA (US); Florence Wagner, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/345,471

(22) Filed: Jun. 11, 2021

(65) Prior Publication Data

US 2021/0332012 A1 Oct. 28, 2021

Related U.S. Application Data

(63) Continuation of application No. PCT/US2020/019856, filed on Feb. 26, 2020.

(60) Provisional application No. 62/958,220, filed on Jan. 7, 2020, provisional application No. 62/811,206, filed on Feb. 27, 2019.

(51) Int. Cl.
| | |
|---|---|
| *C07D 209/08* | (2006.01) |
| *A61P 25/24* | (2006.01) |
| *C07D 209/14* | (2006.01) |
| *C07D 401/06* | (2006.01) |
| *C07D 403/06* | (2006.01) |
| *C07D 491/044* | (2006.01) |
| *A61K 31/4045* | (2006.01) |

(52) U.S. Cl.
CPC ........ *C07D 209/08* (2013.01); *A61K 31/4045* (2013.01); *A61P 25/24* (2018.01); *C07D 209/14* (2013.01); *C07D 401/06* (2013.01); *C07D 403/06* (2013.01); *C07D 491/044* (2013.01)

(58) Field of Classification Search
CPC .. C07D 209/08; C07D 209/14; C07D 401/06; C07D 403/06; C07D 491/044; A61P 25/24; A61K 31/4045; A61K 31/395
See application file for complete search history.

(56) References Cited

U.S. PATENT DOCUMENTS

| | | | |
|---|---|---|---|
| 4,841,056 | A | 6/1989 | Hunter |
| 5,494,928 | A | 2/1996 | Bos |
| 6,380,238 | B1 | 4/2002 | Adams et al. |
| 6,380,242 | B1 | 4/2002 | Arora et al. |
| 6,635,639 | B2 | 10/2003 | Arora et al. |
| 6,828,314 | B2 | 12/2004 | Frank et al. |
| 6,903,090 | B2 | 6/2005 | Frank et al. |
| 8,338,447 | B2 | 12/2012 | Hung et al. |
| 2002/0169322 | A1 | 11/2002 | Arora et al. |
| 2003/0225058 | A1 | 12/2003 | Frank et al. |
| 2005/0070558 | A1 | 3/2005 | Vidal et al. |
| 2005/0250767 | A1 | 11/2005 | Weiner et al. |
| 2006/0105030 | A1 | 5/2006 | Windt-Hanke et al. |
| 2010/0317863 | A1 | 12/2010 | Kuzmich et al. |
| 2011/0229555 | A1 | 9/2011 | Helson et al. |
| 2012/0296569 | A1 | 11/2012 | Shahaf et al. |
| 2013/0195866 | A1 | 8/2013 | Bacskai et al. |
| 2014/0275531 | A1 | 9/2014 | Bollu et al. |
| 2014/0275548 | A1 | 9/2014 | Basinger et al. |
| 2015/0141345 | A1 | 5/2015 | Gozes et al. |
| 2020/0030309 | A1 | 1/2020 | Olson |

FOREIGN PATENT DOCUMENTS

| | | |
|---|---|---|
| AU | 614343 B2 | 8/1991 |
| GB | 2550110 A | 11/2017 |
| WO | 2000038677 | 7/2000 |
| WO | 2001070223 | 9/2001 |
| WO | 2004005389 A1 | 1/2004 |
| WO | 2004064738 A2 | 8/2004 |
| WO | 2008157845 A1 | 12/2008 |
| WO | 2009035473 A2 | 3/2009 |
| WO | 2013007698 A1 | 1/2013 |
| WO | 2017216279 A1 | 12/2017 |
| WO | 2018045178 A1 | 3/2018 |
| WO | 2018064465 A1 | 4/2018 |
| WO | 2018209341 A1 | 11/2018 |
| WO | 2019099402 A1 | 5/2019 |
| WO | 2020169851 A1 | 8/2020 |
| WO | 2020176597 A1 | 9/2020 |
| WO | 2020176599 A1 | 9/2020 |
| WO | 2020181194 A1 | 9/2020 |
| WO | 2021076572 A1 | 4/2021 |

OTHER PUBLICATIONS (2018) Depression The National Institute of Mental Health: www.nimh.nih.gov, 13 pages.
European Search Report for EP Application 17857489.3, dated Apr. 8, 2020, 6 pages.
International Search Report and Written Opinion received for International Application No. PCT/US2020/019858, dated Jul. 15, 2020, 12 pages.
International Search Report and Written Opinion received for International Application No. PCT/US2020/055507, dated Mar. 1, 2021, 12 pages.
International Search Report and Written Opinion received for PCT Application No. PCT/US2017/054277, dated Dec. 14, 2017, 10 pages.
International Search Report and Written Opinion received for PCT Application No. PCT/US2020/019856, dated Jun. 26, 2020, 11 pages.
U.S. Appl. No. 17/345,745, filed Jun. 11, 2021, "Azepino-indoles and Other Heterocycles for Treating Brain Disorders", 119 pages.
Anderson Amy C. (Sep. 2003) "The Process of Structure-based Drug Design", Chemistry and Biology, 10(9):787-797.

(Continued)

*Primary Examiner* — Robert H Havlin
(74) *Attorney, Agent, or Firm* — Mintz, Levin, Cohn, Ferris, Glovsky and Popeo, P.C.

(57) ABSTRACT

The present invention provides N-substituted indoles and other heterocycles and methods of using the compounds for treating brain disorders.

25 Claims, 10 Drawing Sheets

(56) References Cited

OTHER PUBLICATIONS

Antonaci et al. (May 17, 2016) "Recent Advances in Migraine Therapy", SpringerPlus 5:1-14.
Borovac Josip A. (Mar. 24, 2016) "Side Effects of a Dopamine Agonist Therapy for Parkinson's Disease: A Mini-review of Clinical Pharmacology", Yale Journal of Biology and Medicine, 89:37-47.
Cameron et al. (Jan. 21, 2021) "A Non-hallucinogenic Psychedelic Analogue With Therapuetic Potential", Nature, 589:474-479 (24 pages).
Cameron et al. (Jul. 2019) "Chronic, Intermittent Microdoses of the Psychedelic N,N-Dimethyltryptamine (DMT) Produce Positive Effects on Mood and Anxiety in Rodents", ACS Chemical Neuroscience, 10(7):3261-3270.
Cameron et al. (Oct. 2018) "Dark Classics in Chemical Neuroscience: N,N-Dimethyltryptamine (DMT)", ACS Chemical Neuroscience, 9(10):2344-2357.
Cameron et al. (Jul. 2018) "Effects of N,N-Dimethyltryptamine on Rat Behaviors Relevant to Anxiety and Depression", ACS Chemical Neuroscience, 9(7):1582-1590(22 pages).
Cameron et al. (Apr.-Jun. 2020) "Psychedelic Microdosing: Prevalence and Subjective Effects", Jounal of Psychoactive Drugs, 52(2):113-122.
Chiba et al. (May 23, 2010) "Cabergoline, a Dopamine Receptor Agaonist, has an Antidepressant-like Property and Enhances Brain-derived Neurotrophic Factor Signaling", Psychpharmacology 211(3):291-301(23 pages).
Dunlap et al. (Jan. 2020) "Identification of Psychoplastogenic N,N-Dimethylaminoisotryptamine (isoDMT) Analogues through Structure-Activity Relationship Studies", Journal of Medicinal Chemistry, 63(3):1142-1155(36 pages).
Glennon et al. (2000) "Binding of Beta-Carbolines and Related Agents at Serotonin (5-HT(2) and 5-HT(1A)), Dopamine (D(2)) and Benzodiazepine Receptors", Drug & Alcohol Dependence, 60(2):121-132.
Glennon et al. (1983) "DOM-stimulus Generalization to LSD and other Hallucinogenic Indolealkylamines", European Journal of Pharmacology, 86:453-459.
Goadsby et al. (2005) Comparative Efficacy of Eletriptan and Sumatriptan in Reducing Headache Recurrence in High-Risk Migraine Patients, Journal of the Neurological Sciences, 238(Suppl. 1):S940.
Golda et al. (Jun. 1987) "Animal Model of Depression: Drug Induced Changes Independent of Changes in Exploratory Activity", Activitas Nervosa Superior, 29(2):114-115.
Golda et al. (1986) "Animal Model of Depression: Imipramine, Bromocriptine and Lisuride Alleviate Motor Depression", Activitas Nervosa Superior, 28(1):26-27(4 pages).
Golda et al. (1984) "Reactivity to the Electric Shocks and Motor Depression as a Consequence of Inescapable Shocking: the Effect of Acute Lisuride Treatment", 27(4):377-392.
Halford Bethany (Dec. 2020) "Ibogaine Inspires Potential Neuropsychiatric Treatment", C&E News, 3 pages.

Harris et al. (2012) "Cabergoline Associated with First Episode Mania", Psychosomatics, 53(6):595-600(10 pages).
Hougaku et al. (Jan. 1994) "Therapeutic Effect of Lisuride Maleate on Post-stroke Depression", Journal of Geriatrics, 31:52-59.
Izumi et al. (2000) "Open Pergolide Treatment of Tricyclic and Heterocyclic Antidepressant-resistant Depression", Journal of Affective Disorders, 61:127-132.
Konopaske et al. (Dec. 2014) "Prefrontal Cortical Dendritic Spine Pathology in Schizophrenia and Bipolar disorder", JAMA Psychiatry, 71(12):1323-1331.
Lieberman et al. (Nov. 1981) "Use of Lisuride in Advanced Parkinson's Disease. Potent Dopamine and Serotonin Agonist", New York State Journal of Medicine, 81(12):1751-1755.
Luquin et al. (1987) "Parenteral Administration of Lisuride In Parkinson's Disease", Advances in Neurology, 45:561-568.
Ly et al. (Jun. 12, 2018) "Psychedelics Promote Structural and Functional Neural Plasticity", Cell Reports, 23(11):3170-3182.
Meintzschel et al. (Oct. 12, 2005) "Modification of Practice-dependent Plasticity in Human Motor Cortex by Neuromodulators", Cerebral Cortex, 16(8):1106-1115.
Meyer et al. (Jan. 2001) "The Effect of Paroxetine on 5-HT 2A Receptors in Depression: An [18F]Setoperone PET Imaging Study", The American Journal of Psychiatry, 158(1):78-85.
Moyer et al. (2015) "Dendritic Spine Alterations in Schizophrenia", Neuroscience Letters, 601:46-53(18 pages).
Nakamura et al. (1989) "Effects in Animal Models of Depression of Lisuride Along and Upon Co-administration with antidepressants", Folia pharmacol.japon, 94(1):81-89.
Odaka et al. (Jun. 2014) "Cabergoline, Dopamine D2 REceptor Agonist, Prevents Neuronal Cell Death under Oxidative Stress via Reducing Excitotoxicity", PLoS One, 9(6):12 pages.
Penzes et al. (Mar. 2011) "Dendritic Spine Pathology in Neuropsychiatric Disorders", Nature Neuroscience Review, 14(3):285-293(22 pages).
Pfizer Canana, Inc. (Jul. 23, 2013) "Product Monograph", Pfizer Cananda Inc., pp. 1-2.
PubChem (Oct. 20, 2014) "1,2,3,4-Tetrahydropyrrolo[2,3-b]Indole", PubChem CID 82415753, 8 pages.
PubChem (Jun. 16, 2016) "3,4-Trimethylen-inden", PubChem SID 314981250, 5 pages.
PubChem (Aug. 8, 2005) "Carbazole, 9-(1-methyl-2-piperidyl)methyl-", PubChem CID 43403, 10 pages.
Sharma Gitanjali (Nov. 6, 2019) "Intranasal Cabergoline: Pharmacokinetic and Pharmacodynamic Studies", AAPS PHarSciTech, 10(4):1321-1330.
Thiel Karl A. (May 2004) "Structure-Aided Drug Design's Next Generation", Nature Biology, 22(5):513-519.
Tittarelli et al. (2015) "Recreational Use, Analysis and Toxicity of Tryptamines", Current Neuropharmacology, 13(1):26-46.
Zetler et al. (1972) "Refractory Period and Strophanthin Actions, as Influenced by Four Indole Alkaloids and Two Synthetic Azepinoindoles", Pharmacology, 8:235-243.
Chang-Fong et al., "Evaluation of Isotryptamine Derivatives at 5-HT2 Serotonin Receptors", Bioorg. Med. Chem. Lett. 2002, 12, 155-158.
Glennon, R. et al., "Synthesis and Evaluation of a Novel Series of N,N Dimethylisotryptamines", J. Med. Chem. 1984, 27, 41-45.
Vargas, "Psychedelics and Other Psychoplastogens for Treating Mental Illness" Frontiers in Psychiatry 2021, p. 1-19.

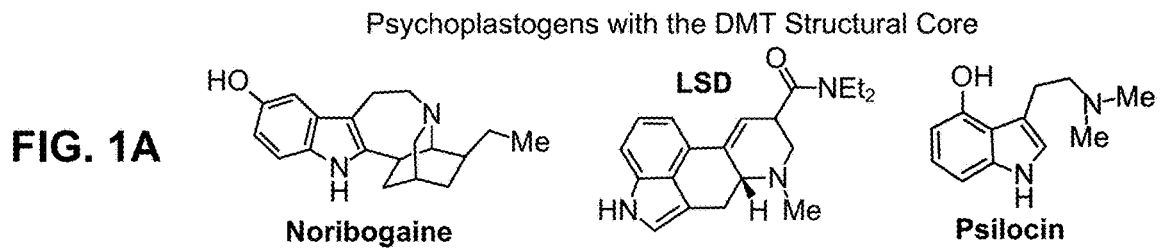
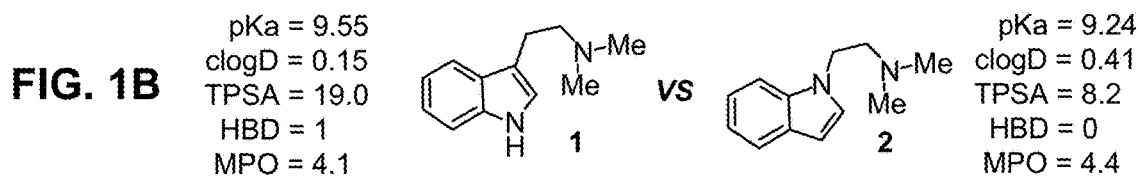
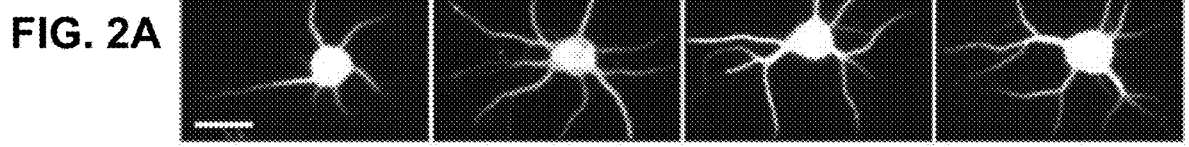
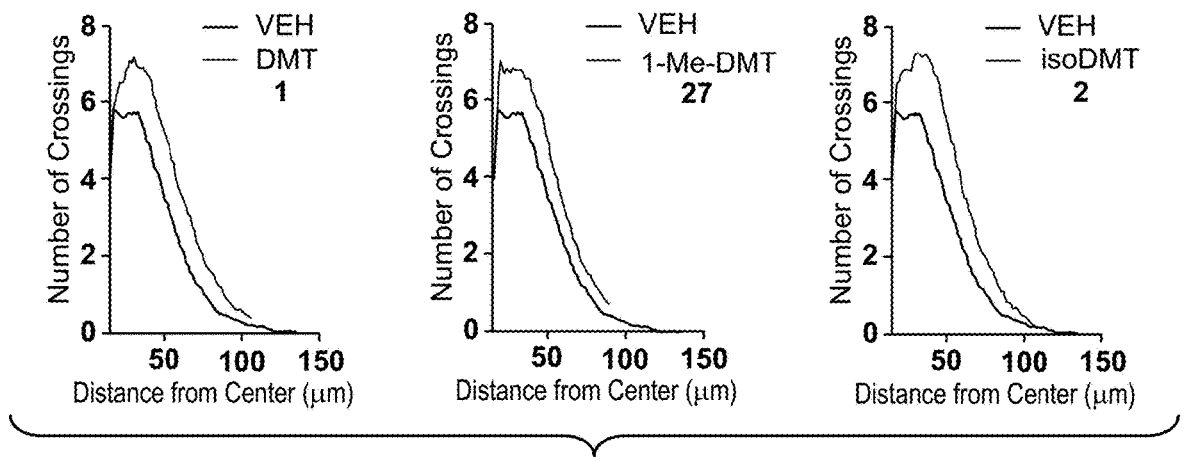
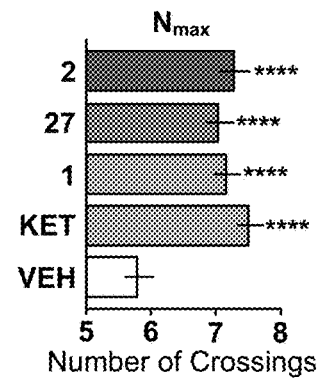

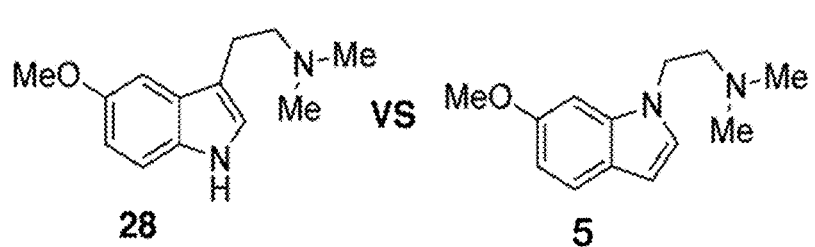
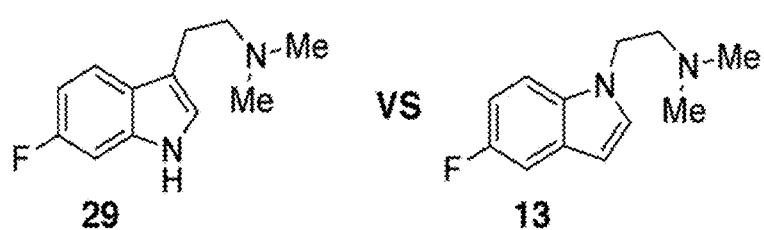
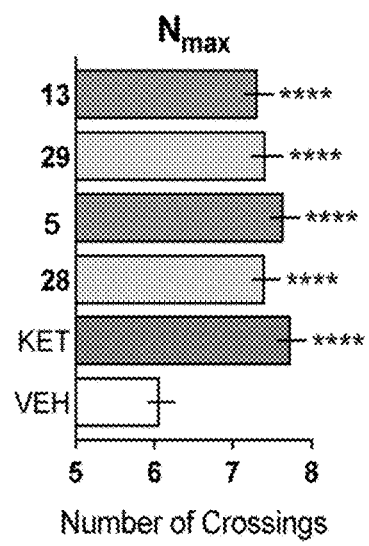
FIG. 3A
FIG. 3B
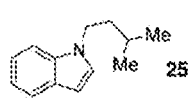
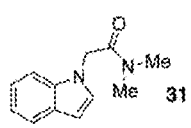
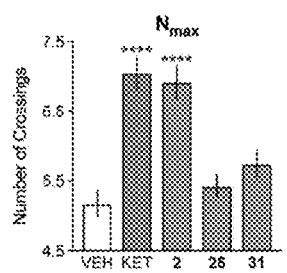
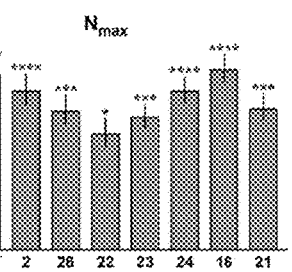
FIG. 4A
FIG. 4B
FIG. 4C

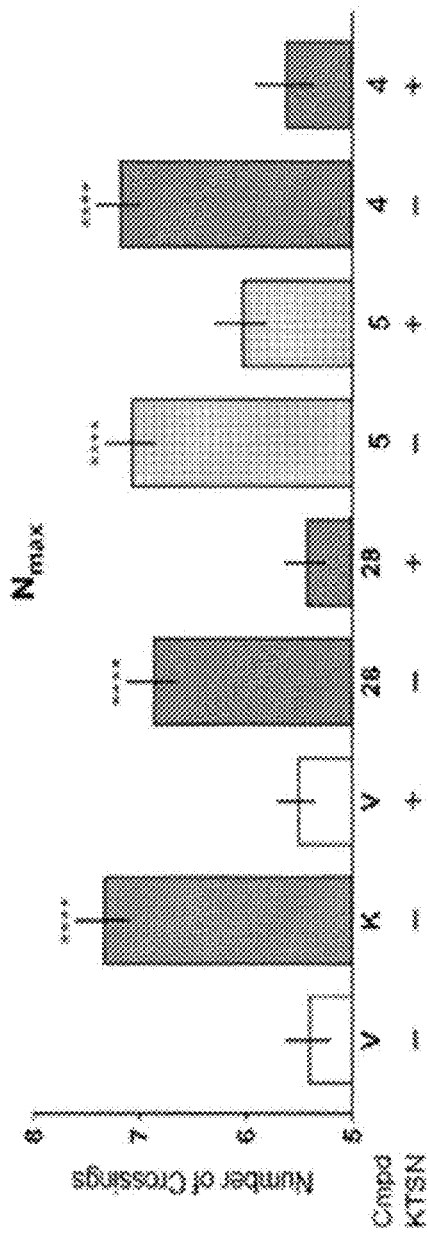
FIG. 7
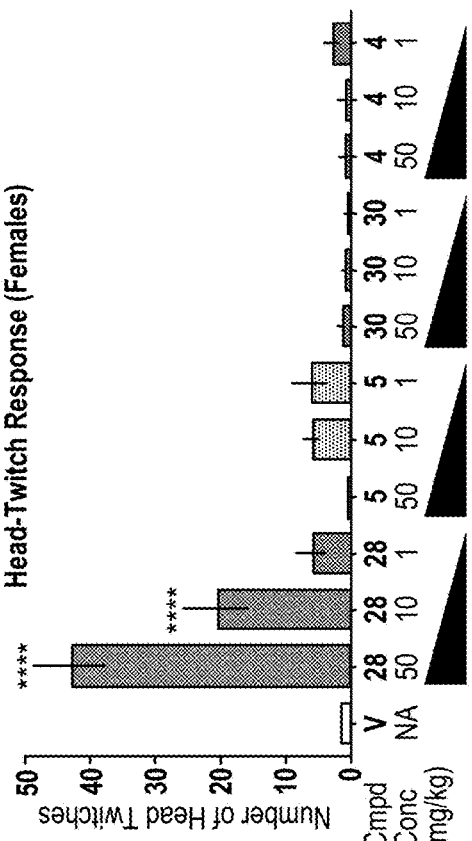
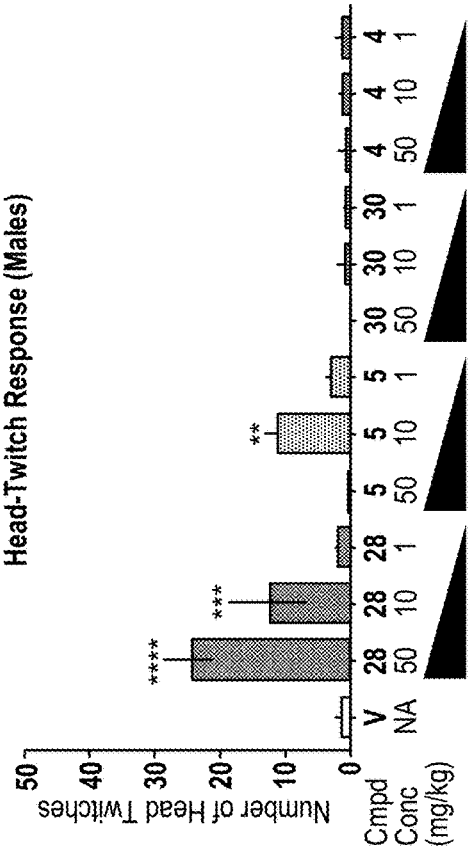
FIG. 8

N-SUBSTITUTED INDOLES AND OTHER HETEROCYCLES FOR TREATING BRAIN DISORDERS

CROSS-REFERENCES TO RELATED APPLICATIONS

This application is a continuation of International PCT Patent Application No. PCT/US2020/019856, filed Feb. 26, 2020, which claims priority to U.S. Provisional Application Nos. 62/811,206, filed Feb. 27, 2019, and 62/958,220, filed Jan. 7, 2020, each of which are incorporated herein by reference in their entirety for all purposes.

BACKGROUND OF THE INVENTION

Ketamine, N,N-dimethyltryptamine (DMT), and other psychoplastogens possess potential as neurotherapeutics due to their ability to promote neuronal growth. Several key features of the psychoplastogenic pharmacophore are disclosed herein. Also disclosed herein are isoDMT psychoplastogens that are easier to synthesize, have improved physicochemical properties, and possess reduced hallucinogenic potential as compared to their DMT counterparts.

Major depressive disorder and related neuropsychiatric diseases are among the leading causes of disability worldwide. Recently, the Food and Drug Administration (FDA) approved the dissociative anesthetic ketamine for treatment-resistant depression, making it the first mechanistically distinct medicine to be introduced to psychiatry in nearly 30 years. In some instances, ketamine is capable of rectifying the deleterious changes in neuronal structure that are associated with depression. Such structural alterations include, for example, the loss of dendritic spines and synapses in the prefrontal cortex (PFC), as well as reductions in dendritic arbor complexity. However, ketamine is an imperfect drug, for example, with potential for abuse and its dissociative effects necessitate the hospitalization of patients during treatment. A therapy without such side effects are needed in the clinic.

Compounds known as psychoplastogens promote neuronal growth through a mechanism involving the activation of AMPA receptors, the tropomyosin receptor kinase B (TrkB), and the mammalian target of rapamycin (mTOR). In addition to ketamine, the tropane alkaloid scopolamine and GLYX-13 (i.e., rapastinel) have demonstrated psychoplastogenic properties, and this class of compounds has potential for treating a variety of neuropsychiatric diseases. As pyramidal neurons in the PFC exhibit top-down control over areas of the brain controlling motivation, fear, and reward, these results provide an explanation for compounds with antidepressant, anxiolytic, and anti-addictive effects of psychedelics in the clinic.

The common pharmacophore in psychedelic compounds appears to be N,N-dimethyltryptamine (DMT, 1) (FIG. 1). As DMT produces antidepressant and anxiolytic behavioral effects in rodents and a DMT-containing tisane has demonstrated clinical efficacy for treatment-resistant depression, DMT was used as the starting point for identifying novel psychoplastogenic compounds described herein.

Thus, new compounds are needed to treat major depressive disorders and neuropsychiatric diseases. The present invention meets this and other needs.

BRIEF SUMMARY OF THE INVENTION

In one embodiment, the present invention provides a compound of Formula I:

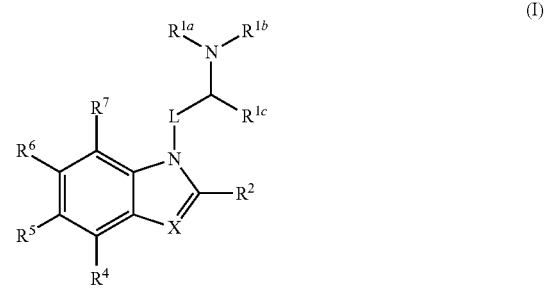

wherein: X is $CR^3$; $R^{1a}$ and $R^{1b}$ are each independently hydrogen, $C_{1-6}$ alkyl, $C_{3-8}$ cycloalkyl, or $C_{4-14}$ alkyl-cycloalkyl; $R^{1c}$ is $C_{1-6}$ alkyl, $C_{3-8}$ cycloalkyl, or $C_{4-14}$ alkyl-cycloalkyl; alternatively, two of $R^{1a}$, $R^{1b}$, and $R^{1c}$ are combined with the atoms to which they are attached to form a $C_{3-12}$ heterocycloalkyl; $R^2$, $R^3$, $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, $-OR^{8a}$, $-NO_2$, $-CN$, $-C(O)R^{8b}$, $-C(O)OR^{8b}$, $-OC(O)R^{8b}$, $-OC(O)OR^{8b}$, $-N(R^{8b}R^{8c})$, $-N(R^{8b})C(O)R^{8c}$, $-C(O)N(R^{8b}R^{8c})$, $-N(R^{8b})C(O)OR^{8c}$, $-OC(O)N(R^{8b}R^{8c})$, $-N(R^{8b})C(O)N(R^{8c}R^{8d})$, $-C(O)C(O)N(R^{8b}R^{8c})$, $-S(O_2)R^{8b}$, $-S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8a}$ is $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8b}$, $R^{8c}$ and $R^{8d}$ are each independently H or $C_{1-6}$ alkyl; alternatively, one of $R^{1a}$, $R^{1b}$, or $R^{1c}$ is combined with $R^2$ to form a $C_{5-12}$ heterocycloalkyl; alternatively, $R^2$ and $R^3$ are combined with the atoms to which they are each attached to form a $C_{4-8}$ cycloalkyl, $C_{4-10}$ heterocycloalkyl, or $C_{6-12}$ aryl; alternatively, $R^4$ and $R^5$, $R^5$ and $R^6$, or $R^6$ and $R^7$ are combined with the atoms to which they are each attached to form a $C_{4-6}$ cycloalkyl, $C_{4-6}$ heterocycloalkyl, $C_{6-12}$ aryl, or $C_{5-10}$ heteroaryl; and L is $C_{1-6}$ alkylene, or pharmaceutically acceptable salts and isomers thereof, wherein when $R^{1a}$, $R^{1b}$ and $R^{1c}$ are each Me, L is methylene, X is $CR^3$ and $R^2$, $R^3$, $R^4$, $R^5$, $R^6$ and $R^7$ are hydrogen, then the compound is

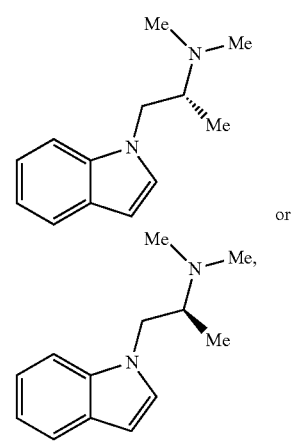

and wherein the compound is other than

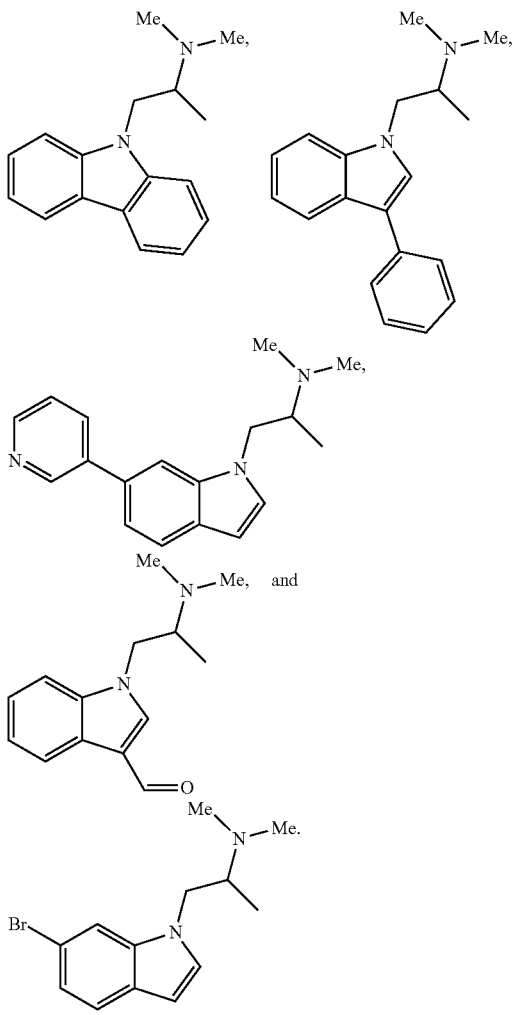

In another embodiments, the present invention provides a compound of Formula II:

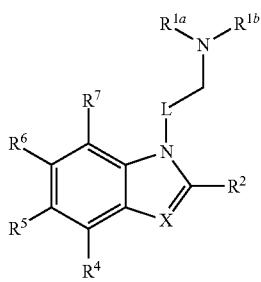
(II)

wherein: X is $CR^3$; $R^{1a}$ and $R^{1b}$ are each independently hydrogen, $C_{1-6}$ alkyl, $C_{3-8}$ cycloalkyl, or $C_{4-14}$ alkyl-cycloalkyl; alternatively, $R^{1a}$ and $R^{1b}$ are combined with the atoms to which they are attached to form a $C_{3-12}$ heterocycloalkyl; $R^2$, $R^3$, $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —$C(O)R^{8b}$, —$C(O)OR^{8b}$, —$OC(O)R^{8b}$, —$OC(O)OR^{8b}$, —$N(R^{8b}R^{8c})$, —$N(R^{8b})C(O)R^{8c}$, —$C(O)N(R^{8b}R^{8c})$, —$N(R^{8b})C(O)OR^{8c}$, —$OC(O)N(R^{8b}R^{8c})$, —$N(R^{8b})C(O)N(R^{8c}R^{8d})$, —$C(O)C(O)N(R^{8b}R^{8c})$, —$S(O_2)R^{8b}$, —$S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8a}$ is $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8b}$, $R^{8c}$ and $R^{8d}$ are each independently H or $C_{1-6}$ alkyl; alternatively, one of $R^{1a}$ or $R^{1b}$ is combined with $R^2$ to form a $C_{5-12}$ heterocycloalkyl; alternatively, $R^2$ and $R^3$ are combined with the atoms to which they are each attached to form a $C_{4-8}$ cycloalkyl, $C_{4-10}$ heterocycloalkyl, or $C_{6-12}$ aryl; alternatively, $R^4$ and $R^5$, $R^5$ and $R^6$, or $R^6$ and $R^7$ are combined with the atoms to which they are each attached to form a $C_{4-6}$ cycloalkyl, $C_{4-6}$ heterocycloalkyl, $C_{6-12}$ aryl, or $C_{5-10}$ heteroaryl; and L is $C_{1-6}$ alkylene, or pharmaceutically acceptable salts and isomers thereof, wherein when $R^{1a}$ and $R^{1b}$ are both Me, and L is methylene, then at least one of $R^2$, $R^3$, $R^4$, $R^5$, $R^6$, and $R^7$ is not hydrogen and the compound is other than:

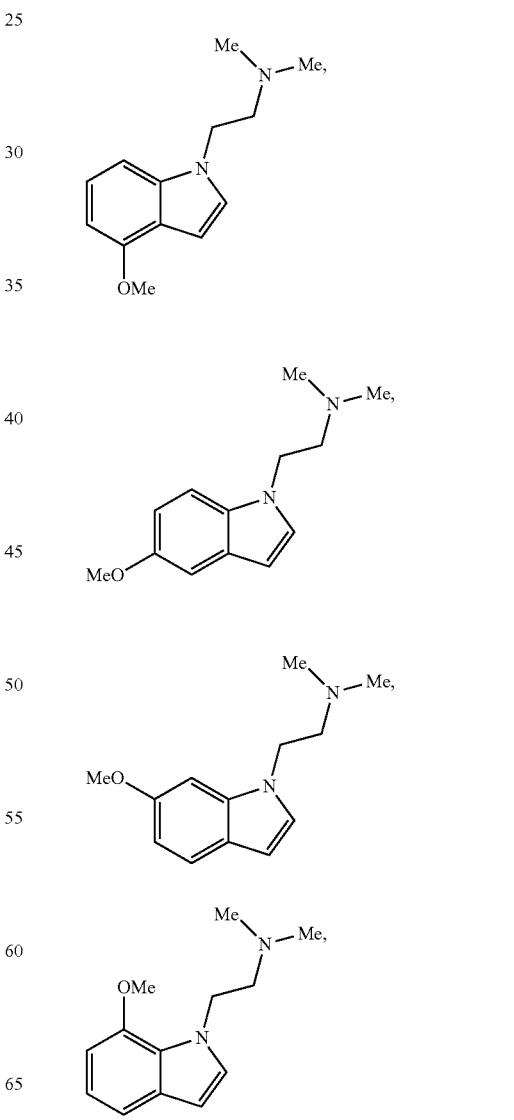

-continued

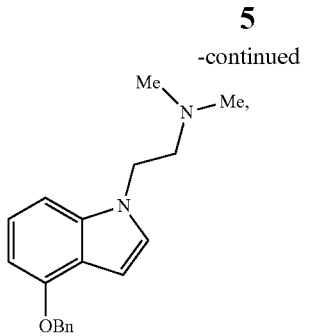

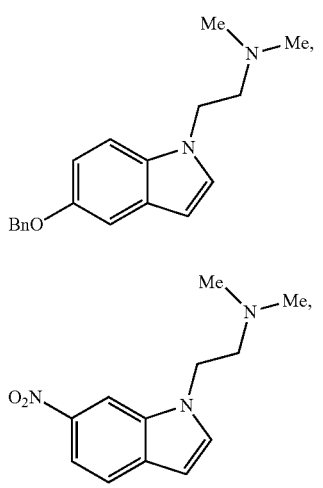

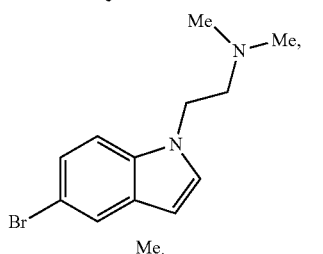

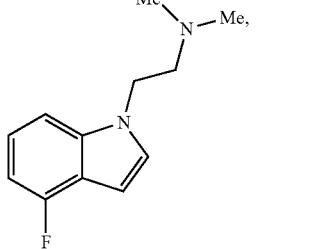

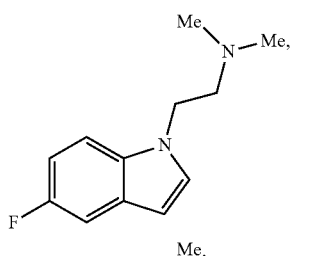

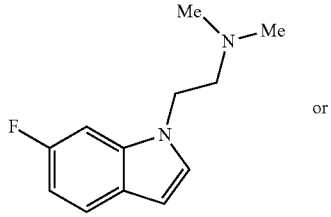

or

-continued

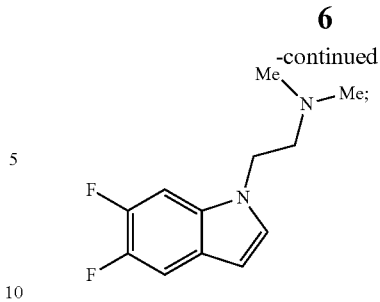

wherein when $R^{1a}$ and $R^{1b}$ are Me, L is ethylene, and X is $CR^3$, then at least one of $R^2$, $R^3$, $R^4$, $R^5$, $R^6$ and $R^7$ is not hydrogen; wherein when $R^{1c}$ is hydrogen, and $R^5$ is Br, Cl, F, —$NH_2$, —$NO_2$, or $C_{1-3}$ alkoxy, then at least one of $R^2$, $R^3$, $R^4$, $R^6$, or $R^7$ is not hydrogen; and wherein when $R^{1c}$ is hydrogen and $R^5$ is F, then at least one of $R^2$, $R^3$, $R^4$, $R^6$, or $R^7$ is not hydrogen and $R^6$ is not F.

In another embodiment, the present invention provides pharmaceutical composition comprising a compound of the present invention, and a pharmaceutically acceptable excipient.

In another embodiment, the present invention provides a method for increasing neuronal plasticity, comprising contacting a neuronal cell with a compound of Formula I:

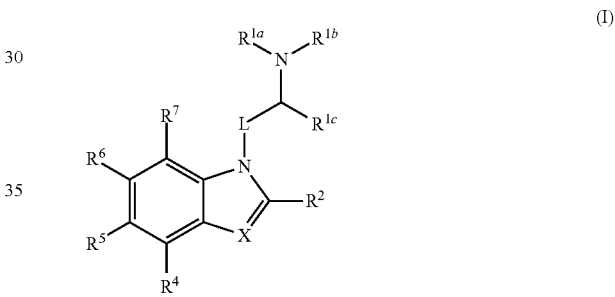

or a pharmaceutically acceptable salt thereof, in an amount sufficient to increase neuronal plasticity of the neuronal cell, wherein: X is N or $CR^3$; $R^{1a}$, $R^{1b}$, and $R^{1c}$ are each independently hydrogen, $C_{1-6}$ alkyl, $C_{3-8}$ cycloalkyl, or $C_{4-14}$ alkyl-cycloalkyl; alternatively, two of $R^{1a}$, $R^{1b}$, and $R^{1c}$ are combined with the atoms to which they are attached to form a $C_{3-12}$ heterocycloalkyl; $R^2$, $R^3$, $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —$C(O)R^{8b}$, —$C(O)OR^{8b}$, —$OC(O)R^{8b}$, —$OC(O)OR^{8b}$, —$N(R^{8b}R^{8c})$, —$N(R^{8b})C(O)R^{8c}$, —$C(O)N(R^{8b}R^{8c})$, —$N(R^{8b})C(O)OR^{8c}$, —$OC(O)N(R^{8b}R^{8c})$, —$N(R^{8b})C(O)N(R^{8c}R^{8d})$, —$C(O)C(O)N(R^{8b}R^{8c})$, —$S(O)_2R^{8b}$, —$S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8a}$ is $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8b}$, $R^{8c}$ and $R^{8d}$ are each independently H or $C_{1-6}$ alkyl; alternatively, one of $R^{1a}$, $R^{1b}$, or $R^{1c}$ is combined with $R^2$ to form a $C_{5-12}$ heterocycloalkyl; alternatively, $R^2$ and $R^3$ are combined with the atoms to which they are each attached to form a $C_{4-8}$ cycloalkyl, $C_{4-10}$ heterocycloalkyl, or $C_{6-12}$ aryl; alternatively, $R^4$ and $R^5$, $R^5$ and $R^6$, or $R^6$ and $R^7$ are combined with the atoms to which they are each attached to form a $C_{3-6}$ cycloalkyl, $C_{3-6}$ heterocycloalkyl, $C_{6-12}$ aryl, or $C_{5-10}$ heteroaryl; and L is $C_{1-6}$ alkylene.

In another embodiment, the present invention provides a method of treating a brain disorder, comprising administering to a subject in need thereof a therapeutically effective amount of a compound of Formula I:

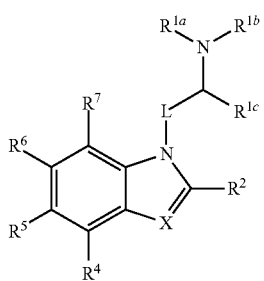

or a pharmaceutically acceptable salt thereof, thereby treating the brain disorder, wherein: X is N or $CR^3$; $R^{1a}$, $R^{1b}$, and $R^{1c}$ are each independently hydrogen, $C_{1-6}$ alkyl, $C_{3-8}$ cycloalkyl, or $C_{4-14}$ alkyl-cycloalkyl; alternatively, two of $R^{1a}$, $R^{1b}$, and $R^{1c}$ are combined with the atoms to which they are attached to form a $C_{3-12}$ heterocycloalkyl; $R^2$, $R^3$, $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —$C(O)R^{8b}$, —$C(O)OR^{8b}$, —$OC(O)R^{8b}$, —$OC(O)OR^{8b}$, —$N(R^{8b}R^{8c})$, —$N(R^{8b})C(O)R^{8c}$, —$C(O)N(R^{8b}R^{8c})$, —$N(R^{8b})C(O)OR^{8c}$, —$OC(O)N(R^{8b}R^{8c})$, —$N(R^{8b})C(O)N(R^{8c}R^{8d})$, —$C(O)C(O)N(R^{8b}R^{8c})$, —$S(O_2)R^{8b}$, —$S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8a}$ is $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8b}$, $R^{8c}$ and $R^{8d}$ are each independently H or $C_{1-6}$ alkyl; alternatively, one of $R^{1a}$, $R^{1b}$, or $R^{1c}$ is combined with $R^2$ to form a $C_{5-12}$ heterocycloalkyl; alternatively, $R^2$ and $R^3$ are combined with the atoms to which they are each attached to form a $C_{4-8}$ cycloalkyl, $C_{4-10}$ heterocycloalkyl, or $C_{6-12}$ aryl; alternatively, $R^4$ and $R^5$, $R^5$ and $R^6$, or $R^6$ and $R^7$ are combined with the atoms to which they are each attached to form a $C_{3-6}$ cycloalkyl, $C_{3-6}$ heterocycloalkyl, $C_{6-12}$ aryl, or $C_{5-10}$ heteroaryl; and L is $C_{1-6}$ alkylene.

In another embodiment, the present invention provides a method for increasing at least one of translation, transcription or secretion of neurotrophic factors, comprising contacting a neuronal cell with a compound of Formula I:

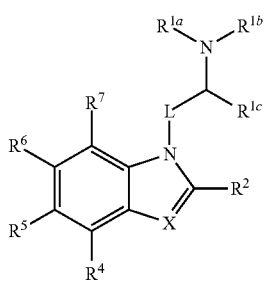

or a pharmaceutically acceptable salt thereof, in an amount sufficient to increase neuronal plasticity of the neuronal cell, wherein: X is N or $CR^3$; $R^{1a}$, $R^{1b}$, and $R^{1c}$ are each independently hydrogen, $C_{1-6}$ alkyl, $C_{3-8}$ cycloalkyl, or $C_{4-14}$ alkyl-cycloalkyl; alternatively, two of $R^{1a}$, $R^{1b}$, and $R^{1c}$ are combined with the atoms to which they are attached to form a $C_{3-12}$ heterocycloalkyl; $R^2$, $R^3$, $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —$C(O)R^{8b}$, —$C(O)OR^{8b}$, —$OC(O)R^{8b}$, —$OC(O)OR^{8b}$, —$N(R^{8b}R^{8c})$, —$N(R^{8b})C(O)R^{8c}$, —$C(O)N(R^{8b}R^{8c})$, —$N(R^{8b})C(O)OR^{8c}$, —$OC(O)N(R^{8b}R^{8c})$, —$N(R^{8b})C(O)N(R^{8c}R^{8d})$, —$C(O)C(O)N(R^{8b}R^{8c})$, —$S(O_2)R^{8b}$, —$S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8a}$ is $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8b}$, $R^{8c}$ and $R^{8d}$ are each independently H or $C_{1-6}$ alkyl; alternatively, one of $R^{1a}$, $R^{1b}$, or $R^{1c}$ is combined with $R^2$ to form a $C_{5-12}$ heterocycloalkyl; alternatively, $R^2$ and $R^3$ are combined with the atoms to which they are each attached to form a $C_{4-8}$ cycloalkyl, $C_{4-10}$ heterocycloalkyl, or $C_{6-12}$ aryl; alternatively, $R^4$ and $R^5$, $R^5$ and $R^6$, or $R^6$ and $R^7$ are combined with the atoms to which they are each attached to form a $C_{3-6}$ cycloalkyl, $C_{3-6}$ heterocycloalkyl, $C_{6-12}$ aryl, or $C_{5-10}$ heteroaryl; and L is $C_{1-6}$ alkylene.

BRIEF DESCRIPTION OF THE DRAWINGS

FIG. 1A and FIG. 1B shows structure of compounds possessing the DMT pharmacophore. FIG. 1A shows the DMT structure (highlighted in black) is the core scaffold of several known psychoplastogenic compounds. FIG. 1B shows the only difference between the chemical structures of DMT (1) and isoDMT (2) is that the $C_1$ and $C_3$ atoms of the indole are transposed. Predicted chemical properties and calculated MPO scores are shown. clogD=calculated log D; TPSA=total polar surface area; HBD=hydrogen bond donor; MPO=multiparameter optimization score.

FIG. 2A, FIG. 2B and FIG. 2C show the indole N—H of tryptamine derivatives is not necessary to promote dendritogenesis. FIG. 2A shows representative images of cortical neurons (DIV6) treated with compounds. FIG. 2B shows sholl analysis demonstrating that 1-Me-DMT (27) and isoDMT (2) increase dendritic arbor complexity to a comparable extent as DMT (1) (n=46-79 neurons). FIG. 2C shows maximum number of crossings (Nmax) of the Sholl plots in B. Data are represented as mean±SEM. *p<0.05, p<0.01, *p<0.001, ****p<0.0001, as compared to vehicle control following a one-way ANOVA with Dunnett's post hoc test (F=9.702; DFn=4; DFd=304; p-value<0.0001). VEH=vehicle, KET=ketamine. Scale bar=20 µm.

FIG. 3A and FIG. 3B shows DMT and isoDMT analogs produce comparable effects on dendritic arbor complexity. FIG. 3A shows chemical structures of DMT derivatives and analogous isoDMTs. FIG. 3B shows maximum number of crossings ($N_{max}$) of the Sholl analysis for cortical neurons treated with compounds (n=82-95 neurons). Data are represented as mean±SEM. *p<0.05, p<0.01, *p<0.001, ****p<0.0001, as compared to vehicle control following a one-way ANOVA with Dunnett's post hoc test (F=11.17; DFn=5; DFd=524; p-value <0.0001). VEH=vehicle, KET=ketamine.

FIG. 4A to FIG. 4C shows establishment of the essential psychoplastogen pharmacophore. FIG. 4A Chemical structures of non-basic analogs of isoDMT 2. FIG. 4B and FIG. 4C shows maximum number of crossings ($N_{max}$) of the Sholl plots for cortical neurons treated with compounds (n=46-85 neurons). The effects of nitrogen basicity and modifications to the aromatic ring were assessed in FIG. 4B and FIG. 4C, respectively. Data are represented as mean±SEM. *p<0.05, p<0.01, *p<0.001, ****p<0.0001, as compared to vehicle control following a one-way ANOVA with Dunnett's post hoc test (For B: F=19.03; DFn=4; DFd=273; p-value<0.0001. For C:F=6.933; DFn=8; DFd=599; p-value<0.0001). VEH=vehicle, KET=ketamine.

FIG. 7 shows the psychoplastogenic effects of isoDMTs are blocked by a 5-HT2A antagonist. Maximum number of crossings ($N_{max}$) of the Sholl plots for cortical neurons treated with compounds (n=45-63 neurons) in the presence (+) or absence (−) of the 5-HT2A antagonist ketanserin. Data are represented as mean±SEM. ****p<0.0001, as compared to vehicle control following a one-way ANOVA with Dunnett's post hoc test (F=13.92; DFn=8; DFd=461; p-value<0.0001). V=vehicle, K=ketamine, KTSN=ketanserin.

FIG. 8 shows mouse HTR assays demonstrate that psychoplastogenic isoDMTs exhibit reduced hallucinogenic potential. Male and female mice were administered drugs via intraperitoneal injection, and the number of head-twitches were recorded over the next 20 mins (n=3-8 mice per condition). Data are represented as mean±SEM. *p<0.05, p<0.01, *p<0.001, ****p<0.0001, as compared to vehicle control following a one-way ANOVA with Dunnett's post hoc test. V=vehicle.

DETAILED DESCRIPTION OF THE INVENTION

I. General

Figure 5:
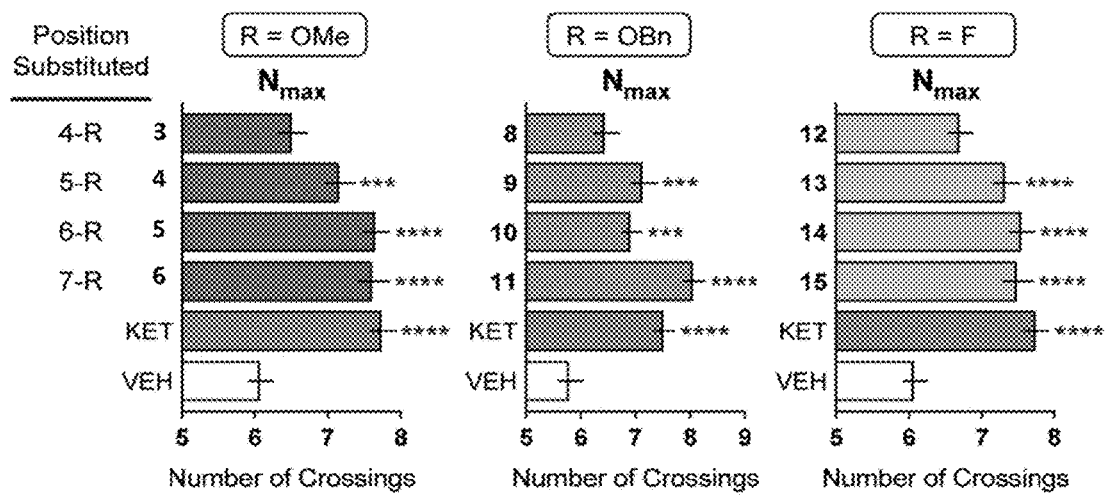
FIG. 5 shows the impact of indole substitution on the ability of isoDMTs to promote neuronal growth. Maximum number of crossings ($N_{max}$) of the Sholl plots for cortical neurons treated with compounds (n=39-93 neurons). Data are represented as mean±SEM. *p<0.05, p<0.01, *p<0.001, ****p<0.0001, as compared to vehicle control following a one-way ANOVA with Dunnett's post hoc test (For R=OMe: F=13.85; DFn=5; DFd=493; p-value<0.0001. For R=OBn: F=15.44; DFn=5; DFd=372; p-value<0.0001. For R=F: F=13.24; DFn=5; DFd=506; p-value<0.0001). VEH=vehicle, KET=ketamine.

The present invention provides N-substituted indoles and other heterocyclic non-hallucinogenic compounds useful for the treatment of a variety of brain disorders and other conditions, as well as increasing neuronal plasticity, and increasing at least one of translation, transcription, or secretion of neurotrophic factors.

Compounds capable of modifying neural circuits that control motivation, anxiety, and drug-seeking behavior have potential for treating depression, post-traumatic stress disorder (PTSD), and substance abuse disorder (SUD). Moreover, such psychoplastogenic medicines are likely to produce sustained therapeutic effects because, for example, of the potential to treat the underlying pathological changes in circuitry. Psychedelic compounds have distinguished themselves in this regard because, for example, they promote structural and functional neural plasticity in key circuits, elicit therapeutic responses in multiple neuropsychiatric disorders, and produce beneficial effects that can last for months following a single administration.

In some instances, hallucinogenic $5-HT_{2A}$ agonists (e.g., DMT, LSD, DOI, etc.) are potential therapeutics for neurological diseases, such as, for example, neuropsychiatric diseases. (Ly et al., 2018) However, the hallucinogenic and dissociative potential of such compounds has limited the use of these compounds in the clinic. $5-HT_{2A}$ antagonists abrogate the neuritogenesis and spinogenesis effects of hallucinogenic compounds with $5-HT_{2A}$ agonist activity, e.g., DMT, LSD, and DOI, demonstrating the correlation of $5-HT_{2A}$ agonism and the promotion of neural plasticity (Ly et al., 2018; Dunlap et al., 2020).

Provided herein are non-hallucinogenic psychoplastogens. Additionally, several isoDMT compounds possess comparable affinity for serotonin receptors (e.g., $5HT_{2A}$) as compared to their DMT counterparts. In some embodiments, the isoDMT analogs described herein have improved physiochemical properties as a result of the loss of a hydrogen bond donor, decreasing total polar surface area and improving central nervous system multiparameter optimization (MPO) scores (FIG. 1). Described herein in some embodiments are non-hallucinogenic compounds that demonstrate similar therapeutic potential as hallucinogenic $5-HT_{2A}$ agonists. In some embodiments, the non-hallucinogenic compounds described herein provide better therapeutic potential than hallucinogenic $5-HT_{2A}$ agonists for neurological diseases.

II. Definitions

Unless specifically indicated otherwise, all technical and scientific terms used herein have the same meaning as commonly understood by those of ordinary skill in the art to which this invention belongs. In addition, any method or material similar or equivalent to a method or material described herein can be used in the practice of the present invention. For purposes of the present invention, the following terms are defined.

"A," "an," or "the" refers to not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

Abbreviations used: DMT, N,N'-dimethyltryptamine; PFC, prefrontal cortex; 5-HT2A, serotonin 2A; MPO, multiparameter optimization; LSD, lysergic acid diethylamide; TPSA, total polar surface area; MAP2, microtubule-associated protein 2; $N_{max}$, maximum number of crossings; 5-HT2B, serotonin 2B; DIV, days in vitro; VEH, vehicle; KET, ketamine; SEM, standard error of the mean; ANOVA, analysis of variance; DOM, 2,5-dimethoxy-4-methylamphetamine; OMe, methoxy; OBn, benzyloxy; F, fluoro; µM, micromolar; nM, nanomolar; pM, picomolar; V, vehicle; K, ketamine; ATR, attenuated total reflectance; FT-IR, Fourier transform infrared spectroscopy; UHPLC, ultra-high performance liquid chromatography; LRMS, low-resolution mass spectrometry; IACUC, institutional animal care and use committee; AAALAC, Association for Assessment and Accreditation of Laboratory Animal Care; BSA, bovine serum albumin; DPBS, Dulbecco's phosphate-buffered saline; mTOR, mammalian target of rapamycin; AMPA, α-amino-3-hydroxy-5-methyl-4-isoxazolepropionic acid; TrkB, tropomyosin receptor kinase B; HTR, head-twitch response.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —$(CH_2)_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene. Alkylene groups can be substituted or unsubstituted.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted.

"Cycloalkyl" refers to a saturated or partially unsaturated, monocyclic, bicyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Bicyclic compounds include spirocyclic compounds, fused bicyclic compounds and bridged bicyclic compounds. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted.

"Alkyl-cycloalkyl" refers to a radical having an alkyl component and a cycloalkyl component, where the alkyl component links the cycloalkyl component to the point of attachment. The alkyl component is as defined above, except that the alkyl component is at least divalent, an alkylene, to link to the cycloalkyl component and to the point of attachment. In some instances, the alkyl component can be absent. The alkyl component can include any number of carbons, such as $C_{1-6}$, $C_{1-2}$, $C_{1-3}$, $C_{1-4}$, $C_{1-5}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. The cycloalkyl component is as defined within. Exemplary alkyl-cycloalkyl groups include, but are not limited to, methyl-cyclopropyl, methyl-cyclobutyl, methyl-cyclopentyl and methyl-cyclohexyl.

"Heterocycloalkyl" refers to a cycloalkyl as defined above, having from 3 to 12 ring members and from 1 to 4 heteroatoms of N, O and S. Heterocycloalkyl includes bicyclic compounds which include a heteroatom. Bicyclic compounds includes spirocyclic compounds, fused bicyclic compounds, and bridged bicyclic compounds The heteroatoms can also be oxidized, such as, but not limited to, —S(O)— and —S(O)$_2$—. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. The heterocycloalkyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline. Heterocycloalkyl groups can be unsubstituted or substituted. For example, heterocycloalkyl groups can be substituted with $C_{1-6}$ alkyl or oxo (=O), among many others.

"Alkyl-heterocycloalkyl" refers to a radical having an alkyl component and a heterocycloalkyl component, where the alkyl component links the heterocycloalkyl component to the point of attachment. The alkyl component is as defined above, except that the alkyl component is at least divalent, an alkylene, to link to the heterocycloalkyl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The heterocycloalkyl component is as defined above. Alkyl-heterocycloalkyl groups can be substituted or unsubstituted.

"Halogen" refers to fluorine, chlorine, bromine and iodine.

"Haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, haloalkyl includes trifluoromethyl, flouromethyl, etc. In some instances, the term "perfluoro" can be used to define a compound or radical where all the hydrogens are replaced with fluorine. For example, perfluoromethyl refers to 1,1,1-trifluoromethyl.Alkylamine "Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc. The alkoxy groups can be further substituted with a variety of substituents described within. Alkoxy groups can be substituted or unsubstituted.

"Haloalkoxy" refers to an alkoxy group where some or all of the hydrogen atoms are substituted with halogen atoms. As for an alkyl group, haloalkoxy groups can have any suitable number of carbon atoms, such as $C_{1-6}$. The alkoxy groups can be substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2,-trifluoroethoxy, perfluoroethoxy, etc.

"Amine" refers to an —N(R)$_2$ group where the R groups can be hydrogen, alkyl, alkenyl, alkynyl, cycloalkyl, heterocycloalkyl, aryl, or heteroaryl, among others. The R groups can be the same or different. The amino groups can be primary (each R is hydrogen), secondary (one R is hydrogen) or tertiary (each R is other than hydrogen).

"Alkyl amine" refers to an alkyl group as defined within, having one or more amino groups. The amino groups can be primary, secondary or tertiary. The alkyl amine can be further substituted with a hydroxy group to form an amino-hydroxy group. Alkyl amines useful in the present invention include, but are not limited to, ethyl amine, propyl amine, isopropyl amine, ethylene diamine and ethanolamine. The amino group can link the alkyl amine to the point of attachment with the rest of the compound, be at the omega position of the alkyl group, or link together at least two carbon atoms of the alkyl group. One of skill in the art will appreciate that other alkyl amines are useful in the present invention.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted.

"Alkyl-aryl" refers to a radical having an alkyl component and an aryl component, where the alkyl component links the aryl component to the point of attachment. The alkyl component is as defined above, except that the alkyl component is at least divalent, an alkylene, to link to the aryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The aryl component is as defined above. Examples of alkyl-aryl groups include, but are not limited to, benzyl and ethyl-benzene. Alkyl-aryl groups can be substituted or unsubstituted.

"Heteroaryl" refers to a monocyclic or fused bicyclic or tricyclic aromatic ring assembly containing 5 to 16 ring atoms, where from 1 to 5 of the ring atoms are a heteroatom such as N, O or S. Heteroaryl groups can include any number of ring atoms, such as, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

"Alkyl-heteroaryl" refers to a radical having an alkyl component and a heteroaryl component, where the alkyl component links the heteroaryl component to the point of attachment. The alkyl component is as defined above, except that the alkyl component is at least divalent, an alkylene, to link to the heteroaryl component and to the point of attachment. The alkyl component can include any number of carbons, such as $C_{0-6}$, $C_{1-2}$, $C_{1-3}$, $C_{1-4}$, $C_{1-5}$, $C_{1-6}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. In some instances, the alkyl component can be absent. The heteroaryl component is as defined within. Alkyl-heteroaryl groups can be substituted or unsubstituted.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (fumaric acid, acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

"Pharmaceutically acceptable salt" refers to a compound in salt form, wherein the compound are suitable for administration to a subject. Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like "Pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

"Composition" refers to a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation.

"Isomers" refers to compounds with same chemical formula but different connectivity between the atoms in the molecule, leading to distinct chemical structures. Isomers include structural isomers and stereoisomers. Examples of structural isomers include, but are not limited to tautomers and regioisomers. Examples of stereoisomers include but are not limited to diastereomers and enantiomers.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Subject" refers to animals such as mammals, including, but not limited to, primates (e.g., humans), cows, sheep, goats, horses, dogs, cats, rabbits, rats, mice and the like. In certain embodiments, the subject is a human.

"Therapeutically effective amount" or "therapeutically sufficient amount" or "effective or sufficient amount" refers to a dose that produces therapeutic effects for which it is administered. The exact dose will depend on the purpose of the treatment, and will be ascertainable by one skilled in the art using known techniques (see, e.g, Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington; The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

"Neuronal plasticity" refers to the ability of the brain to change its structure and/or function continuously throughout a subject's life. Examples of the changes to the brain include, but are not limited to, the ability to adapt or respond to internal and/or external stimuli, such as due to an injury, and the ability to produce new neurites, dendritic spines, and synapses.

"Brain disorder" refers to a neurological disorder which affects the brain's structure and function. Brain disorders can include, but are not limited to, Alzheimer's, Parkinson's disease, psychological disorder, depression, treatment resistant depression, addiction, anxiety, post-traumatic stress disorder, suicidal ideation, major depressive disorder, bipolar disorder, schizophrenia, stroke, traumatic brain injury, and substance use disorder.

"Combination therapy" refers to a method of treating a disease or disorder, wherein two or more different pharmaceutical agents are administered in overlapping regimens so that the subject is simultaneously exposed to both agents. For example, the compounds of the invention can be used in combination with other pharmaceutically active compounds. The compounds of the invention can be administered simultaneously (as a single preparation or separate preparation) or sequentially to the other drug therapy. In general, a combination therapy envisions administration of two or more drugs during a single cycle or course of therapy.

"Neurotrophic factors" refers to a family of soluble peptides or proteins which support the survival, growth, and differentiation of developing and mature neurons.

"Modulate" or "modulating" or "modulation" refers to an increase or decrease in the amount, quality, or effect of a particular activity, function or molecule. By way of illustration and not limitation, agonists, partial agonists, antagonists, and allosteric modulators (e.g., a positive allosteric modulator) of a G protein-coupled receptor (e.g., $5HT_{2A}$) are modulators of the receptor.

"Agonism" refers to the activation of a receptor or enzyme by a modulator, or agonist, to produce a biological response.

"Agonist" refers to a modulator that binds to a receptor or enzyme and activates the receptor to produce a biological response. By way of example only, "$5HT_{2A}$ agonist" can be used to refer to a compound that exhibits an $EC_{50}$ with respect to $5HT_{2A}$ activity of no more than about 100 μM. In some embodiments, the term "agonist" includes full agonists or partial agonists. "Full agonist" refers to a modulator that binds to and activates a receptor with the maximum response that an agonist can elicit at the receptor. "Partial agonist" refers to a modulator that binds to and activates a given receptor, but has partial efficacy, that is, less than the maximal response, at the receptor relative to a full agonist.

"Positive allosteric modulator" refers to a modulator that binds to a site distinct from the orthosteric binding site and enhances or amplifies the effect of an agonist.

"Antagonism" refers to the inactivation of a receptor or enzyme by a modulator, or antagonist. Antagonism of a receptor, for example, is when a molecule binds to the receptor and does not allow activity to occur.

"Antagonist" or "neutral antagonist" refers to a modulator that binds to a receptor or enzyme and blocks a biological response. An antagonist has no activity in the absence of an agonist or inverse agonist but can block the activity of either, causing no change in the biological response.

III. Compounds

The present invention provides N-substituted indoles and other heterocyclic compounds useful for the treatment of a variety of brain disorders and other conditions. In some embodiments, the N-substituted indoles and other heterocyclic compounds provided herein are $5\text{-HT}_{2A}$ modulators and promote neural plasticity (e.g., cortical structural plasticity).

In some embodiments, the present invention provides a compound of Formula I:

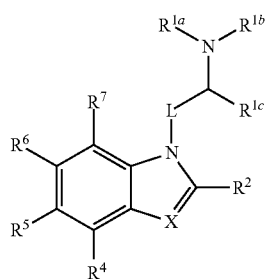

wherein X is N or $CR^3$; $R^{1a}$, $R^{1b}$ and $R^{1c}$ are each independently hydrogen, $C_{1-6}$ alkyl, $C_{3-8}$ cycloalkyl, or $C_{4-14}$ alkyl-cycloalkyl; alternatively, two of $R^{1a}$, $R^{1b}$ and $R^{1c}$ are combined with the atoms to which they are attached to form a $C_{3-6}$ heterocycloalkyl; $R^2$, $R^3$, $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —$C(O)R^{8b}$, —$C(O)OR^{8b}$, —$OC(O)R^{8b}$, —$OC(O)OR^{8b}$, —$N(R^{8b}R^{8c})$, —$N(R^{8b})C(O)R^{8c}$, —$C(O)N(R^{8b}R^{8c})$, —$N(R^{8b})C(O)OR^{8c}$, —$OC(O)N(R^{8b}R^{8c})$, —$N(R^{8b})C(O)N(R^{8c}R^{8d})$, —$C(O)C(O)N(R^{8b}R^{8c})$, —$S(O_2)R^{8b}$, —$S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8a}$ is $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8b}$, $R^{8c}$ and $R^{8d}$ are each independently H or $C_{1-6}$ alkyl; alternatively, one of $R^{1a}$, $R^{1b}$ and $R^{1c}$ is combined with one of $R^2$, $R^3$, $R^4$, $R^5$, $R^6$ and $R^7$ to form a $C_{5-6}$ cycloalkyl or $C_{5-6}$ heterocycloalkyl; alternatively, $R^2$ and $R^3$ can be combined with the atoms to which they are each attached to form a $C_{6-12}$ aryl; alternatively, $R^4$ and $R^5$, $R^5$ and $R^6$, or $R^6$ and $R^7$ can be combined with the atoms to which they are each attached to form a $C_{3-6}$ cycloalkyl or a $C_{3-6}$ heterocycloalkyl; and L is $C_{1-6}$ alkylene, or salts and isomers thereof.

In some embodiments, the present invention provides a compound of Formula I:

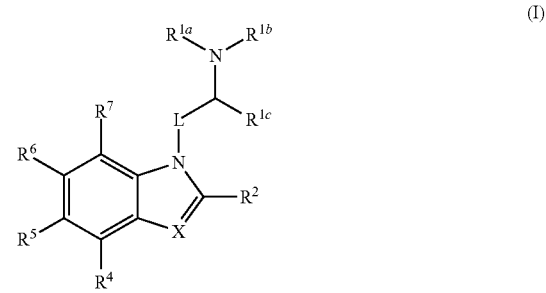

wherein: X is N or $CR^3$; $R^{1a}$, $R^{1b}$, and $R^{1c}$ are each independently hydrogen, $C_{1-6}$ alkyl, $C_{3-8}$ cycloalkyl, or $C_{4-14}$ alkyl-cycloalkyl; alternatively, two of $R^{1a}$, $R^{1b}$, and $R^{1c}$ are combined with the atoms to which they are attached to form a $C_{3-12}$ heterocycloalkyl; $R^2$, $R^3$, $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —$C(O)R^{8b}$, —$C(O)OR^{8b}$, —$OC(O)R^{8b}$, —$OC(O)OR^{8b}$, —$N(R^{8b}R^{8c})$, —$N(R^{8b})C(O)R^{8c}$, —$C(O)N(R^{8b}R^{8c})$, —$N(R^{8b})C(O)OR^{8c}$, —$OC(O)N(R^{8b}R^{8c})$, —$N(R^{8b})C(O)N(R^{8c}R^{8d})$, —$C(O)C(O)N(R^{8b}R^{8c})$, —$S(O_2)R^{8b}$, —$S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8a}$ is $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8b}$, $R^{8c}$ and $R^{8d}$ are each independently H or $C_{1-6}$ alkyl; alternatively, one of $R^{1a}$, $R^{1b}$, or $R^{1c}$ is combined with one of $R^2$, $R^3$, $R^4$, $R^5$, $R^6$ or $R^7$ to form a $C_{5-12}$ heterocycloalkyl; alternatively, $R^2$ and $R^3$ are combined with the atoms to which they are each attached to form a $C_{4-8}$ cycloalkyl, $C_{4-10}$ heterocycloalkyl, or $C_{6-12}$ aryl; alternatively, $R^4$ and $R^5$, $R^5$ and $R^6$, or $R^6$ and $R^7$ are combined with the atoms to which they are each attached to form a $C_{3-6}$ cycloalkyl, $C_{3-6}$ heterocycloalkyl, $C_{6-12}$ aryl, or $C_{5-10}$ heteroaryl; and L is $C_{1-6}$ alkylene, or pharmaceutically acceptable salts and isomers thereof, wherein when $R^{1a}$ and $R^{1b}$ are both Me, $R^{1c}$ is hydrogen, and L is methylene, then at least one of $R^2$, $R^3$, $R^4$, $R^5$, $R^6$, and $R^7$ is not hydrogen and the compound is other than:

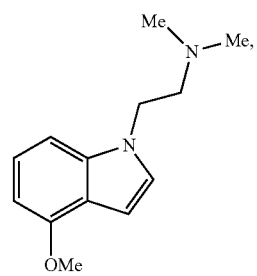

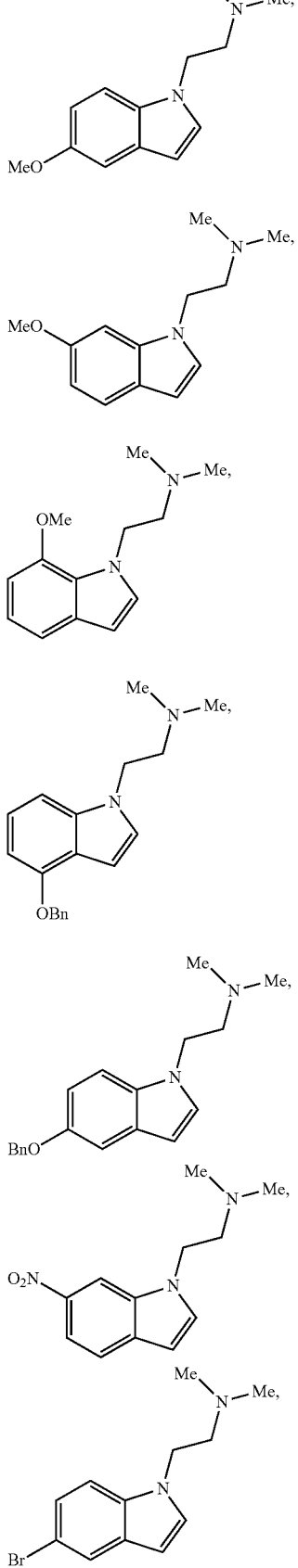

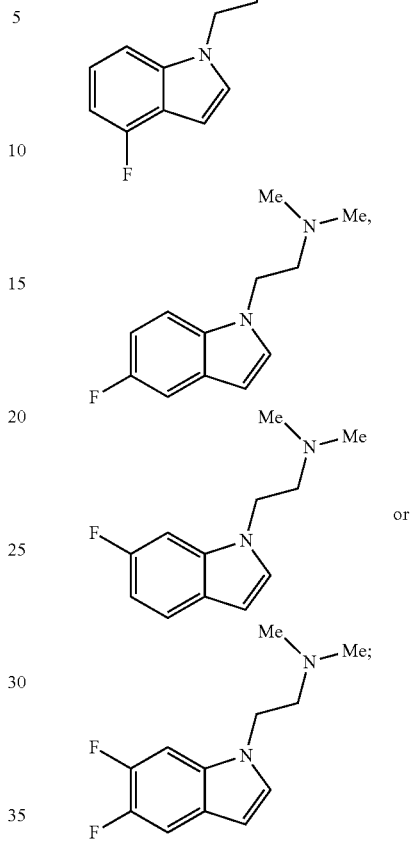

wherein when $R^{1a}$ and $R^{1b}$ are Me, $R^{1c}$ is hydrogen, L is ethylene, and X is $CR^3$, then at least one of $R^2$, $R^3$, $R^4$, $R^5$, $R^6$ and $R^7$ is not hydrogen; wherein when $R^{1c}$ is hydrogen, and $R^5$ is Br, Cl, F, —$NH_2$, —$NO_2$, or $C_{1-3}$ alkoxy, then at least one of $R^2$, $R^3$, $R^4$, $R^6$, or $R^7$ is not hydrogen; wherein when $R^{1c}$ is hydrogen and $R^5$ is F, then at least one of $R^2$, $R^3$, $R^4$, $R^6$, or $R^7$ is not hydrogen and $R^6$ is not F; and wherein when $R^{1a}$, $R^{1b}$ and $R^{1c}$ are each Me, L is methylene, X is $CR^3$ and $R^2$, $R^3$, $R^4$, $R^5$, $R^6$ and $R^7$ are hydrogen, then the compound is

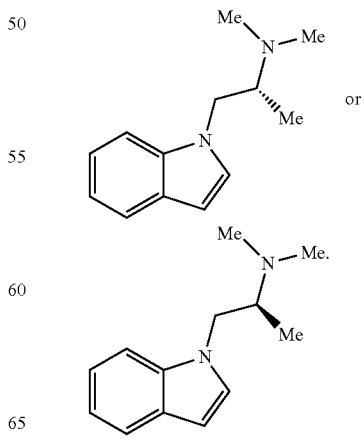

In some embodiments, the present invention provides a compound of Formula I:

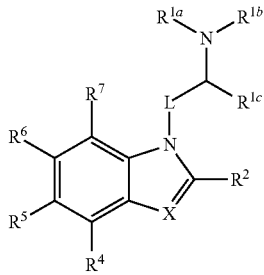

(I)

wherein: X is $CR^3$; $R^{1a}$ and $R^{1b}$ are each independently hydrogen, $C_{1-6}$ alkyl, $C_{3-8}$ cycloalkyl, or $C_{4-14}$ alkyl-cycloalkyl; $R^{1c}$ is $C_{1-6}$ alkyl, $C_{3-8}$ cycloalkyl, or $C_{4-14}$ alkyl-cycloalkyl; alternatively, two of $R^{1a}$, $R^{1b}$, and $R^{1c}$ are combined with the atoms to which they are attached to form a $C_{3-12}$ heterocycloalkyl; $R^2$, $R^3$, $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —$C(O)R^{8b}$, —$C(O)OR^{8b}$, —$OC(O)R^{8b}$, —$OC(O)OR^{8b}$, —$N(R^{8b}R^{8c})$, —$N(R^{8b})C(O)R^{8c}$, —$C(O)N(R^{8b}R^{8c})$, —$N(R^{8b})C(O)OR^{8c}$, —$OC(O)N(R^{8b}R^{8c})$, —$N(R^{8b})C(O)N(R^{8c}R^{8d})$, —$C(O)C(O)N(R^{8b}R^{8c})$, —$S(O_2)R^{8b}$, —$S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8a}$ is $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8b}$, $R^{8c}$ and $R^{8d}$ are each independently H or $C_{1-6}$ alkyl; alternatively, one of $R^{1a}$, $R^{1b}$, or $R^{1c}$ is combined with $R^2$ to form a $C_{5-12}$ heterocycloalkyl; alternatively, $R^2$ and $R^3$ are combined with the atoms to which they are each attached to form a $C_{4-8}$ cycloalkyl, $C_{4-10}$ heterocycloalkyl, or $C_{6-12}$ aryl; alternatively, $R^4$ and $R^5$, $R^5$ and $R^6$, or $R^6$ and $R^7$ are combined with the atoms to which they are each attached to form a $C_{4-6}$ cycloalkyl, $C_{4-6}$ heterocycloalkyl, $C_{6-12}$ aryl, or $C_{5-10}$ heteroaryl; and L is $C_{1-6}$ alkylene, or pharmaceutically acceptable salts and isomers thereof, wherein when $R^{1a}$, $R^{1b}$ and $R^{1c}$ are each Me, L is methylene, X is $CR^3$ and $R^2$, $R^3$, $R^4$, $R^5$, $R^6$ and $R^7$ are hydrogen, then the compound is

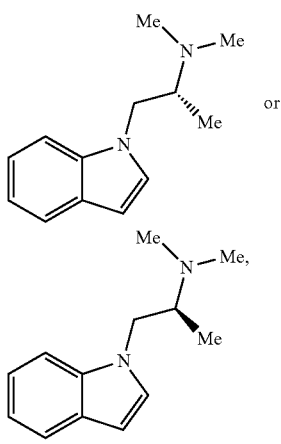

and wherein the compound is other than

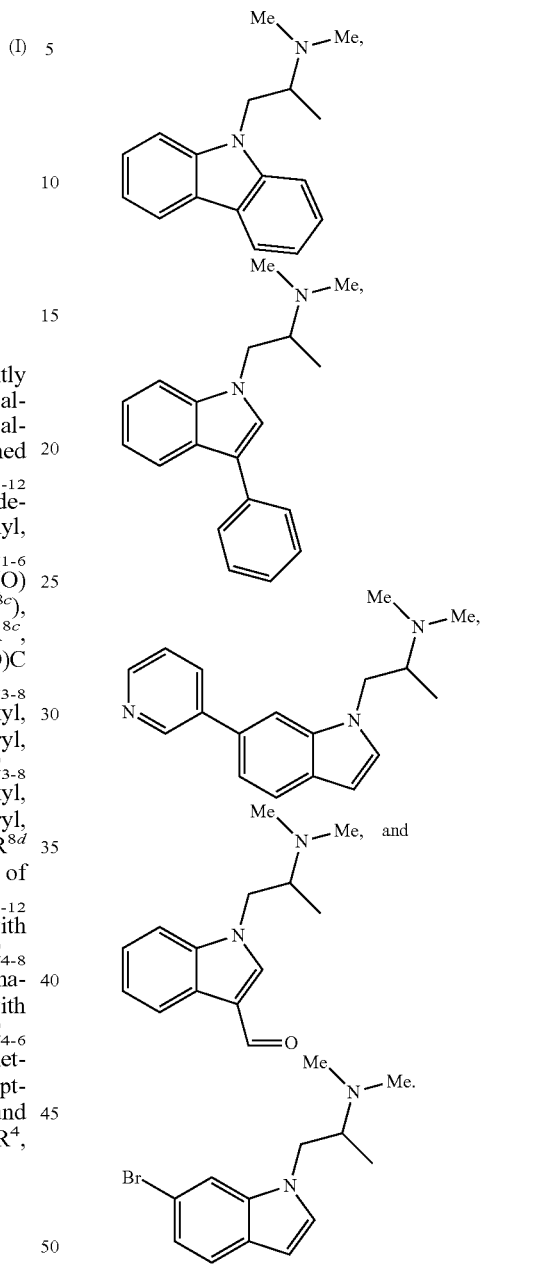

In some embodiments, the present invention provides a compound, or a pharmaceutically acceptable salt thereof, X is N or $CR^3$. In some embodiments, the present invention provides a compound, or a pharmaceutically acceptable salt thereof, X is $CR^3$. In some embodiments, the present invention provides a compound, or a pharmaceutically acceptable salt thereof, X is N.

In some embodiments, the present invention provides a compound, or a pharmaceutically acceptable salt thereof, wherein X is $CR^3$; $R^2$ and $R^3$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —$C(O)R^{8b}$, —$C(O)OR^{8b}$, —$OC(O)R^{8b}$, —$OC(O)OR^{8b}$, —$N(R^{8b}R^{8c})$, —$N(R^{8b})C(O)R^{8c}$, —$C(O)N(R^{8b}R^{8c})$, —$N(R^{8b})C(O)OR^{8c}$, —OC(O)N($R^{8b}R^{8c}$), —N($R^{8b}$)C(O)N($R^{8c}R^{8d}$), —C(O)C(O)N($R^{8b}R^{8c}$), —S($O_2$)$R^{8b}$, —S(O)$_2$N($R^{8b}R^{8c}$), $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8a}$ is $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; and $R^{8b}$, $R^{8c}$ and $R^{8d}$ are each independently H or $C_{1-6}$ alkyl; wherein when $R^{1a}$, $R^{1b}$ and $R^{1c}$ are each Me, L is methylene, and $R^2$, $R^3$, $R^4$, $R^5$, $R^6$ and $R^7$ are hydrogen, then the compound is

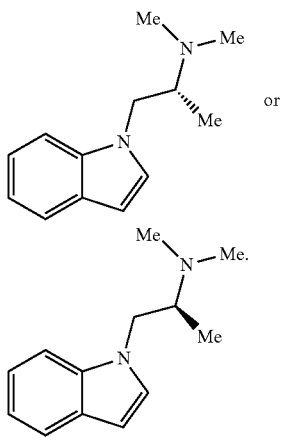

In some embodiments, the present invention provides a compound, or a pharmaceutically acceptable salt thereof, wherein the compound of Formula I has the following structure:

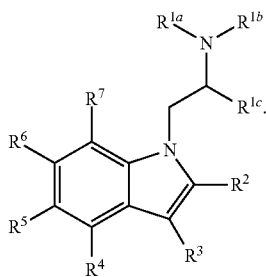

In some embodiments, the present invention provides a compound, or a pharmaceutically acceptable salt thereof, wherein $R^{1a}$, $R^{1b}$, and $R^{1c}$ are each independently $C_{1-6}$ alkyl, $C_{3-8}$ cycloalkyl, or $C_{4-14}$ alkyl-cycloalkyl; alternatively, two of $R^{1a}$, $R^{1b}$, and $R^{1c}$ are combined with the atoms to which they are attached to form a $C_{3-12}$ heterocycloalkyl; $R^2$, $R^3$, $R^4$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —OR$^{8a}$, —NO$_2$, —CN, —C(O)$R^{8b}$, —C(O)O$R^{8b}$, —OC(O)$R^{8b}$, —OC(O)O$R^{8b}$, —N($R^{8b}R^{8c}$), —N($R^{8b}$)C(O)$R^{8c}$, —C(O)N($R^{8b}R^{8c}$), —N($R^{8b}$)C(O)O$R^{8c}$, —OC(O)N($R^{8b}R^{8c}$), —N($R^{8b}$)C(O)N($R^{8c}R^{8d}$), —C(O)C(O)N($R^{8b}R^{8c}$), —S($O_2$)$R^{8b}$, —S(O)$_2$N($R^{8b}R^{8c}$), $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^5$ is $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —OR$^{8a}$, —NO$_2$, —CN, —C(O)$R^{8b}$, —C(O)O$R^{8b}$, —OC(O)$R^{8b}$, —OC(O)O$R^{8b}$, —N($R^{8b}R^{8c}$), —N($R^{8b}$)C(O)$R^{8c}$, —C(O)N($R^{8b}R^{8c}$), —N($R^{8b}$)C(O)O$R^{8c}$, —OC(O)N($R^{8b}R^{8c}$), —N($R^{8b}$)C(O)N($R^{8c}R^{8d}$), —C(O)C(O)N($R^{8b}R^{8c}$), —S($O_2$)$R^{8b}$, —S(O)$_2$N($R^{8b}R^{8c}$), $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8a}$ is $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; and $R^{8b}$, $R^{8c}$ and $R^{8d}$ are each independently H or $C_{1-6}$ alkyl; alternatively, $R^4$ and $R^5$, $R^5$ and $R^6$, or $R^6$ and $R^7$ are combined with the atoms to which they are each attached to form a $C_{4-6}$ cycloalkyl, $C_{4-6}$ heterocycloalkyl, $C_{6-12}$ aryl, or $C_{5-10}$ heteroaryl.

In some embodiments, the present invention provides a compound, or a pharmaceutically acceptable salt thereof, wherein $R^{1a}$ and $R^{1b}$ are each independently hydrogen or $C_{1-6}$ alkyl; $R^{1c}$ is $C_{1-6}$ alkyl; $R^2$ and $R^3$ are each independently hydrogen, $C_{1-6}$ alkyl, $C_{1-6}$ alkoxy, halogen, or —C(O)C(O)N($R^{8b}R^{8c}$); $R^4$, $R^5$, $R^6$ and $R^7$ are each independently hydrogen, $C_{1-6}$ alkyl, halogen, $C_{1-6}$ haloalkyl, $C_{1-6}$ alkoxy, $C_{1-6}$ haloalkoxy, or —OR$^{8a}$, wherein at least one of $R^4$, $R^5$, $R^6$ and $R^7$ is not H; and $R^{8a}$ is $C_{7-18}$ alkyl-aryl; alternatively, $R^5$ and $R^6$ can be combined with the atoms to which they are each attached to form a $C_{4-6}$ heterocycloalkyl.

In some embodiments, the present invention provides a compound, wherein X is $CR^3$; $R^{1a}$, $R^{1b}$ and $R^{1c}$ are each independently hydrogen or $C_{1-6}$ alkyl; $R^2$ and $R^3$ are each independently hydrogen, $C_{1-6}$ alkyl, or —C(O)C(O)N($R^{8b}R^{8c}$); alternatively, $R^2$ and $R^3$ can be combined with the atoms to which they are each attached to form a $C_{6-12}$ aryl; $R^4$, $R^5$, $R^6$ and $R^7$ are each independently hydrogen, $C_{1-6}$ alkyl, halogen, $C_{1-6}$ haloalkyl, $C_{1-6}$ alkoxy, $C_{1-6}$ haloalkoxy, or —OR$^{8a}$, wherein at least one of $R^4$, $R^5$, $R^6$ and $R^7$ is not H; and $R^{8a}$ is $C_{7-18}$ alkyl-aryl; alternatively, $R^5$ and $R^6$ can be combined with the atoms to which they are each attached to form a $C_{3-6}$ heterocycloalkyl.

In some embodiments, the present invention provides a compound, or a pharmaceutically acceptable salt thereof, $R^{1a}$, and $R^{1b}$ are each independently hydrogen, $C_{1-6}$ alkyl, $C_{3-8}$ cycloalkyl, or $C_{4-14}$ alkyl-cycloalkyl; alternatively, two of $R^{1a}$, $R^{1b}$, and $R^{1c}$ are combined with the atoms to which they are attached to form a $C_{3-12}$ heterocycloalkyl. In some embodiments, $R^{1a}$ and $R^{1b}$ are each independently hydrogen, or $C_{1-6}$ alkyl. In some embodiments, $R^{1a}$ and $R^{1b}$ are each independently hydrogen, methyl, ethyl, or propyl. In some embodiments, $R^{1a}$ and $R^{1b}$ are each independently hydrogen or methyl.

In some embodiments, the present invention provides a compound, or a pharmaceutically acceptable salt thereof, $R^{1a}$ and $R^{1b}$ are independently hydrogen or methyl, and $R^{1c}$ is methyl; alternatively, two of $R^{1a}$, $R^{1b}$, and $R^{1c}$ are combined with the atoms to which they are attached to form a $C_{3-8}$ heterocycloalkyl. In some embodiments, the present invention provides a compound, or a pharmaceutically acceptable salt thereof, wherein $R^{1a}$ and $R^{1b}$ are each independently hydrogen or methyl; and $R^{1c}$ is methyl; alternatively, two of $R^{1a}$, $R^{1b}$, and $R^{1c}$ are combined with the atoms to which they are attached to form a $C_{3-8}$ heterocycloalkyl.

In some embodiments, the present invention provides a compound, or a pharmaceutically acceptable salt thereof, wherein $R^{1c}$ is $C_{1-6}$ alkyl, $C_{3-8}$ cycloalkyl, or $C_{4-14}$ alkyl-cycloalkyl. In some embodiments, the present invention provides a compound, or a pharmaceutically acceptable salt thereof, wherein $R^{1c}$ is $C_{1-6}$ alkyl. In some embodiments, $R^{1c}$ is methyl, ethyl, or propyl. In some embodiments, the present invention provides a compound, or a pharmaceutically acceptable salt thereof, wherein $R^{1c}$ is methyl. In some embodiments, $R^{1c}$ is methyl.

In some embodiments, the present invention provides a compound, or a pharmaceutically acceptable salt thereof, wherein $R^{1a}$, $R^{1b}$, and $R^{1c}$ are each methyl; alternatively, two of $R^{1a}$, $R^{1b}$, and $R^{1c}$ are combined with the atoms to which they are attached to form a $C_{3-8}$ heterocycloalkyl. In some embodiments, the present invention provides a compound, or a pharmaceutically acceptable salt thereof, wherein $R^{1a}$, $R^{1b}$ and $R^{1c}$ are each Me; alternatively, two of $R^{1a}$, $R^{1b}$, and $R^{1c}$ are combined with the atoms to which they are attached to form a $C_{3-8}$ heterocycloalkyl.

In some embodiments, the present invention provides a compound, or a pharmaceutically acceptable salt thereof, wherein one of $R^{1a}$, $R^{1b}$, or $R^{1c}$ is combined with one of $R^2$, $R^3$, $R^4$, $R^5$, $R^6$ or $R^7$ to form a $C_{5-12}$ heterocycloalkyl. In some embodiments, the present invention provides a compound, or a pharmaceutically acceptable salt thereof, wherein one of $R^{1a}$, $R^{1b}$, or $R^{1c}$ is combined with one of $R^2$ or $R^7$ to form a $C_{5-8}$ heterocycloalkyl. In some embodiments, the present invention provides a compound, or a pharmaceutically acceptable salt thereof, wherein one of $R^{1a}$, $R^{1b}$, or $R^{1c}$ is combined with $R^2$ to form a $C_{5-8}$ heterocycloalkyl.

In some embodiments, the present invention provides a compound, or a pharmaceutically acceptable salt thereof, wherein $R^2$, $R^3$, $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —$C(O)R^{8b}$, —$C(O)OR^{8b}$, —$OC(O)R^{8b}$, —$OC(O)OR^{8b}$, —$N(R^{8b}R^{8c})$, —$N(R^{8b})C(O)R^{8c}$, —$C(O)N(R^{8b}R^{8c})$, —$N(R^{8b})C(O)OR^{8c}$, —$OC(O)N(R^{8b}R^{8c})$, —$N(R^{8b})C(O)N(R^{8c}R^{8d})$, —$C(O)C(O)N(R^{8b}R^{8c})$, —$S(O_2)R^{8b}$, —$S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl. In some embodiments, $R^{8a}$ is $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; and $R^{8b}$, $R^{8c}$ and $R^{8d}$ are each independently H or $C_{1-6}$ alkyl.

In some embodiments, the present invention provides a compound, or a pharmaceutically acceptable salt thereof, wherein $R^2$ and $R^3$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —$C(O)R^{8b}$, —$C(O)OR^{8b}$, —$OC(O)R^{8b}$, —$OC(O)OR^{8b}$, —$N(R^{8b}R^{8c})$, —$N(R^{8b})C(O)R^{8c}$, —$C(O)N(R^{8b}R^{8c})$, —$N(R^{8b})C(O)OR^{8c}$, —$OC(O)N(R^{8b}R^{8c})$, —$N(R^{8b})C(O)N(R^{8c}R^{8d})$, —$C(O)C(O)N(R^{8b}R^{8c})$, —$S(O_2)R^{8b}$, —$S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl.

In some embodiments, the present invention provides a compound, or a pharmaceutically acceptable salt thereof, wherein $R^2$ is hydrogen, $C_{1-6}$ alkyl, halogen, or $C_{1-6}$ alkoxy. In some embodiments, the present invention provides a compound, or a pharmaceutically acceptable salt thereof, wherein $R^2$ is hydrogen, methyl, ethyl, propyl, F, Cl, Br, I, methoxy, or ethoxy. In some embodiments, the present invention provides a compound, or a pharmaceutically acceptable salt thereof, wherein $R^2$ is hydrogen, Me, F or —OMe.

In some embodiments, the present invention provides a compound, or a pharmaceutically acceptable salt thereof, wherein $R^3$ is hydrogen, $C_{1-6}$ alkyl, $C_{1-6}$ alkoxy, halogen, or —$C(O)C(O)N(R^{8b}R^{8c})$ and $R^{8b}$ and $R^{8c}$ are each independently H or $C_{1-6}$ alkyl. In some embodiments, the present invention provides a compound, or a pharmaceutically acceptable salt thereof, wherein $R^3$ is hydrogen, methyl, ethyl, propyl, F, Cl, Br, I, methoxy, ethoxy, or —$C(O)C(O)N(R^{8b}R^{8c})$, and $R^{8b}$ and $R^{8c}$ are each independently methyl, ethyl, or propyl.

In some embodiments, the present invention provides a compound, or a pharmaceutically acceptable salt thereof, wherein $R^3$ is hydrogen, $C_{1-6}$ alkyl, $C_{1-6}$ alkoxy, halogen, or —$C(O)C(O)N(R^{8b}R^{8c})$; and $R^{8b}$ and $R^{8c}$ are each independently H or $C_{1-6}$ alkyl. In some embodiments, the present invention provides a compound, or a pharmaceutically acceptable salt thereof, wherein $R^3$ is hydrogen, Me, F, —OMe or —$C(O)C(O)NMe_2$.

In some embodiments, the present invention provides a compound, or a pharmaceutically acceptable salt thereof, wherein the compound of Formula I has the following structure:

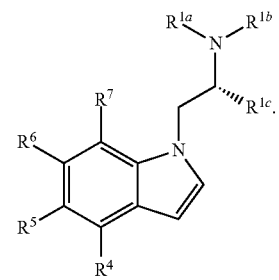

In some embodiments, the present invention provides a compound, or a pharmaceutically acceptable salt thereof, wherein the compound of Formula I has the following structure:

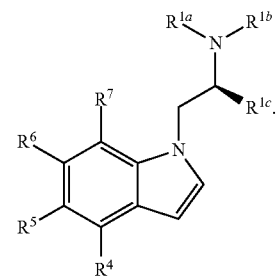

In some embodiments, the present invention provides a compound, or a pharmaceutically acceptable salt thereof, wherein $R^{1a}$ and $R^{1b}$ are combined with the atoms to which they are attached to form a $C_{3-12}$ heterocycloalkyl. In some embodiments, the present invention provides a compound, or a pharmaceutically acceptable salt thereof, wherein $R^{1a}$ and $R^{1b}$ are combined with the atoms to which they are attached to form a $C_{3-8}$ heterocycloalkyl. In some embodiments, the present invention provides a compound, or a pharmaceutically acceptable salt thereof, wherein $R^{1a}$ and $R^{1b}$ are combined with the atoms to which they are attached to form a $C_{3-8}$ heterocycloalkyl.

In some embodiments, the present invention provides a compound, or a pharmaceutically acceptable salt thereof, wherein $R^{1a}$ and $R^{1c}$ are combined with the atoms to which they are attached to form a $C_{5-12}$ heterocycloalkyl. In some embodiments, the present invention provides a compound, or a pharmaceutically acceptable salt thereof, wherein $R^{1a}$ and $R^{1c}$ are combined with the atoms to which they are attached to form a $C_{5-8}$ heterocycloalkyl. In some embodiments, the present invention provides a compound, or a pharmaceutically acceptable salt thereof, wherein $R^{1a}$ and $R^{1c}$ are combined with the atoms to which they are attached to form a $C_{5-6}$ heterocycloalkyl. In some embodiments, the present invention provides a compound, or a pharmaceutically acceptable salt thereof, wherein $R^{1a}$ and $R^{1c}$ are combined with the atoms to which they are attached to form a $C_{5-8}$ heterocycloalkyl.

In some embodiments, the present invention provides a compound of Formula (Ia), or a pharmaceutically acceptable salt or solvate thereof:

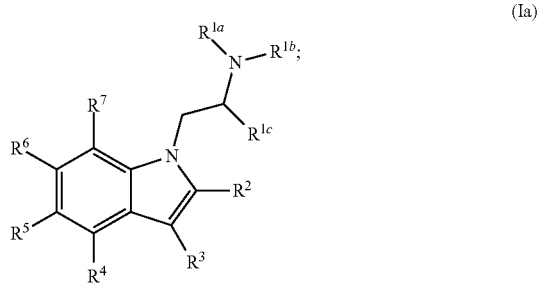

(Ia)

wherein: $R^{1a}$ and $R^{1b}$ are each independently $C_{1-6}$ alkyl, $C_{3-8}$ cycloalkyl, or $C_{4-14}$ alkyl-cycloalkyl; $R^{1c}$ is hydrogen, $C_{1-6}$ alkyl, $C_{3-8}$ cycloalkyl, or $C_{4-14}$ alkyl-cycloalkyl; alternatively, two of $R^{1a}$, $R^{1b}$, and $R^{1c}$ are combined with the atoms to which they are attached to form a $C_{3-12}$ heterocycloalkyl; $R^2$, $R^3$, $R^4$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —$C(O)R^{8b}$, —$C(O)OR^{8b}$, —$OC(O)R^{8b}$, —$OC(O)OR^{8b}$, —$N(R^{8b}R^{8c})$, —$N(R^{8b})C(O)R^{8c}$, —$C(O)N(R^{8b}R^{8c})$, —$N(R^{8b})C(O)OR^{8c}$, —$OC(O)N(R^{8b}R^{8c})$, —$N(R^{8b})C(O)N(R^{8c}R^{8d})$, —$C(O)C(O)N(R^{8b}R^{8c})$, —$S(O_2)R^{8b}$, —$S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^5$ is F, Cl, Br, $C_{1-6}$ alkyl, $C_{1-6}$ haloalkoxy, —$OR^{8a}$, —$NO_2$, —CN, $C_{2-6}$ alkenyl, $C_{2-6}$ alkynyl, —$C(O)R^{8b}$, —$N(R^{8b}R^{8c})$, —$N(R^{8b})C(O)R^{8c}$, —$C(O)N(R^{8b}R^{8c})$, —$N(R^{8b})C(O)OR^{8c}$, —$OC(O)N(R^{8b}R^{8c})$, —$N(R^{8b})C(O)N(R^{8c}R^{8d})$, —$C(O)C(O)N(R^{8b}R^{8c})$, —$S(O_2)R^{8b}$, —$S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, or $C_{4-16}$ alkyl-heteroaryl; $R^{8a}$ is $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8b}$, $R^{8c}$ and $R^{8d}$ are each independently H or $C_{1-6}$ alkyl; alternatively, one of $R^{1a}$, $R^{1b}$, and $R^{1c}$ is combined with one of $R^2$ or $R^7$ to form a $C_{5-6}$ cycloalkyl or $C_{5-6}$ heterocycloalkyl; and alternatively, $R^2$ and $R^3$ are combined with the atoms to which they are each attached to form a $C_{6-12}$ aryl; alternatively, $R^4$ and $R^5$, $R^5$ and $R^6$, or $R^6$ and $R^7$ are combined with the atoms to which they are each attached to form a $C_{3-6}$ cycloalkyl or a $C_{3-6}$ heterocycloalkyl; or salts and isomers thereof; wherein if $R^{1c}$ is H and $R^5$ is Br, Cl, F, —$NH_2$, —$NO_2$, or $C_1$-$C_3$alkoxy, then at least one of $R^2$, $R^3$, $R^4$, $R^6$, or $R^7$ is not H; and wherein when $R^5$ is F, then $R^6$ is not F.

In some embodiments, the present invention provides a compound of Formula (Ia), or a pharmaceutically acceptable salt or solvate thereof: wherein: $R^{1a}$ and $R^{1b}$ are each independently $C_{1-6}$ alkyl, $C_{3-8}$ cycloalkyl, or $C_{4-14}$ alkyl-cycloalkyl; $R^{1c}$ is $C_{1-6}$ alkyl, $C_{3-8}$ cycloalkyl, or $C_{4-14}$ alkyl-cycloalkyl; alternatively, two of $R^{1a}$, $R^{1b}$, and $R^{1c}$ are combined with the atoms to which they are attached to form a $C_{3-12}$ heterocycloalkyl; $R^2$, $R^3$, $R^4$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —$C(O)R^{8b}$, —$C(O)OR^{8b}$, —$OC(O)R^{8b}$, —$OC(O)OR^{8b}$, —$N(R^{8b}R^{8c})$, —$N(R^{8b})C(O)R^{8c}$, —$C(O)N(R^{8b}R^{8c})$, —$N(R^{8b})C(O)OR^{8c}$, —$OC(O)N(R^{8b}R^{8c})$, —$N(R^{8b})C(O)N(R^{8c}R^{8d})$, —$C(O)C(O)N(R^{8b}R^{8c})$, —$S(O_2)R^{8b}$, —$S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^5$ is $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —$C(O)R^{8b}$, —$C(O)OR^{8b}$, —$OC(O)R^{8b}$, —$OC(O)OR^{8b}$, —$N(R^{8b}R^{8c})$, —$N(R^{8b})C(O)R^{8c}$, —$C(O)N(R^{8b}R^{8c})$, —$N(R^{8b})C(O)OR^{8c}$, —$OC(O)N(R^{8b}R^{8c})$, —$N(R^{8b})C(O)N(R^{8c}R^{8d})$, —$C(O)C(O)N(R^{8b}R^{8c})$, —$S(O_2)R^{8b}$, —$S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8a}$ is $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8b}$, $R^{8c}$ and $R^{8d}$ are each independently H or $C_{1-6}$ alkyl; alternatively, one of $R^{1a}$, $R^{1b}$, and $R^{1c}$ is combined with one of $R^2$ or $R^7$ to form a $C_{5-6}$ cycloalkyl or $C_{5-6}$ heterocycloalkyl; alternatively, $R^2$ and $R^3$ are combined with the atoms to which they are each attached to form a $C_{6-12}$ aryl; and alternatively, $R^4$ and $R^5$, $R^5$ and $R^6$, or $R^6$ and $R^7$ are combined with the atoms to which they are each attached to form a $C_{3-6}$ cycloalkyl or a $C_{3-6}$ heterocycloalkyl; or salts and isomers thereof.

In some embodiments, the present invention provides a compound, or a pharmaceutically acceptable salt thereof, wherein the compound of Formula I has the following structure:

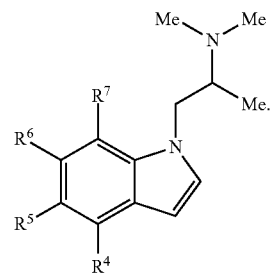

In some embodiments, the present invention provides a compound, or a pharmaceutically acceptable salt thereof, wherein the compound of Formula I has the following structure:

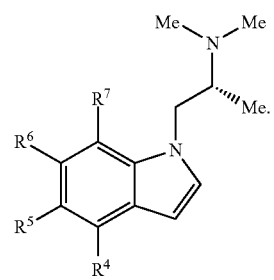

In some embodiments, the present invention provides a compound, or a pharmaceutically acceptable salt thereof, wherein the compound of Formula I has the following structure:

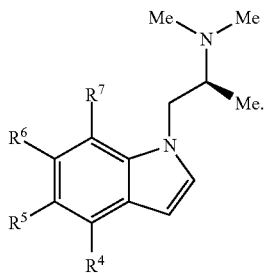

In some embodiments, $R^2$ and $R^3$ are combined with the atoms to which they are each attached to form a $C_{4-8}$ cycloalkyl, $C_{4-10}$ heterocycloalkyl, or $C_{6-12}$ aryl.

In some embodiments, the present invention provides a compound, or a pharmaceutically acceptable salt thereof, wherein $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, $-OR^{8a}$, $-NO_2$, $-CN$, $-C(O)R^{8b}$, $-C(O)OR^{8b}$, $-OC(O)R^{8b}$, $-OC(O)OR^{8b}$, $-N(R^{8b}R^{8c})$, $-N(R^{8b})C(O)R^{8c}$, $-C(O)N(R^{8b}R^{8c})$, $-N(R^{8b})C(O)OR^{8c}$, $-OC(O)N(R^{8b}R^{8c})$, $-N(R^{8b})C(O)N(R^{8c}R^{8d})$, $-C(O)C(O)N(R^{8b}R^{8c})$, $-S(O_2)R^{8b}$, $-S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; alternatively, $R^4$ and $R^5$, $R^5$ and $R^6$, or $R^6$ and $R^7$ are combined with the atoms to which they are each attached to form a $C_{4-6}$ cycloalkyl, $C_{4-6}$ heterocycloalkyl, $C_{6-12}$ aryl, or $C_{5-10}$ heteroaryl;. In some embodiments, the present invention provides a compound, or a pharmaceutically acceptable salt thereof, wherein $R^4$, $R^5$, $R^6$ and $R^7$ are each independently hydrogen, $C_{1-6}$ alkyl, halogen, $C_{1-6}$ haloalkyl, $C_{1-6}$ alkoxy, $C_{1-6}$ haloalkoxy, $-OR^{8a}$, $-NO_2$, $-CN$, $C_{3-8}$ cycloalkyl, or $C_{3-14}$ alkyl-cycloalkyl.

In some embodiments, the present invention provides a compound, or a pharmaceutically acceptable salt thereof, wherein $R^{8a}$ is $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; and $R^{8b}$, $R^{8c}$ and $R^{8d}$ are each independently H or $C_{1-6}$ alkyl. In some embodiments, the present invention provides a compound, or a pharmaceutically acceptable salt thereof, wherein $R^{8a}$ is $C_{3-8}$ cycloalkyl, $C_{3-14}$ alkyl-cycloalkyl, $C_{4-16}$ alkyl-heterocycloalkyl, $C_{7-18}$ alkyl-aryl, or $C_{4-16}$ alkyl-heteroaryl.

In some embodiments, the present invention provides a compound, or a pharmaceutically acceptable salt thereof, wherein $R^4$ and $R^5$, $R^5$ and $R^6$, or $R^6$ and $R^7$ are combined with the atoms to which they are each attached to form a $C_{4-6}$ cycloalkyl, $C_{4-6}$ heterocycloalkyl, $C_{6-12}$ aryl, or $C_{5-10}$ heteroaryl. In some embodiments, the present invention provides a compound, or a pharmaceutically acceptable salt thereof, wherein $R^4$ and $R^5$ are combined with the atoms to which they are each attached to form a $C_{4-6}$ heterocycloalkyl. In some embodiments, the present invention provides a compound, or a pharmaceutically acceptable salt thereof, wherein $R^5$ and $R^6$ are combined with the atoms to which they are each attached to form a $C_{4-6}$ heterocycloalkyl. In some embodiments, the present invention provides a compound, or a pharmaceutically acceptable salt thereof, wherein $R^6$ and $R^7$ are combined with the atoms to which they are each attached to form a $C_{4-6}$ heterocycloalkyl. In some embodiments, the present invention provides a compound, or a pharmaceutically acceptable salt thereof, wherein $R^5$ and $R^6$ are combined with the atoms to which they are each attached to form a $C_{5-6}$ heterocycloalkyl. In some embodiments, the present invention provides a compound, or a pharmaceutically acceptable salt thereof, wherein $R^5$ and $R^6$ are combined with the atoms to which they are each attached to form a 1,3-dioxole ring or 1,4-dioxane ring.

In some embodiments, the present invention provides a compound, or a pharmaceutically acceptable salt thereof, wherein $R^4$, $R^5$, $R^6$ and $R^7$ are each independently hydrogen, $C_{1-6}$ alkyl, halogen, $C_{1-6}$ haloalkyl, $C_{1-6}$ alkoxy, $C_{1-6}$ haloalkoxy, $-OR^{8a}$, $-NO_2$, $-CN$, $C_{3-8}$ cycloalkyl, or $C_{3-14}$ alkyl-cycloalkyl; alternatively, $R^4$ and $R^5$, $R^5$ and $R^6$, or $R^6$ and $R^7$ can be combined with the atoms to which they are each attached to form a $C_{5-6}$ heterocycloalkyl; and $R^{8a}$ is $C_{3-8}$ cycloalkyl, $C_{3-14}$ alkyl-cycloalkyl, $C_{4-16}$ alkyl-heterocycloalkyl, $C_{7-18}$ alkyl-aryl, or $C_{4-16}$ alkyl-heteroaryl. In some embodiments, the present invention provides a compound, or a pharmaceutically acceptable salt thereof, wherein $R^4$, $R^5$, $R^6$ and $R^7$ are each independently hydrogen, $C_{1-6}$ alkyl, halogen, $C_{1-6}$ alkoxy, $C_{1-6}$ haloalkoxy, $-OR^{8a}$, or $-NO_2$; alternatively, $R^4$ and $R^5$, $R^5$ and $R^6$, or $R^6$ and $R^7$ are combined with the atoms to which they are each attached to form a $C_5$ heterocycloalkyl; and $R^{8a}$ is $C_{7-18}$ alkyl-aryl. In some embodiments, the present invention provides a compound, or a pharmaceutically acceptable salt thereof, wherein $R^4$, $R^6$ and $R^7$ are each independently hydrogen, $C_{1-6}$ alkyl, halogen, $C_{1-6}$ alkoxy, $C_{1-6}$ haloalkoxy, $-OR^{8a}$, or $-NO_2$; $R^5$ is $C_{1-6}$ alkyl, halogen, $C_{1-6}$ alkoxy, $C_{1-6}$ haloalkoxy, $-OR^{8a}$, or $-NO_2$; alternatively, $R^4$ and $R^5$, $R^5$ and $R^6$, or $R^6$ and $R^7$ are combined with the atoms to which they are each attached to form a $C_5$ heterocycloalkyl; and $R^{8a}$ is $C_{7-18}$ alkyl-aryl. In some embodiments, the present invention provides a compound, or a pharmaceutically acceptable salt thereof, wherein $R^4$, $R^5$, $R^6$ and $R^7$ are each independently hydrogen, Me, F, Cl, Br, $-OMe$, $-OCF_3$, $-O-CH_2$-phenyl or $-NO_2$; alternatively, $R^5$ and $R^6$ are combined with the atoms to which they are each attached to form a 1,3-dioxole ring or 1,4-dioxane ring.

In some embodiments, the present invention provides a compound, or a pharmaceutically acceptable salt thereof, wherein $R^5$ is $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, $-OR^{8a}$, $-NO_2$, $-CN$, $-C(O)R^{8b}$, $-C(O)OR^{8b}$, $-OC(O)R^{8b}$, $-OC(O)OR^{8b}$, $-N(R^{8b}R^{8c})$, $-N(R^{8b})C(O)R^{8c}$, $-C(O)N(R^{8b}R^{8c})$, $-N(R^{8b})C(O)OR^{8c}$, $-OC(O)N(R^{8b}R^{8c})$, $-N(R^{8b})C(O)N(R^{8c}R^{8d})$, $-C(O)C(O)N(R^{8b}R^{8c})$, $-S(O_2)R^{8b}$, $-S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl. In some embodiments, the present invention provides a compound, or a pharmaceutically acceptable salt thereof, wherein $R^5$ is $C_{1-6}$ alkyl, halogen, $C_{1-6}$ alkoxy, $C_{1-6}$ haloalkoxy, or $-NO_2$. In some embodiments, the present invention provides a compound, or a pharmaceutically acceptable salt thereof, wherein $R^5$ is methyl, ethyl, propyl, F, Cl, Br, I, methoxy, ethoxy, $-OCF_3$, $-O$-benzyl, or $-NO_2$. In some embodiments, the present invention provides a compound, or a pharmaceutically acceptable salt thereof, wherein $R^5$ is methyl, F, Cl, Br, methoxy, $-OCF_3$, $-O$-benzyl, or $-NO_2$.

In some embodiments, the present invention provides a compound, or a pharmaceutically acceptable salt thereof, wherein $R^4$, $R^6$ and $R^7$ are each hydrogen; and $R^5$ is Me, F, Cl, Br, —OMe, —$CF_3$, —$OCF_3$, —O-benzyl or —$NO_2$. In some embodiments, the present invention provides a compound, or a pharmaceutically acceptable salt thereof, wherein $R^5$ is Me, F, Cl, Br, —OMe, —$CF_3$, —$OCF_3$, —O-benzyl or —$NO_2$; and $R^6$ and $R^7$ are each independently hydrogen, Me, F, Cl, Br, —OMe, —$OCF_3$, —O—$CH_2$-phenyl or —$NO_2$, wherein at least one of $R^6$ and $R^7$ is not hydrogen.

In some embodiments, the present invention provides a compound, wherein X is $CR^3$; $R^{1a}$, $R^{1b}$ and $R^{1c}$ are each independently hydrogen or $C_{1-6}$ alkyl; $R^2$ and $R^3$ are each independently hydrogen, $C_{1-6}$ alkyl, or —C(O)C(O)N($R^{8b}R^{8c}$); alternatively, $R^2$ and $R^3$ can be combined with the atoms to which they are each attached to form a $C_{6-12}$ aryl; $R^4$, $R^5$, $R^6$ and $R^7$ are each independently hydrogen, $C_{1-6}$ alkyl, halogen, $C_{1-6}$ haloalkyl, $C_{1-6}$ alkoxy, $C_{1-6}$ haloalkoxy, or —$OR^{8a}$, wherein at least one of $R^4$, $R^5$, $R^6$ and $R^7$ is not H; and $R^{8a}$ is $C_{7-18}$ alkyl-aryl; alternatively, $R^5$ and $R^6$ can be combined with the atoms to which they are each attached to form a $C_{3-6}$ heterocycloalkyl.

In some embodiments, the present invention provides a compound, wherein X is $CR^3$; $R^{1a}$ and $R^{1b}$ are each Me; $R^{1c}$ is hydrogen or Me; $R^2$ is H, Me or —C(O)—C(O)N(Me)$_2$; alternatively, $R^2$ and $R^3$ are combined to form a phenyl ring; and $R^4$, $R^5$, $R^6$ and $R^7$ are each independently H, F, Br, —$NO_2$, —OMe, —$CF_3$, —$OCF_3$, or —O-benzyl; alternatively, $R^5$ and $R^6$ are combined to form a 1,3-dioxole ring.

In some embodiments, the present invention provides a compound, wherein X is $CR^3$; $R^{1a}$ and $R^{1b}$ are each Me; $R^{1c}$ is hydrogen or Me; $R^2$ is H or Me; $R^3$ is H or —C(O)—C(O)N(Me)$_2$; $R^4$ is H, F, —OMe or —O-benzyl; $R^5$ is H, F, Br, —OMe, —$CF_3$—$OCF_3$ or —O-benzyl; $R^6$ is H, —$NO_2$, —OMe, —$OCF_3$, or —O-benzyl; alternatively, $R^2$ and $R^3$ are combined to form a phenyl ring; alternatively, $R^5$ and $R^6$ are combined to form a 1,3-dioxole ring; and $R^7$ is H, F, —OMe, or —O-benzyl.

In some embodiments, the present invention provides a compound, or a pharmaceutically acceptable salt thereof, wherein X is $CR^3$; $R^{1a}$ and $R^{1b}$ are each Me; $R^{1c}$ is Me, Et, or Pr; $R^2$ is H, Me, —OMe, —F, or —C(O)—C(O)N(Me)$_2$; $R^3$ is H, Me, —OMe, —F, or —C(O)—C(O)N(Me)$_2$; and $R^4$, $R^5$, $R^6$ and $R^7$ are each independently H, Me, —F, —Cl, —Br, —$NO_2$, —OMe, —$CF_3$, —$OCF_3$, or —O-benzyl; alternatively, $R^5$ and $R^6$ are combined to form a 1,3-dioxole ring or 1,4-dioxane ring. In some embodiments, the present invention provides a compound, or a pharmaceutically acceptable salt thereof, wherein X is $CR^3$; $R^{1a}$ and $R^{1b}$ are each Me; $R^{1c}$ is Me, Et, or Pr; $R^2$ is H, Me, —F, —OMe; $R^3$ is H, Me, —F, —OMe, or —C(O)—C(O)N(Me)$_2$; $R^4$ is H, Me, —F, —OMe or —O-benzyl; $R^5$ is H, Me, —F, —Cl, —Br, —OMe, —$CF_3$—$OCF_3$ or —O-benzyl; $R^6$ is H, Me, —F, —$NO_2$, —OMe, —$OCF_3$, or —O-benzyl; alternatively, $R^5$ and $R^6$ are combined to form a 1,3-dioxole ring or 1,4-dioxane ring; and $R^7$ is H, Me, —F, —OMe, or —O-benzyl.

In some embodiments, the present invention provides a compound, or a pharmaceutically acceptable salt thereof, wherein L is $C_{1-6}$ alkylene. In some embodiments, the present invention provides a compound, or a pharmaceutically acceptable salt thereof, wherein L is methylene, ethylene, propylene, or butylene. In some embodiments, the present invention provides a compound, or a pharmaceutically acceptable salt thereof, wherein L is methylene or ethylene. In some embodiments, the present invention provides a compound, or a pharmaceutically acceptable salt thereof, wherein L is ethylene. In some embodiments, the present invention provides a compound, or a pharmaceutically acceptable salt thereof, wherein L is methylene.

In some embodiments, the present invention provides a compound, wherein the compound is

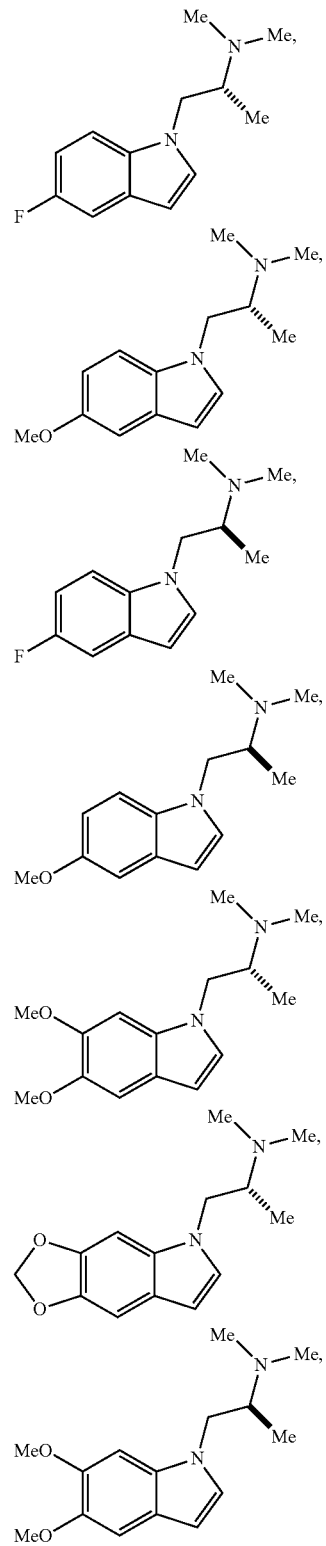

-continued
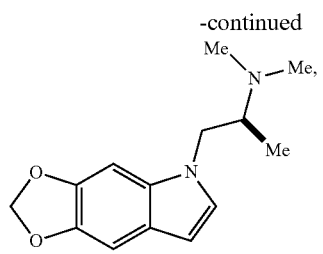
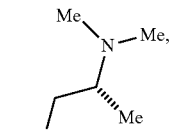
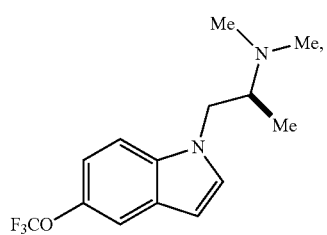
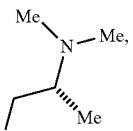
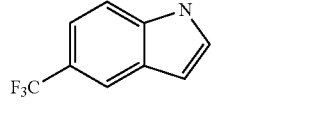
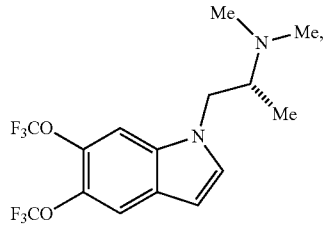
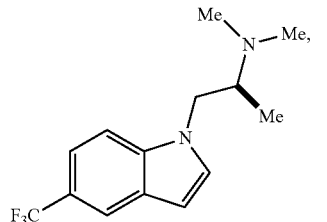
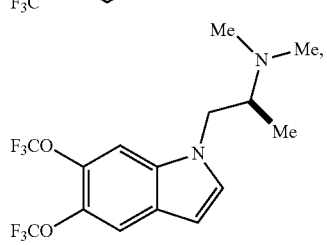
-continued
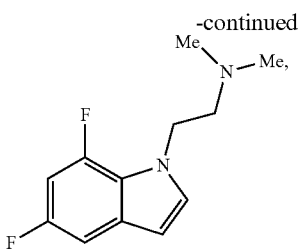
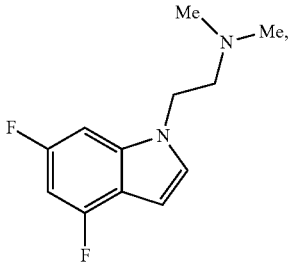
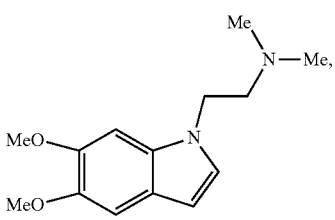
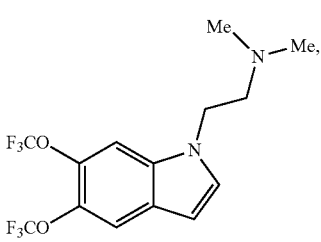
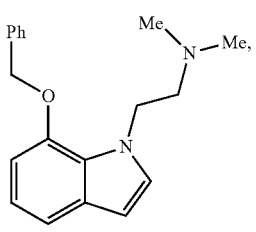
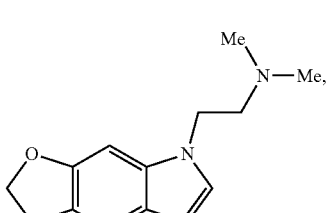
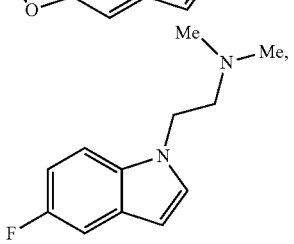

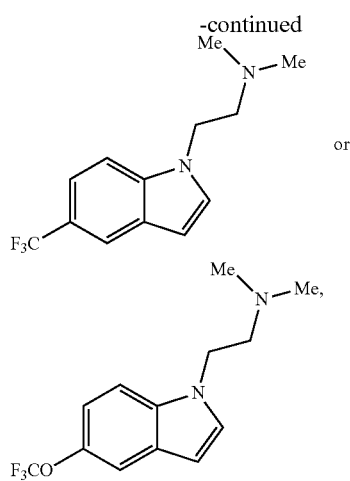
or
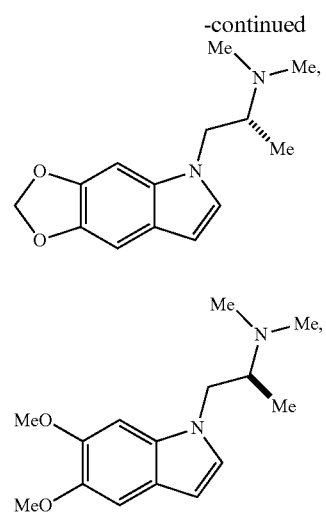
or a pharmaceutically acceptable salt thereof.
In some embodiments, the present invention provides a compound, wherein the compound is
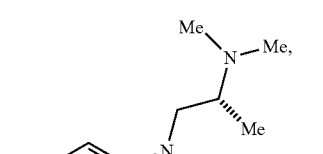
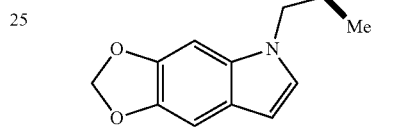
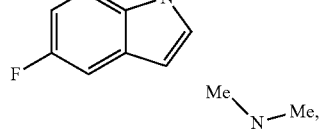
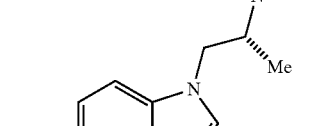
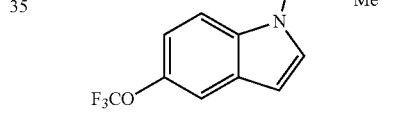
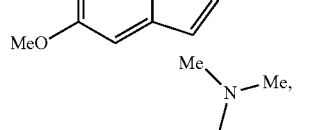
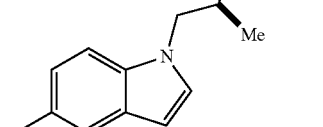
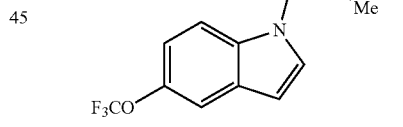
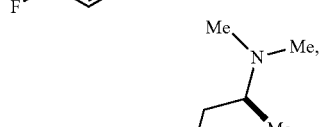
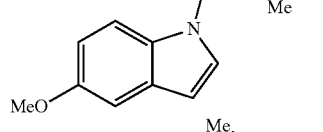
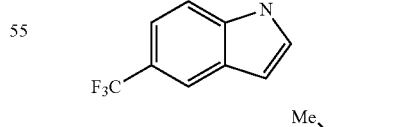
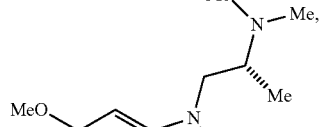
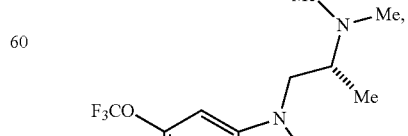
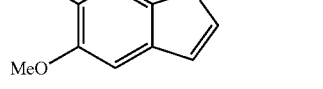
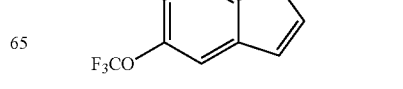

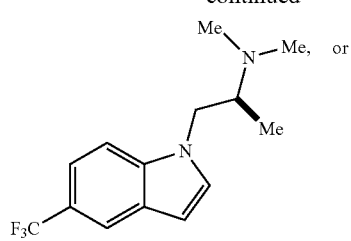
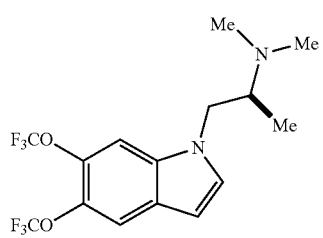
or a pharmaceutically acceptable salt thereof.
In some embodiments, the present invention provides a compound, wherein the compound is
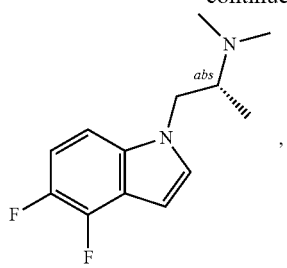
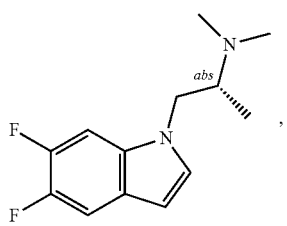
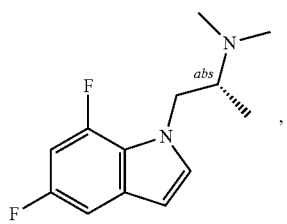
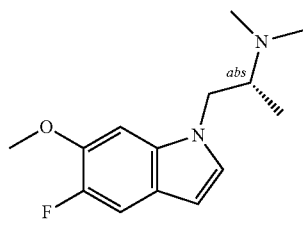
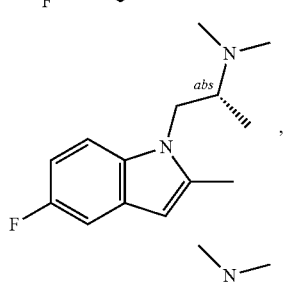
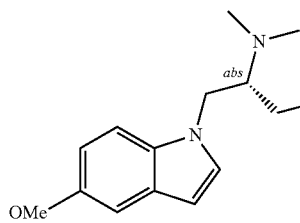

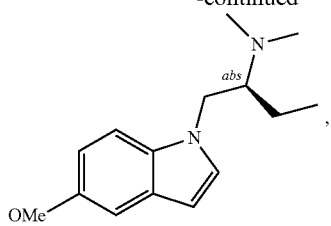
,
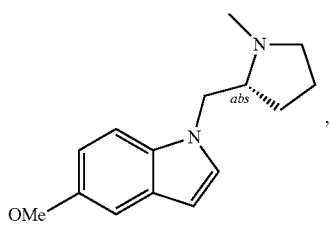
,
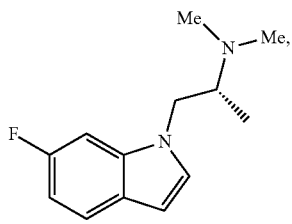
,
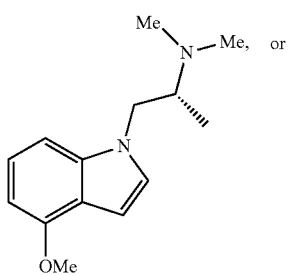
or
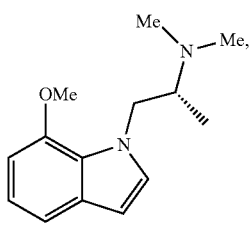
,
or a pharmaceutically acceptable salt thereof.
In some embodiments, the present invention provides wherein the compound is
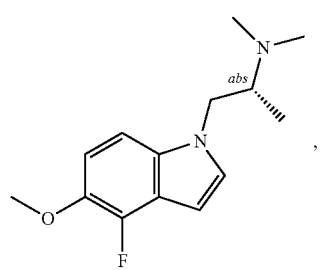
,
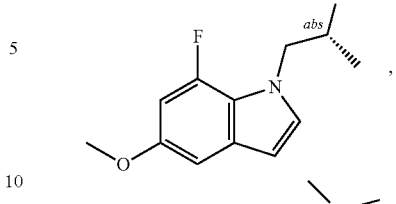
,
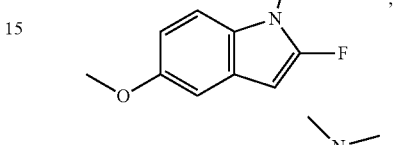
,
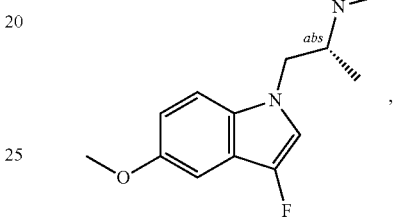
,
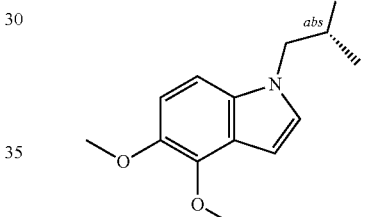
,
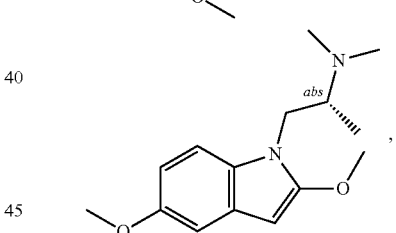
,
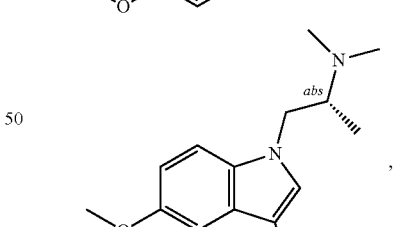
,
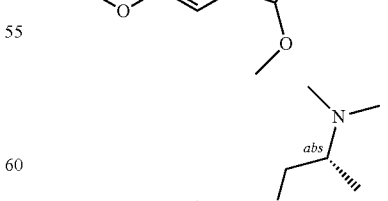
,
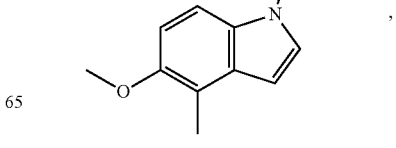
, -continued
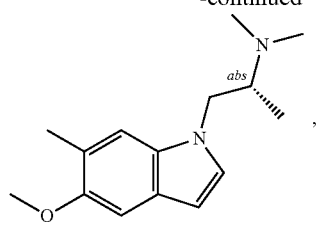,
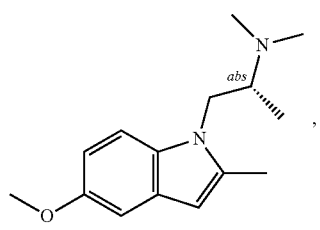,
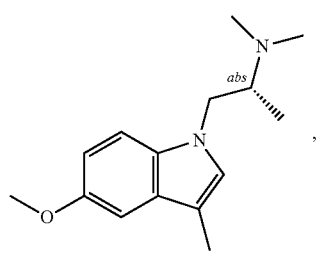,
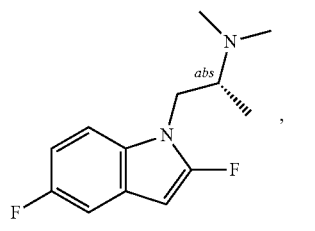,
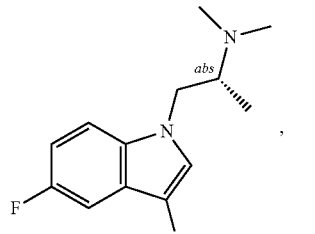,
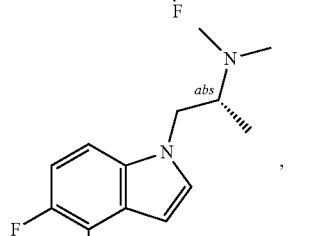,
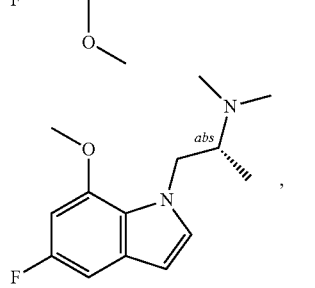,
-continued
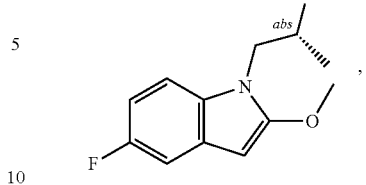,
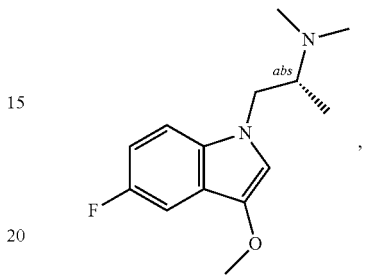,
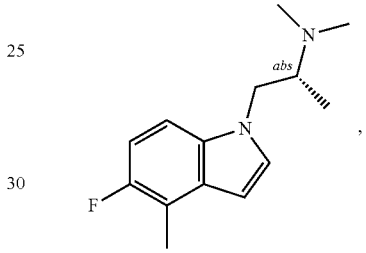,
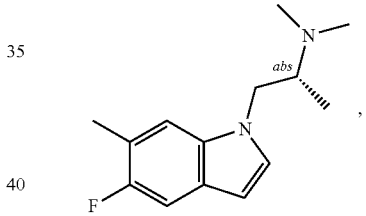,
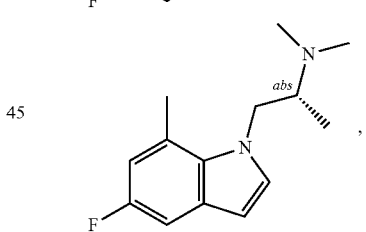,
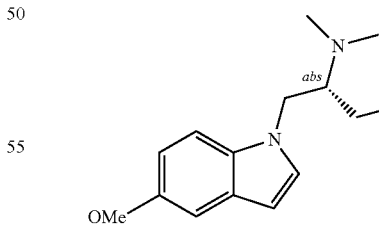,
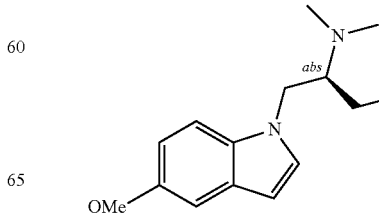,

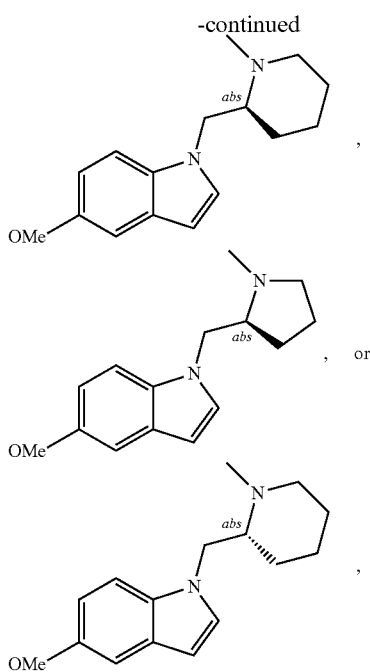

or a pharmaceutically acceptable salt thereof.

In some embodiments, the present invention provides a compound of Formula II:

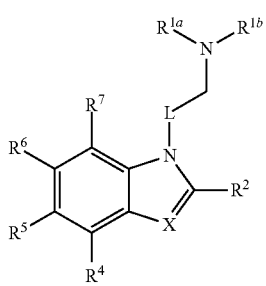

(II)

wherein: X is $CR^3$; $R^{1a}$ and $R^{1b}$ are each independently hydrogen, $C_{1-6}$ alkyl, $C_{3-8}$ cycloalkyl, or $C_{4-14}$ alkyl-cycloalkyl; alternatively, $R^{1a}$ and $R^{1b}$ are combined with the atoms to which they are attached to form a $C_{3-12}$ heterocycloalkyl; $R^2$, $R^3$, $R^4$, $R^5$, $R^6$ and $R^7$ are each independently hydrogen, $C_{1-6}$ alkyl, $C_{2-6}$ alkenyl, $C_{2-6}$ alkynyl, halogen, $C_{1-6}$ haloalkyl, $C_{1-6}$ alkylamine, $C_{1-6}$ alkoxy, $C_{1-6}$ haloalkoxy, —$OR^{8a}$, —$NO_2$, —CN, —$C(O)R^{8b}$, —$C(O)OR^{8b}$, —$OC(O)R^{8b}$, —$OC(O)OR^{8b}$, —$N(R^{8b}R^{8c})$, —$N(R^{8b})C(O)R^{8c}$, —$C(O)N(R^{8b}R^{8c})$, —$N(R^{8b})C(O)OR^{8c}$, —$OC(O)N(R^{8b}R^{8c})$, —$N(R^{8b})C(O)N(R^{8c}R^{8d})$, —$C(O)C(O)N(R^{8b}R^{8c})$, —$S(O_2)R^{8b}$, —$S(O)_2N(R^{8b}R^{8c})$, $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8a}$ is $C_{3-8}$ cycloalkyl, $C_{3-14}$ alkyl-cycloalkyl, $C_{4-10}$ heterocycloalkyl, $C_{4-16}$ alkyl-heterocycloalkyl, $C_{6-12}$ aryl, $C_{7-18}$ alkyl-aryl, $C_{5-10}$ heteroaryl, or $C_{4-16}$ alkyl-heteroaryl; $R^{8b}$, $R^{8c}$ and $R^{8d}$ are each independently H or $C_{1-6}$ alkyl; alternatively, one of $R^{1a}$ or $R^{1b}$ is combined with $R^2$ to form a $C_{5-12}$ heterocycloalkyl; alternatively, $R^2$ and $R^3$ are combined with the atoms to which they are each attached to form a $C_{4-8}$ cycloalkyl, $C_{4-10}$ heterocycloalkyl, or $C_{6-12}$ aryl; alternatively, $R^4$ and $R^5$, $R^5$ and $R^6$, or $R^6$ and $R^7$ are combined with the atoms to which they are each attached to form a $C_{4-6}$ cycloalkyl, $C_{4-6}$ heterocycloalkyl, $C_{6-12}$ aryl, or $C_{5-10}$ heteroaryl; and L is $C_{1-6}$ alkylene, or pharmaceutically acceptable salts and isomers thereof, wherein when $R^{1a}$ and $R^{1b}$ are both Me, and L is methylene, then at least one of $R^2$, $R^3$, $R^4$, $R^5$, $R^6$, and $R^7$ is not hydrogen and the compound is other than:

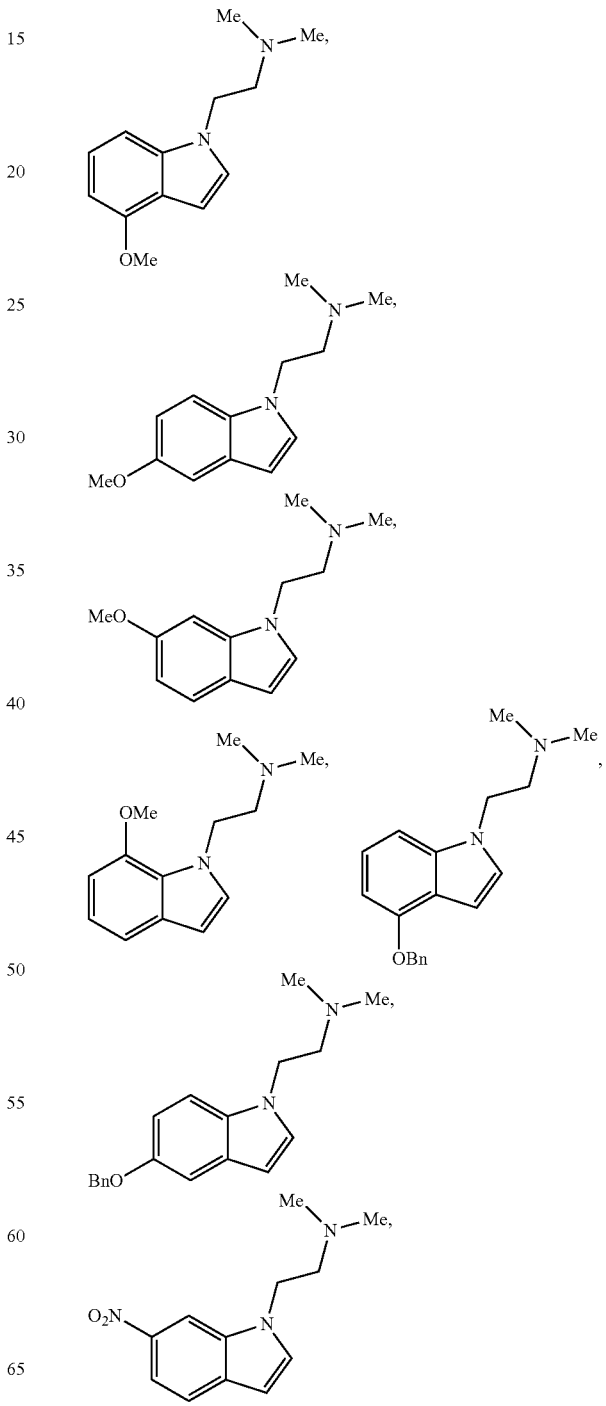

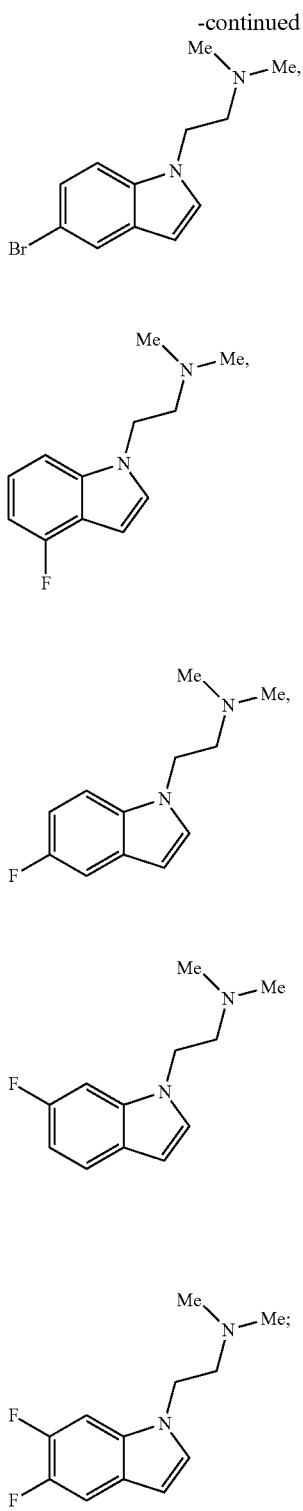

wherein when $R^{1a}$ and $R^{1b}$ are Me, L is ethylene, and X is $CR^3$, then at least one of $R^2$, $R^3$, $R^4$, $R^5$, $R^6$ and $R^7$ is not hydrogen; wherein when $R^{1c}$ is hydrogen, and $R^5$ is Br, Cl, F, —NH$_2$, —NO$_2$, or C$_{1-3}$ alkoxy, then at least one of $R^2$, $R^3$, $R^4$, $R^6$, or $R^7$ is not hydrogen; and wherein when $R^{1c}$ is hydrogen and $R^5$ is F, then at least one of $R^2$, $R^3$, $R^4$, $R^6$, or $R^7$ is not hydrogen and $R^6$ is not F.

In some embodiments, the present invention provides a compound, or a pharmaceutically acceptable salt thereof, wherein the compound of Formula II has the following structure:

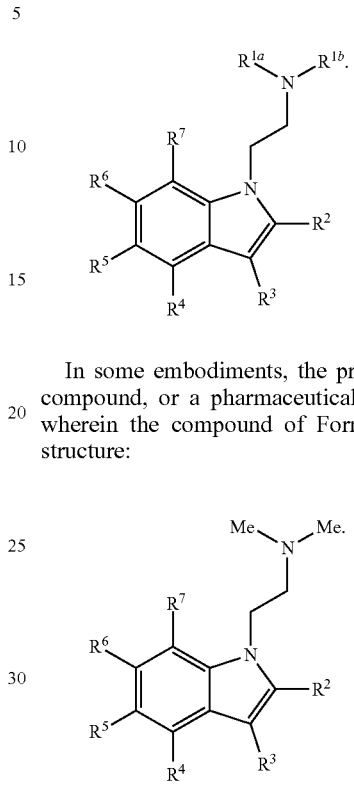

In some embodiments, the present invention provides a compound, or a pharmaceutically acceptable salt thereof, wherein the compound of Formula II has the following structure:

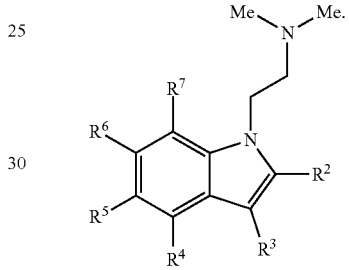

In some embodiments, the present invention provides a compound, or a pharmaceutically acceptable salt thereof, wherein at least one of $R^2$, $R^3$, $R^4$, $R^5$, $R^6$ and $R^7$ is not H.

In some embodiments, the present invention provides a compound, or a pharmaceutically acceptable salt thereof, wherein $R^4$, $R^5$, $R^6$ and $R^7$ are each independently hydrogen, C$_{1-6}$ alkyl, halogen, C$_{1-6}$ haloalkyl, C$_{1-6}$ alkoxy, C$_{1-6}$ haloalkoxy, —OR$^{8a}$, —NO$_2$, —CN, C$_{3-8}$ cycloalkyl, or C$_{3-14}$ alkyl-cycloalkyl; alternatively, $R^4$ and $R^5$, $R^5$ and $R^6$, or $R^6$ and $R^7$ can be combined with the atoms to which they are each attached to form a C$_{5-6}$ heterocycloalkyl; and $R^{8a}$ is C$_{3-8}$ cycloalkyl, C$_{3-14}$ alkyl-cycloalkyl, C$_{4-16}$ alkyl-heterocycloalkyl, C$_{7-18}$ alkyl-aryl, or C$_{4-16}$ alkyl-heteroaryl. In some embodiments, the present invention provides a compound, or a pharmaceutically acceptable salt thereof, wherein $R^4$, $R^5$, $R^6$ and $R^7$ are each independently hydrogen, C$_{1-6}$ alkyl, halogen, C$_{1-6}$ alkoxy, C$_{1-6}$ haloalkoxy, —OR$^{8a}$, or —NO$_2$; alternatively, $R^4$ and $R^5$, $R^5$ and $R^6$, or $R^6$ and $R^7$ are combined with the atoms to which they are each attached to form a C$_5$ heterocycloalkyl; and $R^{8a}$ is C$_{7-18}$ alkyl-aryl.

In some embodiments, the present invention provides a compound, or a pharmaceutically acceptable salt thereof, wherein $R^4$, $R^5$, $R^6$ and $R^7$ are each independently hydrogen, F, Cl, —OMe, —OCF$_3$ or —O-benzyl; alternatively, $R^5$ and $R^6$ are combined with the atoms to which they are each attached to form a 1,3-dioxole ring or 1,4-dioxane ring. In some embodiments, the present invention provides a compound, or a pharmaceutically acceptable salt thereof, wherein $R^5$ is F, Cl, —OMe, —OCF$_3$ or —O-benzyl; alternatively, $R^5$ and $R^6$ are combined with the atoms to which they are each attached to form a 1,3-dioxole ring or 1,4-dioxane ring.

In some embodiments, the present invention provides a compound, or a pharmaceutically acceptable salt thereof, wherein $R^5$ is F, Cl, —OMe, —OCF$_3$ or —O-benzyl; $R^6$ and $R^7$ are each independently hydrogen, F, Cl, —OMe, —OCF$_3$ or —O-benzyl, wherein at least one of $R^6$ and $R^7$ is not hydrogen; alternatively, $R^5$ and $R^6$ are combined with the atoms to which they are each attached to form a 1,3-dioxole ring or 1,4-dioxane ring.

In some embodiments, the present invention provides a compound, wherein the compound is

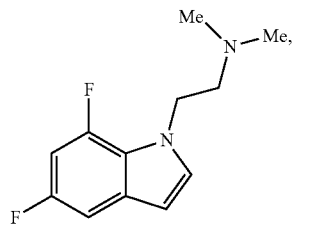

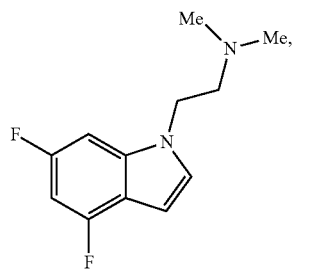

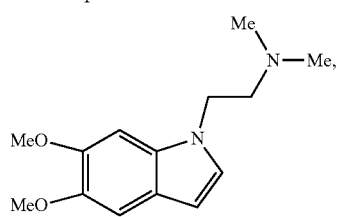

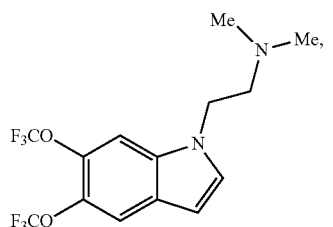

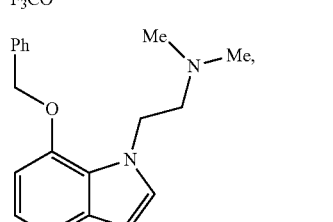

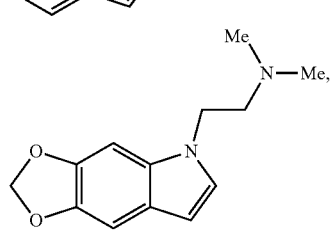

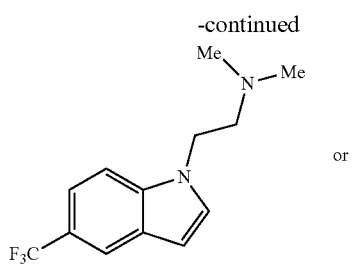

or

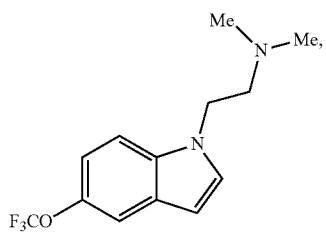

or a pharmaceutically acceptable salt thereof.

In some embodiments, the present invention provides a compound, wherein the compound is

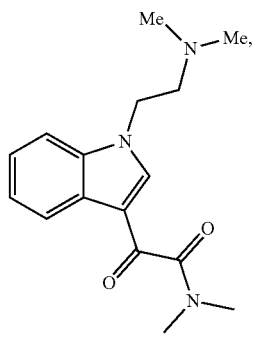

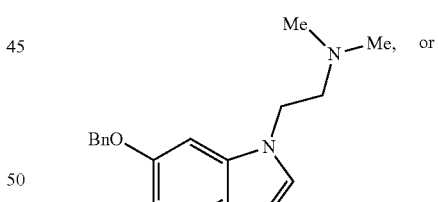

or

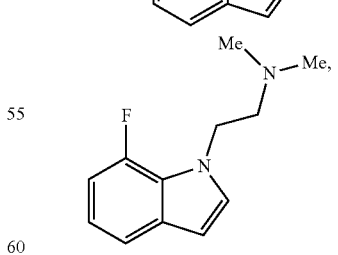

or a pharmaceutically acceptable salt thereof.

In some embodiments, the present invention provides a compound, or a pharmaceutically acceptable salt thereof, wherein $R^{1a}$ and $R^{1b}$ are combined with the atoms to which they are attached to form a $C_{3-8}$ heterocycloalkyl.

In some embodiments, the present invention provides a compound, wherein the compound is
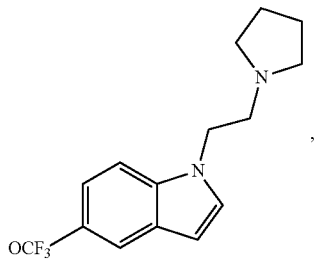
,
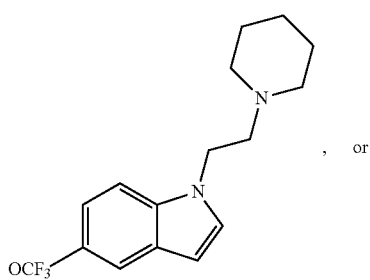
, or
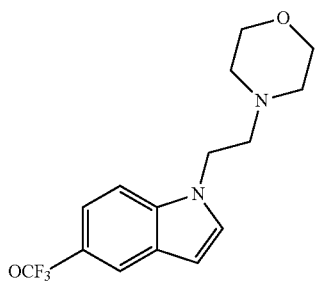
or a pharmaceutically acceptable salt thereof.
In some embodiments, the present invention provides a compound, wherein the compound is
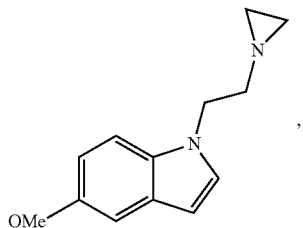
,
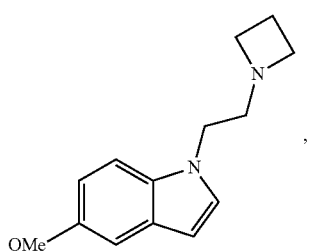
,
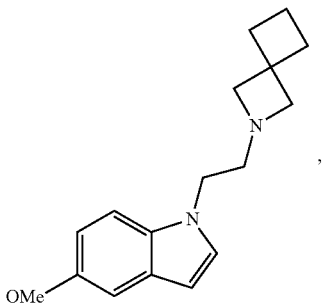
,
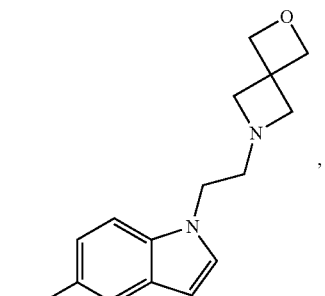
,
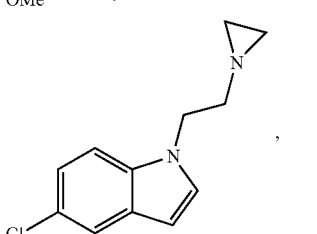
,
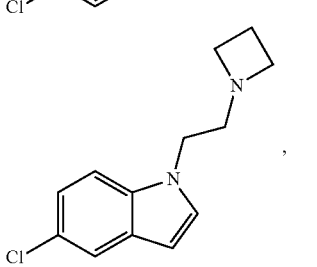
,
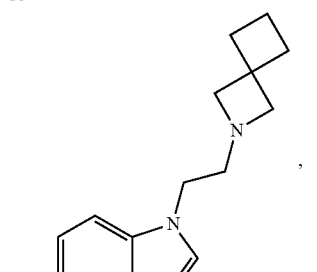
,
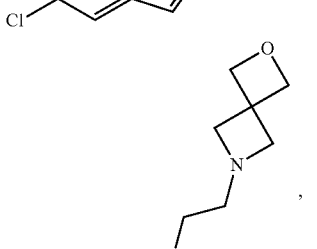
,
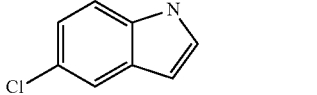

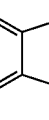

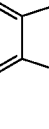

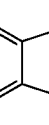

, or 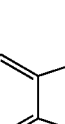

or a pharmaceutically acceptable salt thereof.

The compounds of the present invention can also be in the salt forms, such as acid or base salts of the compounds of the present invention. Illustrative examples of pharmaceutically acceptable salts are mineral acid (hydrochloric acid, hydrobromic acid, phosphoric acid, and the like) salts, organic acid (fumaric acid, acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

In some embodiments, the compound of the present invention is a salt comprising fumaric acid. In some embodiments, the present invention provides a compound, wherein the compound is a salt comprising fumaric acid or a pharmaceutically acceptable salt.

The present invention also includes isotopically-labeled compounds of the present invention, wherein one or more atoms are replaced by one or more atoms having specific atomic mass or mass numbers. Examples of isotopes that can be incorporated into compounds of the invention include, but are not limited to, isotopes of hydrogen, carbon, nitrogen, oxygen, fluorine, sulfur, and chlorine (such as $^2$H, $^3$H, $^{13}$C, $^{14}$C, $^{15}$N, $^{18}$O, $^{17}$O, $^{18}$F, $^{35}$S and $^{36}$Cl). Isotopically-labeled compounds of the present invention are useful in assays of the tissue distribution of the compounds and their prodrugs and metabolites; preferred isotopes for such assays include $^3$H and $^{14}$C. In addition, in certain circumstances substitution with heavier isotopes, such as deuterium ($^2$H), can provide increased metabolic stability, which offers therapeutic advantages such as increased in vivo half-life or reduced dosage requirements. Isotopically-labeled compounds of this invention can generally be prepared according to the methods known by one of skill in the art by substituting an isotopically-labeled reagent for a non-isotopically labeled reagent. Compounds of the present invention can be isotopically labeled at positions adjacent to the basic amine, in aromatic rings, and the methyl groups of methoxy substituents.

The present invention includes all tautomers and stereoisomers of compounds of the present invention, either in admixture or in pure or substantially pure form. The compounds of the present invention can have asymmetric centers at the carbon atoms, and therefore the compounds of the present invention can exist in diastereomeric or enantiomeric forms or mixtures thereof. All conformational isomers (e.g., cis and trans isomers) and all optical isomers (e.g., enantiomers and diastereomers), racemic, diastereomeric and other mixtures of such isomers, as well as solvates, hydrates, isomorphs, polymorphs and tautomers are within the scope of the present invention. Compounds according to the present invention can be prepared using diastereomers, enantiomers or racemic mixtures as starting materials. Furthermore, diastereomer and enantiomer products can be separated by chromatography, fractional crystallization or other methods known to those of skill in the art.

IV. Pharmaceutical Compositions and Formulations

In some embodiments, the present invention provides a pharmaceutical composition comprising a compound of the present invention, and a pharmaceutically acceptable excipient.

The pharmaceutical compositions of the present invention can be prepared in a wide variety of oral, parenteral and topical dosage forms. Oral preparations include tablets, pills, powder, capsules, liquids, lozenges, cachets, gels, syrups, slurries, suspensions, etc., suitable for ingestion by the patient. The compositions of the present invention can also be administered by injection, that is, intravenously, intramuscularly, intracutaneously, subcutaneously, intraduodenally, or intraperitoneally. Also, the compositions described herein can be administered by inhalation, for example, intranasally. Additionally, the compositions of the present invention can be administered transdermally. The compositions of this invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present invention also provides pharmaceutical compositions including a pharmaceutically acceptable carrier or excipient and the compounds of the present invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa. ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% to 70% or 10% to 70% of the compounds of the present invention.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

For preparing suppositories, a low melting wax, such as a mixture of fatty acid glycerides or cocoa butter, is first melted and the compounds of the present invention are dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the compounds of the present invention in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending the compound of the present invention in a vegetable oil, such as *arachis* oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention can also be delivered as microspheres for slow release in the body. For example, microspheres can be formulated for administration via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

In some embodiments, the pharmaceutical compositions of the present invention can be formulated for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose, any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In some embodiments, the formulations of the compositions of the present invention can be delivered by the use of liposomes which fuse with the cellular membrane or are endocytosed, i.e., by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

V. Administration

The compositions of the present invention can be delivered by any suitable means, including oral, parenteral and topical methods. Transdermal administration methods, by a topical route, can be formulated as applicator sticks, solutions, suspensions, emulsions, gels, creams, ointments, pastes, jellies, paints, powders, and aerosols.

The pharmaceutical preparation is preferably in unit dosage form. In such form the preparation is subdivided into unit doses containing appropriate quantities of the compounds of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compound of the present invention can be present in any suitable amount, and can depend on various factors including, but not limited to, weight and age of the subject, state of the disease, etc. Suitable dosage ranges for the compound of the present invention include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the compound of the present invention include about 1 mg, 5, 10, 20, 30, 40, 50, 60, 70, 80, 90, 100, 200, 300, 400, 500, 600, 700, 800, 900 or 1000 mg.

The compounds of the present invention can be administered at any suitable frequency, interval and duration. For example, the compound of the present invention can be administered once an hour, or two, three or more times an hour, once a day, or two, three, or more times per day, or once every 2, 3, 4, 5, 6, or 7 days, so as to provide the preferred dosage level. When the compound of the present invention is administered more than once a day, representative intervals include 5, 10, 15, 20, 30, 45 and 60 minutes, as well as 1, 2, 4, 6, 8, 10, 12, 16, 20, and 24 hours. The compound of the present invention can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

The composition can also contain other compatible therapeutic agents. The compounds described herein can be used in combination with one another, with other active agents known to be useful in modulating a glucocorticoid receptor, or with adjunctive agents that may not be effective alone, but may contribute to the efficacy of the active agent.

The compounds of the present invention can be co-administered with another active agent. Co-administration includes administering the compound of the present invention and active agent within 0.5, 1, 2, 4, 6, 8, 10, 12, 16, 20, or 24 hours of each other. Co-administration also includes administering the compound of the present invention and active agent simultaneously, approximately simultaneously (e.g., within about 1, 5, 10, 15, 20, or 30 minutes of each other), or sequentially in any order. Moreover, the compound of the present invention and the active agent can each be administered once a day, or two, three, or more times per day so as to provide the preferred dosage level per day.

In some embodiments, co-administration can be accomplished by co-formulation, i.e., preparing a single pharmaceutical composition including both the compound of the present invention and the active agent. In other embodiments, the compound of the present invention and the active agent can be formulated separately.

The compound of the present invention and the active agent can be present in the compositions of the present invention in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). The compound of the present invention and the other active agent can be present in any suitable weight ratio, such as about 1:100 (w/w), 1:50, 1:25, 1:10, 1:5, 1:4, 1:3, 1:2, 1:1, 2:1, 3:1, 4:1, 5:1, 10:1, 25:1, 50:1 or 100:1 (w/w). Other dosages and dosage ratios of the compound of the present invention and the active agent are suitable in the compositions and methods of the present invention.

VI. Methods of Treatment

The compounds of the present invention can be used for increasing neuronal plasticity. The compounds of the present invention can also be used to treat any brain disease. The compounds of the present invention can also be used for increasing at least one of translation, transcription or secretion of neurotrophic factors.

In some embodiments, a compound of the present invention is used to treat neurological diseases. In some embodiments, the compounds have, for example, anti-addictive properties, antidepressant properties, anxiolytic properties, or a combination thereof. In some embodiments, the neurological disease is a neuropsychiatric disease. In some embodiments, the neuropsychiatric disease is a mood or anxiety disorder. In some embodiments, the neurological disease is a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, traumatic brain injury, and addiction (e.g., substance use disorder). In some embodiments, the neurological disease is a migraine or cluster headache. In some embodiments, the neurological disease is a neurodegenerative disorder, Alzheimer's disease, or Parkinson's disease. In some embodiments, the neurological disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease or neurological disease is post-traumatic stress disorder (PTSD), addiction (e.g., substance use disorder), schizophrenia, depression, or anxiety. In some embodiments, the neuropsychiatric disease or neurological disease is addiction (e.g., substance use disorder). In some embodiments, the neuropsychiatric disease or neurological disease is depression. In some embodiments, the neuropsychiatric disease or neurological disease is anxiety. In some embodiments, the neuropsychiatric disease or neurological disease is post-traumatic stress disorder (PTSD). In some embodiments, the neurological disease is stroke or traumatic brain injury. In some embodiments, the neuropsychiatric disease or neurological disease is schizophrenia.

In some embodiments, a compound of the present invention is used for increasing neuronal plasticity. In some embodiments, the compounds described herein are used for treating a brain disorder. In some embodiments, the compounds described herein are used for increasing at least one of translation, transcription, or secretion of neurotrophic factors.

In some embodiments, the compounds of the present invention have activity as 5-HT$_{2A}$ modulators. In some embodiments, the compounds of the present invention have activity as 5-HT$_{2A}$ modulators. In some embodiments, the compounds of the present invention elicit a biological response by activating the 5-HT$_{2A}$ receptor (e.g., allosteric modulation or modulation of a biological target that activates the 5-HT$_{2A}$ receptor). 5-HT$_{2A}$ agonism has been correlated with the promotion of neural plasticity (Ly et al., 2018). As depicted in FIG. 7, 5-HT$_{2A}$ antagonists abrogate the neuritogenesis and spinogenesis effects of hallucinogenic compounds with 5-HT$_{2A}$ agonist activity, e.g., DMT, LSD, and DOI. In some embodiments, the compounds of the present invention are 5-HT$_{2A}$ modulators and promote neural plasticity (e.g., cortical structural plasticity). In some embodiments, the compounds of the present invention are selective 5-HT$_{2A}$ modulators and promote neural plasticity (e.g., cortical structural plasticity). In some embodiments, promotion of neural plasticity includes, for example, increased dendritic spine growth, increased synthesis of synaptic proteins, strengthened synaptic responses, increased dendritic arbor complexity, increased dendritic branch content, increased spinogenesis, increased neuritogenesis, or any combination thereof. In some embodiments, increased neural plasticity includes, for example, increased cortical structural plasticity in the anterior parts of the brain.

In some embodiments, the 5-HT$_{2A}$ modulators (e.g., 5-HT$_{2A}$ agonists) are non-hallucinogenic. In some embodiments, non-hallucinogenic 5-HT$_{2A}$ modulators (e.g., 5-HT$_{2A}$ agonists) are used to treat neurological diseases, which modulators do not elicit dissociative side-effects. In some embodiments, the hallucinogenic potential of the compounds described herein is assessed in vitro. In some embodiments, the hallucinogenic potential assessed in vitro of the compounds described herein is compared to the hallucinogenic potential assessed in vitro of hallucinogenic homologs. In some embodiments, the compounds described herein elicit less hallucinogenic potential in vitro than the hallucinogenic homologs.

In some embodiments, non-hallucinogenic 5-HT$_{2A}$ modulators (e.g., 5-HT$_{2A}$ agonists) are used to treat neurological diseases. In some embodiments, the neurological diseases comprise decreased neural plasticity, decreased cortical structural plasticity, decreased 5-HT$_{2A}$ receptor content, decreased dendritic arbor complexity, loss of dendritic spines, decreased dendritic branch content, decreased spinogenesis, decreased neuritogenesis, retraction of neurites, or any combination thereof.

In some embodiments, non-hallucinogenic 5-HT$_{2A}$ modulators (e.g., 5-HT$_{2A}$ agonists) are used for increasing neuronal plasticity. In some embodiments, non-hallucinogenic 5-HT$_{2A}$ modulators (e.g., 5-HT$_{2A}$ agonists) are used for treating a brain disorder. In some embodiments, non-hallucinogenic 5-HT$_{2A}$ modulators (e.g., 5-HT$_{2A}$ agonists) are used for increasing at least one of translation, transcription, or secretion of neurotrophic factors.

A. Methods for Increasing Neuronal Plasticity

Neuronal plasticity refers to the ability of the brain to change structure and/or function throughout a subject's life. New neurons can be produced and integrated into the central nervous system throughout the subject's life. Increasing neuronal plasticity includes, but is not limited to, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing neuronal plasticity comprises promoting neuronal growth, promoting neuritogenesis, promoting synaptogenesis, promoting dendritogenesis, increasing dendritic arbor complexity, and increasing dendritic spine density.

In some embodiments, increasing neuronal plasticity can treat neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In some embodiments, the present invention provides methods for increasing neuronal plasticity, comprising contacting a neuronal cell with any of the compounds of the present invention. In some embodiments, increasing neuronal plasticity improves a brain disorder described herein.

In some embodiments, a compound of the present invention is used to increase neuronal plasticity. In some embodiments, the compounds used to increase neuronal plasticity have, for example, anti-addictive properties, antidepressant properties, anxiolytic properties, or a combination thereof. In some embodiments, decreased neuronal plasticity is associated with a neuropsychiatric disease. In some embodiments, the neuropsychiatric disease is a mood or anxiety disorder. In some embodiments, the neuropsychiatric disease includes, for example, migraine, cluster headache, post-traumatic stress disorder (PTSD), schizophrenia, anxiety, depression, and addiction (e.g., substance abuse disorder). In some embodiments, brain disorders include, for example, migraines, addiction (e.g., substance use disorder), depression, and anxiety.

In some embodiments, the experiment or assay to determine increased neuronal plasticity of any compound of the present invention is a phenotypic assay, a dendritogenesis assay, a spinogenesis assay, a synaptogenesis assay, a Sholl analysis, a concentration-response experiment, a 5-HT$_{2A}$ agonist assay, a 5-HT$_{2A}$ antagonist assay, a 5-HT$_{2A}$ binding assay, or a 5-HT$_{2A}$ blocking experiment (e.g., ketanserin blocking experiments). In some embodiments, the experiment or assay to determine the hallucinogenic potential of any compound of the present invention is a mouse head-twitch response (HTR) assay.

In some embodiments, the present invention provides a method for increasing neuronal plasticity, comprising contacting a neuronal cell with a compound of Formula I:

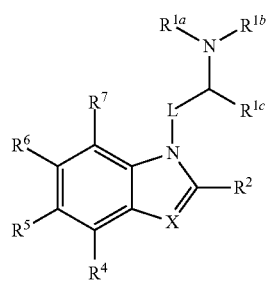

(I)

or a pharmaceutically acceptable salt thereof, in an amount sufficient to increase neuronal plasticity of the neuronal cell, wherein: X is N or CR$^3$; R$^{1a}$, R$^{1b}$, and R$^{1c}$ are each independently hydrogen, C$_{1-6}$ alkyl, C$_{3-8}$ cycloalkyl, or C$_{4-14}$ alkyl-cycloalkyl; alternatively, two of R$^{1a}$, R$^{1b}$, and R$^{1c}$ are combined with the atoms to which they are attached to form a C$_{3-12}$ heterocycloalkyl; R$^2$, R$^3$, R$^4$, R$^5$, R$^6$ and R$^7$ are each independently hydrogen, C$_{1-6}$ alkyl, C$_{2-6}$ alkenyl, C$_{2-6}$ alkynyl, halogen, C$_{1-6}$ haloalkyl, C$_{1-6}$ alkylamine, C$_{1-6}$ alkoxy, C$_{1-6}$ haloalkoxy, —OR$^{8a}$, —NO$_2$, —CN, —C(O)R$^{8b}$, —C(O)OR$^{8b}$, —OC(O)R$^{8b}$, —OC(O)OR$^{8b}$, —N(R$^{8b}$R$^{8c}$), —N(R$^{8b}$)C(O)R$^{8c}$, —C(O)N(R$^{8b}$R$^{8c}$), —N(R$^{8b}$)C(O)OR$^{8c}$, —OC(O)N(R$^{8b}$R$^{8c}$), —N(R$^{8b}$)C(O)N(R$^{8c}$R$^{8d}$), —C(O)C(O)N(R$^{8b}$R$^{8c}$), —S(O$_2$)R$^{8b}$, —S(O)$_2$N(R$^{8b}$R$^{8c}$), C$_{3-8}$ cycloalkyl, C$_{3-14}$ alkyl-cycloalkyl, C$_{4-10}$ heterocycloalkyl, C$_{4-16}$ alkyl-heterocycloalkyl, C$_{6-12}$ aryl, C$_{7-18}$ alkyl-aryl, C$_{5-10}$ heteroaryl, or C$_{4-16}$ alkyl-heteroaryl; R$^{8a}$ is C$_{3-8}$ cycloalkyl, C$_{3-14}$ alkyl-cycloalkyl, C$_{4-10}$ heterocycloalkyl, C$_{4-16}$ alkyl-heterocycloalkyl, C$_{6-12}$ aryl, C$_{7-18}$ alkyl-aryl, C$_{5-10}$ heteroaryl, or C$_{4-16}$ alkyl-heteroaryl; R$^{8b}$, R$^{8c}$ and R$^{8d}$ are each independently H or C$_{1-6}$ alkyl; alternatively, one of R$^{1a}$, R$^{1b}$, or R$^{1c}$ is combined with R$^2$ to form a C$_{5-12}$ heterocycloalkyl; alternatively, R$^2$ and R$^3$ are combined with the atoms to which they are each attached to form a C$_{4-8}$ cycloalkyl, C$_{4-10}$ heterocycloalkyl, or C$_{6-12}$ aryl; alternatively, R$^4$ and R$^5$, R$^5$ and R$^6$, or R$^6$ and R$^7$ are combined with the atoms to which they are each attached to form a C$_{3-6}$ cycloalkyl, C$_{3-6}$ heterocycloalkyl, C$_{6-12}$ aryl, or C$_{5-10}$ heteroaryl; and L is C$_{1-6}$ alkylene.

In some embodiments, the present invention provides a method for increasing neuronal plasticity, comprising contacting a neuronal cell with a compound of Formula I wherein, X is N or CR$^3$; R$^{1a}$, R$^{1b}$ and R$^{1c}$ are each independently hydrogen, C$_{1-6}$ alkyl, C$_{3-8}$ cycloalkyl, or C$_{4-14}$ alkyl-cycloalkyl; alternatively, two of R$^{1a}$, R$^{1b}$ and R$^{1c}$ are combined with the atoms to which they are attached to form a C$_{3-6}$ heterocycloalkyl; R$^2$, R$^3$, R$^4$, R$^5$, R$^6$ and R$^7$ are each independently hydrogen, C$_{1-6}$ alkyl, C$_{2-6}$ alkenyl, C$_{2-6}$ alkynyl, halogen, C$_{1-6}$ haloalkyl, C$_{1-6}$ alkylamine, C$_{1-6}$ alkoxy, C$_{1-6}$ haloalkoxy, —OR$^{8a}$, —NO$_2$, —CN, —C(O)R$^{8b}$, —C(O)OR$^{8b}$, —OC(O)R$^{8b}$, —OC(O)OR$^{8b}$, —N(R$^{8b}$R$^{8c}$), —N(R$^{8b}$)C(O)R$^{8c}$, —C(O)N(R$^{8b}$R$^{8c}$), —N(R$^{8b}$)C(O)OR$^{8c}$, —OC(O)N(R$^{8b}$R$^{8c}$), —N(R$^{8b}$)C(O)N(R$^{8c}$R$^{8d}$), —C(O)C(O)N(R$^{8b}$R$^{8c}$), —S(O$_2$)R$^{8b}$, —S(O)$_2$N(R$^{8b}$R$^{8c}$), C$_{3-8}$ cycloalkyl, C$_{3-14}$ alkyl-cycloalkyl, C$_{4-10}$ heterocycloalkyl, C$_{4-16}$ alkyl-heterocycloalkyl, C$_{6-12}$ aryl, C$_{7-18}$ alkyl-aryl, C$_{5-10}$ heteroaryl, or C$_{4-16}$ alkyl-heteroaryl; R$^{8a}$ is C$_{3-8}$ cycloalkyl, C$_{3-14}$ alkyl-cycloalkyl, C$_{4-10}$ heterocycloalkyl, C$_{4-16}$ alkyl-heterocycloalkyl, C$_{6-12}$ aryl, C$_{7-18}$ alkyl-aryl, C$_{5-10}$ heteroaryl, or C$_{4-16}$ alkyl-heteroaryl; R$^{8b}$, R$^{8c}$ and R$^{8d}$ are each independently H or C$_{1-6}$ alkyl; alternatively, one of R$^{1a}$, R$^{1b}$ and R$^{1c}$ is combined with one of R$^2$, R$^3$, R$^4$, R$^5$, R$^6$ and R$^7$ to form a C$_{5-6}$ cycloalkyl or C$_{5-6}$ heterocycloalkyl; alternatively, R$^2$ and R$^3$ can be combined with the atoms to which they are each attached to form a C$_{6-12}$ aryl; alternatively, R$^4$ and R$^5$, R$^5$ and R$^6$, or R$^6$ and R$^7$ can be combined with the atoms to which they are each attached to form a C$_{3-6}$ cycloalkyl or a C$_{3-6}$ heterocycloalkyl; and L is C$_{1-6}$ alkylene, or salts and isomers thereof, in an amount sufficient to increase neuronal plasticity of the neuronal cell.

B. Methods of Treating a Brain Disorder

In some embodiments, the present invention provides a method of treating a disease, including administering to a subject in need thereof, a therapeutically effective amount of a compound of the present invention. In some embodiments, the present invention provides a method of treating a brain disorder, including administering to a subject in need thereof, a therapeutically effective amount of a compound of the present invention. In some embodiments, the present invention provides a method of treating a brain disorder with combination therapy, including administering to a subject in need thereof, a therapeutically effective amount of a compound of the present invention and at least one additional therapeutic agent.

In some embodiments, 5-HT$_{2A}$ modulators (e.g., 5-HT$_{2A}$ agonists) are used to treat a brain disorder. In some embodiments, the brain disorders comprise decreased neural plasticity, decreased cortical structural plasticity, decreased 5-HT$_{2A}$ receptor content, decreased dendritic arbor complexity, loss of dendritic spines, decreased dendritic branch content, decreased spinogenesis, decreased neuritogenesis, retraction of neurites, or any combination thereof.

In some embodiments, a compound of the present invention is used to treat brain disorders. In some embodiments, the compounds have, for example, anti-addictive properties, antidepressant properties, anxiolytic properties, or a combination thereof. In some embodiments, the brain disorder is a neuropsychiatric disease. In some embodiments, the neuropsychiatric disease is a mood or anxiety disorder. In some embodiments, brain disorders include, for example, migraine, cluster headache, post-traumatic stress disorder (PTSD), anxiety, depression, schizophrenia, and addiction (e.g., substance abuse disorder). In some embodiments, brain disorders include, for example, migraines, addiction (e.g., substance use disorder), depression, and anxiety.

In some embodiments, the present invention provides a method of treating a brain disorder, comprising administering to a subject in need thereof a therapeutically effective amount of a compound of Formula I:

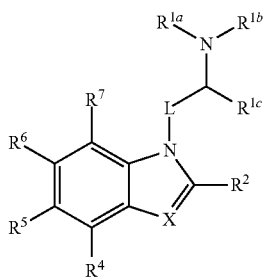

(I)

or a pharmaceutically acceptable salt thereof, thereby treating the brain disorder, wherein: X is N or CR$^3$; R$^{1a}$, R$^{1b}$, and R$^{1c}$ are each independently hydrogen, C$_{1-6}$ alkyl, C$_{3-8}$ cycloalkyl, or C$_{4-14}$ alkyl-cycloalkyl; alternatively, two of R$^{1a}$, R$^{1b}$, and R$^{1c}$ are combined with the atoms to which they are attached to form a C$_{3-12}$ heterocycloalkyl; R$^2$, R$^3$, R$^4$, R$^5$, R$^6$ and R$^7$ are each independently hydrogen, C$_{1-6}$ alkyl, C$_{2-6}$ alkenyl, C$_{2-6}$ alkynyl, halogen, C$_{1-6}$ haloalkyl, C$_{1-6}$ alkylamine, C$_{1-6}$ alkoxy, C$_{1-6}$ haloalkoxy, —OR$^{8a}$, —NO$_2$, —CN, —C(O)R$^{8b}$, —C(O)OR$^{8b}$, —OC(O)R$^{8b}$, —OC(O)OR$^{8b}$, —N(R$^{8b}$R$^{8c}$), —N(R$^{8b}$)C(O)R$^{8c}$, —C(O)N(R$^{8b}$R$^{8c}$), —N(R$^{8b}$)C(O)OR$^{8c}$, —OC(O)N(R$^{8b}$R$^{8c}$), —N(R$^{8b}$)C(O)N(R$^{8c}$R$^{8d}$), —C(O)C(O)N(R$^{8b}$R$^{8c}$), —S(O$_2$)R$^{8b}$, —S(O)$_2$N(R$^{8b}$R$^{8c}$), C$_{3-8}$ cycloalkyl, C$_{3-14}$ alkyl-cycloalkyl, C$_{4-10}$ heterocycloalkyl, C$_{4-16}$ alkyl-heterocycloalkyl, C$_{6-12}$ aryl, C$_{7-18}$ alkyl-aryl, C$_{5-10}$ heteroaryl, or C$_{4-16}$ alkyl-heteroaryl; R$^{8a}$ is C$_{3-8}$ cycloalkyl, C$_{3-14}$ alkyl-cycloalkyl, C$_{4-10}$ heterocycloalkyl, C$_{4-16}$ alkyl-heterocycloalkyl, C$_{6-12}$ aryl, C$_{7-18}$ alkyl-aryl, C$_{5-10}$ heteroaryl, or C$_{4-16}$ alkyl-heteroaryl; R$^{8b}$, R$^{8c}$ and R$^{8d}$ are each independently H or C$_{1-6}$ alkyl; alternatively, one of R$^{1a}$, R$^{1b}$, or R$^{1c}$ is combined with R$^2$ to form a C$_{5-12}$ heterocycloalkyl; alternatively, R$^2$ and R$^3$ are combined with the atoms to which they are each attached to form a C$_{4-8}$ cycloalkyl, C$_{4-10}$ heterocycloalkyl, or C$_{6-12}$ aryl; alternatively, R$^4$ and R$^5$, R$^5$ and R$^6$, or R$^6$ and R$^7$ are combined with the atoms to which they are each attached to form a C$_{3-6}$ cycloalkyl, C$_{3-6}$ heterocycloalkyl, C$_{6-12}$ aryl, or C$_{5-10}$ heteroaryl; and L is C$_{1-6}$ alkylene.

In some embodiments, the present invention provides a method of treating a brain disorder, comprising administering to a subject in need thereof a therapeutically effective amount of a compound of Formula I wherein X is N or CR$^3$; R$^{1a}$, R$^{1b}$ and R$^{1c}$ are each independently hydrogen, C$_{1-6}$ alkyl, C$_{3-8}$ cycloalkyl, or C$_{4-14}$ alkyl-cycloalkyl; alternatively, two of R$^{1a}$, R$^{1b}$ and R$^{1c}$ are combined with the atoms to which they are attached to form a C$_{3-6}$ heterocycloalkyl; R$^2$, R$^3$, R$^4$, R$^5$, R$^6$ and R$^7$ are each independently hydrogen, C$_{1-6}$ alkyl, C$_{2-6}$ alkenyl, C$_{2-6}$ alkynyl, halogen, C$_{1-6}$ haloalkyl, C$_{1-6}$ alkylamine, C$_{1-6}$ alkoxy, C$_{1-6}$ haloalkoxy, —OR$^{8a}$, —NO$_2$, —CN, —C(O)R$^{8b}$, —C(O)OR$^{8b}$, —OC(O)R$^{8b}$, —OC(O)OR$^{8b}$, —N(R$^{8b}$R$^{8c}$), —N(R$^{8b}$)C(O)R$^{8c}$, —C(O)N(R$^{8b}$R$^{8c}$), —N(R$^{8b}$)C(O)OR$^{8c}$, —OC(O)N(R$^{8b}$R$^{8c}$), —N(R$^{8b}$)C(O)N(R$^{8c}$R$^{8d}$), —C(O)C(O)N(R$^{8b}$R$^{8c}$), —S(O$_2$)R$^{8b}$, —S(O)$_2$N(R$^{8b}$R$^{8c}$), C$_{3-8}$ cycloalkyl, C$_{3-14}$ alkyl-cycloalkyl, C$_{4-10}$ heterocycloalkyl, C$_{4-16}$ alkyl-heterocycloalkyl, C$_{6-12}$ aryl, C$_{7-18}$ alkyl-aryl, C$_{5-10}$ heteroaryl, or C$_{4-16}$ alkyl-heteroaryl; R$^{8a}$ is C$_{3-8}$ cycloalkyl, C$_{3-14}$ alkyl-cycloalkyl, C$_{4-10}$ heterocycloalkyl, C$_{4-16}$ alkyl-heterocycloalkyl, C$_{6-12}$ aryl, C$_{7-18}$ alkyl-aryl, C$_{5-10}$ heteroaryl, or C$_{4-16}$ alkyl-heteroaryl; R$^{8b}$, R$^{8c}$ and R$^{8d}$ are each independently H or C$_{1-6}$ alkyl; alternatively, one of R$^{1a}$, R$^{1b}$ and R$^{1c}$ is combined with one of R$^2$, R$^3$, R$^4$, R$^5$, R$^6$ and R$^7$ to form a C$_{5-6}$ cycloalkyl or C$_{5-6}$ heterocycloalkyl; alternatively, R$^2$ and R$^3$ can be combined with the atoms to which they are each attached to form a C$_{6-12}$ aryl; alternatively, R$^4$ and R$^5$, R$^5$ and R$^6$, or R$^6$ and R$^7$ can be combined with the atoms to which they are each attached to form a C$_{3-6}$ cycloalkyl or a C$_{3-6}$ heterocycloalkyl; and L is C$_{1-6}$ alkylene, or salts and isomers thereof, thereby treating the brain disorder.

In some embodiments, the brain disorder is a neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In some embodiments, the brain disorder is a neurodegenerative disorder, Alzheimer's, or Parkinson's disease. In some embodiments, the brain disorder is a psychological disorder, depression, addiction, anxiety, or a post-traumatic stress disorder. In some embodiments, the brain disorder is depression. In some embodiments, the brain disorder is addiction. In some embodiments, the brain disorder is treatment resistant depression, suicidal ideation, major depressive disorder, bipolar disorder, schizophrenia, stroke, traumatic brain injury or substance use disorder. In some embodiments, the brain disorder is treatment resistant depression, suicidal ideation, major depressive disorder, bipolar disorder, schizophrenia, or substance use disorder. In some embodiments, the brain disorder is stroke or traumatic brain injury. In some embodiments, the brain disorder is treatment resistant depression, suicidal ideation, major depressive disorder, bipolar disorder, or substance use disorder. In some embodiments, the brain disorder is schizophrenia. In some embodiments, the brain disorder is alcohol use disorder.

In some embodiments, the method further comprises administering one or more additional therapeutic agent that is lithium, Olanzapine (Zyprexa), Quetiapine (Seroquel), Risperidone (Risperdal), Ariprazole (Abilify), Ziprasidone (Geodon), Clozapine (Clozaril), divalproex sodium (Depakote), lamotrigine (Lamictal), valproic acid (Depakene), carbamazepine (Equetro), topiramate (Topamax), levomilnacipran (Fetzima), duloxetine (Cymbalta, Yentreve), venlafaxine (Effexor), citalopram (Celexa), fluvoxamine (Luvox), escitalopram (Lexapro), fluoxetine (Prozac), paroxetine (Paxil), sertraline (Zoloft), clomipramine (Anafranil), amitriptyline (Elavil), desipramine (Norpramin), imipramine (Tofranil), nortriptyline (Pamelor), phenelzine (Nardil), tranylcypromine (Parnate), diazepam (Valium), alprazolam (Xanax), or clonazepam (Klonopin).

In some embodiments, the compounds of the present invention are used in combination with the standard of care therapy for a neurological disease described herein. Non-limiting examples of the standard of care therapies, may include, for example, lithium, olanzapine, quetiapine, risperidone, ariprazole, ziprasidone, clozapine, divalproex sodium, lamotrigine, valproic acid, carbamazepine, topiramate, levomilnacipran, duloxetine, venlafaxine, citalopram, fluvoxamine, escitalopram, fluoxetine, paroxetine, sertraline, clomipramine, amitriptyline, desipramine, imipramine, nortriptyline, phenelzine, tranylcypromine, diazepam, alprazolam, clonazepam, or any combination thereof. Non-limiting examples of standard of care therapy for depression are sertraline, fluoxetine, escitalopram, venlafaxine, or aripiprazole. Non-limiting examples of standard of care therapy for depression are citralopram, escitalopram, fluoxetine, paroxetine, diazepam, or sertraline.

C. Methods of Increasing at Least One of Translation, Transcription, or Secretion of Neurotrophic Factors Neurotrophic factors refers to a family of soluble peptides or proteins which support the survival, growth, and differentiation of developing and mature neurons. Increasing at least one of translation, transcription, or secretion of neurotrophic factors can be useful for, but not limited to, increasing neuronal plasticity, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing at least one of translation, transcription, or secretion of neurotrophic factors can increasing neuronal plasticity. In some embodiments, increasing at least one of translation, transcription, or secretion of neurotrophic factors can promoting neuronal growth, promoting neuritogenesis, promoting synaptogenesis, promoting dendritogenesis, increasing dendritic arbor complexity, and/or increasing dendritic spine density.

In some embodiments, 5-HT$_{2A}$ modulators (e.g., 5-HT$_{2A}$ agonists) are used to increase at least one of translation, transcription, or secretion of neurotrophic factors. In some embodiments, a compound of the present invention is used to increase at least one of translation, transcription, or secretion of neurotrophic factors. In some embodiments, increasing at least one of translation, transcription or secretion of neurotrophic factors treats a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, traumatic brain injury, and addiction (e.g., substance use disorder).

In some embodiments, the experiment or assay used to determine increase translation of neurotrophic factors includes ELISA, western blot, immunofluorescence assays, proteomic experiments, and mass spectrometry. In some embodiments, the experiment or assay used to determine increase transcription of neurotrophic factors includes gene expression assays, PCR, and microarrays. In some embodiments, the experiment or assay used to determine increase secretion of neurotrophic factors includes ELISA, western blot, immunofluorescence assays, proteomic experiments, and mass spectrometry.

In some embodiments, the present invention provides a method for increasing at least one of translation, transcription or secretion of neurotrophic factors, comprising contacting a neuronal cell with a compound of Formula I:

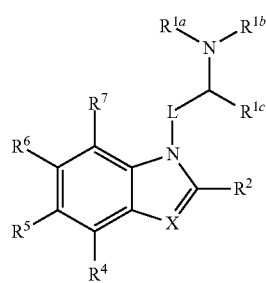

(I)

or a pharmaceutically acceptable salt thereof, in an amount sufficient to increase neuronal plasticity of the neuronal cell, wherein: X is N or CR$^3$; R$^{1a}$, R$^{1b}$, and R$^{1c}$ are each independently hydrogen, C$_{1-6}$ alkyl, C$_{3-8}$ cycloalkyl, or C$_{4-14}$ alkyl-cycloalkyl; alternatively, two of R$^{1a}$, R$^{1b}$, and R$^{1c}$ are combined with the atoms to which they are attached to form a C$_{3-12}$ heterocycloalkyl; R$^2$, R$^3$, R$^4$, R$^5$, R$^6$ and R$^7$ are each independently hydrogen, C$_{1-6}$ alkyl, C$_{2-6}$ alkenyl, C$_{2-6}$ alkynyl, halogen, C$_{1-6}$ haloalkyl, C$_{1-6}$ alkylamine, C$_{1-6}$ alkoxy, C$_{1-6}$ haloalkoxy, —OR$^{8a}$, —NO$_2$, —CN, —C(O)R$^{8b}$, —C(O)OR$^{8b}$, —OC(O)R$^{8b}$, —OC(O)OR$^{8b}$, —N(R$^{8b}$R$^{8c}$), —N(R$^{8b}$)C(O)R$^{8c}$, —C(O)N(R$^{8b}$R$^{8c}$), —N(R$^{8b}$)C(O)OR$^{8c}$, —OC(O)N(R$^{8b}$R$^{8c}$), —N(R$^{8b}$)C(O)N(R$^{8c}$R$^{8d}$), —C(O)C(O)N(R$^{8b}$R$^{8c}$), —S(O$_2$)R$^{8b}$, —S(O)$_2$N(R$^{8b}$R$^{8c}$), C$_{3-8}$ cycloalkyl, C$_{3-14}$ alkyl-cycloalkyl, C$_{4-10}$ heterocycloalkyl, C$_{4-16}$ alkyl-heterocycloalkyl, C$_{6-12}$ aryl, C$_{7-18}$ alkyl-aryl, C$_{5-10}$ heteroaryl, or C$_{4-16}$ alkyl-heteroaryl; R$^{8a}$ is C$_{3-8}$ cycloalkyl, C$_{3-14}$ alkyl-cycloalkyl, C$_{4-10}$ heterocycloalkyl, C$_{4-16}$ alkyl-heterocycloalkyl, C$_{6-12}$ aryl, C$_{7-18}$ alkyl-aryl, C$_{5-10}$ heteroaryl, or C$_{4-16}$ alkyl-heteroaryl; R$^{8b}$, R$^{8c}$ and R$^{8d}$ are each independently H or C$_{1-6}$ alkyl; alternatively, one of R$^{1a}$, R$^{1b}$, or R$^{1c}$ is combined with R$^2$ to form a C$_{5-12}$ heterocycloalkyl; alternatively, R$^2$ and R$^3$ are combined with the atoms to which they are each attached to form a C$_{4-8}$ cycloalkyl, C$_{4-10}$ heterocycloalkyl, or C$_{6-12}$ aryl; alternatively, R$^4$ and R$^5$, R$^5$ and R$^6$, or R$^6$ and R$^7$ are combined with the atoms to which they are each attached to form a C$_{3-6}$ cycloalkyl, C$_{3-6}$ heterocycloalkyl, C$_{6-12}$ aryl, or C$_{5-10}$ heteroaryl; and L is C$_{1-6}$ alkylene.

In some embodiments, the present invention provides a method for increasing at least one of translation, transcription or secretion of neurotrophic factors, comprising contacting a neuronal cell with a compound of Formula I, wherein X is N or CR$^3$; R$^{1a}$, R$^{1b}$ and R$^{1c}$ are each independently hydrogen, C$_{1-6}$ alkyl, C$_{3-8}$ cycloalkyl, or C$_{4-14}$ alkyl-cycloalkyl; alternatively, two of R$^{1a}$, R$^{1b}$ and R$^{1c}$ are combined with the atoms to which they are attached to form a C$_{3-6}$ heterocycloalkyl; R$^2$, R$^3$, R$^4$, R$^5$, R$^6$ and R$^7$ are each independently hydrogen, C$_{1-6}$ alkyl, C$_{2-6}$ alkenyl, C$_{2-6}$ alkynyl, halogen, C$_{1-6}$ haloalkyl, C$_{1-6}$ alkylamine, C$_{1-6}$ alkoxy, C$_{1-6}$ haloalkoxy, —OR$^{8a}$, —NO$_2$, —CN, —C(O)R$^{8b}$, —C(O)OR$^{8b}$, —OC(O)R$^{8b}$, —OC(O)OR$^{8b}$, —N(R$^{8b}$R$^{8c}$), —N(R$^{8b}$)C(O)R$^{8c}$, —C(O)N(R$^{8b}$R$^{8c}$), —N(R$^{8b}$)C(O)OR$^{8c}$, —OC(O)N(R$^{8b}$R$^{8c}$), —N(R$^{8b}$)C(O)N(R$^{8c}$R$^{8d}$), —C(O)C(O)N(R$^{8b}$R$^{8c}$), —S(O$_2$)R$^{8b}$, —S(O)$_2$N(R$^{8b}$R$^{8c}$), C$_{3-8}$ cycloalkyl, C$_{3-14}$ alkyl-cycloalkyl, C$_{4-10}$ heterocycloalkyl, C$_{4-16}$ alkyl-heterocycloalkyl, C$_{6-12}$ aryl, C$_{7-18}$ alkyl-aryl, C$_{5-10}$ heteroaryl, or C$_{4-16}$ alkyl-heteroaryl; R$^{8a}$ is C$_{3-8}$ cycloalkyl, C$_{3-14}$ alkyl-cycloalkyl, C$_{4-10}$ heterocycloalkyl, C$_{4-16}$ alkyl-heterocycloalkyl, C$_{6-12}$ aryl, C$_{7-18}$ alkyl-aryl, C$_{5-10}$ heteroaryl, or C$_{4-16}$ alkyl-heteroaryl; R$^{8b}$, R$^{8c}$ and R$^{8d}$ are each independently H or C$_{1-6}$ alkyl; alternatively, one of R$^{1a}$, R$^{1b}$ and R$^{1c}$ is combined with one of R$^2$, R$^3$, R$^4$, R$^5$, R$^6$ and R$^7$ to form a C$_{5-6}$ cycloalkyl or C$_{5-6}$ heterocycloalkyl; alternatively, R$^2$ and R$^3$ can be combined with the atoms to which they are each attached to form a C$_{6-12}$ aryl; alternatively, R$^4$ and R$^5$, R$^5$ and R$^6$, or R$^6$ and R$^7$ can be combined with the atoms to which they are each attached to form a C$_{3-6}$ cycloalkyl or a C$_{3-6}$ heterocycloalkyl; and L is C$_{1-6}$ alkylene, or salts and isomers thereof, in an amount sufficient to increase neuronal plasticity of the neuronal cell.

VII. Examples

General. All reagents were obtained commercially and used without purification unless otherwise noted. DMSO was purified by passage under 12 psi N2 through activated alumina columns. Reactions were performed using glassware that was flame-dried under reduced pressure (~1 Torr).

Compounds purified by chromatography were adsorbed to the silica gel before loading. Thin layer chromatography was performed on Millipore silica gel 60 $F_{254}$ Silica Gel plates. Visualization of the developed chromatogram was accomplished by fluorescence quenching or by staining with ninhydrin or aqueous ceric ammonium molybdate (CAM).

Nuclear magnetic resonance (NMR) spectra were acquired on either a Bruker 400 operating at 400 and 100 MHz, a Varian 600 operating at 600 and 150 MHz, or a Bruker 800 operating at 800 and 200 MHz for $^1$H and $^{13}$C, respectively, and are referenced internally according to residual solvent signals. Data for $^1$H NMR are recorded as follows: chemical shift (δ, ppm), multiplicity (s, singlet; d, doublet; t, triplet; q, quartet; m, multiplet), integration, coupling constant (Hz). Data for $^{13}$C NMR are reported in terms of chemical shift (δ, ppm). Infrared spectra were recorded using a Thermo Nicolet iS10 FT-IR spectrometer with a Smart iTX Accessory (diamond ATR) and are reported in frequency of absorption (v, cm$^{-1}$). Liquid chromatography-mass spectrometry (LC-MS) was performed using a Waters LC-MS with an ACQUITY Arc QDa detector. Ketamine was purchased from Fagron. DMT (1) and 6-F-DMT (29) were synthesized using previously published methods (Purity >99% as determined by UHPLC)(Cameron, L. P.; Benson, C. J.; Dunlap, L. E.; Olson, D. E. Effects of N,N-Dimethyltryptamine (DMT) on Rodent Behaviors Relevant to Anxiety and Depression. *ACS Chem. Neurosci.* 2018, 97, 1582-1590; Tombari, R. J.; Saunders, C. M.; Wu, C. Y.; Dunlap, L. E.; Tantillo, D. J.; Olson, D. E. Ex Vivo Analysis of Tryptophan Metabolism Using 19F NMR, *ACS Chem. Biol.*, 2019, 14, 1866-1873.). For cellular plasticity assays (i.e., dendritogenesis), all compounds were dissolved in DMSO and stored as 10 mM stock solutions in the dark at −20° C.

All compounds tested in cellular assays were confirmed to be of >95% purity based on UHPLC analysis (Waters ACQUITY Arc) measuring absorbance at 254 and 280 nm. Mobile phase A consisted of 0.01% formic acid in water, and mobile phase B consisted of 0.01% formic acid in acetonitrile. All samples were injected at a volume of 5 μL and the column temperature was maintained at 40° C. One of three methods was used depending on the specific compound. Method A utilized a CORTECS C18, 2.7 μm, 4.6×50 mm column, a flow rate of 0.6 mL/min, and a gradient from 10% to 90% mobile phase B over 3 minutes, which was maintained for an additional 2 minutes. Method B utilized an XBridge BEH C18 2.5 μm, 2.1×100 mm column, a flow rate of 0.6 mL/min, and a gradient from 10% to 90% mobile phase B over 0.5 minutes, which was maintained for an additional 4.5 minutes. Method C utilized a CORTECS C18, 2.7 μm, 4.6×50 mm column, a flow rate of 0.2 mL/min, and a gradient from 10% to 90% mobile phase B over 4 minutes, which was maintained for an additional 2 minutes. As most compounds reported in this study were isolated as the fumarate salts, peaks in UHPLC traces corresponding to fumaric acid were not included in the calculation of purity.

Synthesis of isoDMTs

Chemistry. An operationally simple and robust method for synthesizing a variety of isoDMTs under mild reaction conditions is described herein. Compound 2 was obtained in good yield using KOH as the base and KI to enhance reactivity via an in-situ Finkelstein reaction. Maintaining the reaction at 0.4 M proved optimal with both higher and lower concentrations resulting in a reduction in yield.

Procedure A

In some embodiments, intermediates used in the preparation of compounds described herein are prepared as outlined in Scheme 1.

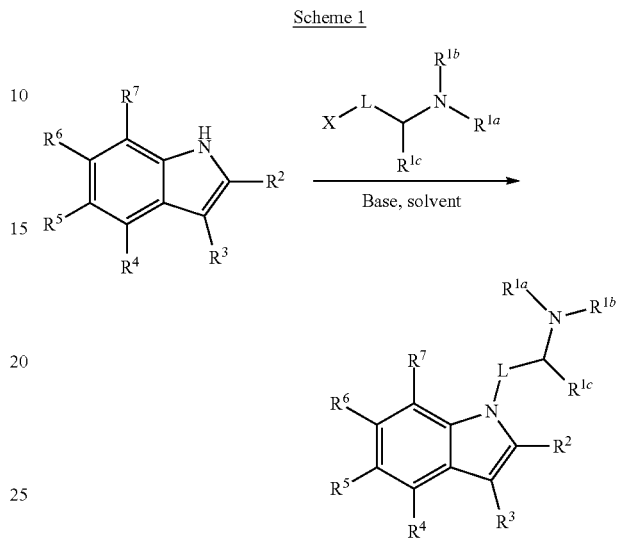

Scheme 1

In Scheme 1, L, $R^{1a-1c}$, and $R^2$-$R^7$ are as described herein. In some embodiments, X is halo or a sulfone. In some embodiments, halo is iodo, bromo, or chloro. In some embodiments, halo is chloro. In some embodiments, the sulfone is a tosylate, a nosylate, a brosylate, or a mesylate. In some embodiments, X is chloro.

In some embodiments, indole I-1 is reacted with I-2 under suitable condensation reaction conditions, optionally, followed by suitable salt formation conditions to provide substituted IsoDMT I-3. In some embodiments, suitable condensation reaction conditions include an appropriate base, an appropriate additive, an appropriate solvent, for an appropriate time at an appropriate temperature. In some embodiments, the appropriate base is a hydroxide base, a carbonate base, or a bicarbonate base. In some embodiments, the appropriate base is a hydroxide base or a hydride base. In some embodiments, the appropriate hydroxide base is sodium hydroxide or potassium hydroxide. In some embodiments, the appropriate hydroxide base is potassium hydroxide. In some embodiments, the appropriate hydride base is sodium hydride. In some embodiments, the appropriate additive is a salt. In some embodiments, the salt is potassium iodide, sodium iodide, or lithium iodide. In some embodiments, the appropriate salt is potassium iodide. In some embodiments, the appropriate solvent is a polar aprotic solvent. In some embodiments, the polar aprotic solvent is dichloromethane (DCM), tetrahydrofuran (THF), ethyl acetate (EtOAc), acetone, dimethylformamide (DMF), or acetonitrile (MeCN). In some embodiments, the polar aprotic solvent is DMSO, DMF, MeCN, or acetone. In some embodiments, the polar aprotic solvent is DMSO. In some embodiments, the appropriate time and appropriate temperature are overnight and about 25° C.

In some embodiments, the appropriate salt formation conditions include an appropriate acid in an appropriate solvent at an appropriate temperature for an appropriate time. In some embodiments, the appropriate acid is a carboxylic acid. In some embodiments, the carboxylic acid is fumaric acid. In some embodiments, the appropriate solvent is acetone. In some embodiments, the appropriate time and temperature are 5 minutes to 1 hour and 55° C.

For example, to a solution of respective indole or related heterocycle in DMSO (0.4 M) was added 2-chloro-N,N-dimethylethylamine hydrochloride (1.1 equiv), potassium iodide (1.1 equiv), and potassium hydroxide pellets (5.0 equiv). The reaction was stirred at room temperature for 24 h before being diluted with 1.0 M NaOH$_{(aq)}$. The aqueous phase was extracted three times with DCM. The organic extracts were combined, dried over Na$_2$SO$_4$, filtered, and concentrated under reduced pressure to yield an oil. The unpurified oil was dissolved in a minimal amount of acetone and added dropwise to a boiling solution of fumaric acid (1.0 equiv) in acetone. In most cases, a precipitate formed immediately, which was stored at −20° C. overnight. The resulting crystals were filtered and washed with several portions of ice-cold acetone to yield the desired product. In cases where the desired product did not readily crystalize as the fumarate salt, the oil was subjected to column chromatography (9:1 CH$_2$Cl$_2$:MeOH:1% NH$_4$OH$_{(aq)}$) unless noted otherwise.

Example 1. N,N-dimethyltryptamine (DMT)

The DMT compound below can be prepared by what is known in the art.

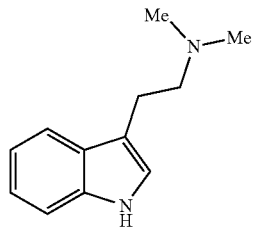 [SMILES: CN(C)CCc1c[nH]c2ccccc12]

Example 2. 2-(1H-indol-1-yl)-N,N-dimethylethan-1-amine fumarate salt (1:1) (2, isoDMT)

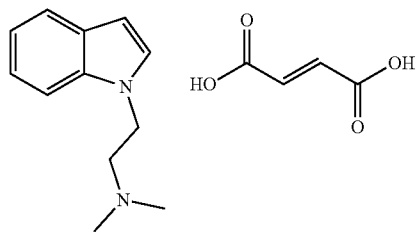

Indole (100 mg, 0.85 mmol), 2-Chloro-N,N-dimethylethylamine hydrochloride (135 mg, 0.94 mmol, 1.1 equiv), potassium iodide (156 mg, 0.94 mmol, 1.1 equiv), and potassium hydroxide (140 mg, 4.2 mmol, 5.0 equiv) were stirred in DMSO (2.15 mL) until the 2-Chloro-N,N-dimethylethylamine was completely consumed (17-24 h) as determined by TLC. The reaction mixture was diluted with 1.0 M NaOH$_{(aq)}$ (100 mL). The aqueous phase was extracted 3× with DCM (25 mL). The organic extracts were combined, dried over Na$_2$SO$_4$, filtered, and concentrated under reduced pressure to yield a colorless oil. The unpurified oil was dissolved in acetone (2 mL) and added dropwise to a boiling solution of fumaric acid (99 mg, 0.85 mmol, 1.0 equiv) in acetone (4 mL). A precipitate formed immediately which was then stored at −20° C. overnight. The crystals were filtered and washed with several portions of ice-cold acetone to yield the desired product. (1:1 isoDMT: fumaric acid) (175 mg, 67%). Purity >99%. TLC R$_f$ (free base)=0.50 (9:1 CH$_2$Cl$_2$:MeOH:1% NH$_4$OH$_{(aq)}$); $^1$H NMR (600 MHz, DMSO-d6) δ 7.54 (d, 1H, J=7.6 Hz), 7.48 (d, 1H, J=7.6 Hz), 7.38 (d, 1H, J=3.1 Hz), 7.13 (ddd, 1H, J=7.6, 1.0 Hz), 7.01 (dd, 1H, J=7.6, 1.0 Hz), 6.61 (s, 2H), 6.42 (d, 1H J=3.1 Hz), 4.29 (t, 2H, J=6.7 Hz), 2.70 (t, 2H, J=6.7 Hz), 2.26 (s, 6H). $^{13}$C NMR (150 MHz, DMSO-d$_6$) δ 166.32, 135.66, 134.20, 128.82, 128.06, 120.96, 120.38, 118.88, 109.68, 100.54, 58.09, 44.83, 43.11 ppm; IR (diamond, ATR) v 3100, 2923, 2393, 1705 cm$^{-1}$; LRMS (ES+) calcd for C$_{12}$H$_{16}$N$_2$+ 188.13, found 189.38 (MH+); MP=147-149° C.

Example 3. 2-(4-methoxy-1H-indol-1-yl)-N,N-dimethylethan-1-amine fumarate salt (1:1) (3)

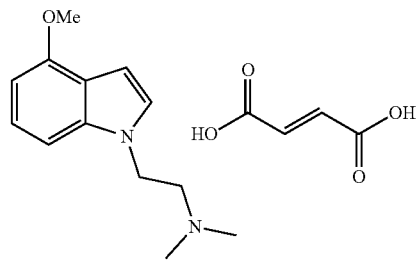 [SMILES: COc1cccc2c1ccn2CCN(C)C ; O=C(O)/C=C/C(=O)O]

Synthesized according to Procedure A. Reaction performed using 4-methoxyindole (100 mg, 0.68 mmol) and purified via crystallization. Yield=95 mg, 42%. Purity=96%. TLC R$_f$ (free base)=0.35 (9:1 CH$_2$Cl$_2$:MeOH:1% NH$_4$OH$_{(aq)}$); $^1$H NMR (600 MHz, DMSO-d$_6$) δ 7.26 (d, 1H, J=3.1 Hz), 7.10 (d, 1H, J=7.8 Hz), 6.90 (t, 1H, J=7.8 Hz), 6.66 (d, 1H, J=7.8 Hz), 6.60 (s, 2H), 6.35 (d, 1H, J=3.1 Hz), 4.49 (t, 2H, J=7.0 Hz), 3.89 (s, 3H), 2.76 (t, 2H, J=7.0 Hz), 2.32 (s, 6H) ppm; $^{13}$C NMR (150 MHz, DMSO-d$_6$) δ 166.30, 146.96, 134.17, 130.46, 129.79, 124.94, 119.64, 113.33, 102.42, 100.93, 59.61, 55.32, 45.63, 44.63 ppm; IR (diamond, ATR) v 2929, 2455, 1712, 1644 cm$^{-1}$. LRMS (ES+) calcd for C$_{13}$H$_{18}$N$_2$O+ 219.15, found 220.33 (MH+); MP=140-145° C.

Example 4. 2-(5-methoxy-1H-indol-1-yl)-N,N-dimethylethan-1-amine fumarate salt (1:1) (4)

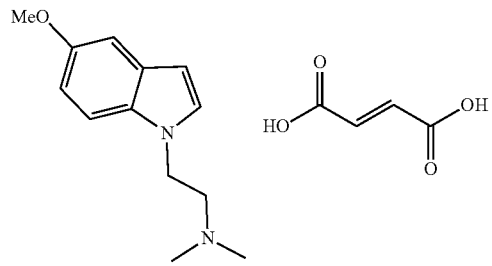 [SMILES: COc1ccc2c(ccn2CCN(C)C)c1 ; O=C(O)/C=C/C(=O)O]

Synthesized according to Procedure A. Reaction performed using 5-methoxyindole (100 mg, 0.68 mmol) and purified via crystallization. Yield=111 mg, 49%. Purity=98%. TLC R$_f$ (free base)=0.66 (9:1 CH$_2$Cl$_2$:MeOH:

1% NH$_4$OH$_{(aq)}$); $^1$H NMR (600 MHz, DMSO-d$_6$) δ 7.38 (d, 1H, J=8.9 Hz), 7.33 (d, 1H, J=3.0 Hz), 7.04 (d, 1H, J=2.4 Hz), 6.77 (dd, 1H, J=8.9, 2.4 Hz), 6.6 (s, 2H), 6.33 (d, 1H, J=3.0 Hz), 4.29 (t, 2H, J=6.8 Hz), 3.74 (s, 3H), 2.79 (t, 2H, J=6.8 Hz), 2.30 (s, 6H) ppm; $^{13}$C NMR (150 MHz, DMSO-d$_6$) δ 166.58, 153.42, 134.32, 130.90, 129.20, 128.48, 111.12, 110.39, 102.13, 100.34, 57.68, 55.30, 44.44, 42.91 ppm; IR (diamond, ATR) v 3035, 2923, 2446, 1715 cm$^{-1}$. LRMS (ES+) calcd for C$_{13}$H$_{18}$N$_2$O+ 219.15, found 220.19 (MH+); MP=140-142° C.

Example 5. 2-(6-methoxy-1H-indol-1-yl)-N,N-dimethylethan-1-amine (5)

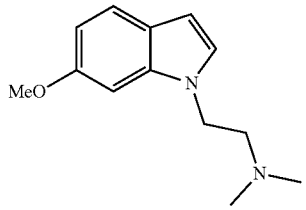 [SMILES: COc1ccc2ccn(CCN(C)C)c2c1]

Synthesized according to Procedure A. Reaction performed using 6-methoxyindole (147 mg, 1.0 mmol) and purified via chromatography. Yield=148 mg, 68%. Purity >99%. TLC R$_f$ (free base)=0.32 (9:1 CH$_2$Cl$_2$:MeOH: 1% NH$_4$OH$_{(aq)}$); $^1$H NMR (600 MHz, CDCl$_3$) δ 7.49 (d, 1H, J=7.8 Hz), 7.02 (d, 1H, J=8.2 Hz), 6.82 (s, 2H), 6.78 (dd, 1H, J=7.5 Hz), 6.42 (d, 1H, J=7.8 Hz), 4.17 (t, 2H, J=7.0 Hz), 2.31 (s, 3H), 2.69 (t, 2H, J=7.0 Hz), 2.31 (s, 6H) ppm; $^{13}$C NMR (150 MHz, CDCl$_3$) δ 156.30, 136.77, 127.04, 123.00, 121.67, 109.22, 101.31, 93.14, 59.00, 55.91, 45.94, 44.91 ppm; IR (diamond, ATR) v 2940, 2859, 2769, 1602 cm$^{-1}$. LRMS (ES+) calcd for C$_{13}$H$_{18}$N$_2$O+ 219.15, found 220.33 (MH+). The freebase was used for dendritogenesis assays.

Example 5'. 2-(6-methoxy-1H-indol-1-yl)-N,N-dimethylethan-1-amine oxalate (5')

Synthesized according to Procedure A. Reaction performed using 6-methoxyindole (250 mg, 1.7 mmol) and purified via crystallization. Yield=221 mg, 42%. Purity=98%. $^1$H NMR (600 MHz, CD$_3$OD) δ 7.42 (d, 1H, J=8.5 Hz), 7.16 (d, 1H, J=2.9 Hz), 7.02 (s, 2H), 6.74 (d, 1H, J=8.5 Hz), 6.44 (d, 1H, J=2.9 Hz), 4.58 (t, 2H, J=6.8 Hz), 3.87 (s, 3H), 3.56 (t, 2H, J=7.0 Hz), 2.86 (s, 6H) ppm; $^{13}$C NMR (150 MHz, CD$_3$OD) δ 166.72, 158.20, 138.02, 127.52, 124.45, 122.61, 111.06, 103.58, 93.83, 57.22, 56.19, 44.04, 42.17 ppm; IR (diamond, ATR) v 3129, 3014, 2641, 1727 cm$^{-1}$. LRMS (ES+) calcd for C$_{13}$H$_{18}$N$_2$O+ 219.15, found 220.05 (MH+). MP=165-167° C. The oxalate salt was used for HTR assays.

Example 6. 2-(7-methoxy-1H-indol-1-yl)-N,N-dimethylethan-1-amine fumarate salt (1:1) (6)

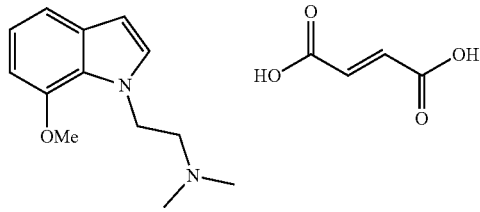 [SMILES: COc1cccc2ccn(CCN(C)C)c12 ; O=C(O)/C=C/C(=O)O]

Synthesized according to Procedure A. Reaction performed using 7-methoxyindole (100 mg, 0.68 mmol) and purified via crystallization. Yield=162 mg, 72%. Purity >99%. TLC R$_f$ (free base)=0.44 (9:1 CH$_2$Cl$_2$:MeOH: 1% NH$_4$OH$_{(aq)}$); $^1$H NMR (600 MHz, DMSO-d$_6$) δ 7.26 (d, 1H, J=3.1 Hz), 7.09-7.03 (m, 2H), 6.60 (s, 2H), 6.52 (dd, 1H, J=6.1, 1.3 Hz), 6.41 (dd, 1H, J=3.0, 0.7 Hz), 4.29 (t, 2H, J=6.8 Hz), 3.86 (s, 3H), 2.75 (t, 2H, J=6.8 Hz), 2.29 (s, 6H) ppm; $^{13}$C NMR (150 MHz, DMSO-d$_6$) δ 166.46, 152.80, 137.02, 134.24, 127.14, 121.98, 118.38, 103.09, 99.16, 97.88, 57.83, 54.89, 44.60, 43.15 ppm; IR (diamond, ATR) v 3435, 3034, 2653, 1705 cm$^{-1}$. LRMS (ES+) calcd for C$_{13}$H$_{18}$N$_2$O+ 219.15, found 220.40 (MH+); Mp 120-123° C.

Example 7. Benzyloxy Indoles

The 4-, 5-, 6-, and 7-OBn indoles were synthesized using methods published previously.

Example 8. 2-(4-(benzyloxy)-1H-indol-1-yl)-N,N-dimethylethan-1-amine fumarate salt (1:1) (8)

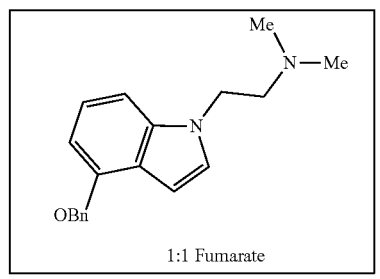 [SMILES: CN(C)CCn1ccc2c(OCc3ccccc3)cccc21]

Synthesized according to Procedure A. Reaction performed using 4-benzyloxyindole (200 mg, 0.89 mmol) and purified via crystallization. Yield=120 mg, 46%. Purity >99%. TLC R$_f$ (free base)=0.42 (9:1 CH$_2$Cl$_2$:MeOH: 1% NH$_4$OH$_{(aq)}$); $^1$H NMR (400 MHz, CD$_3$OD) δ 7.49 (d, 2H, J=7.5 Hz), 7.37 (t, 2H, J=7.5 Hz), 7.31 (t, 1H, J=7.5 Hz), 7.20 (d, 1H, J=3.26 Hz), 7.12 (m, 2H), 6.72 (s, 1H), 6.66 (m, 1H), 5.22 (s, 2H), 4.57 (t, 2H, J=6.7 Hz), 3.50 (t, 2H, J=6.7 Hz), 2.81 (s, 6H) ppm; $^{13}$C NMR (100 MHz, CD$_3$OD) δ 169.90, 153.99, 139.05, 138.85, 135.75, 129.47, 128.78, 128.47, 127.21, 124.18, 121.16, 103.87, 102.67, 101.07, 70.95, 57.32, 43.90, 42.46 ppm; IR (diamond, ATR) v 2918, 2493, 1701, 1639 cm$^{-1}$. LRMS (ES+) calcd for C$_{19}$H$_{22}$N$_2$O+ 294.17, found 295.24 (MH+); MP=145-150° C.

Example 9. 2-(5-(benzyloxy)-1H-indol-1-yl)-N,N-dimethylethan-1-amine fumarate salt (1:1) (9)

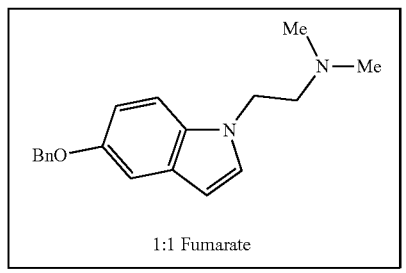 [SMILES: CN(C)CCn1ccc2cc(OCc3ccccc3)ccc21]

Synthesized according to Procedure A. Reaction performed using 5-benzyloxyindole (287 mg, 1.3 mmol) and purified via crystallization. Yield=133 mg, 25%. Purity >99%. TLC $R_f$ (free base)=0.47 (9:1 CH$_2$Cl$_2$:MeOH: 1% NH$_4$OH$_{(aq)}$); $^1$H NMR (400 MHz, CD$_3$OD) δ 7.44 (d, 2H, J=7.5 Hz), 7.36 (m, 3H), 7.29 (d, 2H, J=7.5 Hz), 7.24 (d, 1H, J=3.2 Hz), 7.15 (d, 1H, J=2.4 Hz), 6.95 (dd, 1H, J=2.4, 8.9 Hz), 6.72 (s, 2H), 6.43 (d, 1H, J=3.2 Hz), 5.07 (s, 2H), 4.54 (t, 2H, J=6.8 Hz), 3.45 (t, 2H, J=6.8 Hz), 2.78 (s, 6H) ppm; $^{13}$C NMR (200 MHz, CD$_3$OD) δ 171.06, 154.78, 139.26, 136.11, 132.77, 130.89, 130.81, 129.44, 128.73, 128.61, 113.97, 110.95, 105.71, 103.24, 71.86, 57.66, 44.16, 42.77 ppm; IR (diamond, ATR) v 2916, 2516, 1698, 1639 cm$^{-1}$. LRMS (ES+) calcd for C$_{19}$H$_{22}$N$_2$O+ 294.17, found 295.17 (MH+); MP=133-135° C.

Example 10. 2-(6-(benzyloxy)-1H-indol-1-yl)-N,N-dimethylethan-1-amine (10)

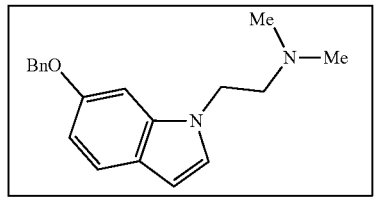 [SMILES: CN(C)CCn1ccc2ccc(OCc3ccccc3)cc21]

Synthesized according to Procedure A. Reaction performed using 6-benzyloxyindole (370 mg, 1.7 mmol) and purified via chromatography. Yield=184 mg, 38%. Purity >97%. TLC $R_f$ (free base)=0.45 (9:1 CH$_2$Cl$_2$:MeOH: 1% NH$_4$OH$_{(aq)}$); $^1$H NMR (600 MHz, CD$_3$OD) δ 7.47 (d, 2H, J=7.4 Hz), 7.40 (d, 2H, J=8.6 Hz), 7.37 (t, 1H, J=7.4 Hz), 7.30 (t, 1H, J=7.4 Hz), 7.08 (d, 1H, J=3.8 Hz), 6.96 (s, 1H), 6.78 (d, 1H, J=8.6 Hz), 6.35 (d, 1H, J=3.8 Hz), 5.15 (s, 2H), 4.22 (t, 2H, J=7.3 Hz), 2.66 (t, 2H, J=7.3 Hz), 2.26 (s, 6H) ppm; $^{13}$C NMR (150 MHz, CDCl$_3$) δ 156.39, 137.60, 136.66, 128.69, 127.97, 127.67, 127.22, 123.24, 121.68, 109.95, 101.31, 94.71, 70.87, 58.92, 45.91, 44.90 ppm; IR (diamond, ATR) v 3030, 2952, 2768, 1621 cm$^{-1}$. LRMS (ES+) calcd for C$_{19}$H22N$_2$O+ 294.17, found 295.10 (MH+).

Example 11. 2-(7-(benzyloxy)-1H-indol-1-yl)-N,N-dimethylethan-1-amine (11)

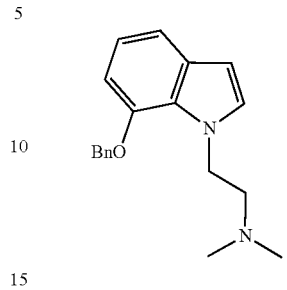

Synthesized according to Procedure A. Reaction performed using 7-benzyloxyindole (119 mg, 0.53 mmol) and purified via chromatography. Yield=51 mg, 23%. Purity >99%. TLC $R_f$ (free base)=0.48 (9:1 CH$_2$Cl$_2$:MeOH: 1% NH$_4$OH$_{(aq)}$); $^1$H NMR (600 MHz, CDCl$_3$) δ 7.49 (d, 2H, J=7.4 Hz), 7.40 (t, 2H, J=7.4 Hz), 7.34 (t, 1H, J=7.4 Hz), 7.22 (d, 1H, J=7.9 Hz), 7.01 (d, 1H, J=3.0 Hz), 6.97 (t, 1H, J=7.8 Hz), 6.70 (d, 1H, J=7.8 Hz), 5.19 (s, 2H), 4.45 (t, 2H, J=7.4 Hz), 2.62 (t, 2H, J=7.4 Hz), 2.09 (s, 6H) ppm; $^{13}$C NMR (150 MHz, CDCl$_3$) δ 150.59, 146.71, 137.11, 131.25, 129.45, 128.75, 128.24, 128.15, 119.82, 114.16, 103.35, 101.60, 70.55, 61.02, 47.54, 45.64 ppm; IR (diamond, ATR) v 2940, 2821, 1575, 1439 cm$^{-1}$. LRMS (ES+) calcd for C$_{19}$H$_{22}$N$_2$O+ 294.17, found 295.24 (MH+).

Example 12. 2-(4-fluoro-1H-indol-1-yl)-N,N-dimethylethan-1-amine fumarate salt (1:1) (12)

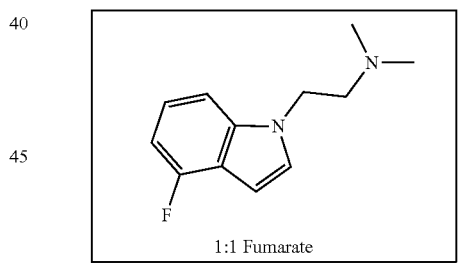

Synthesized according to Procedure A. Reaction performed using 4-fluoroindole (135 mg, 1.0 mmol) and purified via crystallization. Yield=164 mg, 51%. Purity >99%. TLC $R_f$ (free base)=0.39 (9:1 CH$_2$Cl$_2$:MeOH:1% NH$_4$OH$_{(aq)}$); $^1$H NMR (400 MHz, DMSO-d$_6$) δ 7.44 (d, 1H, J=2.3 Hz), 7.35 (d, 2H, J=8.3 Hz), 7.10 (dd, 2H, J=7.4, 7.25 Hz), 6.79 (t, 2H, J=9.5 Hz), 6.60 (s, 2H), 6.49 (d, 2H, J=2.3 Hz), 4.32 (t, 2H, J=6.7 Hz), 2.74 (t, 2H, J=6.8 Hz), 2.28 (s, 6H) ppm; $^{13}$C NMR (150 MHz, DMSO-d$_6$) δ 166.37, 156.67, 154.34, 138.56, 138.44, 134.21, 129.35, 121.63, 121.55, 116.74, 116.51, 106.48, 106.45, 103.70, 103.51, 96.24, 57.90, 44.73, 43.40 ppm; IR (diamond, ATR) v 3123, 2389, 1702, 1660 cm$^{-1}$. LRMS (ES+) calcd for C$_{12}$H$_{16}$FN$_2$+ 207.13, found 208.32 (MH+); MP=145-149° C.

Example 13. 2-(5-fluoro-1H-indol-1-yl)-N,N-dimethylethan-1-amine fumarate salt (1:1) (13)

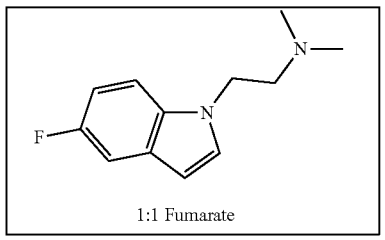

1:1 Fumarate

Synthesized according to Procedure A. Reaction performed using 5-fluoroindole (135 mg, 1.0 mmol) and purified via crystallization. Yield=145 mg, 45%. Purity >99%. TLC $R_f$ (free base)=0.35 (9:1 CH$_2$Cl$_2$:MeOH:1% NH$_4$OH$_{(aq)}$); $^1$H NMR (400 MHz, DMSO-d$_6$) δ 7.50 (dd, 1H, J=4.5, 4.3 Hz), 7.46 (d, 1H, J=2.1 Hz), 7.29 (d, 1H, J=9.5 Hz), 6.97 (t, 1H, J=9.5 Hz), 6.60 (s, 2H), 6.41 (d, 1H, J=2.1 Hz), 4.32 (t, 2H, J=6.7 Hz), 2.79 (t, 2H, J=6.7 Hz), 2.31 (s, 6H) ppm; $^{13}$C NMR (150 MHz, DMSO-d$_6$) δ 166.59, 159.61, 158.06, 135.77, 135.69, 134.33, 129.54, 129.51, 124.72, 121.39, 121.32, 107.48, 107.32, 100.97, 96.32, 96.15, 57.66, 44.58, 43.00 ppm; IR (diamond, ATR) v 3036, 2049, 1723, 1663 cm$^{-1}$. LRMS (ES+) calcd for C$_{12}$H$_{16}$FN$_2$+ 207.13, found 207.40 (MH+); MP=145-148° C.

Example 14. 2-(6-fluoro-1H-indol-1-yl)-N,N-dimethylethan-1-amine fumarate salt (1:1) (14)

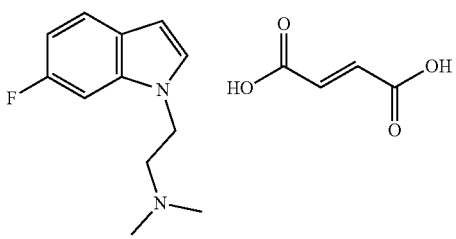

Synthesized according to Procedure A. Reaction performed using 6-fluoroindole (100 mg, 0.739 mmol) and purified via crystallization. Yield=145 mg, 61%. Purity=97%. TLC $R_f$ (free base)=0.45 (9:1 CH$_2$Cl$_2$:MeOH: 1% NH$_4$OH$_{(aq)}$); $^1$H NMR (600 MHz, DMSO-d$_6$) δ 7.52 (dd, 1H, J=7.0, 3.0 Hz), 7.39-7.37 (m, 2H), 6.88-6.85 (m, 1H), 6.59 (s, 2H), 6.44 (d, 1H, J=3.1 Hz), 4.29 (t, 2H, J=6.8 Hz), 2.77 (t, 2H, J=6.8 Hz), 2.30 (s, 6H) ppm; $^{13}$C NMR (150 MHz, DMSO-d$_6$) δ 166.59, 159.61, 158.06, 136.16, 134.75, 129.95, 125.14, 121.78, 107.91, 107.74, 101.39, 96.74, 96.57, 57.66, 44.58, 43.00 ppm; IR (diamond, ATR) v 3058, 2385, 1698, 1634 cm$^{-1}$. LRMS (ES+) calcd for C$_{12}$H$_{16}$FN$_2$+ 207.13, found 208.39 (MH+); MP=141-147° C.

Example 15. 2-(7-fluoro-1H-indol-1-yl)-N,N-dimethylethan-1-amine fumarate salt (1:1) (15)

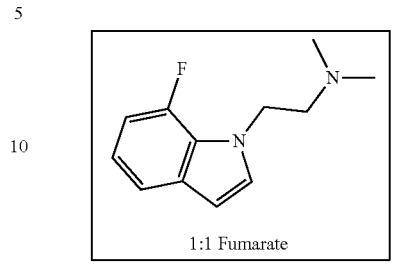

1:1 Fumarate

Synthesized according to Procedure A. Reaction performed using 7-fluoroindole (135 mg, 1.0 mmol) and purified via crystallization. Yield=172 mg, 53%. Purity=98%. TLC $R_f$ (free base)=0.45 (9:1 CH$_2$Cl$_2$:MeOH:1% NH$_4$OH$_{(aq)}$); $^1$H NMR (400 MHz, DMSO-d$_6$) δ 7.41 (s, 1H), 7.35 (d, 1H, J=7.6 Hz), 6.98-6.88 (m, 2H), 6.61 (s, 2H), 6.48 (s, 1H), 4.37 (t, 2H, J=6.7 Hz), 2.69 (t, 2H, J=6.7 Hz), 2.23 (s, 6H) ppm; $^{13}$C NMR (100 MHz, CD$_3$OD) δ 169.37, 134.60, 133.26, 129.51, 119.90, 119.46, 116.82, 116.79, 107.06, 106.88, 102.78, 57.61, 57.61, 43.71, 43.67, 42.90 ppm; IR (diamond, ATR) v 3040, 2429, 1718. 1661 cm$^{-1}$. LRMS (ES+) calcd for C$_{12}$H$_{16}$FN$_2$+ 207.13, found 207.33 (MH+); MP=168-170° C.

Example 16. N,N-dimethyl-2-(2-methyl-1H-indol-1-yl)ethan-1-amine fumarate salt (1:1) (16)

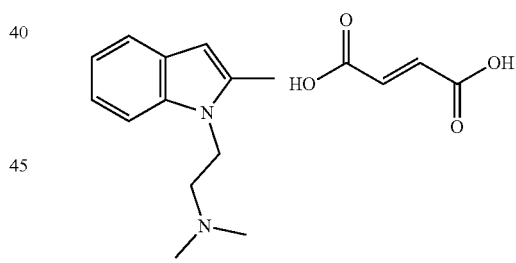

Synthesized according to Procedure A. Reaction performed using 2-methylindole (100 mg, 0.76 mmol) and purified via crystallization. Yield (172 mg, 71%). Purity >99%. TLC $R_f$ (free base)=0.47 (9:1 CH$_2$Cl$_2$:MeOH: 1% NH$_4$OH$_{(aq)}$); $^1$H NMR (400 MHz, DMSO-d$_6$) δ 7.41 (d, 1H, J=7.8 Hz), 7.37 (d, 1H, J=7.8 Hz), 7.06 (t, 1H, J=7.8 Hz), 6.96 (t, 1H, J=7.8 Hz), 6.61 (s, 2H), 6.20 (d, J=1.3 Hz, 1H), 4.24 (t, 2H, J=7.0 Hz), 2.65 (t, 2H, J=7.0 Hz), 2.42 (s, 3H), 2.31 (s, 6H) ppm; $^{13}$C NMR (150 MHz, DMSO-d$_6$) 167.03, 137.08, 136.72, 134.75, 128.09, 120.58, 119.65, 119.62, 119.40, 109.61, 100.14, 57.82, 45.18, 12.76 ppm; IR (diamond, ATR) v 3040, 2489, 1700, 1606 cm$^{-1}$. LRMS (ES+) calcd for C$_{13}$H$_{18}$N$_2$+ 203.15, found 204.43 (MH+); MP=131-133° C.

Example 17. 2-(5,6-difluoro-1H-indol-1-yl)-N,N-dimethylethan-1-amine fumarate salt (1:1) (17)

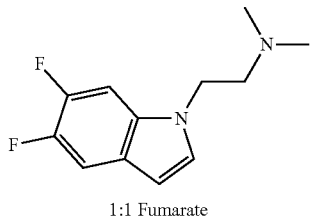 [SMILES: CN(C)CCn1ccc2cc(F)c(F)cc21]

1:1 Fumarate

Synthesized according to Procedure A. Reaction performed using 5,6-difluoroindole (153 mg, 1.0 mmol) and purified via crystallization. Yield=147 mg, 43%. Purity=98%. TLC $R_f$ (free base)=0.35 (9:1 CH$_2$Cl$_2$:MeOH: 1% NH$_4$OH$_{(aq)}$); $^1$H NMR (400 MHz, DMSO-d$_6$) δ 7.64 (dd, 1H, J=7.0, 4.7 Hz), 7.51 (dd, 1H, J=8.5, 2.1 Hz), 7.45 (d, 1H, J=2.1 Hz), 6.60 (s, 2H), 6.43 (d, 1H, J=2.1 Hz), 4.28 (t, 2H, J=6.5 Hz), 2.73 (t, 2H, J=6.5 Hz), 2.27 (s, 6H) ppm; $^{13}$C NMR (150 MHz, DMSO-d$_6$) δ 166.37, 134.21, 131.09, 130.99, 134.70, 130.67, 123.21, 123.12, 106.86, 106.67, 100.98, 100.94, 98.30, 98.08, 57.86, 44.71, 43.36 ppm; IR (diamond, ATR) v 3051, 2392, 1712, 1658 cm$^{-1}$. LRMS (ES+) calcd for C$_{12}$H$_{16}$F$_2$N$_2$+ 224.11, found 225.28 (MH+); MP=162-165° C.

Example 18. 2-(4,6-difluoro-1H-indol-1-yl)-N,N-dimethylethan-1-amine fumarate salt (1:1) (18)

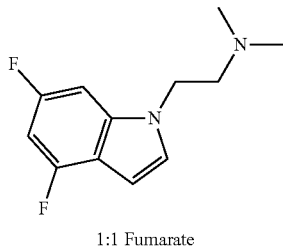 [SMILES: CN(C)CCn1ccc2c(F)cc(F)cc21]

1:1 Fumarate

Synthesized according to Procedure A. Reaction performed using 4,6-difluoroindole (153 mg, 1.0 mmol) and purified via crystallization. Yield=265 mg, 78%. Purity=>99%. TLC $R_f$ (free base)=0.35 (9:1 CH$_2$Cl$_2$:MeOH: 1% NH$_4$OH$_{(aq)}$); $^1$H NMR (400 MHz, DMSO-d$_6$) δ 7.44 (d, 1H, J=2.8 Hz), 7.32 (d, 1H, J=10.1 Hz), 6.83 (t, 1H, J=10.1 Hz), 6.60 (s, 2H), 6.49 (d, 1H, J=2.8 Hz), 4.31 (t, 2H, J=6.6 Hz), 2.78 (t, 2H, J=6.6 Hz), 2.31 (s, 6H) ppm; $^{13}$C NMR (150 MHz, DMSO-d$_6$) δ 166.55, 159.33, 159.21, 156.99, 156.87, 156.03, 155.88, 153.58, 153.43, 137.50, 137.36, 137.22, 134.29, 129.82, 129.79, 113.42, 113.20, 96.61, 94.53, 94.30, 94.24, 94.00, 93.32, 93.28, 93.06, 93.02, 57.49, 44.49, 43.23 ppm; IR (diamond, ATR) v 3026, 2398, 1706, 1640 cm$^{-1}$. LRMS (ES+) calcd for C$_{12}$H$_{16}$F$_2$N$_2$+ 224.11, found 225.28 (MH+); MP=141-145° C.

Example 19. N,N-dimethyl-2-(6-nitro-1H-indol-1-yl)ethan-1-amine fumarate salt (1:1) (19)

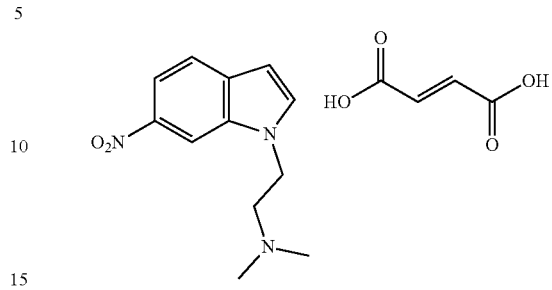

Synthesized according to Procedure A. Reaction performed using 6-nitroindole (43.6 mg, 0.269 mmol) and purified via crystallization. Yield=52 mg, 55%. Purity >96%. TLC $R_f$ (free base)=0.48 (9:1 CH$_2$Cl$_2$:MeOH: 1% NH$_4$OH$_{(aq)}$); $^1$H NMR (400 MHz, DMSO-d$_6$) δ 8.54 (d, 1H, J=2.0 Hz), 7.90 (dd, 1H, J=8.8, 2.0 Hz), 7.82 (d, 1H, J=3.0 Hz), 7.72 (d, 1H, J=8.8 Hz), 7.74 (s, 1H), 6.65 (d, 1H, J=3.0 Hz), 6.60 (s, 2H), 4.44 (t, 2H, J=6.3 Hz), 2.68 (t, 2H, J=6.3 Hz), 2.23 (s, 6H) ppm; $^{13}$C NMR (600 MHz, DMSO-d$_6$) δ 166.66, 136.18, 134.76, 134.59, 133.41, 121.04, 114.52, 107.53, 102.25, 58.98, 45.50, 44.18 ppm; IR (diamond, ATR) v 3048, 2922, 1704, 1607 cm$^{-1}$. LRMS (ES+) calcd for C$_{12}$H$_{16}$N$_3$O$_2$+ 233.12, found 234.25 (MH+); MP=159-164° C.

Example 20. 2-(5-bromo-1H-indol-1-yl)-N,N-dimethylethan-1-amine fumarate salt (1:1) (20)

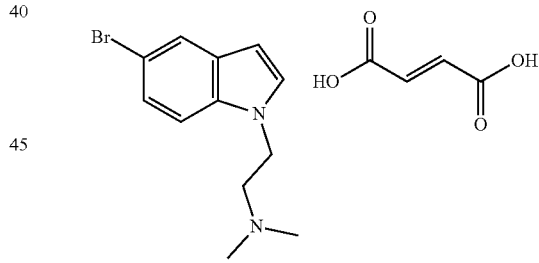

Synthesized according to Procedure A. Reaction performed using 5-bromoindole (56.1 mg, 0.281 mmol) and purified via crystallization. Yield=60 mg, 55%. Purity >99%. TLC $R_f$ (free base)=0.49 (9:1 CH$_2$Cl$_2$:MeOH:1% NH$_4$OH$_{(aq)}$); $^1$H NMR (600 MHz, DMSO-d$_6$) δ 7.72 (d, J=1.9 Hz, 1H), 7.48 (d, 1H, J=8.7 Hz), 7.44 (d, 1H, J=3.1 Hz), 7.23 (dd, 1H, J=8.7, 1.9 Hz), 6.60 (s, 3H), 6.41 (d, 1H, J=3.1 Hz), 4.27 (t, 2H, J=6.6 Hz), 2.67 (t, 2H, J=6.6 Hz), 2.22 (s, 6H) ppm; $^{13}$C NMR (600 MHz, DMSO-d$_6$) δ 166.24, 134.47, 134.15, 130.46, 129.89, 123.81, 122.54, 111.87, 111.56, 100.28, 58.09, 44.86, 43.32 ppm; IR (diamond, ATR) v 2959, 2443, 1705, 1661 cm$^{-1}$. LRMS (ES+) calcd for C$_{12}$H$_{16}$BrN$_2$+ 266.04, found 267.26 (MH+); MP=140-142° C.

Example 21. 2-(1-(2-(dimethylamino)ethyl)-1H-indol-3-yl)-N,N-dimethyl-2-oxoacetamide (21)

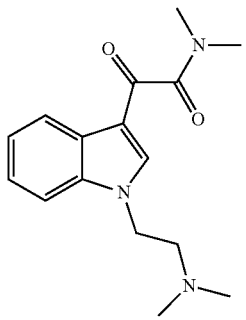 [SMILES: CN(C)CCn1cc(C(=O)C(=O)N(C)C)c2ccccc21]

Reaction performed using 2-(1H-indol-3-yl)-N,N-dimethyl-2-oxoacetamide (synthesized using the method developed by Speeter et. al. (Speeter, M. E.; Anthony, W. C. The Action of Oxalyl Chloride on Indoles: a New Approach to Tryptamines. *J. Am. Chem. Soc.* 1954, 76, 6208-6210.) (200 mg, 0.92 mmol) and purified via chromatography. Yield=92 mg, 35%. Purity=98%. TLC $R_f$ (free base)=0.38 (9:1 $CH_2Cl_2$:MeOH:1% $NH_4OH_{(aq)}$); $^1$H NMR (600 MHz, $CDCl_3$) δ 8.32 (s, 1H), 7.92 (s, 1H), 7.37-7.29 (m, 3H), 4.21 (t, 2H, J=7.0 Hz), 3.08 (s, 3H), 3.04 (s, 3H), 2.71 (t, 2H, J=7.0 Hz), 2.27 (s, 6H) ppm; $^{13}$C NMR (150 MHz, $CDCl_3$) δ 185.64, 167.70, 138.82, 137.01, 126.36, 124.00, 123.28, 122.48, 113.45, 110.06, 58.40, 45.68 45.42, 37.59, 34.51 ppm; IR (diamond, ATR) v 2981, 1734 1631, 1525 cm$^{-1}$. LRMS (ES+) calcd for $C_{16}H_{21}N_3O_2$+ 287.16, found 288.25 (MH+).

Example 22. 2-(1H-benzo[d]imidazol-1-yl)-N,N-dimethylethan-1-amine fumarate salt (1:1) (22)

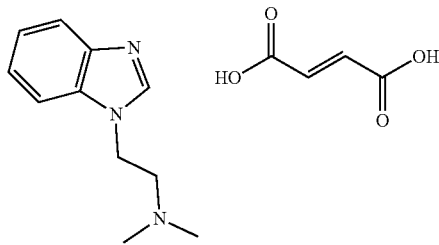

Synthesized according to Procedure A. Reaction performed using benzimidazole (200 mg, 1.6 mmol) and purified via crystallization. Yield=218 mg, 45%. Purity=98%. TLC $R_f$ (free base)=0.42 (9:1 $CH_2Cl_2$:MeOH:1% $NH_4OH_{(aq)}$); $^1$H NMR (400 MHz, DMSO-$d_6$) δ 8.23 (s, 1H), 7.71-7.56 (m, 2H), 7.34-7.10 (m, 2H), 6.61 (s, 2H), 4.41 (t, 2H, J=6.5 Hz), 2.83 (dd, 2H, J=7.0, 6.0 Hz), 2.32 (s, 6H) ppm; $^{13}$C NMR (100 MHz, $CD_3OD$) δ 170.14, 144.78, 143.90, 135.81, 134.62, 124.80, 124.04, 120.36, 111.29, 57.46, 44.39, 41.80 ppm; IR (diamond, ATR) v 3054, 2384, 1707, 1654 cm$^{-1}$. LRMS (ES+) calcd for $C_{11}H_{15}N_3$+ 189.13, found 190.23 (MH+); MP=171-178° C.

Example 23. N,N-dimethyl-2-(1H-pyrrol-1-yl)ethan-1-amine fumarate salt (1:1) (23)

Synthesized according to Procedure A. Reaction performed using pyrrole (0.103 ml, 1.5 mmol) and purified via crystallization. Yield=126 mg, 33%. Purity >99%. TLC $R_f$ (free base)=0.45 (9:1 $CH_2Cl_2$:MeOH:1% $NH_4OH_{(aq)}$); $^1$H NMR (600 MHz, $CD_3OD$) δ 6.80 (t, 2H, J=2.2, Hz), 6.72 (s, 2H), 6.14 (t, 2H. J=2.2, Hz), 4.34 (t, 2H, J=6.4 Hz), 3.50 (dd, 2H, J=6.4 Hz), 2.78 (s, 6H) ppm; $^{13}$C NMR (100 MHz, $CD_3OD$) δ 170.26, 136.21, 122.18, 110.89, 59.35, 45.83, 44.45 ppm; IR (diamond, ATR) v 2998, 2532, 1662, 1421 cm$^{-1}$. LRMS (ES+) calcd for $C_8H_{14}N_2$+ 138.12, found 139.29 (MH+); MP=174-180° C.

Example 24. 2-(9H-carbazol-9-yl)-N,N-dimethyl-ethan-1-amine fumarate salt (1:1) (24)

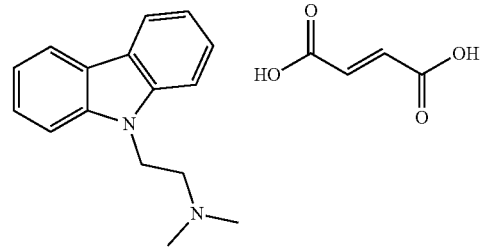 [SMILES: CN(C)CCn1c2ccccc2c2ccccc21 ; O=C(O)/C=C/C(=O)O]

Synthesized according to Procedure A. Reaction performed using carbazole (100 mg, 0.57 mmol) and purified via crystallization. Yield=102 mg, 51%. Purity >99%. TLC $R_f$ (free base)=0.42 (9:1 $CH_2Cl_2$:MeOH:1% $NH_4OH_{(aq)}$); $^1$H NMR (600 MHz, DMSO-$d_6$) δ 8.15 (d, 2H, J=7.8 Hz), 7.61 (d, 2H, J=8.2 Hz), 7.48-7.44 (m, 2H), 7.23-7.19 (m, 2H), 6.61 (s, 2H), 4.52 (t, 2H, J=7.0 Hz), 2.73 (t, 2H, J=7.0 Hz), 2.31 (s, 6H) ppm; $^{13}$C NMR (100 MHz, DMSO-$d_6$) δ 169.78, 139.86, 134.76, 125.83, 123.17, 119.99, 119.39, 108.34, 54.39, 42.61, 37.85 ppm; IR (diamond, ATR) v 3053, 2405, 1720, 1660 cm$^{-1}$. LRMS (ES+) calcd for $C_{16}H_{18}N_2$+ 238.15, found 239.34 (MH+); MP=182-184° C.

Example 25. 1-isopentyl-1H-indole (25)

Synthesized according to Procedure A. Reaction performed using indole (100 mg, 0.85 mmol) and 1-chloro-3-methylbutane (0.11 mL mg, 0.94 mmol, 1.1 equiv) and purified via chromatography (4:1 hexanes:EtOAc). Yield=85 mg, 53%. Purity=97%. TLC $R_f$=0.70 (7:3 hexanes:EtOAc); $^1$H NMR (600 MHz, $CDCl_3$) δ 7.65 (d, 1H, J=8.0 Hz), 7.36 (d, 1H, J=8.0 Hz), 7.22 (t, 1H, J=6.9 Hz), 7.11 (m, 2H), 6.49 (d, 1H, J=3.1 Hz), 4.15 (t, 2H, J=7.5 Hz), 1.74 (dd, 2H, J=6.7 Hz), 1.62 (quint, 2H, J=6.7 Hz), 0.98 (d, 1H, J=6.7 Hz) ppm; $^{13}$C NMR (150 MHz, $CDCl_3$) δ 135.78, 128.46, 127.58, 121.20, 120.83, 119.05, 109.28, 100.78, 44.44, 40.72, 38.92, 25.61, 22.37 ppm; IR (diamond, ATR) v 3054, 2955, 2927, 2869 cm$^{-1}$. LRMS (ES+) calcd for $C_{13}H_{17}N$+ 187.14 found 188.39 (MH+).

Example 26. 3-(1H-indol-1-yl)-N,N-dimethylpropan-1-amine fumarate salt (1:1) (26)

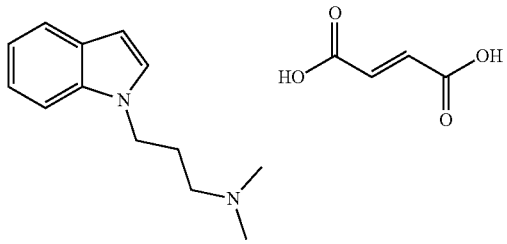

Synthesized according to Procedure A. Reaction performed using indole (100 mg, 0.85 mmol) and 3-chloro-N,N-dimethylpropan-1-amine (160 mg, 0.98 mmol, 1.1 equiv) and purified via crystallization Yield=107 mg, 48%. Purity=98%. TLC $R_f$ (free base)=0.38 (9:1 $CH_2Cl_2$:MeOH: 1% $NH_4OH_{(aq)}$); $^1H$ NMR (600 MHz, DMSO-$d_6$) δ 7.54 (d, 1H, J=7.8 Hz), 7.48 (d, 1H, J=7.8 Hz), 7.36 (d, 1H, J=3.1 Hz), 7.13 (td, 1H, J=7.4, 1.0 Hz), 7.01 (td, 1H, J=7.4, 1.0 Hz), 6.55 (s, 2H), 6.43 (dd, 1H, J=3.1, 1.0 Hz), 4.21 (t, 2H, J=6.8 Hz), 2.56 (t, 2H, J=7.4 Hz), 2.40 (s, 6H), 2.00 (tt, 2H, J=7.4, 6.8 Hz) ppm; $^{13}C$ NMR (150 MHz, DMSO-$d_6$) δ 167.19, 135.60, 134.62, 128.49, 128.07, 120.99, 120.41, 118.90, 109.67, 100.61, 54.88, 43.41, 43.07, 26.26 ppm; IR (diamond, ATR) v 3435, 3034, 2653, 1705 cm$^{-1}$. LRMS (ES+) calcd for $C_{13}H_{18}N_2$+ 203.15, found 204.36 (MH+); MP=129-131° C.

Example 27. N,N-dimethyl-2-(1-methyl-1H-indol-3-yl)ethan-1-amine fumarate salt (1:1) (1-Me-DMT 27)

To an ice-cold solution of N-methyl-2-(1-methyl-1H-indol-3-yl)ethan-1-amine (0.14 g, 0.70 mmol) and glacial acetic acid (0.22 mL, 11 mmol, 5.0 equiv) in MeOH (12 mL) was added sodium cyanoborohydride (0.10 g, 1.6 mmol, 2.1 equiv) followed by 37% formaldehyde$_{(aq)}$ (0.16 mL, 1.9 mmol, 2.6 equiv). The reaction was stirred at room temperature for 5 h before being concentrated under reduced pressure. The unpurified material was then diluted with $CH_2Cl_2$ (50 mL) and 1 M $NaOH_{(aq)}$ (100 mL). The phases were separated, and the aqueous phase was extracted with $CH_2Cl_2$ (2×50 mL). The organic extracts were combined, dried over $Na_2SO_4$, and concentrated under reduced pressure. The unpurified material was dissolved in acetone (5 mL) and added to a boiling solution of fumaric acid (0.088 g, 1 mmol, 1 equiv) in acetone (20 mL). A precipitate formed immediately, and the solution was cooled to room temperature prior to being filtered. The resulting white solid was dried under reduced pressure to yield the pure compound as the fumarate salt (1:1). Yield=0.108 g, 65%. Purity >99%. TLC $R_f$ (free base)=0.19 (9:1 $CH_2Cl_2$:MeOH: 1% $NH_4OH_{(aq)}$); $^1H$ NMR (600 MHz, $CD_3OD$) δ 7.60 (d, 1H, J=8.0 Hz), 7.37 (d, 1H, J=8.0 Hz), 7.20 (t, 1H, J=8.0 Hz), 7.14 (s, 1H), 7.09 (t, 1H, J=8.0 Hz), 6.69 (s, 2H), 3.78 (s, 3H), 3.42 (t, 2H, J=7.8 Hz), 3.20 (t, 2H, J=7.8 Hz), 2.91 (s, 6H) ppm; $^{13}C$ NMR (150 MHz, $CD_3OD$) δ 171.44, 138.80, 136.23, 128.67, 128.59, 122.95, 120.20, 119.27, 110.53, 109.11, 59.12, 43.41, 32.77, 21.72 ppm; IR (diamond, ATR) v 3435, 3034, 2653, 1705 cm$^{-1}$ LRMS (ES+) m/z calcd for $C_{13}H_{18}N_2$+ 202.15, found 203.37 (MH+); MP=167-170° C.

Example 28. 2-(5-methoxy-1H-indol-3-yl)-N,N-dimethylethan-1-amine fumarate salt (2:1) (5-MeO-DMT, 28)

To an ice-cold solution of 5-methoxytryptamine (0.50 g, 2.2 mmol) and glacial acetic acid (0.60 mL, 11 mmol, 5.0 equiv) in MeOH (44 mL) was added sodium cyanoborohydride (0.305 g, 4.8 mmol, 2.2 equiv) followed by 37% formaldehyde$_{(aq)}$ (0.46 mL, 5.7 mmol, 2.6 equiv). The reaction was stirred at room temperature for 5 h before being concentrated under reduced pressure. The residue was diluted with $CH_2Cl_2$ (50 mL) and 1 M $NaOH_{(aq)}$ (100 mL). The phases were separated, and the aqueous phase was extracted with $CH_2Cl_2$ (2×50 mL). The organic extracts were combined, dried over $Na_2SO_4$, filtered, and concentrated under reduced pressure. The unpurified material was dissolved in acetone (5 mL) and added to a boiling solution of fumaric acid (0.26 g, 2.2 mmol, 0.7 equiv) in acetone (35 mL). A precipitate formed immediately, and the solution was cooled to room temperature prior to being filtered. The resulting white solid was dried under reduced pressure to yield the pure compound as the fumarate salt (2:1). Yield=0.49 g, 80%. Purity=98%. TLC $R_f$ (free base)=0.20 (9:1 $CH_2Cl_2$:MeOH:1% $NH_4OH_{(aq)}$); $^1H$ NMR (600 MHz, $CD_3OD$) δ 7.24 (d, 1H, J=8.8 Hz), 7.14 (s, 1H), 7.07 (s, 1H), 6.78 (d, 1H, J=8.8 Hz), 6.70 (s, 1H), 3.83 (s, 3H), 3.29 (m, 2H), 3.13 (t, 2H, J=7.9 Hz), 2.83 (s, 6H) ppm; $^{13}C$ NMR (150 MHz, $CD_3OD$) δ 174.36, 155.27, 137.09, 133.44, 128.49, 124.79, 113.20, 112.96, 110.05, 101.05, 59.25, 56.37, 43.56, 22.12 ppm; IR (diamond, ATR) v 3436, 3034 2654, 1705 cm$^{-1}$. LRMS (ES+) m/z calcd for $C_{13}H_{18}N_2O$+ 218.14, found 219.34 (MH+); MP=175-177° C.

Example 29. 2-(6-fluoro-1H-indol-3-yl)-N,N-dimethylethan-1-amine (6-F-DMT, 29)

Example 29 below can be prepared by what is known in the art.

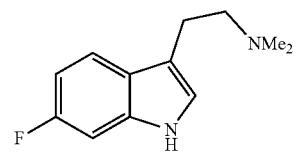 [SMILES: CN(C)CCc1c[nH]c2cc(F)ccc12]

Example 30. 2-(6-methoxy-1H-indol-3-yl)-N,N-dimethylethan-1-amine fumarate salt (2:1) (6-MeO-DMT, 30)

To an ice-cold solution of 6-methoxytryptamine (0.40 g, 2.1 mmol) and glacial acetic acid (0.60 mL, 10 mmol, 5.0 equiv) in MeOH (42 mL) was added sodium cyanoborohydride (0.29 g, 4.6 mmol, 2.2 equiv) followed by 37% formaldehyde$_{(aq)}$ (0.44 mL, 5.5 mmol, 2.6 equiv). The reaction was stirred at room temperature for 5 h before being concentrated under reduced pressure. The residue was diluted with $CH_2Cl_2$ (45 mL) and 1 M $NaOH_{(aq)}$ (100 mL). The phases were separated, and the aqueous phase was extracted with $CH_2Cl_2$ (2×45 mL). The organic extracts were combined, dried over $Na_2SO_4$, filtered, and concentrated under reduced pressure. The unpurified material was dissolved in acetone (5 mL) and added to a boiling solution of fumaric acid (0.26 g, 2.2 mmol, 0.7 equiv) in acetone (35 mL). A precipitate formed immediately, and the solution was cooled to room temperature prior to being filtered. The resulting white solid was dried under reduced pressure to yield the pure compound as the fumarate salt (2:1). Yield=0.320 g, 55%. Purity=95%. TLC $R_f$ (free base)=0.31 (9:1 $CH_2Cl_2$:MeOH:1% $NH_4OH_{(aq)}$); $^1$H NMR (600 MHz, $CD_3OD$) δ 7.44 (d, 1H, J=8.6 Hz), 7.04 (s, 1H), 6.88 (s, 1H), 6.70 (m, 2H), 3.78 (s, 3H), 3.32 (t, 2H, J=7.5 Hz), 3.12 (t, 2H, J=7.5 Hz), 2.84 (s, 6H) ppm; $^{13}$C NMR (150 MHz, $CD_3OD$) δ 173.79, 157.87, 138.97, 136.93, 122.89, 122.53, 119.64, 110.40, 109.99, 95.62, 59.12, 55.94, 43.36, 21.96 ppm; IR (diamond, ATR) ν 2915, 2836, 1691, 1559 $cm^{-1}$. LRMS (ES+) m/z calcd for $C_{13}H_{18}N_2O+$ 218.14, found 219.29 (MH+); MP=173-176° C.

Example 31.
2-(1H-indol-1-yl)-N,N-dimethylacetamide (31)

To a solution of indole (117 mg, 1.0 mmol) in DMSO (2.5 mL, 0.4 M) was added 2-chloro-N,N-dimethylacetamide (0.11 mL, 1.1 mmol, 1.1 equiv), potassium iodide (182 mg, 1.1 mmol, 1.1 equiv), and potassium hydroxide pellets (280 mg, 5 mmol, 5.0 equiv). The reaction was stirred at room temperature for 24 h before being diluted with 1.0 M $NaOH_{(aq)}$. The aqueous phase was extracted three times with DCM. The organic extracts were combined, dried over $Na_2SO_4$, filtered, and concentrated under reduced pressure to yield an oil. The oil was purified via chromatography (3:2 hexanes:EtOAc). Yield=175 mg, 57%. Purity=99%. TLC $R_f$=0.15 (3:2 hexanes:EtOAc); $^1$H NMR (600 MHz, $CD_3OD$) δ 7.53 (d, 1H, J=7.9 Hz), 7.27 (d, 1H, J=7.9 Hz), 7.12 (m, 2H), 7.01 (t, 1H, J=7.5, Hz), 6.46 (d, 1H, J=2.9 Hz), 5.01 (s, 2H), 3.15 (s, 3H), 2.96 (s, 3H) ppm; $^{13}$C NMR (150 MHz, $CDCl_3$) δ 167.4, 136.7, 128.7, 128.5, 122.0, 121.2, 119.8, 109.1, 102.4, 48.2, 36.7, 36.1 ppm; IR (diamond, ATR) ν 3021, 2922, 2877, 1648 $cm^{-1}$. LRMS (ES+) calcd for $C_{12}H_{14}N_2O+$ 202.11 found 203.17 (MH+); MP=58-61° C.

Example 32. (R)-1-(5-methoxy-1H-indol-1-yl)-N,N-dimethylpropan-2-amine, fumaric acid salt

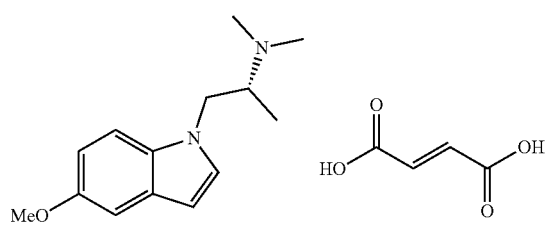 [SMILES: COc1ccc2c(ccn2C[C@@H](C)N(C)C)c1 ; O=C(O)/C=C/C(=O)O]

5-Methoxy-indole (500 mg, 3.40 mmol), (R)-1-chloro-N,N-dimethylpropan-2-amine (1.074 g, 6.79 mmol, 2 equiv), potassium iodide (1.128 mg, 6.79 mmol, 2 equiv), and potassium hydroxide (0.953 g, 16.9 mmol, 5.0 equiv) were stirred in DMSO (8.49 mL) for 24 h. The reaction mixture was diluted with 1.0 M $NaOH_{(aq)}$ (800 mL). The aqueous phase was extracted 3× with DCM (75 mL). The organic extracts were combined, dried over $Na_2SO_4$, filtered, and concentrated under reduced pressure to yield a colorless oil. The crude oil was purified by flash chromatography eluting with 9:1 DCM:MeOH with 1% ammonium hydroxide$_{(aq)}$. The purified oil was dissolved in acetone (2 mL) and added dropwise to a boiling solution of fumaric acid (0.394 g, 3.39 mmol, 1.0 equiv) in acetone (15 mL). A precipitate formed immediately and was filtered and washed with ice-cold portions of acetone to yield the desired product. If no precipitate formed the mixture was concentrated down to facilitate crystal formation to yield the desired product. (1:1 hybrid:fumaric acid) $^1$H NMR (400 MHz, DMSO-d6) δ 7.37 (d, 1H, J=8.8 Hz), 7.30 (s, 1H), 7.03 (s, 1H, J=3.1 Hz), 6.76 (d, 1H, J=8.8 Hz), 6.61 (s, 2H), 6.32 (s, 1H), 4.25 (dd, 1H, J=6.3, 7.8 Hz), 4.02 (dd, 1H, J=6.3, 7.8 Hz), 3.74 (s, 3H) 3.11 (q, 1H, J=6.3, 6.6, Hz), 2.30 (s, 6H), 0.84 (d, 3H, J=6.6 Hz). $^{13}$C NMR (100 MHz, MeOD-d4) δ 171.0, 155.8, 136.1, 132.8, 130.9, 129.7, 113.3, 111.2, 103.8, 103.3, 61.6, 56.2, 47.5, 39.9, 11.7 ppm.

Example 33. (R)-1-(5-fluoro-1H-indol-1-yl)-N,N-dimethylpropan-2-amine, fumaric acid salt

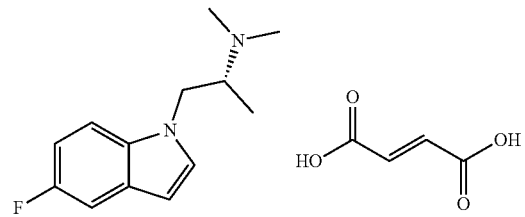 [SMILES: C[C@H](Cn1ccc2cc(F)ccc21)N(C)C ; O=C(O)/C=C/C(=O)O]

5-Fluoro-indole (100 mg, 0.739 mmol), (R)-1-chloro-N,N-dimethylpropan-2-amine (128 mg, 0.814 mmol, 1.1 equiv), potassium iodide (135 mg, 0.814 mmol, 1.1 equiv), and potassium hydroxide (166 mg, 15.8 mmol, 5.0 equiv) were stirred in DMSO (1.85 mL) for 24 h. The reaction mixture was diluted with 1.0 M $NaOH_{(aq)}$ (100 mL). The aqueous phase was extracted 3× with DCM (25 mL). The organic extracts were combined, dried over $Na_2SO_4$, filtered, and concentrated under reduced pressure to yield a colorless oil. The crude oil was purified by flash chromatography eluting with 9:1 DCM:MeOH with 1% ammonium hydroxide$_{(aq)}$. The purified oil was dissolved in acetone (2 mL) and added dropwise to a boiling solution of fumaric acid (86.8 mg, 0.739 mmol, 1.0 equiv) in acetone (5 mL). A precipitate formed immediately and was filtered and washed with ice-cold portions of acetone to yield the desired product. If no precipitate formed the mixture was concentrated down to facilitate crystal formation to yield the desired product. (1:1 hybrid:fumaric acid) (111 mg, 68%) $^1$H NMR (400 MHz, MeOD-d4) δ 7.50 (dd, 1H, J=4.3, 4.6 Hz), 7.36 (d, 1H, J=3.0 Hz), 7.28 (dd, 1H, J=2.0, 9.2 Hz), 7.01 (td, 1H, J=2.0, 9.2 Hz), 6.74 (s, 1H), 6.55 (d, 1H, J=3.0 Hz), 4.63 (dd, 1H J=6.9, 8.5, 5.2 Hz), 4.38 (dd, 1H, J=8.8, 5.7, 8.59 Hz), 3.92 (m, 1H) 2.89 (s, 6H), 1.25 (d, 3H, J=6.7 Hz). $^{13}$C NMR (100 MHz, MeOD-d4) δ 170.9, 136.0, 131.0, 111.4, 111.3, 111.1, 106.7, 106.5, 103.6, 103.5, 61.6, 47.7, 40.2, 11.8 ppm.

Example 34.
1-(1H-indol-1-yl)-N,N-dimethylpropan-2-amine

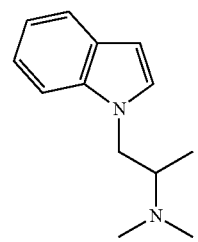

Synthesized according to Procedure A. ¹H NMR (600 MHz, CD3OD) δ 7.59 (d, 1H, J=7.6 Hz), 7.50 (d, 1H, J=7.6 Hz), 7.29 (d, 1H, J=3.1 Hz), 7.23 (t, 1H, J=7.6 Hz), 7.09 (t, 1H, J=7.6 Hz), 6.56 (d, 1H, J=3.1 Hz), 4.64 (dd, 1H, J=8.5, 6.4 Hz), 4.40 (dd, 1H, J=8.5, 6.8 Hz), 3.97 (m), 2.90 (s, 6H), 1.27 (d, 3H, J=6.7 Hz).

Example 35. (R)-1-(1H-indol-1-yl)-N,N-dimethylpropan-2-amine

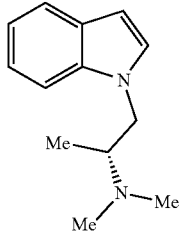 [SMILES: C[C@H](Cn1ccc2ccccc21)N(C)C]

Synthesized according to Procedure A. ¹H NMR (600 MHz, CDCl3) δ 7.62 (d, 1H, J=8.0 Hz), 7.36 (d, 1H, J=8.0 Hz), 7.21 (t, 1H, J=8.0 Hz), 7.10 (m, 1H), 6.50 (d, 1H, J=3.0 Hz), 6.56 (d, 1H, J=3.1 Hz), 4.34 (dd, 1H, J=9.0, 5.0 Hz), 3.92 (dd, 1H, J=9.0, 5.0 Hz), 3.07 (m, 1H), 2.36 (s, 6H), 0.91 (d, 3H, J=6.7 Hz).

Example 36. (R)-1-(6-fluoro-1H-indol-1-yl)-N,N-dimethylpropan-2-amine

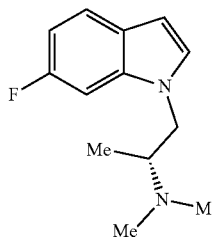

Synthesized according to Procedure A. ¹H NMR (600 MHz, CDCL3) δ 7.40 (dd, 1H, J=5.5, 3.1 Hz), 6.98 (d, 1H, J=3.1 Hz), 6.91 (d, 1H, J=11.8 Hz), 6.74 (t, 1H, J=9.0 Hz), 6.35 (d, 1H, J=3.1 Hz) 4.10 (dd, 1H, J=8.5, 5.6 Hz), 3.74 (dd, 1H, J=8.5, 5.6 Hz), 2.91 (m, 1H), 2.20 (s, 6H), 0.79 (d, 3H, J=6.6 Hz).

Example 37. (R)-1-(4-methoxy-1H-indol-1-yl)-N,N-dimethylpropan-2-amine

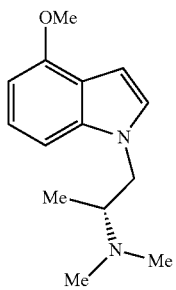 [SMILES: COc1cccc2c1ccn2C[C@@H](C)N(C)C]

Synthesized according to Procedure A. ¹NMR (600 MHz, CDCL3) δ 7.04 (t, 1H, J=7.9 Hz), 6.89 (t, 1H, J=7.9 Hz), 6.50 (d, 1H, J=10.5 Hz), 6.41 (d, 1H, J=8.01 Hz), 4.16 (dd, 1H, J=8.5, 5.5 Hz), 3.83 (s, 3H), 3.77 (dd, 1H, J=8.5, 5.5 Hz), 2.94 (m, 1H), 2.23 (s, 6H), 0.79 (d, 3H, J=6.5 Hz).

Example 38. (R)-1-(7-methoxy-1H-indol-1-yl)-N,N-dimethylpropan-2-amine

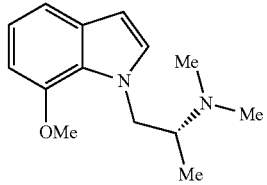 [SMILES: COc1cccc2ccn(C[C@@H](C)N(C)C)c12]

Synthesized according to Procedure A. ¹H NMR (600 MHz, CDCL3) δ 7.02 (d, 1H, J=7.8 Hz), 6.81 (m, 2H), 6.46 (t, 1H, J=6.2 Hz), 6.25 (d, 1H, J=3.0 Hz), 4.44 (dd, 1H, J=8.2, 5.5 Hz), 3.96 (dd, 1H, J=8.2, 5.5 Hz), 3.77 (s, 3H) 2.91 (m, 1H), 2.19 (s, 6H), 0.79 (d, 3H, J=6.7 Hz).

Example 39. (R)-1-(9H-carbazol-9-yl)-N,N-dimethylpropan-2-amine

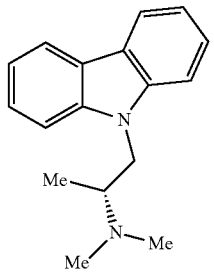 [SMILES: C[C@H](Cn1c2ccccc2c2ccccc21)N(C)C]

Synthesized according to Procedure A. ¹H NMR (600 MHz, CDCL3) δ 8.00 (d, 2H, J=7.7 Hz), 7.34 (m, 4H), 7.13 (d, 1H, J=7.6 Hz), 4.35 (dd, 1H, J=9.8, 4.5 Hz), 4.09 (dd, 1H, J=9.8, 4.5 Hz), 3.12 (m, 1H), 2.33 (s, 6H), 0.82 (d, 3H, J=6.6 Hz).

Example 40. (R)-1-(1H-benzo[d]imidazol-1-yl)-N,N-dimethylpropan-2-amine

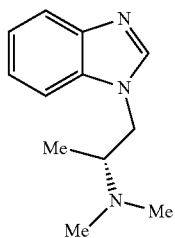 [SMILES: C[C@H](Cn1cnc2ccccc21)N(C)C]

Synthesized according to Procedure A. ¹H NMR (600 MHz, CDCL3) δ 7.72 (s, 1H), 7.16 (d, 1H, J=7.6 Hz), 7.32 (d, 1H, J=11.8 Hz), 6.91 (m, 3H), 4.05 (dd, 1H, J=7.5, 6.7

Hz), 4.10 (dd, 1H, J=7.5, 6.7 Hz), 3.79 (dd, 1H, J=8.5, 5.6 Hz), 2.86 (m, 1H), 2.06 (s, 6H), 0.69 (d, 3H, J=6.6 Hz).

Example 41. N-methyl-2-(1-methyl-1H-indol-3-yl)ethan-1-amine

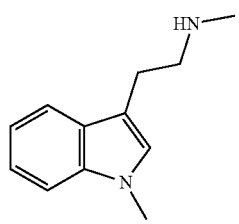

Tert-butyl (2-(1H-indol-3-yl)ethyl)carbamate. To an ice-cold solution of tryptamine (0.50 g, 3.1 mmol) and triethylamine (0.68 mL, 9.4 mmol, 3 equiv) in CH$_2$Cl$_2$ (44 mL) was added Boc$_2$O (0.77 g, 3.7 mmol, 1.2 equiv). The reaction was warmed to room temperature, stirred overnight, and then quenched with H$_2$O (200 mL). The organic phase was separated, and the aqueous phase extracted with CH$_2$Cl$_2$ (2×50 mL). The organic extracts were combined, dried over Na$_2$SO$_4$, filtered, and concentrated under reduced pressure to afford an oil that was purified by chromatography on silica gel (8:2 hexanes:EtOAc); white solid (0.69 g, 85%).

N-methyl-2-(1-methyl-1H-indol-3-yl)ethan-1-amine. To an ice-cold solution of sodium hydride (0.23 g, 5.8 mmol, 2.2 equiv) in DMF (3 mL) was added tert-butyl (2-(1H-indol-3-yl)ethyl)carbamate (0.69 g, 2.6 mmol) in DMF (3 mL). The reaction mixture was allowed to stir at room temperature before being cooled to 0° C. Methyl iodide (0.4 mL, 5.8 mmol, 2.2 equiv) was added dropwise. The reaction was stirred at room temperature for 20 h. Next, the reaction was cooled to 0° C., quenched with TFA (2 mL), and stirred for 30 min. The mixture was diluted with 1.0 M NaOH$_{(aq)}$ (600 mL) and extracted with CH$_2$Cl$_2$ (3×75 mL). The organic phases were combined, dried over Na$_2$SO$_4$, filtered, and concentrated under reduced pressure to afford an oil that was used without further purification (0.45 g, 90%).

Procedure B

General Synthetic Scheme

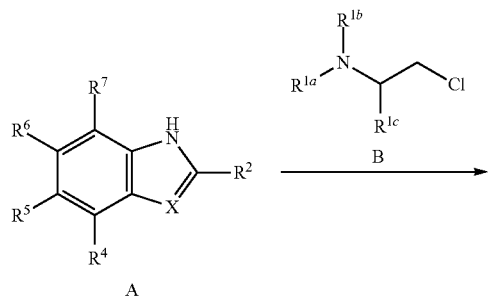

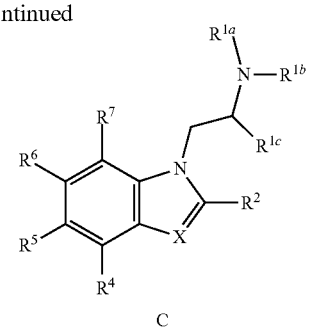

General procedure-1 (GP-B1): To a stirred solution of A (1.0 eq) in DMF (10 vol) was added NaH (60% in mineral oil, 1.2 eq) at 0° C. The reaction mixture was stirred for 20 min at 0° C. To the resultant reaction mixture were added reagent B (1.0 eq) followed by NaI (Cat.). The reaction was slowly warmed to room temperature and stirred for 16 h. The progress of the reaction was monitored by TLC.

General procedure-2 (GP-B2): To a stirred solution of A (1.0 eq) in DMF (10 vol) was added NaH (60% in mineral oil, 1.2 eq) at 0° C. The reaction mixture was stirred for 20 min at 0° C. To the resultant reaction mixture were added reagent B (1.0 eq) followed by NaI (Cat.). The reaction mixture was slowly warmed to room temperature and stirred at 60 to 65° C. for 16 h. The progress of the reaction was monitored by TLC.

General procedure-3 (GP-B3): To a stirred solution of A (1.0 eq) in DMF (10 vol) were added K$_2$CO$_3$ (3.0 eq) followed by reagent B (2.0 eq) and NaI (1.0 eq) at room temperature and then the contents were heated at 70° C. for 16 h. The progress of the reaction was monitored by TLC.

General Work up/purification procedure-B1: The reaction was diluted and quenched with ice cold water. A 2N HCl solution was added until the pH of the solution was 2. The resultant aqueous layer was washed with EtOAc until the unreacted starting material was totally removed (TLC). The aqueous layer was then basified with aq. NaHCO$_3$ solution and extracted with EtOAc. The combined organic layer was washed with water, followed by brine solution and then dried over anhydrous Na$_2$SO$_4$ and concentrated to get the expected product which was sufficiently pure (>95% LC-MS and HPLC purity).

General Work up/purification procedure-B2: The Reaction mixture was quenched with ice cold water and extracted with ethyl acetate. The combined organic layer was washed with ice cold water followed by brine wash. The organic layer was separated, dried over Na$_2$SO$_4$ and concentrated under reduced pressure to get crude material which was purified by combi-flash chromatography using either EtOAc/Heptane or CH$_2$Cl$_2$/MeOH gradients based on the polarity of the compounds. The pure fractions were evaporated and dried to get the compounds with >95% LC-MS and HPLC purity.

Example 42. 2-(5-methoxy-1H-indol-1-yl)-N,N-dimethylethan-1-amine

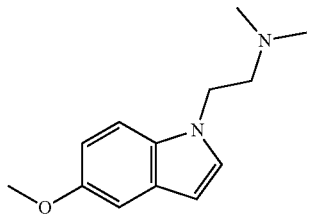

Synthesized according to Procedure B. GP-1 and work up/purification procedure-1 were followed. Yield: 44% (Brown liquid). LC-MS: 97.8%, m/z=219.2 [M+H]$^+$ $^1$H NMR (DMSO-d$_6$, 400 MHz): δ 7.30-7.37 (m, 2H), 7.03 (d, J=2.4 Hz, 1H), 6.76 (dd, J=2.4, 8.8 Hz, 1H), 6.30 (dd, J=0.4, 2.8 Hz, 1H), 4.19 (t, J=6.8 Hz, 2H), 3.74 (s, 3H), 2.57 (t, J=6.8 Hz, 2H), 2.17 (s, 6H).

Example 43. 2-(6-methoxy-1H-indol-1-yl)-N,N-dimethylethan-1-amine

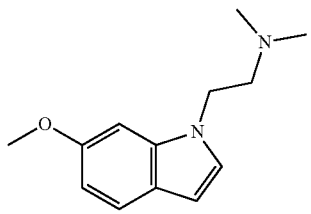

Synthesized according to Procedure B. GP-1 and work up/purification procedure-1 were followed. Yield: 44% (Brown liquid). LC-MS: 95.4%, m/z=219.2 [M+H]$^+$ $^1$H NMR (DMSO-d$_6$, 400 MHz): δ 7.38 (d, J=8.56 Hz, 1H), 7.21 (d, J=3.06 Hz, 1H), 6.98 (d, J=2.20 Hz, 1H), 6.64-6.67 (m, 1H), 6.31 (dd, J=0.73, 3.18 Hz, 1H), 4.19 (t, J=6.66 Hz, 2H), 3.79 (s, 3H), 2.58 (t, J=6.66 Hz, 2H), 2.19 (s, 6H).

Example 44. 5-methoxy-1-(2-(pyrrolidin-1-yl)ethyl)-1H-indole

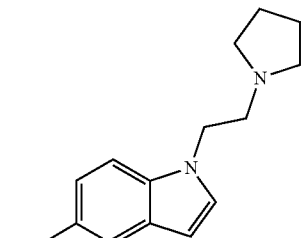

Synthesized according to Procedure B. GP-1 and work up/purification procedure-1 were followed. Yield: 16% (yellow semi solid). LC-MS: 98.2%, m/z=245.2 [M+H]$^+$ $^1$H NMR (DMSO-d$_6$, 400 MHz): δ 7.30-7.36 (m, 2H), 7.03 (d, J=2.45 Hz, 1H), 6.76 (dd, J=2.38, 8.86 Hz, 1H), 6.31 (d, J=3.06 Hz, 1H), 4.21 (t, J=6.79 Hz, 2H), 3.74 (s, 3H), 2.75 (t, J=6.72 Hz, 2H), 2.43-2.47 (m, 4H), 1.65 (td, J=3.15, 6.66 Hz, 4H).

Example 45. 5-methoxy-1-(2-(piperidin-1-yl)ethyl)-1H-indole

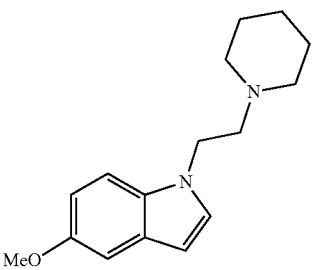 [SMILES: COc1ccc2c(ccn2CCN2CCCCC2)c1]

Synthesized according to Procedure B. GP-1 and work up/purification procedure-1 were followed. Yield: 34% (Brown solid). LC-MS: 99.5%, m/z=259.2 [M+H]$^+$ $^1$H NMR (DMSO-d$_6$, 400 MHz): δ 7.30-7.36 (m, 2H), 7.02 (d, J=2.32 Hz, 1H), 6.75 (dd, J=2.45, 8.80 Hz, 1H), 6.29-6.31 (m, 1H), 4.20 (t, J=6.79 Hz, 2H), 3.74 (s, 3H), 2.55-2.60 (m, 2H), 2.32-2.42 (m, 4H), 1.46 (quin, J=5.41 Hz, 4H), 1.33-1.39 (m, 2H).

Example 46. 4-(2-(5-methoxy-1H-indol-1-yl)ethyl)morpholine

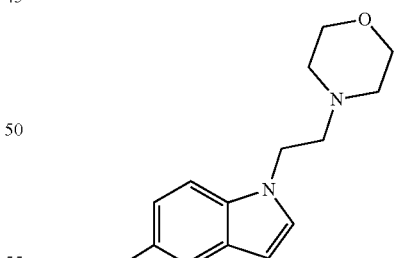

Synthesized according to Procedure B. GP-1 and work up/purification procedure-1 were followed. Yield: 28% (Brown solid). LC-MS: 99.5%, m/z=261.2 [M+H]$^+$ $^1$H NMR (DMSO-d$_6$, 400 MHz): δ 7.31-7.37 (m, 2H), 7.02 (d, J=2.45 Hz, 1H), 6.76 (dd, J=2.45, 8.80 Hz, 1H), 6.31 (dd, J=0.67, 3.00 Hz, 1H), 4.23 (t, J=6.66 Hz, 2H), 3.74 (s, 3H), 3.51-3.55 (m, 4H), 2.62 (t, J=6.66 Hz, 2H), 2.38-2.42 (m, 4H).

Example 47. 5-chloro-1-(2-(pyrrolidin-1-yl)ethyl)-1H-indole

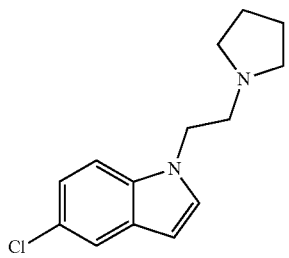 [SMILES: Clc1ccc2c(ccn2CCN2CCCC2)c1]

Synthesized according to Procedure B. GP-1 and work up/purification procedure-1 were followed. Yield: 28% (Brown liquid). LC-MS: 97%, m/z=248.11 [M+H]+ 1H NMR (DMSO-d$_6$, 400 MHz): δ 7.57 (d, J=1.96 Hz, 1H), 7.50 (d, J=8.80 Hz, 1H), 7.46 (d, J=3.06 Hz, 1H), 7.11 (dd, J=2.08, 8.80 Hz, 1H), 6.40 (dd, J=0.61, 3.06 Hz, 1H), 4.27 (t, J=6.60 Hz, 2H), 2.77 (t, J=6.60 Hz, 2H), 2.45 (br s, 4H), 1.64 (td, J=3.16, 6.76 Hz, 4H).

Example 48. 5-chloro-1-(2-(piperidin-1-yl)ethyl)-1H-indole

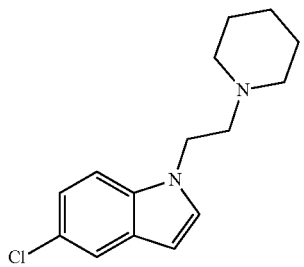 [SMILES: Clc1ccc2c(ccn2CCN2CCCCC2)c1]

Synthesized according to Procedure B. GP-1 and work up/purification procedure-2 were followed. Yield: 20% (Yellow semi solid). LC-MS: 95.18%, m/z=263.2 [M+H]+ 1H NMR (DMSO-d$_6$, 400 MHz): δ 7.57 (d, J=1.96 Hz, 1H), 7.50 (d, J=8.68 Hz, 1H), 7.45 (d, J=3.06 Hz, 1H), 7.11 (dd, J=1.77, 8.74 Hz, 1H), 6.40 (d, J=2.81 Hz, 1H), 4.26 (br s, 2H), 2.53-2.62 (m, 2H), 2.32-2.43 (m, 4H), 1.32-1.50 (m, 6H).

Example 49. 4-(2-(5-chloro-1H-indol-1-yl)ethyl)morpholine

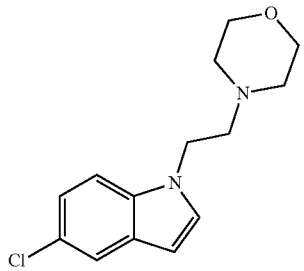 [SMILES: Clc1ccc2c(ccn2CCN2CCOCC2)c1]

Synthesized according to Procedure B. GP-1 and work up/purification procedure-1 were followed. Yield: 28% (Colourless liquid). LC-MS: 98.9%, m/z=265.2 [M+H]+ 1H NMR (DMSO-d$_6$, 400 MHz): δ 7.57 (d, J=1.83 Hz, 1H), 7.52 (d, J=8.80 Hz, 1H), 7.47 (d, J=3.18 Hz, 1H), 7.12 (dd, J=1.83, 8.68 Hz, 1H), 6.41 (d, J=2.81 Hz, 1H), 4.28 (br t, J=5.75 Hz, 2H), 3.52 (br s, 4H), 2.60-2.67 (m, 2H), 2.40 (br s, 4H).

Example 50. 1-(2-(pyrrolidin-1-yl)ethyl)-5-(trifluoromethoxy)-1H-indole

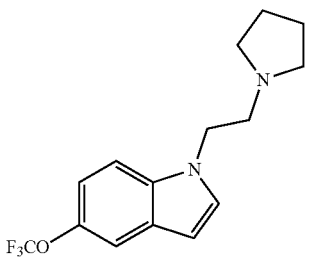

Synthesized according to Procedure B. GP-2 and work up/purification procedure-2 were followed. Yield: 22% (brown semi solid). LC-MS: 99.8%, m/z=299.2 [M+H]+ 1H NMR (CD$_3$OD, 400 MHz): δ 7.43-7.50 (m, 2H), 7.37 (d, J=3.18 Hz, 1H), 7.07 (dd, J=0.98, 8.93 Hz, 1H), 6.52 (d, J=3.18 Hz, 1H), 4.39 (t, J=7.09 Hz, 2H), 3.03 (t, J=7.03 Hz, 2H), 2.68 (br s, 4H), 1.83 (td, J=3.33, 6.79 Hz, 4H).

Example 51. 1-(2-(piperidin-1-yl)ethyl)-5-(trifluoromethoxy)-1H-indole

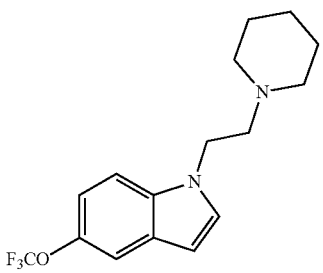 [SMILES: FC(F)(F)Oc1ccc2c(ccn2CCN2CCCCC2)c1]

Synthesized according to Procedure B. GP-1 and work up/purification procedure-2 were followed. Yield: 25% (brown liquid). LC-MS: 99.6%, m/z=313.2 [M+H]+ 1H NMR (DMSO-d$_6$, 400 MHz): δ 7.54-7.59 (m, 1H), 7.51 (d, J=3.06 Hz, 2H), 7.08 (dd, J=1.34, 8.93 Hz, 1H), 6.48 (dd, J=0.61, 3.06 Hz, 1H), 4.28 (t, J=6.66 Hz, 2H), 2.60 (t, J=6.66 Hz, 2H), 2.37 (br d, J=4.40 Hz, 4H), 1.45 (quin, J=5.41 Hz, 4H), 1.32-1.40 (m, 2H).

Example 52. 4-(2-(5-(trifluoromethoxy)-1H-indol-1-yl)ethyl)morpholine

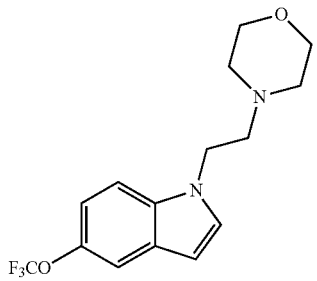 [SMILES: FC(F)(F)Oc1ccc2c(ccn2CCN2CCOCC2)c1]

Synthesized according to Procedure B. GP-2 and work up/purification procedure-2 were followed. Yield: 22% (brown liquid). LC-MS: 98.27%, m/z=315.2 [M+H]$^+$ $^1$H NMR (DMSO-d$_6$, 400 MHz): δ 7.59 (d, J=8.93 Hz, 1H), 7.50-7.54 (m, 2H), 7.09 (dd, J=1.16, 8.99 Hz, 1H), 6.49 (d, J=2.93 Hz, 1H), 4.31 (t, J=6.54 Hz, 2H), 3.50-3.57 (m, 4H), 2.65 (br t, J=6.54 Hz, 2H), 2.42 (br s, 4H).

Example 53. 2-(4-methoxy-1H-indol-1-yl)-N,N-dimethylethan-1-amine

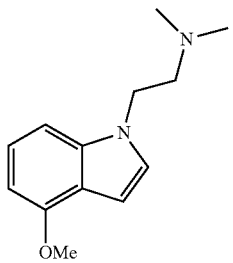 [SMILES: COc1cccc2c1ccn2CCN(C)C]

Synthesized according to Procedure B. GP-1 and work up/purification procedure-1 were followed. Yield: 27% (brown liquid). LC-MS: 98.9%, m/z=219.2 [M+H]$^+$ $^1$H NMR (DMSO-d$_6$, 400 MHz): δ 7.25 (d, J=3.18 Hz, 1H), 7.02-7.07 (m, 2H), 6.49-6.52 (m, 1H), 6.38-6.40 (m, 1H), 4.20 (t, J=6.72 Hz, 2H), 3.85 (s, 3H), 2.55-2.60 (m, 2H), 2.17 (s, 6H).

Example 54. 2-(7-methoxy-1H-indol-1-yl)-N,N-dimethylethan-1-amine

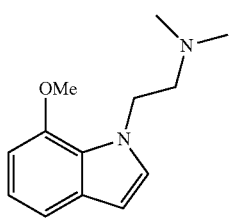 [SMILES: COc1cccc2ccn(CCN(C)C)c12]

Synthesized according to Procedure B. GP-1 and work up/purification procedure-1 were followed. Yield: 27% (Brown liquid). LC-MS: 98.8%, m/z=219.2 [M+H]$^+$ $^1$H NMR (DMSO-d$_6$, 400 MHz): δ 7.24 (d, J=3.06 Hz, 1H), 7.07-7.11 (m, 1H), 6.89 (t, J=7.82 Hz, 1H), 6.64 (d, J=7.70 Hz, 1H), 6.33 (d, J=3.06 Hz, 1H), 4.42 (t, J=6.97 Hz, 2H), 3.88 (s, 3H), 2.56 (t, J=6.97 Hz, 2H), 2.18 (s, 6H).

Example 55. 2-(5-methoxy-1H-benzo[d]imidazol-1-yl)-N,N-dimethylethan-1-amine

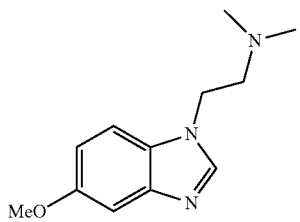 [SMILES: COc1ccc2c(c1)ncn2CCN(C)C]

Example 56. 2-(6-methoxy-1H-benzo[d]imidazol-1-yl)-N,N-dimethylethan-1-amine

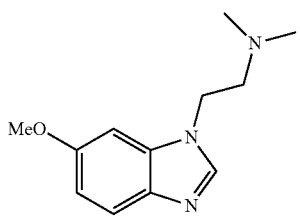 [SMILES: COc1ccc2ncn(CCN(C)C)c2c1]

Synthesized according to Procedure B. The reaction was attempted on Example 55 using GP-2 with a slight modification (using 1 eq of NaI). The work-up/purification procedure-2 was followed to get mixture of regiomers. The mixture was separated by normal phase chiral-HPLC purification using the following method. Both the structures were confirmed by NOE analysis.
Column: Chiralpak IC (250 m×4.6 mm, 5 μm)
Mobile Phase: 0.1% DEA in n-HEXANE
Mobile phase B: DCM:MEOH(80:20)
PROGRAMME: A:B: 80:20
Flow: 1.0 ml/min.
Yield: 10% (pale yellow solid). LCMS: 99.8%, m/z=220.1 [M+H]$^+$ $^1$H NMR (DMSO-d$_6$, 400 MHz): δ 8.11 (s, 1H), 7.48 (d, J=8.80 Hz, 1H), 7.15 (d, J=2.32 Hz, 1H), 6.87 (dd, J=2.32, 8.80 Hz, 1H), 4.27 (t, J=6.30 Hz, 2H), 3.77 (s, 3H), 2.62 (t, J=6.24 Hz, 2H), 2.17 (s, 6H).

Example 57. 2-(1H-benzo[d]imidazol-1-yl)-N,N-dimethylethan-1-amine

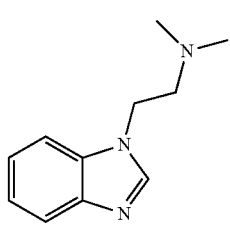

Synthesized according to Procedure B. GP-1 and work up/purification procedure-2 were followed. Yield: 4% (Colorless liquid). LCMS: 99.7%, m/z=190.2 [M+H]+ 1H NMR (DMSO-$d_6$, 400 MHz): δ 8.20 (s, 1H), 7.62 (dd, J=7.95, 12.47 Hz, 2H), 7.16-7.27 (m, 2H), 4.32 (t, J=6.36 Hz, 2H), 2.64 (t, J=6.30 Hz, 2H), 2.18 (s, 6H).

Example 58. N,N-dimethyl-2-(2-methyl-1H-benzo[d]imidazol-1-yl)ethan-1-amine

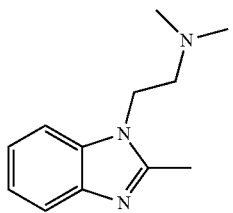

Synthesized according to Procedure B. GP-3 and work up/purification procedure-2 were followed. Yield: 15% (Yellow liquid). LCMS: 98.3%, m/z=204.2 [M+H]+ 1H NMR (DMSO-$d_6$, 400 MHz): δ 7.44-7.51 (m, 2H), 7.09-7.19 (m, 2H), 4.24 (t, J=6.66 Hz, 2H), 2.53-2.57 (m, 5H), 2.19 (s, 6H).

Procedure C slowly warmed to room temperature and then stirred at the same temperature for 16 h. The progress of the reaction was monitored by TLC.

Work up and purification after step-C1: Reaction mixture was quenched with ice cold water and extracted with ethyl acetate. The combined organic layer was washed with ice cold water followed by aq. NaCl solution. The organic layer was separated, dried over $Na_2SO_4$ and concentrated to get crude material which was purified by combi-flash purification using 10 to 20% EtOAc in hexane and then the cleaner fractions (by TLC) were evaporated and dried under reduced pressure to Compound F.

Step-C2: To a stirred solution of Compound F (1 eq) in $CH_2Cl_2$ (10 vol) was added triethylamine (2.5 eq) and the resultant solution was cooled to 0° C. To this was added mesyl chloride (1.5 eq) and warmed to room temperature and stirred for 1 to 2 h. The progress of the reaction was monitored by TLC.

Work up after step-C2: Reaction mixture was quenched with ice cold water and extracted with $CH_2Cl_2$. The combined organic layer was washed with saturated aqueous bicarbonate solution followed by water. The organic layer was separated, dried over $Na_2SO_4$ and concentrated to get crude Compound G which was used in the next step without further purification.

Step-C3: In a sealed tube Compound G (1 eq) followed by DMF (2 vol) and 40% aqueous dimethylamine (10 vol) were General synthetic scheme:

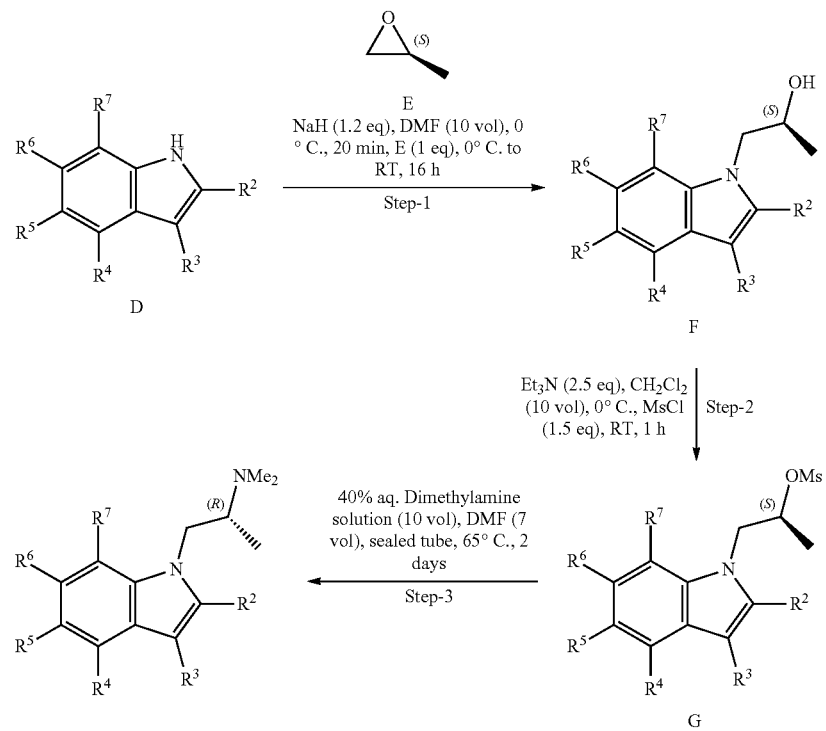

General Synthetic Procedures:

Step-C1: To a stirred solution of Compound D (1.0 eq) in DMF (10 mL) was added NaH (60% in mineral oil, 1.2 eq) at 0° C. The reaction mixture was stirred for 20 min, then Compound E (1.0 eq) was added. The reaction mixture was added and heated at 65° C. for 1 to 2 days. The progress of the reaction was monitored by TLC.

Work up and purification after step-C3: The reaction was quenched with water and extracted with EtOAc. The organic layer was separated, washed with water followed by brine wash. The separated organic layer was dried over anhydrous Na₂SO₄, evaporated to get the crude which was purified by combi-flash purification using 5 to 10% EtOAc in CH₂Cl₂/5 to 10% MeOH in CH₂Cl₂ and then the cleaner fractions (by TLC) were evaporated and dried under reduced pressure to obtain the target compound.

Example 59. (R)-1-(5-methoxy-1H-indol-1-yl)-N,N-dimethylpropan-2-amine

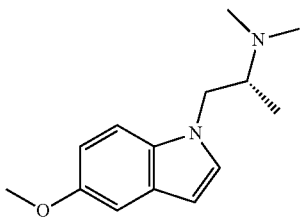

Step-C1: Yield: 71% (pale brown liquid). ¹H NMR (DMSO-d₆, 400 MHz): δ 7.35 (d, J=8.93 Hz, 1H), 7.27 (d, J=3.06 Hz, 1H), 7.02 (d, J=2.32 Hz, 1H), 6.74 (dd, J=2.45, 8.80 Hz, 1H), 6.29-6.32 (m, 1H), 4.85 (d, J=4.77 Hz, 1H), 3.99-4.07 (m, 2H), 3.90-3.98 (m, 1H), 3.74 (s, 3H), 1.01 (d, J=6.11 Hz, 3H).

Step-C2: Yellow solid. ¹H NMR (DMSO-d₆, 400 MHz): δ 7.45 (d, J=8.93 Hz, 1H), 7.33 (d, J=3.06 Hz, 1H), 7.04 (d, J=2.32 Hz, 1H), 6.80 (dd, J=2.32, 8.93 Hz, 1H), 6.38 (d, J=2.93 Hz, 1H), 4.92-5.01 (m, 1H), 4.34-4.40 (m, 2H), 3.75 (s, 3H), 2.54 (s, 3H), 1.33 (d, J=6.24 Hz, 3H).

Step-C3: Yield: 16% (over two steps, brown liquid). [α]$_D^{20}$=−14.6 (C 0.5, CH₂Cl₂). LC-MS: 99.4%, m/z=233.2 [M+H]⁺ ¹H NMR (DMSO-d₆, 400 MHz): δ 7.27-7.36 (m, 2H), 7.02 (d, J=2.32 Hz, 1H), 6.75 (dd, J=2.38, 8.86 Hz, 1H), 6.28-6.32 (m, 1H), 4.18 (dd, J=6.72, 14.18 Hz, 1H), 3.92-3.99 (m, 1H), 3.74 (s, 3H), 2.92-3.02 (m, 1H), 2.19 (s, 6H), 0.79 (d, J=6.60 Hz, 3H).

Example 60. (R)-1-(5-fluoro-1H-indol-1-yl)-N,N-dimethylpropan-2-amine

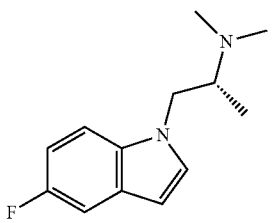 [SMILES: C[C@H](Cn1ccc2cc(F)ccc21)N(C)C]

Step-C1: Yield: 50% (pale brown liquid). ¹H NMR (DMSO-d₆, 400 MHz): δ 7.50 (dd, J=4.52, 8.93 Hz, 1H), 7.41 (d, J=3.06 Hz, 1H), 7.26-7.31 (m, 1H), 6.92-6.99 (m, 1H), 6.39-6.42 (m, 1H), 3.93-4.03 (m, 2H), 3.12-3.21 (m, 1H), 0.92 (d, J=6.36 Hz, 3H).

Step-C2: The mesylate was prepared using the general procedure shown above and then it was treated with NaN₃ (1.5 eq) in DMF (10 vol) at 70° C. for 2 h. The progress of the reaction was monitored by TLC. After completion of the reaction, the reaction mixture was diluted with water and extracted with EtOAc. The combined organic layer was washed with cold water for twice and evaporated to get the crude. This was treated with 10% Pd/C (50% wet) in MeOH under hydrogen atmosphere to the get the crude amine. The crude was purified by combi-flash using 1% MeOH in CH₂Cl₂ and the cleaner fractions were evaporated to get the amine. This was treated with Paraformaldehyde (10 eq) in MeOH/DCM (10 vol, 2:1) and then AcOH (Cat.), followed by NaBH₃CN (6.0 eq) were added and stirred for 1 h. The progress of the reaction was monitored by TLC. After aqueous work up the crude was purified by prep-HPLC followed by combi-flash purification to get the above compound with 30% isolated yield.

The prep-HPLC purification method is shown below:
Preparative HPLC Column: Ymc triat actus C18 (250*20 mm), 5 um
Mobile Phase A: Acetonitrile
Mobile Phase B: 5 mM Ammonium Bicarbonate
Flow rate: 15.0 mL/min

| Gradient Table: | | |
|---|---|---|
| Time | % A | % B |
| 0.01 | 40 | 60 |
| 3.00 | 40 | 60 |
| 20.00 | 55 | 45 |
| 25.00 | 50 | 50 |
| 25.10 | 100 | 0 |
| 30.00 | 100 | 0 |
| 30.10 | 40 | 60 |
| 35.00 | 40 | 60 |

Solvents used for dilution: Acetonitrile/MeOH
Yield: 30% (brown liquid). [α]$_D^{20}$=−15.9 (C 0.5, CH₂Cl₂). LC-MS: 99.5%, m/z=221.2 [M+H]⁺ ¹H NMR (DMSO-d₆, 400 MHz): δ 7.40-7.49 (m, 2H), 7.28 (dd, J=2.51, 9.96 Hz, 1H), 6.92-6.98 (m, 1H), 6.39 (dd, J=0.61, 3.06 Hz, 1H), 4.18-4.25 (m, 1H), 4.01 (dd, J=7.27, 14.24 Hz, 1H), 2.94-3.03 (m, 1H), 2.19 (s, 6H), 0.81 (d, J=6.60 Hz, 3H). ¹⁹F NMR (DMSO-d₆, 376 MHz): δ −127.18 (s, 1F).

Example 61. (R)-1-(6-fluoro-5-methoxy-1H-indol-1-yl)-N,N-dimethylpropan-2-amine

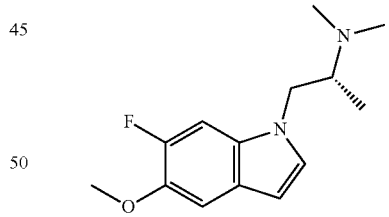

Step-C1: Yield: 74% (brown liquid). ¹H NMR (DMSO-d₆, 400 MHz): δ 7.39 (d, J=12.23 Hz, 1H), 7.27 (d, J=3.06 Hz, 1H), 7.18-7.22 (m, 1H), 6.34 (dd, J=0.61, 3.06 Hz, 1H), 4.84 (d, J=4.77 Hz, 1H), 3.88-4.06 (m, 3H), 3.81 (s, 3H), 1.02 (d, J=6.11 Hz, 3H).

Step-C2: Brown solid. ¹H NMR (DMSO-d₆, 400 MHz): δ 7.52 (d, J=12.23 Hz, 1H), 7.33 (d, J=3.06 Hz, 1H), 7.22 (d, J=8.56 Hz, 1H), 6.41 (dd, J=0.67, 3.12 Hz, 1H), 4.91-5.00 (m, 1H), 4.30-4.39 (m, 2H), 3.82 (s, 3H), 2.56 (s, 3H), 1.32-1.35 (m, 3H).

Step-C3: Yield: 14% (over two steps, Brown liquid). [α]$_D^{20}$=−19.7 (C 0.5, CH₂Cl₂). LC-MS: 98.5%, 251.2 [M+H]⁺ ¹H NMR (DMSO-d₆, 400 MHz): δ 7.38-7.44 (m, 1H), 7.30 (d, J=3.18 Hz, 1H), 7.22 (d, J=8.56 Hz, 1H), 6.35

(d, J=2.57 Hz, 1H), 4.15 (dd, J=7.09, 14.18 Hz, 1H), 3.96 (dd, J=7.15, 14.24 Hz, 1H), 3.83 (s, 3H), 2.93-3.03 (m, 1H), 2.20 (s, 6H), 0.81 (d, J=6.60 Hz, 3H). $^{19}$F NMR (DMSO-d$_6$, 376 MHz): δ −142.08 (s, 1F).

Example 62. (R)-1-(5,6-dimethoxy-1H-indol-1-yl)-N,N-dimethylpropan-2-amine

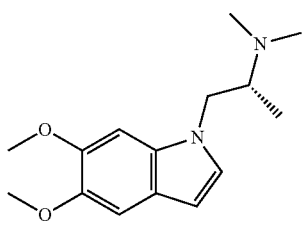

Step-C1: Yield: 50% (Pale brown liquid). $^1$H NMR (DMSO-d$_6$, 400 MHz): δ 7.13 (d, J=3.06 Hz, 1H), 7.03 (d, J=7.21 Hz, 2H), 6.23-6.26 (m, 1H), 4.84 (d, J=4.65 Hz, 1H), 3.91-4.01 (m, 3H), 3.79 (s, 3H), 3.73 (s, 3H), 1.02 (d, J=5.99 Hz, 3H).

Step-C2: Pale brown semi solid. $^1$H NMR (DMSO-d$_6$, 400 MHz): δ 7.18 (d, J=3.18 Hz, 1H), 7.14 (s, 1H), 7.04 (s, 1H), 6.32 (d, J=3.06 Hz, 1H), 4.93-5.02 (m, 1H), 4.30-4.42 (m, 2H), 3.81 (s, 3H), 3.74 (s, 3H), 2.56 (s, 3H), 1.34 (d, J=6.36 Hz, 3H).

Step-C3: Yield: 18% (over two steps, Brown liquid). LC-MS: 94.8%, 263.2[M+H]$^+$ $^1$H NMR (DMSO-d$_6$, 400 MHz): δ 7.14 (d, J=3.06 Hz, 1H), 6.99-7.03 (m, 2H), 6.25 (dd, J=0.61, 3.06 Hz, 1H), 4.12-4.19 (m, 1H), 3.91-3.98 (m, 1H), 3.72-3.81 (m, 6H), 2.93-3.02 (m, 1H), 2.21 (s, 6H), 0.81 (d, J=6.60 Hz, 3H).

Example 63. (R)-1-(5,7-dimethoxy-1H-indol-1-yl)-N,N-dimethylpropan-2-amine

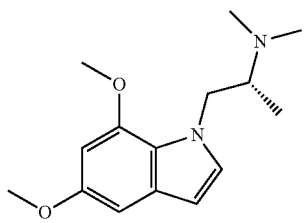

Step-C1: Yield: 35% (Colourless liquid). $^1$H NMR (DMSO-d$_6$, 400 MHz): δ 7.10-7.16 (m, 1H), 6.58-6.61 (m, 1H), 6.27-6.30 (m, 1H), 4.74 (d, J=5.14 Hz, 1H), 4.09-4.32 (m, 2H), 3.83-3.92 (m, 4H), 3.71-3.73 (m, 3H), 0.91-1.00 (m, 3H).

Step-C2: Pale yellow semi solid. $^1$H NMR (DMSO-d$_6$, 400 MHz): δ 7.14-7.20 (m, 1H), 6.61 (d, J=2.08 Hz, 1H), 6.35 (d, J=2.08 Hz, 1H), 6.29-6.32 (m, 1H), 4.87-4.95 (m, 1H), 4.41-4.52 (m, 2H), 3.85-3.89 (m, 3H), 3.72-3.74 (m, 3H), 2.56 (s, 3H), 1.23-1.35 (m, 3H).

Step-C3: Yield: 25% (over two steps, Brown liquid). [α]$_D^{20}$=−22.94 (C 0.25, CH$_2$Cl$_2$). LC-MS: 99.25%, 263.2 [M+H]$^+$ $^1$H NMR (DMSO-d$_6$, 400 MHz): δ 7.13 (d, J=2.93 Hz, 1H), 6.58 (d, J=2.08 Hz, 1H), 6.29 (d, J=1.96 Hz, 1H), 6.23 (d, J=2.93 Hz, 1H), 4.38 (dd, J=6.30, 13.63 Hz, 1H), 4.06 (dd, J=7.83, 13.57 Hz, 1H), 3.85 (s, 3H), 3.72 (s, 3H), 2.88-2.97 (m, 1H), 2.20 (s, 6H), 0.73 (d, J=6.72 Hz, 3H).

Example 64. (R)-1-(5-methoxy-6-methyl-1H-indol-1-yl)-N,N-dimethylpropan-2-amine

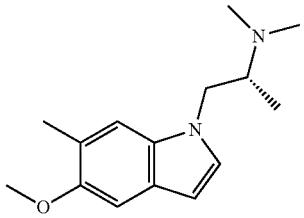

Step-C1: Yield: 83% (Colourless liquid). $^1$H NMR (DMSO-d$_6$, 400 MHz): δ 7.25 (s, 1H), 7.19 (br d, J=2.81 Hz, 1H), 7.00 (s, 1H), 6.29 (br d, J=2.45 Hz, 1H), 4.84 (br d, J=4.40 Hz, 1H), 3.92-4.03 (m, 3H), 3.79 (s, 3H), 2.26 (s, 3H), 1.03 (br d, J=5.87 Hz, 3H).

Step-C2: Pale yellow semi solid. $^1$H NMR (DMSO-d$_6$, 400 MHz): δ 7.34 (s, 1H), 7.23 (d, J=3.06 Hz, 1H), 7.00 (s, 1H), 6.34 (dd, J=0.73, 3.06 Hz, 1H), 4.91-4.98 (m, 1H), 4.31-4.35 (m, 2H), 3.77 (s, 3H), 3.35 (s, 3H), 2.25 (s, 3H), 1.34 (d, J=6.24 Hz, 3H).

Step-C3: Yield: 8% (over two steps, pale brown liquid). [α]$_D^{20}$=−19.10 (C 0.125, CH$_2$Cl$_2$). LC-MS: 99%, 247.2 [M+H]$^+$ $^1$H NMR (DMSO-d$_6$, 400 MHz): δ 7.17-7.22 (m, 2H), 6.98 (s, 1H), 6.26-6.27 (m, 1H), 4.14 (dd, J=6.66, 14.12 Hz, 1H), 3.93 (dd, J=7.58, 14.18 Hz, 1H), 3.77 (s, 3H), 2.93-3.02 (m, 1H), 2.25 (s, 3H), 2.20 (s, 6H), 0.79 (d, J=6.60 Hz, 3H).

Example 65. (R)-1-(5-methoxy-7-methyl-1H-indol-1-yl)-N,N-dimethylpropan-2-amine

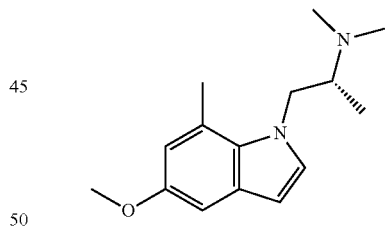

Step-C1: Yield: 75% (pale brown liquid). $^1$H NMR (DMSO-d$_6$, 400 MHz): δ 7.18 (d, J=3.06 Hz, 1H), 6.84 (d, J=2.45 Hz, 1H), 6.49 (d, J=2.08 Hz, 1H), 6.27 (d, J=3.06 Hz, 1H), 4.87 (d, J =5.14 Hz, 1H), 4.16 (dd, J=2.14, 6.17 Hz, 2H), 3.81-3.89 (m, 1H), 3.71 (s, 3H), 2.60 (s, 3H), 1.02 (d, J=6.11 Hz, 3H).

Step-C2: Pale yellow syrup. $^1$H NMR (DMSO-d$_6$, 400 MHz): δ 7.27 (d, J=3.06 Hz, 1H), 6.86 (d, J=2.45 Hz, 1H), 6.54-6.56 (m, 1H), 6.35-6.37 (m, 1H), 4.82-4.90 (m, 1H), 4.48-4.52 (m, 2H), 3.72 (s, 3H), 2.61 (s, 3H), 2.41 (s, 3H), 1.34 (d, J=6.36 Hz, 3H).

Step-C3: Yield: 11% (Over two steps, brown liquid). [α]$_D^{20}$=−6.34 (C 0.5, CH$_2$Cl$_2$). LC-MS: 99.43%, 247.2 [M+H]$^+$ $^1$H NMR (DMSO-d$_6$, 400 MHz): δ 7.17 (d, J=3.06 Hz, 1H), 6.84 (d, J=2.45 Hz, 1H), 6.50 (d, J=1.96 Hz, 1H), 6.26 (d, J=3.06 Hz, 1H), 4.35 (dd, J=6.05, 14.37 Hz, 1H), 4.05-4.12 (m, 1H), 3.71 (s, 3H), 2.81-2.90 (m, 1H), 2.60 (s, 3H), 2.19 (s, 6H), 0.74 (d, J=6.60 Hz, 3H).

Example 66. (R)-1-(5-methoxy-3-methyl-1H-indol-1-yl)-N,N-dimethylpropan-2-amine

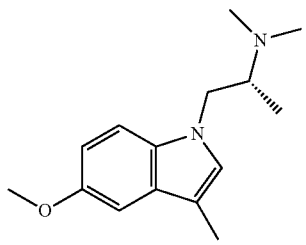

Step-C1: Yield: 70% (Pale brown liquid).

Step-C2: Pale yellow semi solid.

Step-C3: Yield: 19% (over two steps). $[\alpha]_D^{20}$=−1.82 (C 0.5, CH$_2$Cl$_2$). LC-MS: 99.76%, 247.1 [M+H]$^+$ $^1$H NMR (DMSO-d$_6$, 400 MHz): δ 7.28 (d, J=8.80 Hz, 1H), 7.06 (s, 1H), 6.94 (d, J=2.45 Hz, 1H), 6.74 (dd, J=2.45, 8.80 Hz, 1H), 4.07-4.14 (m, 1H), 3.85-3.92 (m, 1H), 3.76 (s, 3H), 2.88-2.98 (m, 1H), 2.18-2.22 (m, 9H), 0.78 (d, J=6.60 Hz, 3H).

Example 67. (R)-1-(4,5-difluoro-1H-indol-1-yl)-N,N-dimethylpropan-2-amine

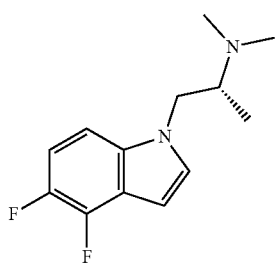 [SMILES: C[C@H](Cn1ccc2c(F)c(F)ccc21)N(C)C]

Step-C1: Yield: 58% (pale brown liquid). $^1$H NMR (DMSO-d$_6$, 400 MHz): δ 7.45 (d, J=3.18 Hz, 1H), 7.33 (dd, J=3.42, 9.05 Hz, 1H), 7.09-7.17 (m, 1H), 6.53 (dd, J=0.79, 3.12 Hz, 1H), 4.89 (d, J=4.77 Hz, 1H), 4.10-4.16 (m, 1H), 4.00-4.07 (m, 1H), 3.90-3.99 (m, 1H), 1.04 (d, J=6.24 Hz, 3H).

Step-C2: Brown liquid. $^1$H NMR (DMSO-d$_6$, 400 MHz): δ 7.51 (d, J=3.18 Hz, 1H), 7.40-7.44 (m, 1H), 7.16-7.24 (m, 1H), 6.61 (dd, J=0.86, 3.18 Hz, 1H), 4.96-5.04 (m, 1H), 4.43-4.47 (m, 2H), 2.65 (s, 3H), 1.34 (d, J=6.36 Hz, 3H).

Step-C3: Yield: 30% (over two steps, Brown liquid). $[\alpha]_D^{20}$=−25.0 (C 0.5, CH$_2$Cl$_2$). LC-MS: 99.08%, m/z=239.2 [M+H]$^+$ $^1$H NMR (DMSO-d$_6$, 400 MHz): δ 7.48 (d, J=3.06 Hz, 1H), 7.30-7.34 (m, 1H), 7.13 (ddd, J=7.89, 8.80, 11.19 Hz, 1H), 6.52 (dd, J=0.73, 3.18 Hz, 1H), 4.19-4.25 (m, 1H), 4.01-4.07 (m, 1H), 2.95-3.04 (m, 1H), 2.18 (s, 6H), 0.82 (d, J=6.60 Hz, 3H).

Example 68. (R)-1-(5,6-difluoro-1H-indol-1-yl)-N,N-dimethylpropan-2-amine

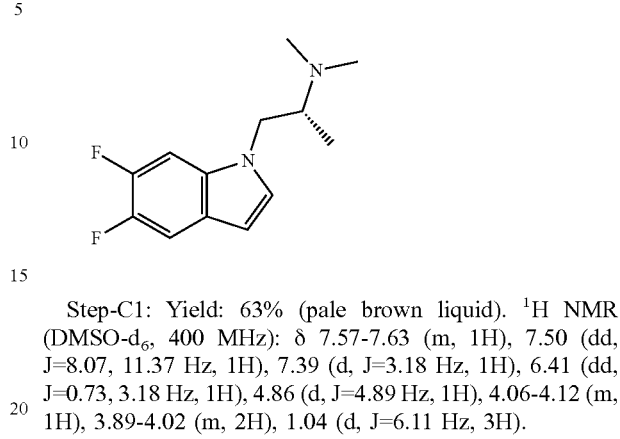

Step-C1: Yield: 63% (pale brown liquid). $^1$H NMR (DMSO-d$_6$, 400 MHz): δ 7.57-7.63 (m, 1H), 7.50 (dd, J=8.07, 11.37 Hz, 1H), 7.39 (d, J=3.18 Hz, 1H), 6.41 (dd, J=0.73, 3.18 Hz, 1H), 4.86 (d, J=4.89 Hz, 1H), 4.06-4.12 (m, 1H), 3.89-4.02 (m, 2H), 1.04 (d, J=6.11 Hz, 3H).

Step-C2: Pale yellow semi solid. $^1$H NMR (DMSO-d$_6$, 400 MHz): δ 7.71 (dd, J=6.97, 11.62 Hz, 1H), 7.51-7.57 (m, 1H), 7.44-7.46 (m, 1H), 6.49 (dd, J=0.73, 3.18 Hz, 1H), 4.94-5.02 (m, 1H), 4.39-4.43 (m, 2H), 2.61 (s, 3H), 1.34 (d, J=6.36 Hz, 3H).

Step-C3: Yield: 30% (over two steps, brown liquid). $[\alpha]_D^{20}$=−21.12 (C 0.5, CH$_2$Cl$_2$). LC-MS: 96.1%, m/z=239.2 [M+H]$^+$ $^1$H NMR (DMSO-d$_6$, 400 MHz): δ 7.58-7.63 (m, 1H), 7.47-7.52 (m, 1H), 7.40-7.42 (m, 1H), 6.41 (dd, J=0.73, 3.06 Hz, 1H), 4.17 (dd, J=7.52, 14.24 Hz, 1H), 3.96-4.03 (m, 1H), 2.94-3.04 (m, 1H), 2.18 (s, 6H), 0.81 (d, J=6.60 Hz, 3H). $^{19}$F NMR (DMSO-d$_6$, 376 MHz): δ −146.8 (d, J=22.5 Hz, 1F), −150.82 (d, J=24.0 Hz, 1F).

Example 69. (R)-1-(5,7-difluoro-1H-indol-1-yl)-N,N-dimethylpropan-2-amine

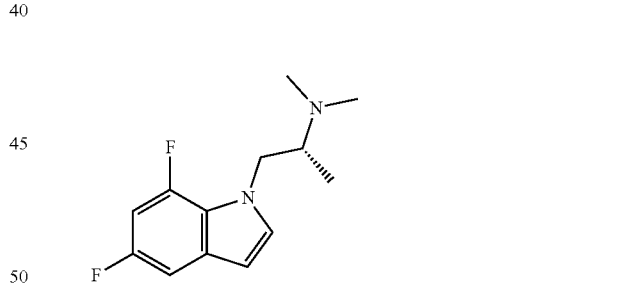

Step-C1: Yield: 57% (colorless liquid). $^1$H NMR (CDCl$_3$, 400 MHz): δ 7.15 (d, J=3.06 Hz, 1H), 7.05 (dd, J=2.20, 9.05 Hz, 1H), 6.67-6.73 (m, 1H), 6.45-6.47 (m, 1H), 4.34 (ddd, J=1.22, 3.30, 14.06 Hz, 1H), 4.14-4.19 (m, 1H), 4.03-4.10 (m, 1H), 1.65 (d, J=4.03 Hz, 1H), 1.24 (d, J=6.11 Hz, 3H).

Step-C2: Yellow semi solid.

Step-C3: Yield: 50% (over two steps, colorless liquid). $[\alpha]_D^{20}$=−28.5 (C 0.5, CH$_2$Cl$_2$). LC-MS: 99.2%, m/z=239.1 [M+H]$^+$ $^1$H NMR (DMSO-d$_6$, 400 MHz): δ 7.44 (d, J=3.06 Hz, 1H), 7.15-7.19 (m, 1H), 6.90-6.97 (m, 1H), 6.47 (t, J=2.69 Hz, 1H), 4.29-4.35 (m, 1H), 4.04-4.10 (m, 1H), 2.91-3.00 (m, 1H), 2.18 (s, 6H), 0.80 (d, J=6.60 Hz, 3H). $^{19}$F NMR (DMSO-d$_6$, 376 MHz): δ −124.28 (s, 1F), −132.87 (s, 1F).

Example 70. (R)-1-(5-fluoro-6-methoxy-1H-indol-1-yl)-N,N-dimethylpropan-2-amine

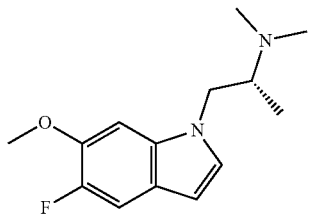

Step-C1: Yield: 46% (colorless liquid).

Step-C2: Yellow semi solid.

Step-C3: Yield: 32% (over two steps, colorless liquid). $[\alpha]_D^{20}=-8.05$ (C 0.5, CH$_2$Cl$_2$). LC-MS: 98.4%, m/z=235.1 [M+H]$^+$ $^1$H NMR (DMSO-d$_6$, 400 MHz): δ 7.24-7.32 (m, 2H), 7.17 (d, J=7.34 Hz, 1H), 6.30 (d, J=2.93 Hz, 1H), 4.18 (dd, J=7.03, 14.24 Hz, 1H), 3.96-4.03 (m, 1H), 3.87 (s, 3H), 2.94-3.05 (m, 1H), 2.21 (s, 6H), 0.82 (d, J=6.60 Hz, 3H). $^{19}$F NMR (DMSO-d$_6$, 376 MHz): δ −146.29 (s, 1F).

Example 71. (R)-1-(5-fluoro-6-methyl-1H-indol-1-yl)-N,N-dimethylpropan-2-amine

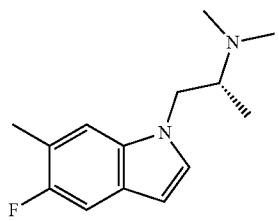 [SMILES: Cc1cc2c(ccn2C[C@@H](C)N(C)C)cc1F]

Step-C1: Yield: 69% (Pale brown liquid). $^1$H NMR (DMSO-d$_6$, 400 MHz): δ 7.33-7.37 (m, 1H), 7.30 (d, J=3.06 Hz, 1H), 7.22 (d, J=10.64 Hz, 1H), 6.32-6.34 (m, 1H), 4.84-4.87 (m, 1H), 3.91-4.08 (m, 3H), 2.32 (d, J=1.83 Hz, 3H), 1.03 (d, J=5.99 Hz, 3H).

Step-C2: Pale yellow solid. $^1$H NMR (DMSO-d$_6$, 400 MHz): δ 7.46 (d, J=6.48 Hz, 1H), 7.36 (d, J=3.06 Hz, 1H), 7.25 (d, J=10.64 Hz, 1H), 6.39-6.41 (m, 1H), 4.94-5.02 (m, 1H), 4.32-4.43 (m, 2H), 2.56 (s, 3H), 2.33 (d, J=1.83 Hz, 3H), 1.34 (d, J=6.36 Hz, 3H).

Step-C3: Yield: 24% (over two steps, pale brown liquid). $[\alpha]_D^{20}=-20.50$ (C 0.5, CH$_2$Cl$_2$). LC-MS: 99.3%, m/z=235.1 [M+H]$^+$ $^1$H NMR (DMSO-d$_6$, 400 MHz): δ 7.30-7.35 (m, 2H), 7.22 (d, J=10.64 Hz, 1H), 6.32 (d, J=3.06 Hz, 1H), 4.17 (dd, J=6.97, 14.18 Hz, 1H), 3.97 (dd, J=7.34, 14.18 Hz, 1H), 2.95-3.04 (m, 1H), 2.33 (d, J=1.59 Hz, 3H), 2.19 (s, 6H), 0.80 (d, J=6.60 Hz, 3H). $^{19}$F NMR (DMSO-d$_6$, 376 MHz): δ −130.78 (s, 1F).

Example 72. (R)-1-(5-fluoro-7-methyl-1H-indol-1-yl)-N,N-dimethylpropan-2-amine

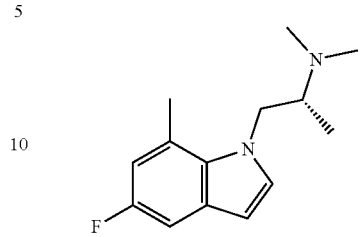

Step-C1: Yield: 72%, pale brown liquid). $^1$H NMR (DMSO-d$_6$, 400 MHz): δ 7.30 (d, J=3.06 Hz, 1H), 7.09 (dd, J=2.51, 9.35 Hz, 1H), 6.72 (dd, J=2.20, 10.39 Hz, 1H), 6.36 (d, J=3.06 Hz, 1H), 4.89 (d, J=5.14 Hz, 1H), 4.16-4.25 (m, 2H), 3.81-3.91 (m, 1H), 2.65 (s, 3H), 1.04 (d, J=6.24 Hz, 3H).

Step-C2: Yellow semi solid. $^1$H NMR (DMSO-d$_6$, 400 MHz): δ 7.39 (d, J=3.06 Hz, 1H), 7.13 (dd, J=2.45, 9.29 Hz, 1H), 6.78 (dd, J=1.96, 10.27 Hz, 1H), 6.44-6.46 (m, 1H), 4.89 (sxt, J=6.24 Hz, 1H), 4.50-4.60 (m, 2H), 2.66 (s, 3H), 2.46 (s, 3H), 1.35 (d, J=6.24 Hz, 3H).

Step-C3: Yield: 19% (over two steps, pale brown liquid). $[\alpha]_D^{20}=-2.43$ (C 0.5, CH$_2$Cl$_2$). LC-MS: 99.8%, m/z=235.1 [M+H]$^+$ $^1$H NMR (DMSO-d$_6$, 400 MHz): δ 7.30 (d, J=3.06 Hz, 1H), 7.09 (dd, J=2.45, 9.29 Hz, 1H), 6.73 (dd, J=2.02, 10.33 Hz, 1H), 6.35 (d, J=3.06 Hz, 1H), 4.38 (dd, J=6.30, 14.49 Hz, 1H), 4.11-4.18 (m, 1H), 2.82-2.92 (m, 1H), 2.65 (s, 3H), 2.19 (s, 6H), 0.76 (d, J=6.60 Hz, 3H). $^{19}$F NMR (DMSO-d$_6$, 376 MHz): δ −127.62 (s, 1F).

The 5-fluoro-7-methyl-1H-indole is prepared from 4-fluoro-2-methyl-1-nitrobenzene using Bartoli Indole synthesis (4-fluoro-2-methyl-1-nitrobenzene in THF (10 vol) was treated with 4 eq of 1M Vinyl Magnesium bromide at −40° C. for 3 h. After completion of the reaction by TLC, the reaction mixture was quenched with saturated NH$_4$Cl and extracted with EtOAc. The combined organic layer washed with brine followed by water to get the crude. The crude was purified by combi-flash using 5% EtOAc in hexane and the cleaner fractions are evaporated to get 5-fluoro-7-methyl-1H-indole with an isolated yield of 27%

Example 73. (R)-1-(5-fluoro-2-methyl-1H-indol-1-yl)-N,N-dimethylpropan-2-amine

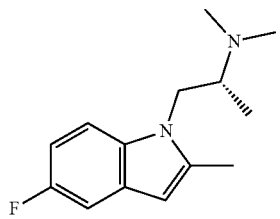 [SMILES: Cc1cc2cc(F)ccc2n1C[C@@H](C)N(C)C]

Step-C1: Yield: 33% (colorless liquid). $^1$H NMR (DMSO-d$_6$, 400 MHz): δ 7.36 (dd, J=4.52, 8.93 Hz, 1H), 7.13-7.17 (m, 1H), 6.81-6.87 (m, 1H), 6.17 (s, 1H), 4.86 (d, J=4.77 Hz, 1H), 3.89-4.05 (m, 3H), 2.40 (d, J=0.73 Hz, 3H), 1.08 (d, J=5.99 Hz, 3H).

Step-C2: Pale brown semi solid.

Step-C3: Yield: 10% (over two steps, colorless liquid). $[\alpha]_D^{20}$=−36.86 (C 0.25, CH$_2$Cl$_2$). LC-MS: 94.4%, m/z=235.2 [M+H]$^+$ $^1$H NMR (DMSO-d$_6$, 400 MHz): δ 7.34 (dd, J=4.52, 8.80 Hz, 1H), 7.15 (dd, J=2.45, 9.90 Hz, 1H), 6.86 (dt, J=2.57, 9.23 Hz, 1H), 6.18 (s, 1H), 4.16 (dd, J=6.42, 14.73 Hz, 1H), 3.93 (dd, J=7.58, 14.67 Hz, 1H), 2.92 (sxt, J=6.80 Hz, 1H), 2.40 (s, 3H), 2.22 (s, 6H), 0.81 (d, J=6.60 Hz, 3H). $^{19}$F NMR (DMSO-d$_6$, 376 MHz): δ −127.21 (s, 1F).

Example 74. (R)-1-(5-fluoro-3-methyl-1H-indol-1-yl)-N,N-dimethylpropan-2-amine

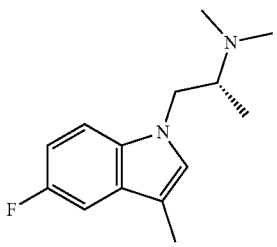 [SMILES: Cc1cn(C[C@@H](C)N(C)C)c2ccc(F)cc12]

Step-C1: Yield: 35% (pale brown liquid). $^1$H NMR (DMSO-d$_6$, 400 MHz): δ 7.41 (dd, J=4.52, 8.93 Hz, 1H), 7.16-7.23 (m, 2H), 6.89-6.95 (m, 1H), 4.85 (d, J=4.65 Hz, 1H), 3.87-4.04 (m, 3H), 2.20 (d, J=0.98 Hz, 3H), 1.02 (d, J=6.11 Hz, 3H).

Step-C2: Brown semi solid. $^1$H NMR (DMSO-d$_6$, 400 MHz): δ 7.49 (dd, J=4.46, 8.92 Hz, 1H), 7.20-7.26 (m, 2H), 6.95-7.01 (m, 1H), 4.91-4.99 (m, 1H), 4.34 (d, J=5.65 Hz, 2H), 2.63 (s, 3H), 2.21 (s, 3H), 1.31 (d, J=6.54 Hz, 3H).

Step-C3: Yield: 44% (over two steps, Brown liquid). $[\alpha]_D^{20}$=−18.4 (C 0.5, CH$_2$Cl$_2$). LC-MS: 95%, m/z=235.2 [M+H]$^+$ $^1$H NMR (DMSO-d$_6$, 400 MHz): δ 7.40 (dd, J=4.46, 8.86 Hz, 1H), 7.17-7.23 (m, 2H), 6.89-6.96 (m, 1H), 4.14 (dd, J=6.91, 14.24 Hz, 1H), 3.90-3.97 (m, 1H), 2.91-3.00 (m, 1H), 2.17-2.23 (m, 9H), 0.80 (d, J=6.60 Hz, 3H). $^{19}$F NMR (DMSO-d$_6$, 376 MHz): δ −127.47 (s, 1F).

Example 75. (R)-1-(5-methoxy-1H-indol-1-yl)-N,N-dimethylbutan-2-amine

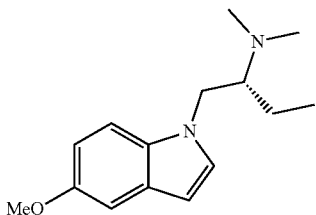 [SMILES: CC[C@H](Cn1ccc2cc(OC)ccc21)N(C)C]

Step-C1: The epoxide used in the reaction is (S)-2-ethyloxirane, the rest of the procedure is same as mentioned in the general procedure. Yield: 44% (pale brown solid). $^1$H NMR (DMSO-d$_6$, 400 MHz): δ 7.34 (d, J=8.93 Hz, 1H), 7.27 (d, J=3.06 Hz, 1H), 7.02 (d, J=2.32 Hz, 1H), 6.73-6.77 (m, 1H), 6.30 (dd, J=0.73, 3.06 Hz, 1H), 4.81 (d, J=5.50 Hz, 1H), 3.95-4.10 (m, 2H), 3.74 (s, 3H), 3.63-3.70 (m, 1H), 1.21-1.42 (m, 2H), 0.88 (t, J=7.40 Hz, 3H).

Step-C2: Pale yellow solid. $^1$H NMR (DMSO-d$_6$, 400 MHz): δ 7.43 (d, J=8.93 Hz, 1H), 7.34 (d, J=3.06 Hz, 1H), 7.04 (d, J=2.32 Hz, 1H), 6.80 (dd, J=2.45, 8.93 Hz, 1H), 6.38 (dd, J=0.73, 3.06 Hz, 1H), 4.81-4.87 (m, 1H), 4.41 (d, J=5.75 Hz, 2H), 3.75 (s, 3H), 2.53 (s, 3H), 1.65-1.76 (m, 1H), 1.54-1.63 (m, 1H), 0.97 (t, J=7.40 Hz, 3H).

Step-C3: Yield: 26% (over two steps, Brown solid). $[\alpha]_D^{20}$=−22.57 (C 0.5, CH$_2$Cl$_2$). LC-MS: 96.7%, m/z=247.2 [M+H]$^+$ $^1$H NMR (DMSO-d$_6$, 400 MHz): δ 7.27-7.33 (m, 2H), 7.03 (d, J=2.32 Hz, 1H), 6.75-6.78 (m, 1H), 6.31 (dd, J=0.73, 3.06 Hz, 1H), 4.17-4.24 (m, 1H), 3.94-4.00 (m, 1H), 3.74 (s, 3H), 2.69-2.76 (m, 1H), 2.23 (s, 6H), 1.40-1.51 (m, 1H), 1.07-1.19 (m, 1H), 0.81 (t, J=7.40 Hz, 3H).

Example 76. (S)-1-(5-methoxy-1H-indol-1-yl)-N,N-dimethylbutan-2-amine

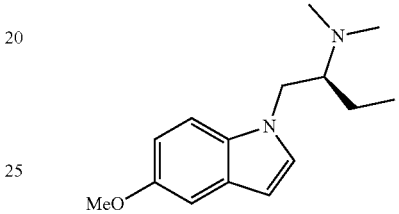

Step-C1: The epoxide used in the reaction is (R)-2-ethyloxirane, the rest of the procedure is same as mentioned in the general procedure. Yield: 34% (Pale brown liquid). $^1$H NMR (DMSO-d$_6$, 400 MHz): δ 7.34 (d, J=8.93 Hz, 1H), 7.27 (d, J=2.93 Hz, 1H), 7.02 (d, J=2.32 Hz, 1H), 6.75 (d, J=2.45, 8.93 Hz, 1H), 6.30 (d, J=2.93 Hz, 1H), 4.82 (d, J=5.50 Hz, 1H), 3.95-4.10 (m, 2H), 3.74 (s, 3H), 3.62-3.70 (m, 1H), 1.21-1.42 (m, 2H), 0.88 (t, J=7.40 Hz, 3H).

Step-C2: Pale brown solid. $^1$H NMR (DMSO-d$_6$, 400 MHz): δ 7.45 (d, J=8.93 Hz, 1H), 7.36 (d, J=3.06 Hz, 1H), 7.06 (d, J=2.45 Hz, 1H), 6.82 (dd, J=2.45, 8.93 Hz, 1H), 6.40 (dd, J=0.61, 3.06 Hz, 1H), 4.82-4.90 (m, 1H), 4.43 (d, J=5.75 Hz, 2H), 3.77 (s, 3H), 2.55 (s, 3H), 1.67-1.78 (m, 1H), 1.55-1.64 (m, 1H), 0.98 (t, J=7.46 Hz, 3H).

Step-C3: Yield: 52% (over two steps, Brown solid). $[\alpha]_D^{20}$=+24.8 (C 0.5, CH$_2$Cl$_2$). LC-MS: 99.68%, m/z=247.2 [M+H]$^+$ $^1$H NMR (DMSO-d$_6$, 400 MHz): δ 7.27-7.33 (m, 2H), 7.02 (d, J=2.38 Hz, 1H), 6.76 (dd, J=2.38, 8.80 Hz, 1H), 6.30-6.32 (m, 1H), 4.21 (dd, J=6.79, 14.31 Hz, 1H), 3.94-4.01 (m, 1H), 3.74 (s, 3H), 2.68-2.76 (m, 1H), 2.23 (s, 6H), 1.41-1.51 (m, 1H), 1.07-1.18 (m, 1H), 0.81 (t, J=7.43 Hz, 3H).

Example 77. (R)-1-(4,5-dimethoxy-1H-indol-1-yl)-N,N-dimethylpropan-2-amine

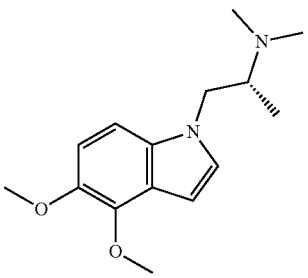

Step-C1: Yield: 75% (Pale brown liquid). ¹H NMR (DMSO-d₆, 400 MHz): δ 7.24 (d, J=3.18 Hz, 1H), 7.12 (dd, J=0.61, 8.80 Hz, 1H), 6.89-6.92 (m, 1H), 6.39 (dd, J=0.67, 3.12 Hz, 1H), 4.84 (d, J=4.65 Hz, 1H), 3.91-4.01 (m, 3H), 3.88 (s, 3H), 3.77 (s, 3H), 1.03 (d, J=5.99 Hz, 3H).

Step-C2: Pale brown liquid.

Step-C3: Yield: 18% (over two steps, brown liquid). $[\alpha]_D^{20}$=-11.7 (C 0.25, CH₂Cl₂). LC-MS: 99.83%, m/z=263.1 [M+H]⁺ ¹H NMR (DMSO-d₆, 400 MHz): δ 7.28 (d, J=3.06 Hz, 1H), 7.11 (d, J=8.80 Hz, 1H), 6.93 (d, J=8.80 Hz, 1H), 6.41 (d, J=3.06 Hz, 1H), 4.17 (dd, J=6.85, 14.18 Hz, 1H), 3.96 (dd, J=7.40, 14.24 Hz, 1H), 3.90 (s, 3H), 3.79 (s, 3H), 2.97-3.03 (m, 1H), 2.19 (s, 6H), 0.83 (d, J=6.60 Hz, 3H).

Example 78. (R)-1-(5-fluoro-3-methoxy-1H-indol-1-yl)-N,N-dimethylpropan-2-amine

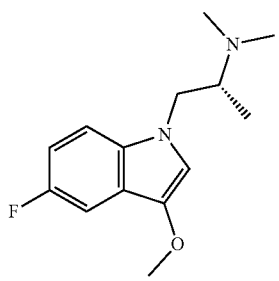 [SMILES: COc1cn(C[C@@H](C)N(C)C)c2ccc(F)cc12]

Step-C1: Yield: 50% (Brown liquid).

Step-C2: Pale yellow solid.

Step-C3: Yield: 3% (over two steps, pale brown liquid). $[\alpha]_D^{20}$=-17.6 (C 0.25, CH₂Cl₂). LC-MS: 99.13%, m/z=251.1 [M+H]⁺ ¹H NMR (DMSO-d₆, 400 MHz): δ 7.41 (dd, J=4.28, 9.05 Hz, 1H), 7.15 (dd, J=2.51, 9.48 Hz, 1H), 7.06 (s, 1H), 6.95 (dt, J=2.57, 9.23 Hz, 1H), 4.11 (dd, J=6.60, 14.18 Hz, 1H), 3.91 (dd, J=7.64, 14.24 Hz, 1H), 3.78 (s, 3H), 2.98 (sxt, J=6.90 Hz, 1H), 2.20 (s, 6H), 0.79 (d, J=6.60 Hz, 3H). ¹⁹F NMR (DMSO-d₆, 376 MHz): δ -127.6 (s, 1F).

Example 79. (R)-1-(5,6-dichloro-1H-indol-1-yl)-N,N-dimethylpropan-2-amine

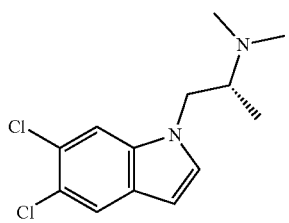 [SMILES: C[C@H](Cn1ccc2cc(Cl)c(Cl)cc21)N(C)C]

Step-C1: Yield: 45% (Pale brown solid). ¹H NMR (DMSO-d₆, 400 MHz): δ 7.85 (s, 1H), 7.78 (s, 1H), 7.45 (d, J=3.18 Hz, 1H), 6.43 (dd, J=0.67, 3.12 Hz, 1H), 4.85 (d, J=4.89 Hz, 1H), 4.11-4.16 (m, 1H), 3.99-4.05 (m, 1H), 3.90-3.97 (m, 1H), 1.05 (d, J=6.24 Hz, 3H).

Step-C2: Pale yellow semi-solid.

Step-C3: Yield: 30% (over two steps, pale brown liquid). $[\alpha]_D^{20}$=-24.14 (C 0.25, CH₂Cl₂). LC-MS: 96.9%, m/z=271.0 [M+H]⁺ ¹H NMR (DMSO-d₆, 400 MHz): δ 7.86 (s, 1H), 7.79 (s, 1H), 7.49 (d, J=3.06 Hz, 1H), 6.45 (d, J=3.06 Hz, 1H), 4.21 (dd, J=7.76, 14.37 Hz, 1H), 4.07 (dd, J=6.60, 14.31 Hz, 1H), 2.98-3.04 (m, 1H), 2.19 (s, 6H), 0.84 (d, J=6.60 Hz, 3H).

Procedure D

General synthetic scheme

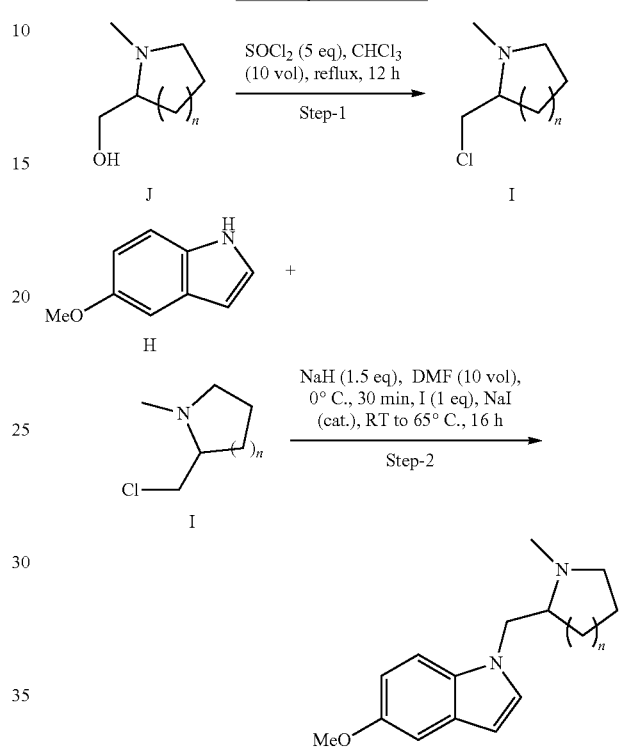

General Synthetic Procedures:

Step-D1: To a stirred solution of Compound J (1 eq) in CHCl₃ (10 vol) was added SOCl₂ (5 eq) at 0° C. and the resultant solution was heated at reflux temperature for 12 h. The progress of the reaction was monitored by TLC.

Work up after step-D1: Reaction mixture was evaporated and then co-evaporated with toluene (10 vol) for twice. Then the obtained crude was directly used in the next step.

Step-D2: To a stirred solution of Compound H (1.0 eq) in DMF (10 vol) was added NaH (60% in mineral oil, 1.5 eq) at 0° C. The reaction mixture was stirred for 30 min, then Compound I (1.0 eq) followed by NaI (cat.) were added. The reaction mixture was slowly warmed to room temperature, then warmed to 65° C. and stirred for 16 h. The progress of the reaction was monitored by TLC.

Work up and purification: Reaction mixture was cooled to RT, quenched with ice cold water and extracted with ethyl acetate. The combined organic layer was washed with ice cold water followed by aq. NaCl solution. The organic layer was separated, dried over Na₂SO₄ and concentrated to get crude material which was purified by combi-flash purification using 2 to 5% MeOH in CH₂Cl₂ and then the cleaner fractions (by TLC) were evaporated and dried under reduced pressure to obtain the desired product.

Example 80. (S)-5-methoxy-1-((1-methylpiperidin-2-yl)methyl)-1H-indole

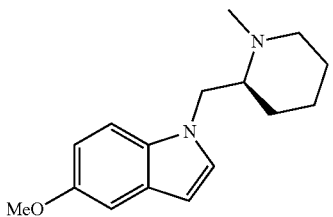 [SMILES: COc1ccc2c(ccn2C[C@@H]2CCCCN2C)c1]

Step-D1: (S)-(1-methylpiperidin-2-yl)methanol was treated with SOCl$_2$ using the general procedure shown above to get the respective chloride.

Step-D2: Yield: 13% (over two steps, pale brown semi solid). $[\alpha]_D^{20}$=−85.8 (C 0.25, CH$_2$Cl$_2$). LC-MS: 99%, m/z=259.1 [M+H]$^+$. $^1$H NMR (DMSO-d$_6$, 400 MHz): δ 7.28-7.35 (m, 2H), 7.03 (d, J=2.32 Hz, 1H), 6.76 (dd, J=2.45, 8.80 Hz, 1H), 6.32 (d, J=2.81 Hz, 1H), 4.44-4.50 (m, 1H), 3.89-3.96 (m, 1H), 3.74 (s, 3H), 2.75-2.82 (m, 1H), 2.36 (br s, 3H), 2.24-2.31 (m, 1H), 1.97-2.08 (m, 1H), 1.37-1.58 (m, 3H), 1.05 (br d, J=9.05 Hz, 3H).

Example 81. (S)-5-methoxy-1-((1-methylpyrrolidin-2-yl)methyl)-1H-indole

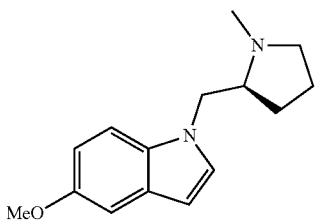 [SMILES: COc1ccc2c(ccn2C[C@@H]2CCCN2C)c1]

Step-D1: (S)-(1-methylpyrrolidin-2-yl)methanol was treated with SOCl$_2$ using the general procedure shown above to get the respective chloride.

Step-D2: Yield: 11% (over two steps, brown liquid). $[\alpha]_D^{20}$=−62.7 (C 0.45, CH$_2$Cl$_2$). LC-MS: 98.14%, m/z=245.2 [M+H]$^+$. $^1$H NMR (DMSO-d$_6$, 400 MHz): δ 7.29-7.38 (m, 2H), 7.02 (d, J=2.45 Hz, 1H), 6.76 (dd, J=2.38, 8.86 Hz, 1H), 6.31 (d, J=2.93 Hz, 1H), 4.19 (dd, J=5.07, 14.12 Hz, 1H), 3.98 (dd, J=6.72, 14.18 Hz, 1H), 3.74 (s, 3H), 2.94 (td, J=4.33, 9.08 Hz, 1H), 2.52-2.58 (m, 1H), 2.10-2.22 (m, 4H), 1.53-1.75 (m, 3H), 1.42-1.50 (m, 1H).

Example 82. (R)-5-methoxy-1-((1-methylpiperidin-2-yl)methyl)-1H-indole

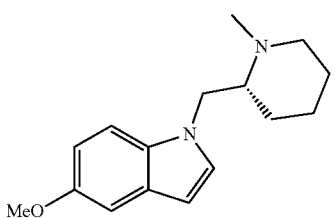 [SMILES: COc1ccc2c(ccn2C[C@H]2CCCCN2C)c1]

Prepared according to Procedure D. Yield: 6% (over two steps, brown solid). $[\alpha]_D^{20}$=+101.19 (C 0.5, CH$_2$Cl$_2$). LC-MS: 97.4%, m/z=259.2 [M+H]$^+$. $^1$H NMR (DMSO-d$_6$, 400 MHz): δ 7.27-7.35 (m, 2H), 7.03 (d, J=2.45 Hz, 1H), 6.76 (dd, J=2.45, 8.93 Hz, 1H), 6.32 (d, J=2.93 Hz, 1H), 4.46 (dd, J=4.28, 14.06 Hz, 1H), 3.92 (dd, J=8.50, 14.12 Hz, 1H), 3.74 (s, 3H), 2.76-2.81 (m, 1H), 2.35 (s, 3H), 2.25-2.30 (m, 1H), 1.99-2.06 (m, 1H), 1.36-1.57 (m, 3H), 1.00-1.10 (m, 3H).

Example 83. (R)-5-methoxy-1-((1-methylpyrrolidin-2-yl)methyl)-1H-indole

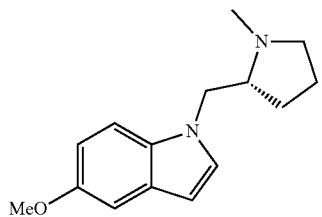 [SMILES: COc1ccc2c(ccn2C[C@H]2CCCN2C)c1]

Step-D1: (R)-(1-methylpyrrolidin-2-yl)methanol was treated with SOCl$_2$ using the general procedure shown above to get the respective chloride.

Step-D2: After combi-flash purification 80% pure product was obtained and this was further purified by prep-HPLC purification to get cleaner final compound.

Prep-HPLC purification details are shown below:
Preparative HPLC Column: Chiralpak IG (250*30 mm, 5 μ)
Mobile Phase A: 0.1% DEA in n-Hexane
Mobile Phase B: EtOH:MeOH (50:50)
Flow rate: 35.0 mL/min

| Isocratic Table: | | |
|---|---|---|
| Time | % A | % B |
| 20 | 20 | 80 |
| 2.00 | 20 | 80 |

Solvents used for dilution: Methanol/Ethanol.

Yield: 11% (over two steps, colorless solid). $[\alpha]_D^{20}$=+79.47 (C 0.5, CH$_2$Cl$_2$). LC-MS: 99.9%, m/z=245.1 [M+H]$^+$. $^1$H NMR (DMSO-d$_6$, 400 MHz): δ 7.29-7.38 (m, 2H), 7.02 (d, J=2.32 Hz, 1H), 6.76 (dd, J=2.38, 8.86 Hz, 1H), 6.31 (d, J=2.93 Hz, 1H), 4.16-4.22 (m, 1H), 3.95-4.01 (m, 1H), 3.74 (s, 3H), 2.94 (td, J=4.37, 9.11 Hz, 1H), 2.52-2.58 (m, 1H), 2.18 (s, 3H), 2.09-2.15 (m, 1H), 1.53-1.72 (m, 3H), 1.41-1.50 (m, 1H).

Procedure E

General synthetic scheme

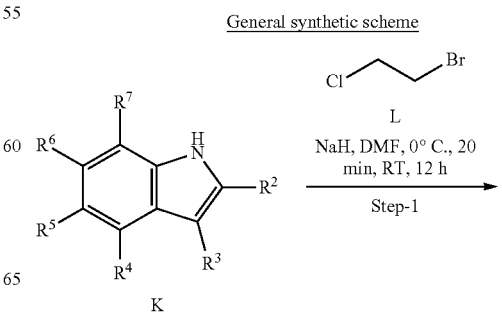

-continued

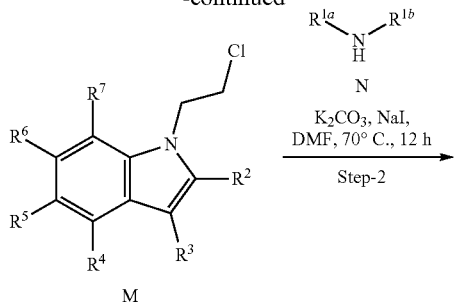

General Synthetic Procedures:

Step-E1: To a stirred solution of K (1.0 eq) in DMF (10 vol) was added NaH (60% in mineral oil, 1.2 eq) at 0° C. and the reaction mixture was stirred for 20 min. Reagent L (1.0 eq) was added to the reaction that was then slowly warmed to room temperature and stirred for 16 h. The progress of the reaction was monitored by TLC. TLC indicated a non-polar spot with respect to K.

Work up after step-E1: The reaction mixture was quenched with ice cold water and extracted with ethyl acetate. The combined organic layer was washed with ice cold water followed by brine wash. The organic layer was separated, dried over $Na_2SO_4$ and concentrated under reduced pressure to get crude material which was purified by combi-flash chromatography using EtOAc/Heptane and then the cleaner fractions are evaporated to obtain M.

Step-E2: To a stirred solution of M (1.0 eq) in DMF (10 vol) were added $K_2CO_3$ (3 eq) followed by reagent N (1.2 eq) and NaI (1 eq) at room temperature and then the reaction mixture was heated at 70° C. for 16 h. The progress of the reaction was monitored by TLC. TLC indicated a polar spot with respect to M.

Work up after Step-E2: The reaction mixture was quenched with ice cold water and extracted with ethyl acetate. The combined organic layer was washed with ice cold water followed by brine wash. The organic layer was separated, dried over $Na_2SO_4$ and concentrated under reduced pressure to get crude material which was purified by combi-flash chromatography using $CH_2Cl_2$/MeOH based and then cleaner fractions (by TLC) were evaporated and dried to obtain the target compound with >95% LC-MS and HPLC purity.

Example 84. 6-(2-(5-methoxy-1H-indol-1-yl)ethyl)-2-oxa-6-azaspiro[3.3]heptane

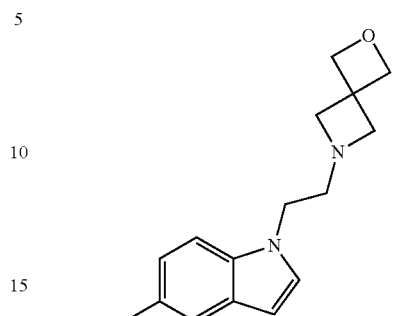

Prepared according to Procedure E. Yield: 38% (over 2-steps), colorless liquid. LC-MS: 99%, m/z=273.2.1 $[M+H]^+$. $^1$H NMR (DMSO-$d_6$, 400 MHz): δ 7.32 (d, J=8.93 Hz, 1H), 7.26 (d, J=3.06 Hz, 1H), 7.02 (d, J=2.32 Hz, 1H), 6.75 (dd, J=2.38, 8.86 Hz, 1H), 6.30 (d, J=2.93 Hz, 1H), 4.52 (s, 4H), 4.04 (t, J=6.30 Hz, 2H), 3.74 (s, 3H), 3.17 (s, 4H), 2.63-2.67 (m, 2H).

Example 85. 6-(2-(5-chloro-1H-indol-1-yl)ethyl)-2-oxa-6-azaspiro[3.3]heptane

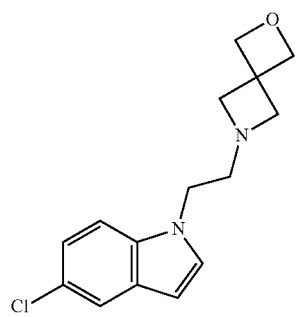 [SMILES: Clc1ccc2c(ccn2CCN2CC3(COC3)C2)c1]

Prepared according to Procedure E. Yield: 25% (over 2-steps), brown liquid. LC-MS: 97.3%, m/z=277.0 $[M+H]^+$. $^1$H NMR (DMSO-$d_6$, 400 MHz): δ 7.57 (d, J=1.96 Hz, 1H), 7.46-7.49 (m, 1H), 7.40 (d, J=3.06 Hz, 1H), 7.09-7.12 (m, 1H), 6.40 (d, J=3.06 Hz, 1H), 4.52 (s, 4H), 4.08-4.11 (m, 2H), 3.18 (s, 4H), 2.67 (t, J=6.11 Hz, 2H).

Example 86. (R)-1-(5-methoxy-2-methyl-1H-indol-1-yl)-N,N-dimethylpropan-2-amine

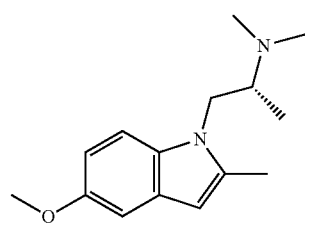

Prepared according to Procedure C. $^1$H NMR (DMSO-$d_6$, 400 MHz): δ 7.20 (d, J=8.8 Hz, 1H), 6.95 (d, J=2.4 Hz, 1H), 6.73 (dd, J=8.8 Hz, J=2.4 Hz, 1H), 6.14 (s, 1H), 4.29 (dd, J=4.8, 14.4 Hz, 1H), 4.06-3.99 (m, 1H), 3.79 (s, 3H), 3.25-3.10 (m, 1H), 2.48 (s, 6H), 2.42 (d, J=0.4 Hz, 3H), 0.92 (d, J=6.4 Hz, 3H). LCMS: 247.1 [M+H]$^+$.

Results and Discussion

SAR studies were performed by comparing the effect of DMT (1) to that of 1-Me-DMT (27) and isoDMT (2). While DMT has the potential to serve as a hydrogen bond donor when bound to its target receptors, 27 and 2 do not. Therefore, this potential hydrogen bonding interaction may not be critical for a compound to induce plasticity, as both 27 and 2 increased dendritic arbor complexity to a comparable extent as 1, despite lacking an indole N—H bond (FIG. 2).

5-MeO-DMT (28) and 6-F-DMT (29) as electron-rich and electron-poor DMT analogs, respectively were chosen. Compound 28 promotes neuritogenesis in the dentate gyrus and alleviate symptoms of depression and anxiety in humans. Compound 29 is predicted to be non-hallucinogenic, as fluorination of DMT analogs attenuates hallucinogenic potential. isoDMT analogs Example 5 and 13 performed identically to 28 and 29 (FIG. 3), suggesting that SAR data related to neuronal growth obtained using derivatives of the isoDMT scaffold may be applied to derivatives of the DMT scaffold through analogy due to the isosteric nature of the two structures.

Various isoDMT analogs were used to establish the key features of the psychoplastogen pharmacophore (FIG. 4). Removing the basic amine of isoDMT to produce 25 yielded a molecule that did not promote dendritogenesis. Furthermore, compound 31—the N,N-dimethylamide analog of isoDMT—did not promote neuronal growth, confirming the hypothesis that a basic nitrogen is necessary to promote plasticity (FIGS. 4A and 4B). Extending the distance between the aromatic ring and the amine by one carbon (26) resulted in only a slight decrease in the $N_{max}$ value (FIG. 4B).

Modification of the aromatic ring was generally well tolerated (FIG. 4C). Converting the indole into a benzimidazole (22), pyrrole (23), or carbazole (24) had a minimal effect on the ability of these molecules to promote neuronal growth. Moreover, substitution at the 2- and 3-positions of the indole (16 and 21, respectively) was well tolerated. Taken together, the minimal psychoplastogen pharmacophore appears to involve a modifiable aromatic ring separated from a basic nitrogen by a short linker.

Substitution on the benzene ring of both DMTs and isoDMTs impacts hallucinogenic potential. For example, 5-MeO-DMT (28) substitutes for the hallucinogen 2,5-dimethoxy-4-methylamphetamine (DOM) in rats trained to discriminate DOM from saline, whereas 6-MeO-DMT does not. Similarly, 6-MeO-isoDMT (5) substitutes for a hallucinogenic training drug while 5-MeO-isoDMT (Example 5) does not. Therefore, three series of analogs substituted with either methoxy (electron-donating; Example 3-6), benzyloxy (electron-donating, but sterically demanding; 8-11), or fluoro (electron-withdrawing; 12-15) groups (FIG. 5) were synthesized and tested. Substitution of the 5-, 6-, and 7-positions were well tolerated regardless of the substituent. However, substitution at the 4-position resulted in compounds incapable of increasing dendritic arbor complexity. Even a fluorine substituent with a very small van der Waals radius (1.2 and 1.47 for H and F, respectively) was not tolerated.

Figure 6:
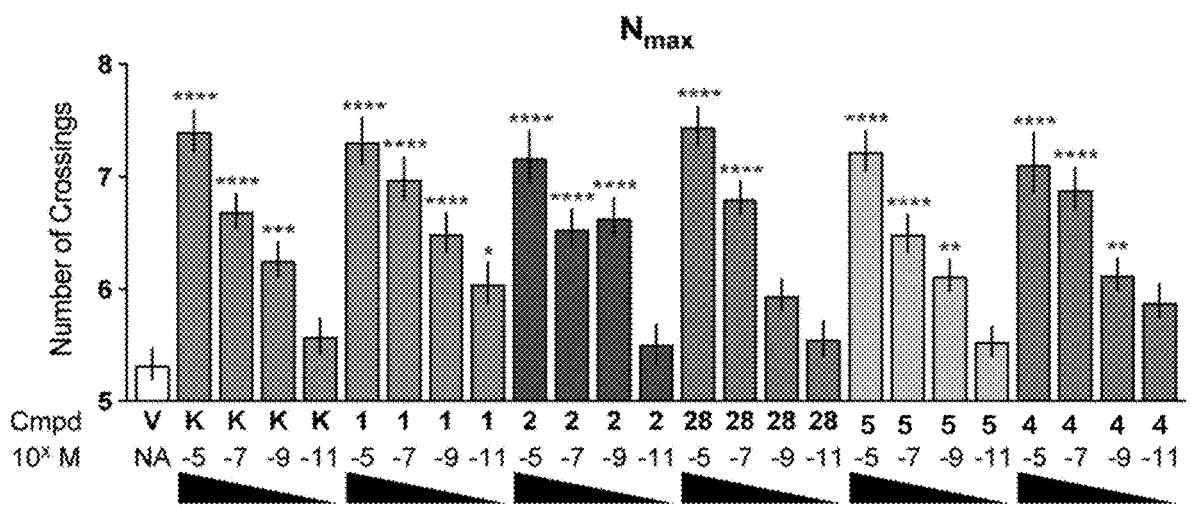
FIG. 6 shows concentration-response experiments demonstrate that DMTs and isoDMTs have similar psychoplastogenic potencies. Maximum number of crossings ($N_{max}$) of the Sholl plots for cortical neurons treated with compounds at concentrations ranging from 10 µM to 10 pM (n=66-123 neurons). Data are represented as mean±SEM. *p<0.05, p<0.01, *p<0.001, ****p<0.0001, as compared to vehicle control following a one-way ANOVA with Dunnett's post hoc test (F=15.40; DFn=24; DFd=2,276; p-value<0.0001). V=vehicle, K=ketamine.

To determine if DMT and isoDMT derivatives exhibited differences in psychoplastogenic potency, concentration-response experiments were performed (FIG. 6). isoDMT analogs (2 and Example 5) produced comparable maximum efficacies and had similar potencies as isosteric DMTs (1 and 28). Moreover, they were capable of increasing dendritic arbor complexity at concentrations as low as 1 nM. These compounds exhibited comparable efficacies and potencies to ketamine, further emphasizing their potential as antidepressants. Finally, compound Example 4 proved to be an exceptional psychoplastogen, which is highly significant due to its low hallucinogenic potential in both drug-discrimination and head-twitch response (HTR) assays (FIG. 8).

DMT and other psychedelic compounds promote increased dendritic arbor complexity, dendritic spine density, and synaptogenesis through a 5-HT$_{2A}$-dependent process. Pretreating cortical cultures with a 5-HT$_{2A}$ antagonist blocked the ability of 5-MeO-DMT (28) to increase dendritic growth (FIG. 7). Importantly, the psychoplastogenic effects of isoDMTs were also blocked under these conditions, implicating the 5-HT$_{2A}$ receptor in their mechanism of action (FIG. 7).

Figure 9:
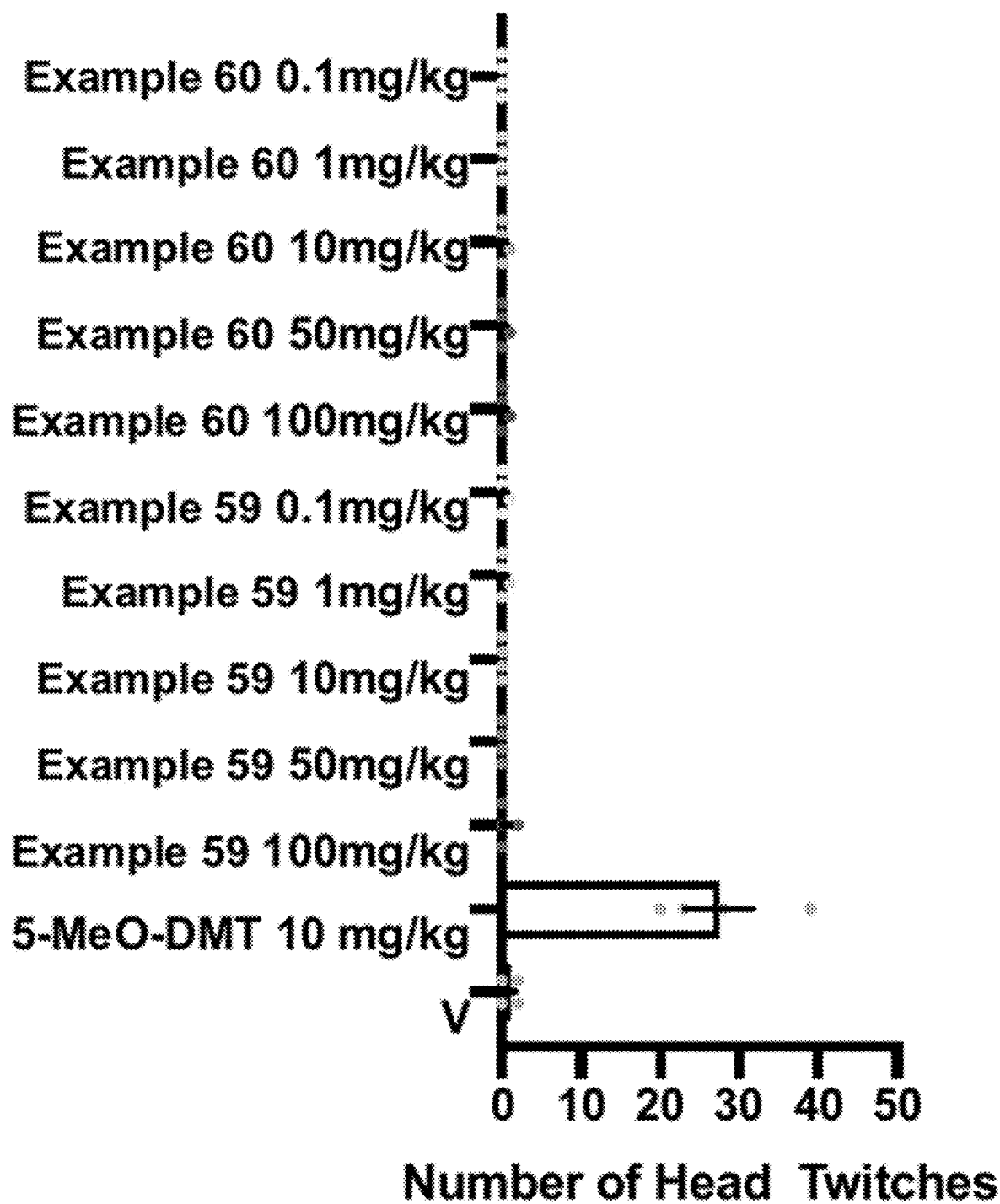
FIG. 9 displays the ability of the compounds of the invention to reduce the head-twitch behavioral response in a head twitch response assay.

Hallucinogenic Potential. Hallucinogenic compound 5-MeO-DMT (28) produces a robust, dose-dependent HTR that was greater in female mice. However, the isosteric compound 6-MeO-isoDMT (Example 5) is significantly less potent (FIG. 8). As expected based on drug-discrimination data, 6-MeO-DMT (30) did not produce a HTR. Finally, potent plasticity-promoting compounds (Example 4, Example 59, and Example 60) did not produce any HTR (FIG. 8 and FIG. 9), demonstrating that hallucinogenic potential and psychoplastogenicity can be decoupled.

Figure 10:
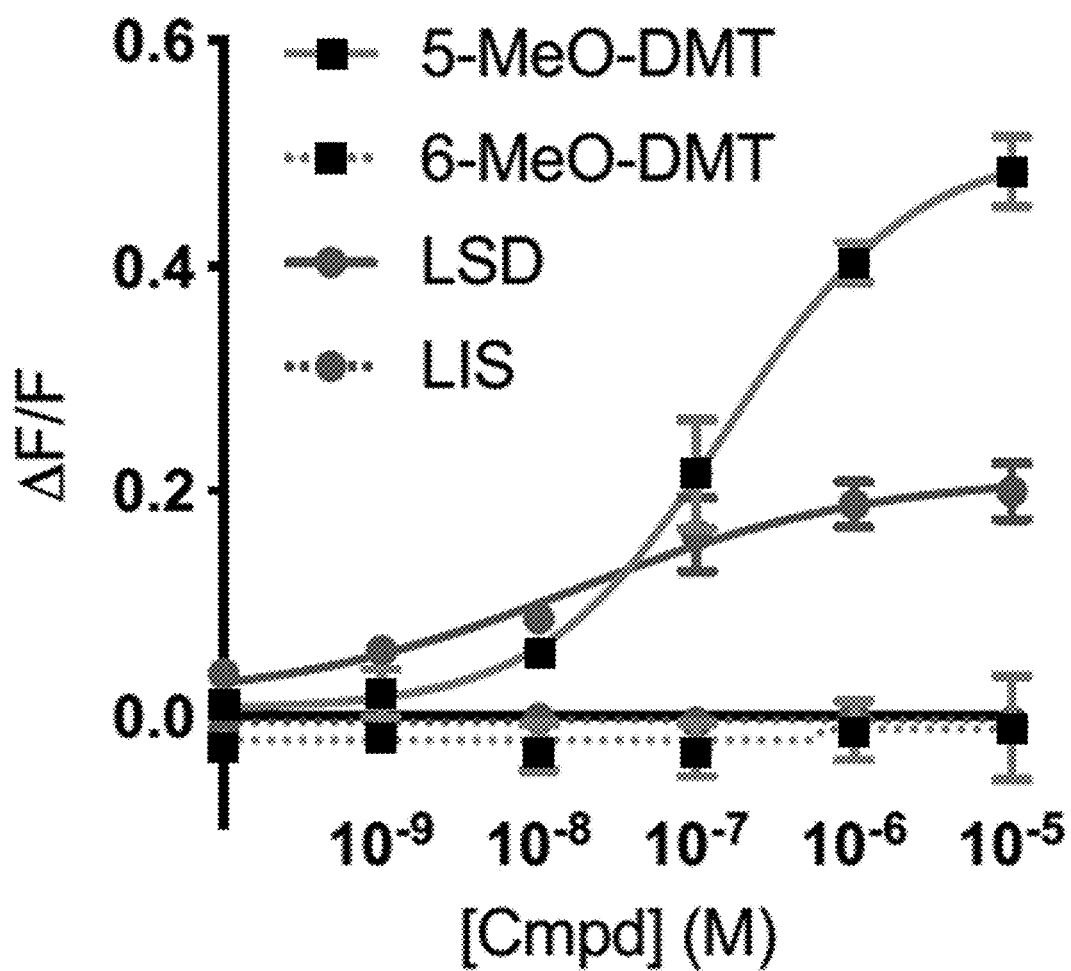
FIG. 10 shows the dose response profile of hallucinogenic and non-hallucinogenic compounds to a $5HT_{2A}$ sensor assay in agonist mode.
Figure 11:
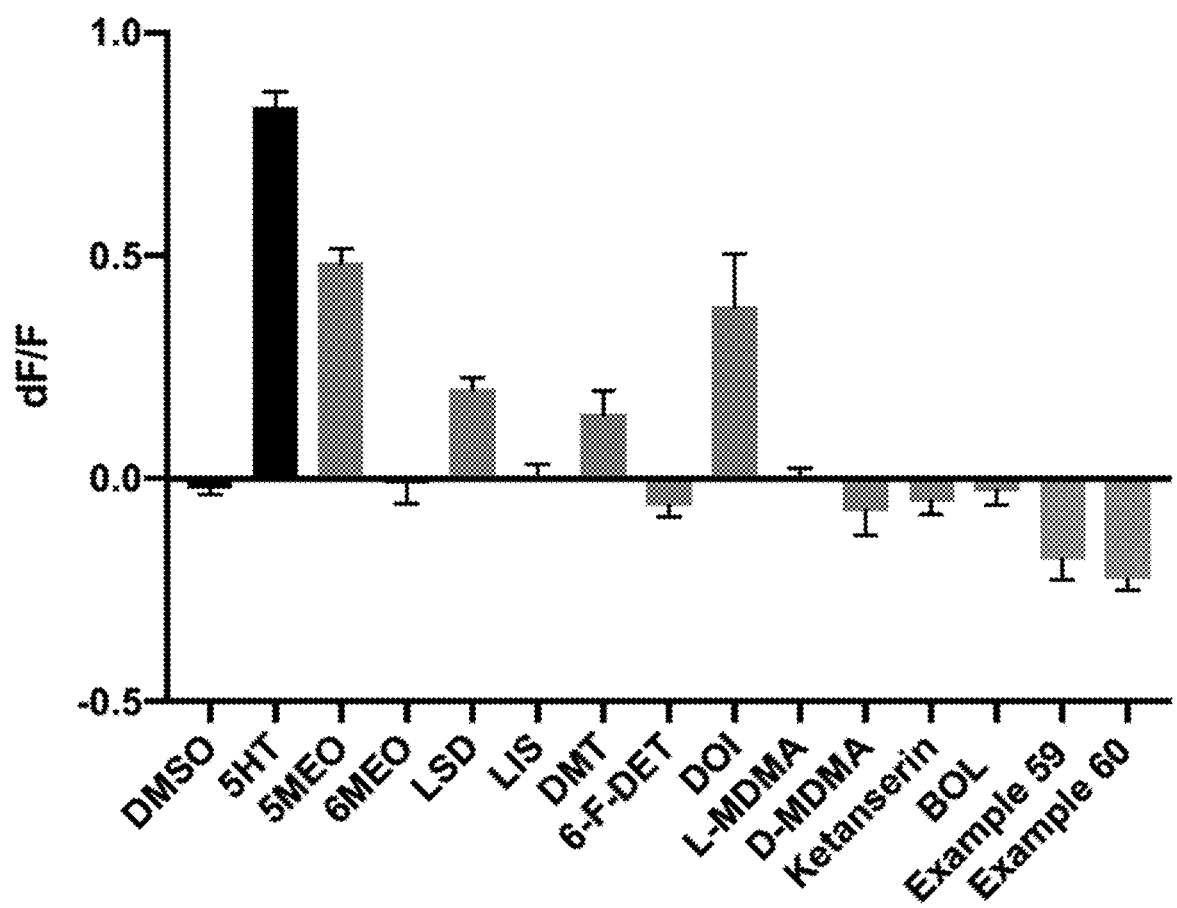
FIG. 11 shows the response profile of hallucinogenic and non-hallucinogenic compounds (at 10 µM) to a $5HT_{2A}$ sensor assay in agonist mode.

Hallucinogens (e.g., LSD and 5-MeO-DMT) activate a 5HT$_{2A}$ sensor assay in agonist mode, but their non-hallucinogenic congeners (lisuride (LIS) and 6-MeO-DMT) do not (FIG. 10). Moreover, compounds, such as, for example, 5-MeO-DMT, LSD, DMT, DOI, which are hallucinogenic in animals (e.g., humans), activate the 5HT$_{2A}$ sensor assay in agonist mode, whereas compounds, such as, for example, 6-MeO-DMT, LIS, 6-F-DET, L-MDMA, R-MDMA, Ketanserin, BOL148, which are non-hallucinogenic in animals (e.g., humans), do not activate the 5HT$_{2A}$ sensor assay in agonist mode (FIG. 11, at 10 µM of compound). In some embodiments, hallucinogenic potential of a compound of the present invention is determined in vitro. In some embodiments, hallucinogenic potential of a compound of the present invention is determined using a 5HT$_{2A}$ sensor assay. In some embodiments, the 5HT$_{2A}$ sensor assay is in an agonist mode or an antagonist mode. In some embodiments, the 5HT$_{2A}$ sensor assay is in an agonist mode. In some embodiments, a compound of the present invention that does not activate the sensor in agonist mode has non-hallucinogenic potential. In some embodiments, a compound of the present invention that does not activate the sensor in agonist mode is a non-hallucinogenic compound.

In some embodiments, the hallucinogenic potential of the compounds assessed in agonist mode is shown in Table 1.

TABLE 1

| Compound | 5HT$_{2A}$ Agonist mean @ 100 µM (%) | 5HT$_{2A}$ Agonist mean @ 10 µM (%) | 5HT$_{2A}$ Agonist mean @ 100 nM (%) |
|---|---|---|---|
| Example 3 | B | B | B |
| Example 4 | A | B | B |
| Example 5 | A | B | B |
| Example 6 | B | B | B |
| Example 44 | B | B | B |
| Example 45 | B | B | B |
| Example 46 | B | B | B |

TABLE 1-continued

| Compound | 5HT$_{2A}$ Agonist mean @ 100 μM (%) | 5HT$_{2A}$ Agonist mean @ 10 μM (%) | 5HT$_{2A}$ Agonist mean @ 100 nM (%) |
|---|---|---|---|
| Example 47 | B | B | B |
| Example 48 | B | B | B |
| Example 49 | A | B | B |
| Example 50 | A | B | B |
| Example 51 | B | B | B |
| Example 52 | A | B | B |
| Example 57 | B | B | B |
| Example 58 | A | B | B |
| Example 59 | B | B | B |
| Example 60 | A | B | B |
| Example 61 | B | B | B |
| Example 62 | A | B | B |
| Example 63 | B | B | B |
| Example 65 | B | B | B |
| Example 67 | B | B | B |
| Example 68 | A | B | B |
| Example 69 | A | B | B |
| Example 70 | B | B | B |
| Example 73 | A | B | B |
| Example 74 | B | B | B |
| Example 75 | B | B | B |
| Example 76 | B | B | B |
| Example 84 | A | B | B |

A: activates 5HT$_{2A}$ sensor assay in agonist mode;
B: does not activate 5HT$_{2A}$ sensor assay in agonist mode.
The percent is relative to the positive control (5-HT at 100 uM for agonist mode).
A compound that produces >15% response is considered to activate the sensor in agonist mode.

Figure 12A:
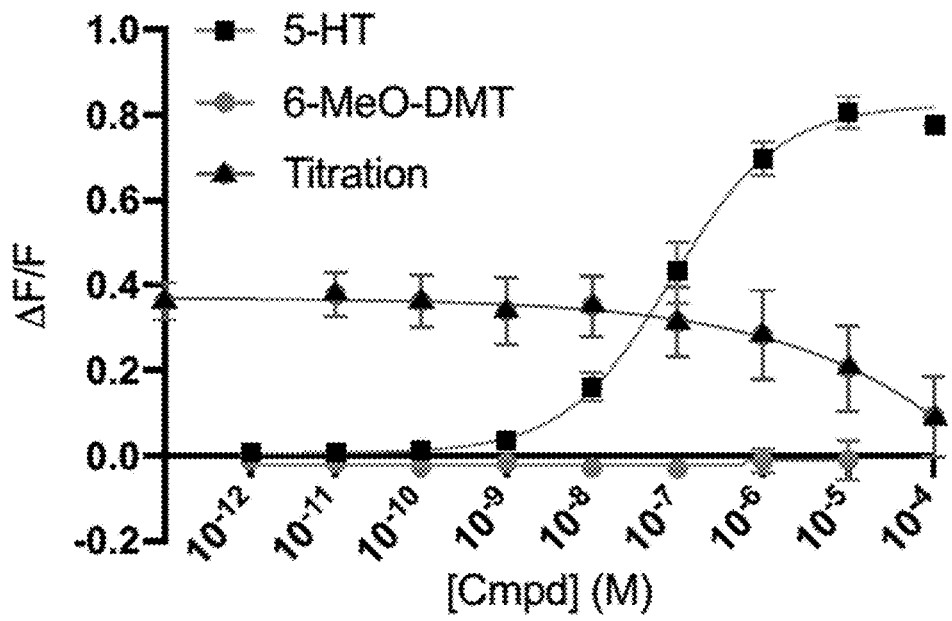
FIG. 12A shows the dose response profile of 5HT, 6-MeO-DMT.
Figure 12B:
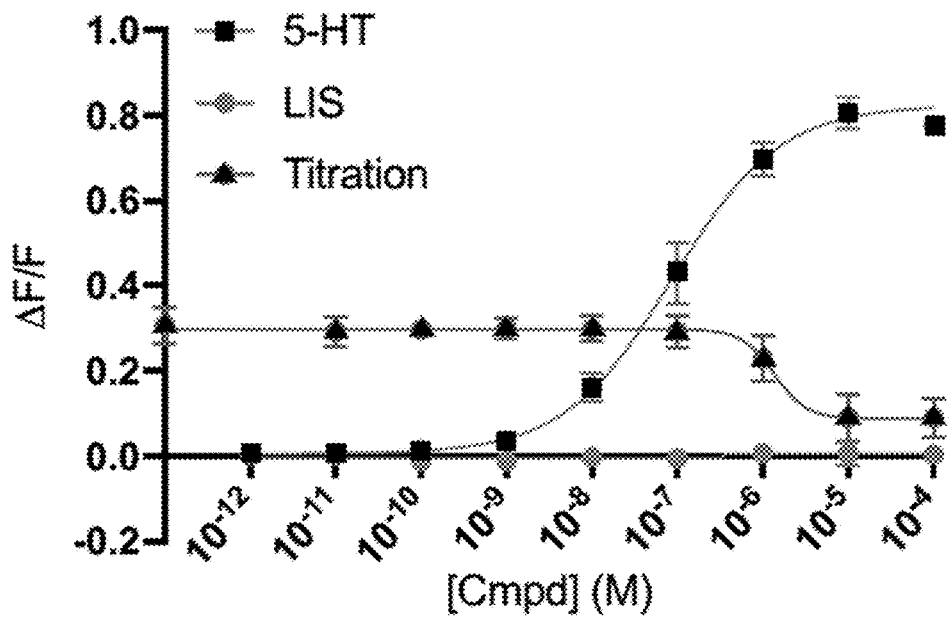
FIG. 12B shows the dose response of lisuride to a $5HT_{2A}$ sensor assay in antagonist mode.
Figure 13:
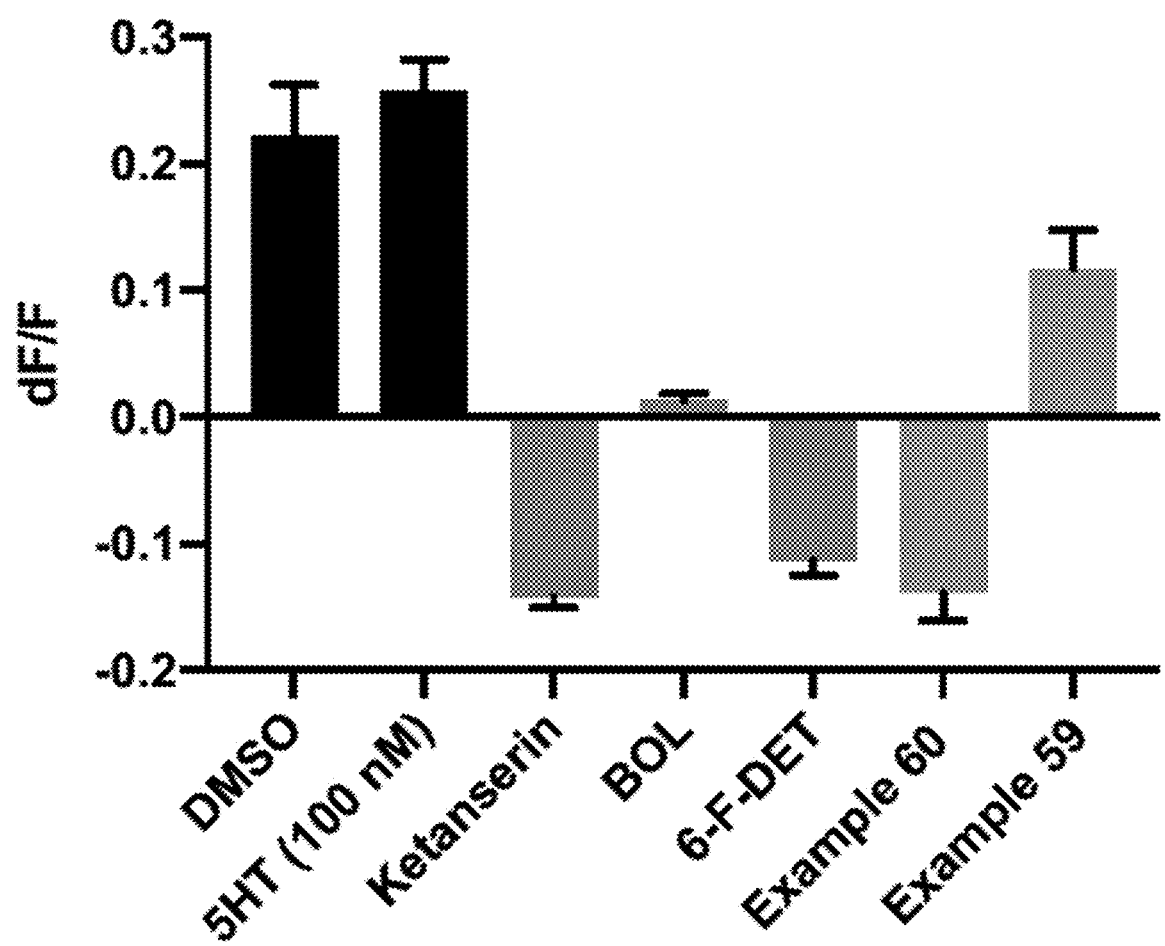
FIG. 13 shows the response profile of hallucinogenic and non-hallucinogenic compounds (at 10 µM) to a $5HT_{2A}$ sensor assay in antagonist mode.

Furthermore, non-hallucinogenic compounds (e.g., lisuride and 6-MeO-DMT) compete off 5-HT when the 5HT$_{2A}$ sensor assay is run in antagonist mode (FIG. 12A and FIG. 12B). Additionally, compounds, such as, for example, 6-F-DET, Ketanserin, BOL148, which are non-hallucinogenic in animals (e.g., humans), compete with 5HT binding to 5HT$_{2A}$ in the antagonist mode sensor assay (FIG. 13, at 10 μM of compound). In some embodiments, a compound of the present invention that prevents binding of 5-HT to 5HT$_{2A}$. In some embodiments, the 5HT$_{2A}$ sensor assay is in an antagonist mode. In some embodiments, a compound of the present invention that prevents binding of 5-HT to 5HT$_{2A}$ and has non-hallucinogenic potential. In some embodiments, a compound of the present invention that prevents binding of 5-HT to 5HT$_{2A}$ and is non-hallucinogenic. In some embodiments, a compound of the present invention that prevents binding of 5-HT to 5HT$_{2A}$ in antagonist mode has non-hallucinogenic potential. In some embodiments, a compound of the present invention that prevents binding of 5-HT in antagonist mode is a non-hallucinogenic compound. In some embodiments, a compound of the present invention that inhibits the response of the sensor assay in antagonist mode has non-hallucinogenic potential. In some embodiments, a compound of the present invention that inhibits the response of the sensor assay in antagonist mode is a non-hallucinogenic compound.

In some embodiments, the results for the agonist mode sensor assay suggests a compound of the present invention is a non-hallucinogenic ligand of the 5-HT$_{2A}$ receptor. In some embodiments, the results for the antagonist mode sensor assay suggests a compound of the present invention is a non-hallucinogenic ligand of the 5-HT$_{2A}$ receptor. In some embodiments, the results for the agonist mode and antagonist mode sensor assay together suggest a compound of the present invention is a non-hallucinogenic ligand of the 5-HT$_{2A}$ receptor.

In some embodiments, the hallucinogenic potential of the compounds assessed in antagonist mode is shown in Table 2.

TABLE 2

| Compound | 5HT$_{2A}$ Antagonist mean @ 100 μM (%) | 5HT$_{2A}$ Antagonist mean @ 10 μM (%) | 5HT$_{2A}$ Antagonist mean @ 100 nM (%) |
|---|---|---|---|
| Example 3 | A | A | A |
| Example 4 | B | B | C |
| Example 5 | B | B | B |
| Example 6 | A | A | A |
| Example 44 | A | A | C |
| Example 45 | A | B | A |
| Example 46 | A | A | A |
| Example 47 | A | A | A |
| Example 48 | A | A | A |
| Example 49 | C | B | A |
| Example 50 | A | B | A |
| Example 51 | A | A | A |
| Example 52 | B | B | A |
| Example 57 | A | A | B |
| Example 58 | A | A | A |
| Example 59 | A | A | B |
| Example 60 | B | B | C |
| Example 61 | A | A | A |
| Example 62 | A | B | B |
| Example 63 | A | B | B |
| Example 65 | A | A | C |
| Example 67 | A | A | A |
| Example 68 | A | A | B |
| Example 69 | B | B | B |
| Example 70 | A | B | B |
| Example 73 | A | B | B |
| Example 74 | B | A | A |
| Example 75 | A | A | A |
| Example 76 | A | A | A |
| Example 84 | B | B | B |

A: inhibits 5HT response by >100%;
B: inhibits 5HT response by 75% to 100%;
inhibits 5HT response by <75%.
the percent is relative to the positive control
(5-HT at 100 nM for antagonist mode).

Calcium Flux Assay. Calcium Secondary Messenger Pathway. The Calcium No Wash$^{PLUS}$ assay monitors the activation of a GPCR (e.g., 5HT$_{2A}$) via Gq secondary messenger signaling in a live cell, non-imaging assay format. Calcium mobilization in PathHunter® cell lines or other cell lines stably expressing Gq-coupled GPCRs (e.g., 5HT$_{2A}$) is monitored using a calcium-sensitive dye that is loaded into cells. GPCR (e.g., 5HT$_{2A}$) activation by a compound results in the release of calcium from intracellular stores and an increase in dye fluorescence that is measured in real-time. In some embodiments, the ability of a compound of the present invention to modulate 5-HT$_{2A}$ function is determined using a calcium flux assay. In some embodiments, a compound of the present invention activates a calcium flux assay. In some embodiments, the activation of a calcium flux assay indicates that a compound of the present invention modulates 5-HT$_{2A}$ function.

In some embodiments, the ability of the compounds of the present invention to modulate 5-HT$_{2A}$ function is assessed from the results of the calcium flux assay (Table 3).

TABLE 3

| Compound | EC$_{50}$ (μM) |
|---|---|
| Example 3 | A |
| Example 4 | A |
| Example 5 | B |
| Example 6 | B |
| Example 44 | A |
| Example 45 | A |

TABLE 3-continued

| Compound | EC$_{50}$ (µM) |
|---|---|
| Example 46 | A |
| Example 47 | B |
| Example 48 | A |
| Example 49 | A |
| Example 50 | A |
| Example 51 | A |
| Example 52 | A |
| Example 57 | A |
| Example 58 | A |
| Example 59 | A |
| Example 60 | A |
| Example 61 | A |
| Example 62 | A |
| Example 63 | A |
| Example 65 | A |
| Example 67 | A |
| Example 68 | A |
| Example 69 | A |
| Example 70 | B |
| Example 73 | A |
| Example 74 | A |
| Example 75 | A |
| Example 76 | A |
| Example 84 | A |

A: >10 µM;
B: <10 µM.

Figure 14A:
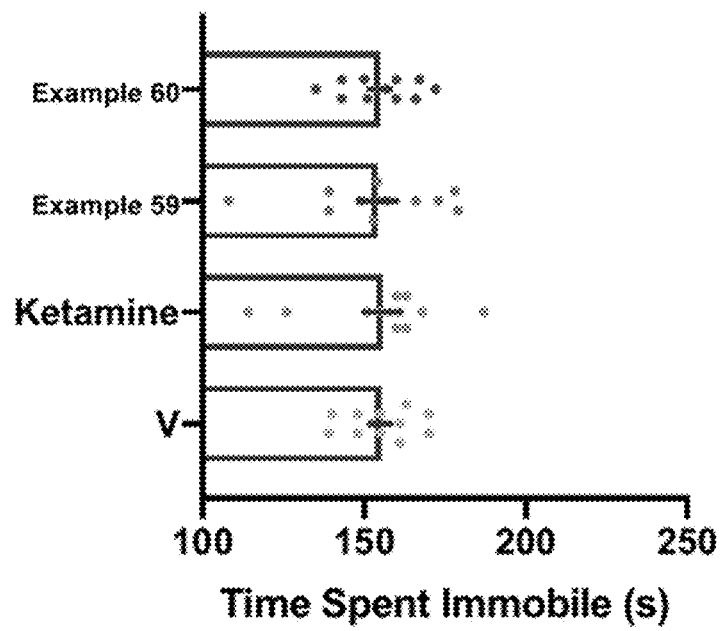
FIG. 14A and FIG. 14B show the anti-depressant characteristics of compounds of the invention in a forced swim test assay in both pretest (FIG. 14A) and acute (FIG. 14B) compound administration.
Figure 14B:
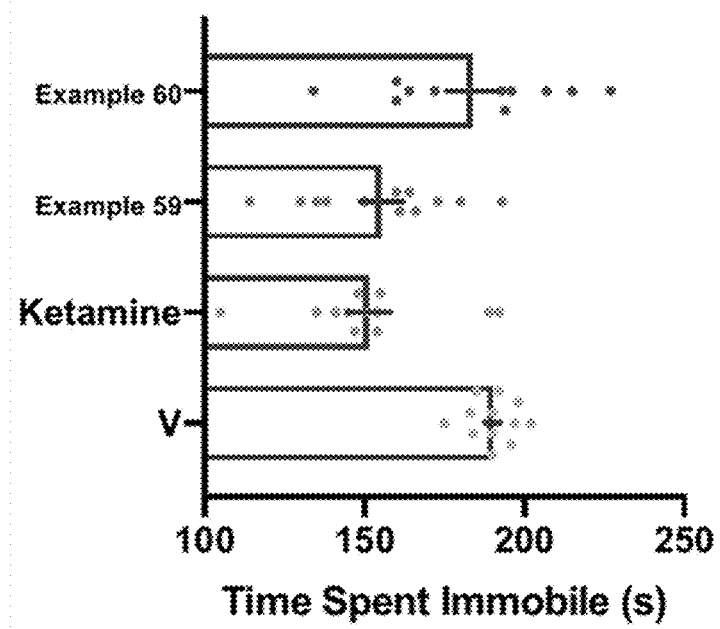

Forced Swim Test. As increased cortical structural plasticity in the anterior parts of the brain mediates the sustained (>24 h) antidepressant-like effects of ketamine and play a role in the therapeutic effects of 5-HT2A agonists, the impact of IsoDMT analogs on forced swim test (FST) behavior (FIG. 14A and FIG. 14B) was evaluated. First, a pretest was used to induce a depressive phenotype. Compounds were administered 24 h after the pre-test, and the FST was performed 24 h and 7 d post drug administration. Both positive control (ketamine) and Example 59 significantly reduced immobility 24 h after drug administration (FIG. 14A vs FIG. 14B).

Neurite outgrowth assay. Changes in the pattern of neurite outgrowth have been implicated in neurodegenerative disorders as well as traumatic injuries. The discovery of new compounds that can positively affect neuritogenesis are important for developing new therapeutics for neurological diseases. Measurement of neurite outgrowth of rat cortical neurons using an automated image-based assay was used to determine the neuroplastic effects of the compounds of the present invention. In some embodiments, a compound of the present invention increases the pattern of neurite outgrowth. In some embodiments, a compound of the present invention increases neurite average length compared to a control. In some embodiments, a compound of the present invention increases neurite branch points compared to a control. In some embodiments, a compound of the present invention increases neurite average length and neurite branch points compared to a control.

In some embodiments, the plastogenic potential of the compounds is shown in Table 4.

TABLE 4

| Compound | Neurite Average Length @ 10 µM | Neurite Branch Points: @ 10 µM |
|---|---|---|
| Example 3 | C | B |
| Example 4 | B | B |
| Example 5 | B | B |
| Example 6 | B | B |
| Example 44 | B | A |
| Example 45 | B | B |
| Example 46 | B | B |
| Example 47 | B | A |
| Example 48 | B | B |
| Example 49 | B | B |
| Example 50 | B | B |
| Example 51 | B | B |
| Example 52 | B | B |
| Example 57 | B | B |
| Example 58 | B | B |
| Example 59 | B | A |
| Example 60 | B | B |
| Example 61 | B | B |
| Example 62 | B | B |
| Example 63 | B | B |
| Example 65 | B | B |
| Example 67 | B | A |
| Example 68 | B | A |
| Example 69 | B | A |
| Example 70 | B | B |
| Example 73 | B | B |
| Example 74 | B | B |
| Example 75 | C | C |
| Example 76 | B | B |
| Example 84 | B | B |

A: >3-fold increase vs DMSO control;
B: 1.5-to 3-fold increase vs DMSO control;
C: <1.5-fold increase vs DMSO control Assays Dendritogenesis Assays. Phenotypic screening has historically proven more successful than target-based approaches for identifying drugs with novel mechanisms of action. Having established a simple and robust method for accessing isoDMT analogs, tested next was their ability to increase dendritic arbor complexity in cultures of cortical neurons using a phenotypic assay. Following treatment, neurons were fixed and visualized using an antibody against MAP2—a cytoskeletal protein localized to the somatodendritic compartment of neurons. Sholl analysis was then performed, and the maximum number of crossings ($N_{max}$) was used as a quantitative metric of dendritic arbor complexity. For statistical comparisons between specific compounds, the raw $N_{max}$ values were compared. Percent efficacies were determined by setting the $N_{max}$ values for the vehicle (DMSO) and positive (ketamine) controls equal to 0% and 100%, respectively.

Animals. For the dendritogenesis experiments, timed pregnant Sprague Dawley rats were obtained from Charles River Laboratories (Wilmington, Mass.). For the head-twitch response assay, male and female C57BL/6J mice were obtained from Jackson Laboratory (Sacramento, Calif.). Mice were housed in a temperature and humidity-controlled room maintained on a 12-h light/dark cycle in groups of 4-5 (same sex). Animals weighed between 17 and 30 g at the time of the experiments. All experimental procedures involving rodents were approved by the UC Davis Institutional Animal Care and Use Committee (IACUC) and adhered to principles described in the National Institutes of Health Guide for the Care and Use of Laboratory Animals. The University of California, Davis and the University of California, San Francisco are accredited by the Association for Assessment and Accreditation of Laboratory Animal Care International (AAALAC).

Dendritogenesis—Sholl Analysis. Dendritogenesis experiments were performed following a previously published method with slight modifications. Neurons were plated in 96-well format (200 µL of media per well) at a density of approximately 15,000 cells/well in Neurobasal (Life Technologies) containing 1% penicillin-streptomycin, 10% heat-inactivated fetal bovine serum, and 0.5 mM glutamine. After 24 h, the medium was replaced with Neurobasal containing 1× B27 supplement (Life Technologies), 1% penicillin-streptomycin, 0.5 mM glutamine, and 12.5 µM glutamate. After 3 days in vitro (DIV3), the cells were treated with compounds. All compounds tested in the dendritogenesis assays were treated at 10 µM unless noted otherwise. Stock solutions of the compounds in DMSO were first diluted 100-fold in Neurobasal before an additional 10-fold dilution into each well (total dilution=1:1000; 0.1% DMSO concentration). Treatments were randomized. After 1 h, the media was removed and replaced with new Neurobasal media containing 1× B27 supplement, 1% penicillin-streptomycin, 0.5 mM glutamine, and 12.5 µM glutamate. The cells were allowed to grow for an additional 71 h. At that time, neurons were fixed by removing 80% of the media and replacing it with a volume of 4% aqueous paraformaldehyde (Alfa Aesar) equal to 50% of the working volume of the well. Then, the cells were incubated at room temperature for 20 min before the fixative was aspirated and each well washed twice with DPBS. Cells were permeabilized using 0.2% Triton X-100 (ThermoFisher) in DPBS for 20 minutes at room temperature without shaking. Plates were blocked with antibody diluting buffer (ADB) containing 2% bovine serum albumin (BSA) in DPBS for 1 h at room temperature. Then, plates were incubated overnight at 4° C. with gentle shaking in ADB containing a chicken anti-MAP2 antibody (1:10,000; EnCor, CPCA-MAP2). The next day, plates were washed three times with DPBS and once with 2% ADB in DPBS. Plates were incubated for 1 h at room temperature in ADB containing an anti-chicken IgG secondary antibody conjugated to Alexa Fluor 488 (Life Technologies, 1:500) and washed five times with DPBS. After the final wash, 100 µL of DPBS was added per well and imaged on an ImageXpress Micro XL High-Content Screening System (Molecular Devices, Sunnyvale, Calif.) with a 20× objective. Images were analyzed using ImageJ Fiji (version 1.51 W). First, images corresponding to each treatment are sorted into individual folders that are then blinded for data analysis. Plate controls (both positive and negative) were used to ensure that the assay is working properly as well as to visually determine appropriate numerical values for brightness/contrast and thresholding to be applied universally to the remainder of the randomized images. Next, the brightness/contrast settings were applied, and approximately 1-2 individual pyramidal-like neurons per image (i.e., no bipolar neurons) were selected using the rectangular selection tool and saved as separate files. Neurons were selected that did not overlap extensively with other cells or extend far beyond the field of view. The threshold settings were then applied to the individual images. The paintbrush tool was used to eliminate artifacts and dendritic processes originating from adjacent neurons (cleanup phaseNext, the point tool was used to select the center of the neuron, and the images were saved and processed using the following Sholl analysis batch macro (Table 5):

run("Sholl Analysis . . . ", "starting=0 ending=NaN radius_step=2 #_samples=1 integration=Mean enclosing=1 #_primary=4 infer fit linear polynomial=[Best fitting degree] most semi-log normalizes Area create background=228 save do");

Sholl analysis circle radii=2 pixel increments=0.67 µm. All images were taken and analyzed by an experimenter blinded to treatment conditions. The number of crossings for each neuron at each distinct radius was averaged to produce an average Sholl plot for each treatment. The $N_{max}$ values were simply determined by identifying the maximum of each plot. For each treatment, neurons were selected from at least 6 wells spread across 2 plates (9 sites/well×3 wells/plate×2 plates). Each plate was prepared using neurons obtained from independent pregnant dams).

TABLE 5

Efficacy in Sholls

| Example No. | % efficacy in sholls |
|---|---|
| Example 1 | 79 |
| Example 2 | 87 |
| Example 3 | 26 |
| Example 4 | 65 |
| Example 5 | 95 |
| Example 6 | 92 |
| Example 8 | 38 |
| Example 9 | 78 |
| Example 10 | 65 |
| Example 11 | 131 |
| Example 12 | 37 |
| Example 13 | 75 |
| Example 14 | 88 |
| Example 15 | 85 |
| Example 16 | 104 |
| Example 17 | 84 |
| Example 18 | 62 |
| Example 19 | 85 |
| Example 20 | 117 |
| Example 21 | 72 |
| Example 22 | 50 |
| Example 23 | 64 |
| Example 24 | 86 |
| Example 25 | 17 |
| Example 26 | 70 |
| Example 27 | 73 |
| Example 28 | 80 |
| Example 29 | 81 |
| Example 30 | 72 |
| Example 32 | 88 |
| Example 33 | 65 |

Ketanserin Blocking Experiments. For the ketaserin blocking experiments (FIG. 7), a slightly modified method was employed. On DIV 3, neurons were first treated with ketanserin (10 µM) for 1 h followed by a 1 h incubation with drug (1 µM) and ketanserin (10 µM) (final concentration of DMSO=0.2%). After 1 h, the media was removed and replaced with new Neurobasal media containing 1× B27 supplement, 1% penicillin-streptomycin, 0.5 mM glutamine, and 12.5 µM glutamate. The cells were allowed to grow for an additional 71 h before being fixed, stained, and imaged.

Neurite Outgrowth Assay. Rat cortical neurons (20,000 cells/well) were freshly isolated from embryonic day 18 rats and cultured in Neurobasal Medium (+B27). The cultured cells were plated in 96 well-plates (avoiding external wells). At DIV 4, the neurons were treated with compound or control (10 µM) for 1 hour followed by complete washout of the compound. At DIV 7, the neurons were analyzed. The experiments were performed in triplicate. Neurite outgrowth was measured analyzing the following parameters: Number of Cell Bodies, total neurite length (pixels), Root Count, Segments, Extremities Count and node points. Changes in the pattern of neurite outgrowth of the neurons were analyzed by immunocytochemistry against β-III-tubulin. Pictures were acquired by the CellInsight CX7 from Thermo Fisher and analyzed using its software. Results generated in the equipment were maximum neurite length, extremity count, root count, dendrite branch points, and total neurite length. The results were compared to DMSO control, representing the fold-change in neuronal outgrowth.

$5HT_{2A}$ Sensor Assays. HEK293T (ATCC) 5HT2A sensor stable line (sLight1.3s) was generated via lentiviral transduction of HIV-EF1α-sLight1.3 and propagated from a single colony. Lentivirus was produced using $2^{nd}$ generation lentiviral plasmids pHIV-EF1α-sLight1.3, pHCMV-G, and pCMV-deltaR8.2.

For the screening of the 41 compounds, sLight1.3s cells were plated in 96-well plates at a density of 40000 24-hours prior to imaging. On the day of imaging, compounds solubilized in DMSO were diluted from the 100 mM stock solution to working concentrations of 1 mM, 100 µM and 1 µM with a DMSO concentration of 1%. Immediately prior to imaging, cells growing in DMEM (Gibco) were washed 2× with HBSS (Gibco) and in agonist mode 180 µL of HBSS or in antagonist mode 160 µL of HBSS was added to each well after the final wash. For agonist mode, images were taken before and after the addition of the 20 µL compound working solution into the wells containing 180 µL HBSS. This produced final compound concentrations of 100 µM, 10 µM and 100 nM with a DMSO concentration of 0.1%. For antagonist mode, images were taken before and after addition of 20 µL of 900 nM 5-HT and again after 20 µL of the compound working solutions to produce final concentrations of 100 nM for 5HT and 100 µM, 10 µM and 100 nM for the compounds with a DMSO concentration of 0.1%. Each compound was tested in triplicates (3 wells) for each concentration (100 µM, 10 µM and 100 nM). Additionally, within each plate, 100 nM 5HT and 0.1% DMSO controls were also imaged.

Imaging was performed using the Leica DMi8 inverted microscope with a 40× objective using the FITC preset with an excitation of 460 nm and emission of 512-542 nm. For each well, the cellular membrane where the 5HT2A sensor is targeted was autofocused using the adaptive focus controls and 5 images from different regions within the well were taken with each image processed from a 2×2 binning.

For data processing, the membranes from each image was segmented and analyzed using a custom algorithm written in MATLAB producing a single raw fluorescence intensity value. For each well the 5 raw fluorescence intensity values generated from the 5 images were averaged and the change in fluorescence intensity (dFF) was calculated as:

$$dFF = (F_{sat} - F_{apo})/F_{apo}$$

For both agonist and antagonist modes, the fluorescence intensity values before compound addition in HBSS only were used as the $F_{apo}$ values while the fluorescence intensity values after compound addition were used as the $F_{sat}$ values.

For agonist mode, data are as percent activation relative to 5HT, where 0 is the average of the DMSO wells and 100 is the average of the 100 uM 5HT wells. For antagonist mode, the inactivation score was calculated as:

$$\text{Inactivation score} = (dFFF(\text{Compound}+5HT) - dFF(5HT))/dFF(5HT)$$

Calcium Secondary Messenger Pathway. Cell lines were expanded from freezer stocks according to standard procedures. Cells were seeded in a total volume of 20 µL into black-walled, clear-bottom, Poly-D-lysine coated 384-well microplates and incubated at 37° C. for the appropriate time prior to testing. Assays were performed in 1× Dye Loading Buffer consisting of 1× Dye, 1× Additive A and 2.5 mM Probenecid in HBSS/20 mM Hepes. Probenicid was prepared fresh. Cells were loaded with dye prior to testing. Media was aspirated from cells and replaced with 20 µL Dye Loading Buffer. Cells were incubated for 30-60 minutes at 37° C.

For agonist determination, cells were incubated with sample to induce response. After dye loading, cells were removed from the incubator and 10 µL HBSS/20 mM Hepes was added. 3× vehicle was included in the buffer when performing agonist dose curves to define the EC80 for subsequent antagonist assays. Cells were incubated for 30 minutes at room temperature in the dark to equilibrate plate temperature. Intermediate dilution of sample stocks was performed to generate 4× sample in assay buffer. Compound agonist activity was measured on a FLIPR Tetra (MDS). Calcium mobilization was monitored for 2 minutes and 10 µL 4× sample in HBSS/20 mM Hepes was added to the cells 5 seconds into the assay.

Compound activity was analyzed using CBIS data analysis suite (ChemInnovation, CA). For agonist mode assays, percentage activity is calculated using the following formula:

$$\% \text{ Activity} = 100\% \times (\text{mean RFU of test sample} - \text{mean RFU of vehicle control})/(\text{mean MAX RFU control ligand} - \text{mean RFU of vehicle control}).$$

Head twitch response experiments. Mice (9-10 weeks old) were injected intraperitoneally with compound (injection volume 5 ml/kg), placed in an empty cage, and filmed for 20 minutes. Cages were cleaned with 70% ethanol between experiments. Each video was scored for the number of head-twitches by two trained observers blinded to treatment condition (Pearson correlation coefficients=0.91 and 0.99 for males and females, respectively), and these results were averaged.

Forced Swim Test (FST). Male C57/BL6J mice (9-10 weeks old at time of experiment) were obtained from the Jackson Lab and housed 4-5 mice/cage in a UCD vivarium following an IACUC approved protocol. After 1 week in the vivarium each mouse was handled for approximately 1 minute by a male experimenter for 3 consecutive days leading up to the first FST. All experiments were carried out by the same male experimenter who performed handling. During the FST, mice underwent a 6 min swim session in a clear Plexiglas cylinder 40 cm tall, 20 cm in diameter, and filled with 30 cm of 24±1° C. water. Fresh water was used for every mouse. After handling and habituation to the experimenter, drug-naïve mice first underwent a pretest swim to more reliably induce a depressive phenotype in the subsequent FST sessions. Immobility scores for all mice were determined after the pre-test and mice were randomly assigned to treatment groups to generate groups with similar average immobility scores to be used for the following two FST sessions. The next day, the animals received intraperitoneal injections of experimental compounds (20 mg/kg), a positive control (ketamine, 3 mg/kg), or vehicle (saline). The animals were subjected to the FST 30 mins after injection and then returned to their home cages. All FSTs were performed between the hours of 8 am and 1 pm. Experiments were video-recorded and manually scored offline. Immobility time—defined as passive floating or remaining motionless with no activity other than that needed to keep the mouse's head above water—was scored for the last 4 min of the 6 min trial.

Statistical analysis. Treatments were randomized, and data were analyzed by experimenters blinded to treatment conditions. Statistical analyses were performed using GraphPad Prism (version 8.1.2). The specific tests used, F-statistics, degrees of freedom, and main effect p-values are indicated in the figure legends where appropriate. All comparisons were planned prior to performing each experiment. For dendritogenesis experiments a one-way ANOVA with Dunnett's post hoc test was deemed most appropriate. Ketamine was included as a positive control to ensure that the assay was working properly.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A compound selected from the group consisting of:

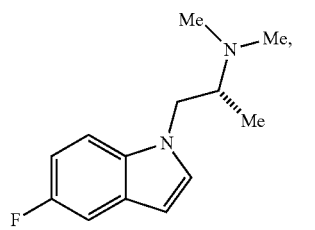 [SMILES: C[C@H](Cn1ccc2cc(F)ccc21)N(C)C]

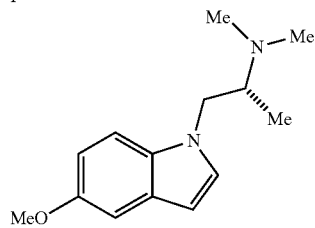

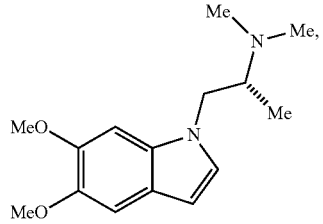

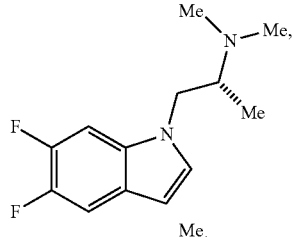

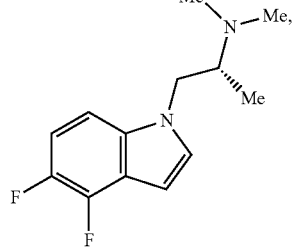

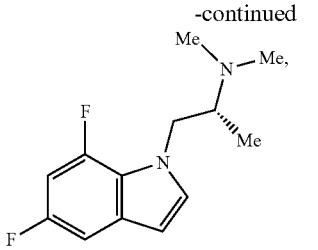

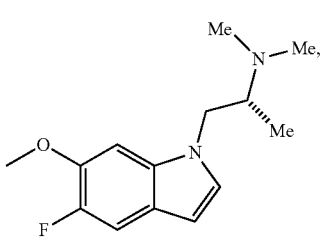

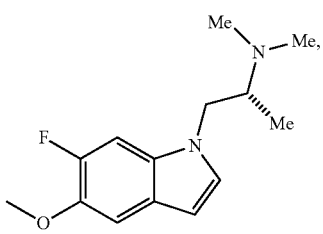

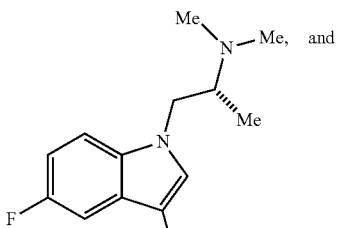

and

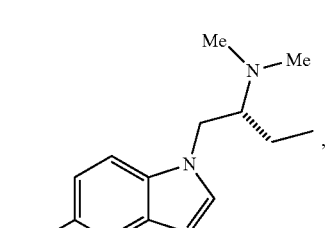

or a pharmaceutically acceptable salt thereof.

2. The compound of claim 1, which is

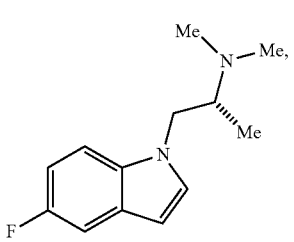

or a pharmaceutically acceptable salt thereof.

3. The compound of claim 1, which is

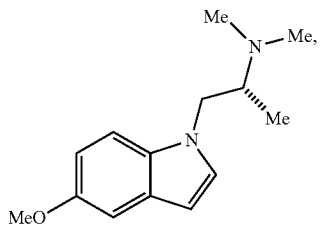 [SMILES: COc1ccc2c(ccn2C[C@@H](C)N(C)C)c1]

or a pharmaceutically acceptable salt thereof.

4. The compound of claim 1, which is

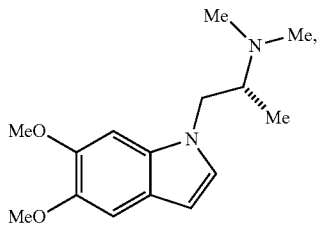 [SMILES: COc1cc2ccn(C[C@@H](C)N(C)C)c2cc1OC]

or a pharmaceutically acceptable salt thereof.

5. The compound of claim 1, which is

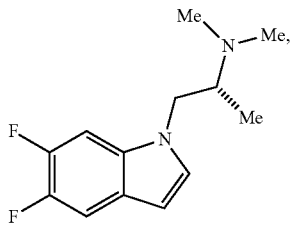 [SMILES: C[C@H](Cn1ccc2cc(F)c(F)cc21)N(C)C]

or a pharmaceutically acceptable salt thereof.

6. The compound of claim 1, which is

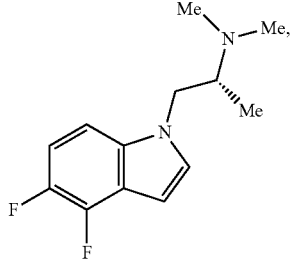 [SMILES: C[C@H](Cn1ccc2c(F)c(F)ccc21)N(C)C]

or a pharmaceutically acceptable salt thereof.

7. The compound of claim 1, which is

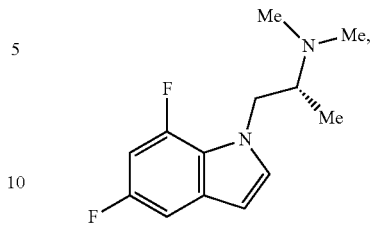

or a pharmaceutically acceptable salt thereof.

8. The compound of claim 1, which is

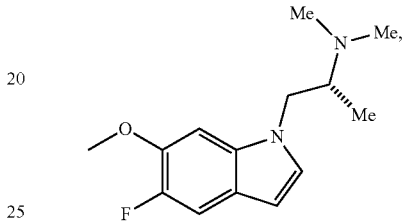

or a pharmaceutically acceptable salt thereof.

9. The compound of claim 1, which is

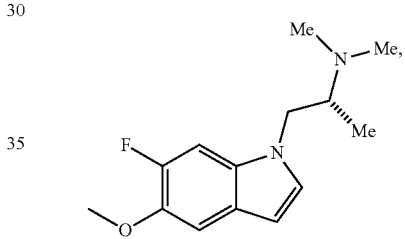

or a pharmaceutically acceptable salt thereof.

10. The compound of claim 1, which is

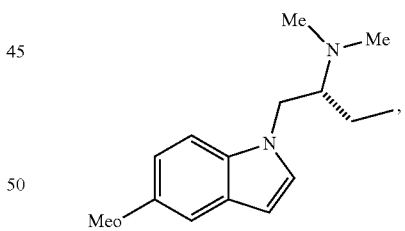

or a pharmaceutically acceptable salt thereof.

11. The compound of claim 1, which is

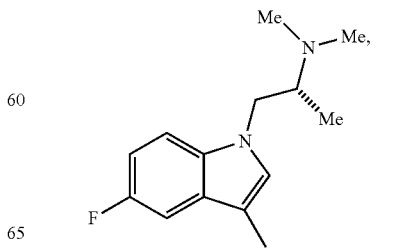

or a pharmaceutically acceptable salt thereof.

12. A method for treating a brain disorder, comprising administering to a subject in need thereof, a therapeutically effective amount of a compound according to claim 1, or a pharmaceutically acceptable salt thereof.

13. The method of claim 12, wherein the brain disorder is a psychological disorder, depression, addiction, anxiety, or post-traumatic stress disorder.

14. The method of claim 13, wherein the brain disorder is depression or addiction.

15. The method of claim 12, wherein the brain disorder is treatment resistant depression, suicidal ideation, major depressive disorder, bipolar disorder, schizophrenia, or substance use disorder.

16. A pharmaceutical composition, comprising a therapeutically effective amount of a compound selected from claim 1, or a pharmaceutically acceptable salt thereof.

17. The pharmaceutical composition of claim 16, selected from the group consisting of:

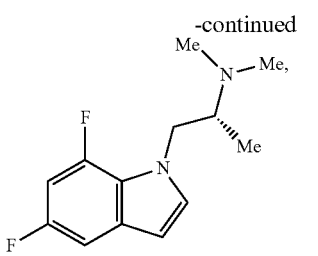

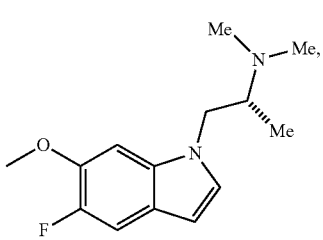 [SMILES: COc1cc2c(ccn2C[C@@H](C)N(C)C)cc1F]

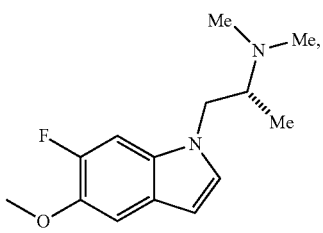 [SMILES: COc1cc2ccn(C[C@@H](C)N(C)C)c2cc1F]

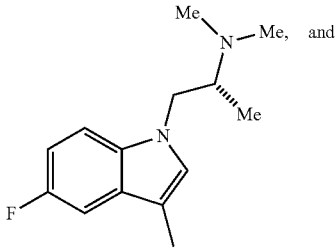

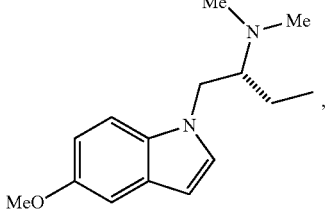

or a pharmaceutically acceptable salt thereof, and a pharmaceutically acceptable excipient.

18. The pharmaceutical composition of claim 17, wherein the compound is

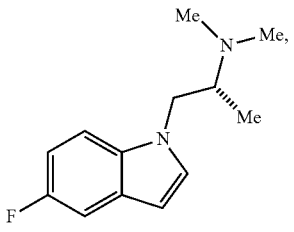

or a pharmaceutically acceptable salt thereof.

19. The pharmaceutical composition of claim 17, wherein the compound is

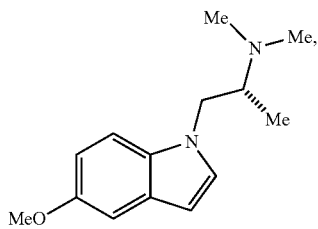 [SMILES: COc1ccc2c(ccn2C[C@@H](C)N(C)C)c1]

or a pharmaceutically acceptable salt thereof.

20. The pharmaceutical composition of claim 17, wherein the compound is

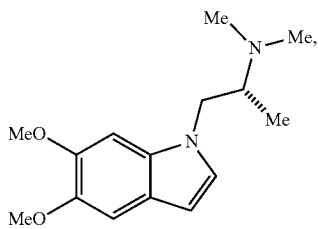 [SMILES: COc1cc2ccn(C[C@@H](C)N(C)C)c2cc1OC]

or a pharmaceutically acceptable salt thereof.

21. The pharmaceutical composition of claim 17, wherein the compound is

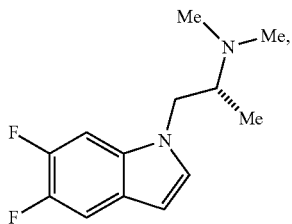 [SMILES: C[C@H](Cn1ccc2cc(F)c(F)cc21)N(C)C]

or a pharmaceutically acceptable salt thereof.

22. The pharmaceutical composition of claim 17, wherein the compound is

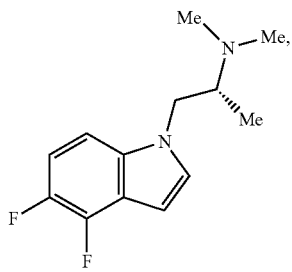 [SMILES: C[C@H](Cn1ccc2c(F)c(F)ccc21)N(C)C]

or a pharmaceutically acceptable salt thereof.

23. The pharmaceutical composition of claim 17, wherein the compound is

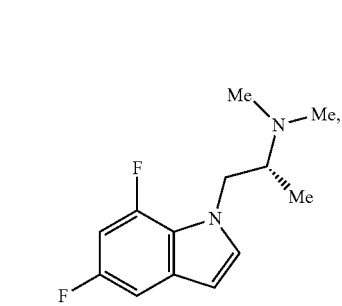 [SMILES: C[C@H](Cn1ccc2cc(F)cc(F)c21)N(C)C]

or a pharmaceutically acceptable salt thereof.

24. The pharmaceutical composition of claim 17, wherein the compound is

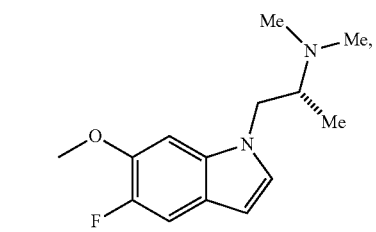 [SMILES: COc1cc2c(ccn2C[C@@H](C)N(C)C)cc1F]

or a pharmaceutically acceptable salt thereof.

25. The pharmaceutical composition of claim 17, wherein the compound is

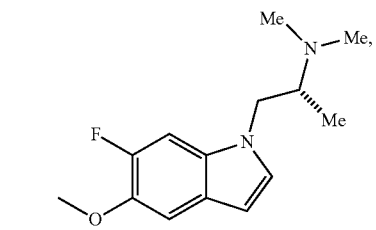 [SMILES: COc1cc2ccn(C[C@@H](C)N(C)C)c2cc1F]

or a pharmaceutically acceptable salt thereof.

* * * * *

UNITED STATES PATENT AND TRADEMARK OFFICE
CERTIFICATE OF CORRECTION

PATENT NO. : 11,254,640 B2  
APPLICATION NO. : 17/345471  
DATED : February 22, 2022  
INVENTOR(S) : David E. Olson, Lee Dunlap and Florence F. Wagner Page 1 of 1

It is certified that error appears in the above-identified patent and that said Letters Patent is hereby corrected as shown below:

On the Title Page

Inventor Name:
Delete "Florence WAGNER" and insert -- Florence F. WAGNER --

Signed and Sealed this
Twenty-second Day of March, 2022

Drew Hirshfeld
*Performing the Functions and Duties of the*
*Under Secretary of Commerce for Intellectual Property and*
*Director of the United States Patent and Trademark Office*